(12) United States Patent
Hermann et al.

(10) Patent No.: US 9,169,259 B2
(45) Date of Patent: Oct. 27, 2015

(54) IMIDAZOPYRIDAZINE COMPOUNDS

(71) Applicant: Hoffmann-La Roche Inc., Nutley, NJ (US)

(72) Inventors: Johannes Cornelius Hermann, Jersey City, NJ (US); Andreas Kuglstatter, Loerrach (DE); Matthew C. Lucas, Lexington, MA (US); Fernando Padilla, Verona, NJ (US); Jutta Wanner, Montclair, NJ (US); Xiaohu Zhang, Jiangsu (CN)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 91 days.

(21) Appl. No.: 13/665,006

(22) Filed: Oct. 31, 2012

(65) Prior Publication Data

US 2013/0109661 A1    May 2, 2013

(30) Foreign Application Priority Data

Nov. 1, 2011   (CN) ................. PCT/CN2011/081614

(51) Int. Cl.
| | | |
|---|---|---|
| A61K 45/06 | (2006.01) |
| A61K 31/625 | (2006.01) |
| C07D 487/04 | (2006.01) |
| A61K 31/5025 | (2006.01) |
| A61K 31/5377 | (2006.01) |

(52) U.S. Cl.
CPC .......... *C07D 487/04* (2013.01); *A61K 31/5025* (2013.01); *A61K 31/5377* (2013.01); *A61K 31/625* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,902,197 B2 | 3/2011 | Elworthy et al. | |
| 7,932,254 B2 | 4/2011 | DuBois et al. | |
| 7,939,531 B2 | 5/2011 | Bamberg et al. | |
| 8,008,298 B2 | 8/2011 | Bamberg et al. | |
| 8,119,636 B2 | 2/2012 | Du Bois et al. | |
| 2011/0230414 A1 | 9/2011 | Hendricks et al. | |
| 2011/0230462 A1 | 9/2011 | Hendricks et al. | |
| 2011/0288067 A1 | 11/2011 | Hendricks et al. | |
| 2011/0288097 A1 | 11/2011 | Hendricks et al. | |

FOREIGN PATENT DOCUMENTS

| | | |
|---|---|---|
| WO | 2007/038314 | 4/2007 |
| WO | 2009/077334 | 6/2009 |
| WO | 2010/068258 | 6/2010 |
| WO | 2010/070008 | 6/2010 |

OTHER PUBLICATIONS (International Search Report PCT/EP2012/071337 Jan. 18, 2013).
Leonard et al., "JAKS and STATS: biological implications" Annual Rev. Immunol 16:293-322 ( 1998).
Turner et al., "Perinatal lethality and blocked B-cell development in mice lacking the tyrosine kinase Syk:" Nature 378:298-302 ( 1995).
Cheng et al., "Syk tyrosine kinase required for mouse viability and B-cell development" Nature 378:303-306 ( 1995).
The English translation of the Chinese Office Action, issued on Apr. 14, 2015, in the relaed Chinese patent application No. 201280064395.0.

*Primary Examiner* — Jeffrey S Lundgren
*Assistant Examiner* — Michael Schmitt

(57) ABSTRACT

The present invention relates to the use of novel compounds of formula I:

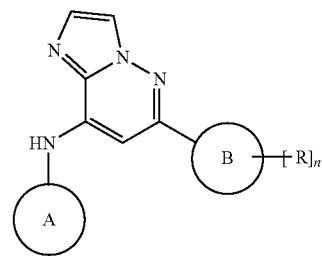

wherein all variable substituents are defined as described herein, which are SYK inhibitors and are useful for the treatment of auto-immune and inflammatory diseases.

21 Claims, No Drawings

IMIDAZOPYRIDAZINE COMPOUNDS

CROSS-REFERENCE TO RELATED APPLICATIONS

This application claims the benefit of International Pat. Appl. No. PCT/CN2011/081614, filed Nov. 1, 2011, which is hereby incorporated by reference in its entirety.

FIELD OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

SYK (Spleen Tyrosine Kinase) is a non-receptor tyrosine kinase that is essential for B-cell activation through BCR signaling. SYK becomes activated upon binding to phosphorylated BCR and thus initiates the early signaling events following BCR activation. Mice deficient in SYK exhibit an early block in B-cell development. Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma. SYK binds to the phosphorylated gamma chain of FcγRI via its SH2 domains and is essential for downstream signaling. SYK deficient mast cells demonstrate defective degranulation, arachidonic acid and cytokine secretion. This also has been shown for pharmacologic agents that inhibit SYK activity in mast cells. Treatment with SYK antisense oligonucleotides inhibits antigen-induced infiltration of eosinophils and neutrophils in an animal model of asthma. SYK deficient eosinophils also show impaired activation in response to FcεR stimulation. Therefore, small molecule inhibitors of SYK will be useful for treatment of allergy-induced inflammatory diseases including asthma.

In view of the numerous conditions that are contemplated to benefit by treatment involving modulation of the SYK pathway it is immediately apparent that new compounds that modulate the SYK pathway and methods of using these compounds should provide substantial therapeutic benefits to a wide variety of patients. Provided herein are novel compounds for use in the therapeutic treatment of auto-immune and inflammatory diseases by targeting the SYK pathway or by inhibition of SYK kinase.

SUMMARY OF THE INVENTION

The application provides a compound of Formula I

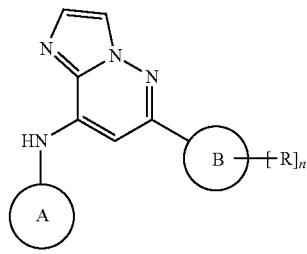

wherein:
A is pyridyl, pyrrolidinyl, or pyrazolyl, substituted with one or more A';
  each A' is independently lower alkyl, lower alkoxy, lower haloalkyl, hydroxy lower alkyl, pyrrolidinyl, piperidinyl, bicyclic heterocycloalkyl, optionally substituted with lower alkyl;
n is 0, 1 or 2;
B is phenyl, pyridyl, pyrrolidinyl, or piperidinyl;
each R is independently halo, hydroxy, lower alkyl, lower alkoxy, lower haloalkyl, cyano, heterocycloalkyl lower alkyl, —NH(C=O)R$^1$, —C(=O)R$^1$, —C(=O)OR$^1$, —O(CH$_2$)$_p$R$^1$, CH$_2$R$^1$, CH$_2$NHR$^1$, or —C(=O)NHR$^1$;
  or two R together form a bicyclic heteroaryl or heterocycloalkyl ring system;
  R$^1$ is H or R$^{1'}$;
  R$^{1'}$ is lower alkyl, phenyl, indolyl, indazolyl, heteroaryl lower alkyl, or heterocycloalkyl, optionally substituted with one or more R$^{1''}$;
    each R$^{1''}$ is hydroxy, lower alkyl, lower alkoxy, carboxy, amido, amino, dialkyl amino, or oxo; and
  p is 0, 1, or 2;
or a pharmaceutically acceptable salt thereof.

The application provides a method for treating an inflammatory or autoimmune condition comprising administering to a patient in need thereof a therapeutically effective amount of the compound of Formula I.

The application provides a pharmaceutical composition comprising a therapeutically effective amount of the compound of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

MeC(=O)OR⁴ wherein

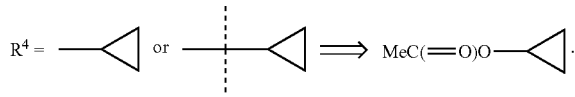

A bond drawn into ring system (as opposed to connected at a distinct vertex) indicates that the bond may be attached to any of the suitable ring atoms The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —$CH_2CH(i\text{-}Pr)CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1\text{-}10}$ alkoxy" as used herein refers to an-O-alkyl wherein alkyl is $C_{1\text{-}10}$.

The term "$PCy_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S($=$O)$_2$R wherein R is alkyl or aryl respectively and alkyl and aryl are as defined herein. The term "heteroalkylsulfonyl" as used herein refers herein denotes a group of formula —S($=$O)$_2$R wherein R is "heteroalkyl" as defined herein.

The terms "alkylsulfonylamino" and "arylsulfonylamino" as used herein refers to a group of formula —NR'S($=$O)$_2$R wherein R is alkyl or aryl respectively, R' is hydrogen or $C_{1\text{-}3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3\text{-}7}$ cycloalkyl" as used herein refers to a cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —$CO_2H$ moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or S(O)$_{0\text{-}2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of SYK

The application provides a compound of Formula I

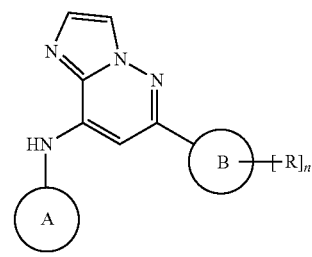

wherein:
A is pyridyl, pyrrolidinyl, or pyrazolyl, substituted with one or more A';

each A' is independently lower alkyl, lower alkoxy, lower haloalkyl, hydroxy lower alkyl, pyrrolidinyl, piperidinyl, bicyclic heterocycloalkyl, optionally substituted with lower alkyl;

n is 0, 1 or 2;

B is phenyl, pyridyl, pyrrolidinyl, or piperidinyl;

each R is independently halo, hydroxy, lower alkyl, lower alkoxy, lower haloalkyl, cyano, heterocycloalkyl lower alkyl, —NH(C=O)R$^1$, —C(=O)R$^1$, —C(=O)OR$^1$, —O(CH$_2$)$_p$R$^1$, CH$_2$R$^1$, CH$_2$NHR$^1$, or —C(=O)NHR$^1$;

or two R together form a bicyclic heteroaryl or heterocycloalkyl ring system;

R$^1$ is H or R$^{1''}$;

R$^{1''}$ is lower alkyl, phenyl, indolyl, indazolyl, heteroaryl lower alkyl, or heterocycloalkyl, optionally substituted with one or more R$^{1'''}$;

each R$^{1'''}$ is hydroxy, lower alkyl, lower alkoxy, carboxy, amido, amino, dialkyl amino, or oxo; and p is 0, 1, or 2;

or a pharmaceutically acceptable salt thereof.

The application provides a compound of Formula I, wherein A is pyridyl, substituted with one or more A'.

The application provides a compound of Formula I, wherein B is phenyl.

The application provides a compound of Formula I, wherein A' is pyrrolidinyl, optionally substituted with one or more lower alkyl.

The application provides a compound of Formula I, wherein A' is methyl pyrrolidinyl or dimethylpyrrolidinyl.

The application provides a compound of Formula I, wherein A' is lower alkoxy.

The application provides a compound of Formula I, wherein R is C(=O)NHR$^1$.

The application provides a compound of Formula I, wherein R is —C(=O)OH.

The application provides a compound of Formula I, wherein R is —NH(C=O)R$^1$.

The application provides a compound of Formula I, wherein n is 0 or two R together form a bicyclic heteroaryl or heterocycloalkyl ring system.

The application provides a compound of Formula I, wherein R$^1$ is phenyl, indolyl, or indazolyl, optionally substituted with one or more R$^{1'''}$.

The application provides a compound selected from the group consisting of:

(6-Phenyl-imidazo[1,2-b]pyridazin-8-yl)-(6-trifluoromethyl-pyridin-2-yl)-amine;
(5-Ethyl-pyridin-2-yl)-(6-phenyl-imidazo[1,2-b]pyridazin-8-yl)-amine;
(6-Phenyl-imidazo[1,2-b]pyridazin-8-yl)-(3,4,5,6-tetrahydro-2H-[1,2']bipyridinyl-6'-yl)-amine;
(6-Phenyl-imidazo[1,2-b]pyridazin-8-yl)-(6-pyrrolidin-1-yl-pyridin-2-yl)-amine;
[6-(2-Methyl-pyrrolidin-1-yl)-pyridin-2-yl]-(6-phenyl-imidazo[1,2-b]pyridazin-8-yl)-amine;
(1-tert-Butyl-1H-pyrazol-3-yl)-(6-phenyl-imidazo[1,2-b]pyridazin-8-yl)-amine;
8-(2,2-Dimethyl-pyrrolidin-1-yl)-6-phenyl-imidazo[1,2-b]pyridazine;
3-{8-[6-(2-Methyl-pyrrolidin-1-yl)-pyridin-2-ylamino]-imidazo[1,2-b]pyridazin-6-yl}-benzoic acid methyl ester;
3-{8-[6-(2-Methyl-pyrrolidin-1-yl)-pyridin-2-ylamino]-imidazo[1,2-b]pyridazin-6-yl}-benzoic acid;
4-(3-{8-[6-(2-Methyl-pyrrolidin-1-yl)-pyridin-2-ylamino]-imidazo[1,2-b]pyridazin-6-yl}-benzoylamino)-benzoic acid;
Sodium 3-(8-(6-(2-methylpyrrolidin-1-yl)pyridin-2-ylamino)imidazo[1,2-b]pyridazin-6-yl)benzoate;
3-{8-[6-(2-Methyl-pyrrolidin-1-yl)-pyridin-2-ylamino]-imidazo[1,2-b]pyridazin-6-yl}-benzamide;
(2-Methyl-3,4,5,6-tetrahydro-2H-[1,2']bipyridinyl-6'-yl)-(6-phenyl-imidazo[1,2-b]pyridazin-8-yl)-amine;
4-{8-[6-(2-Methyl-pyrrolidin-1-yl)-pyridin-2-ylamino]-imidazo[1,2-b]pyridazin-6-yl}-benzoic acid methyl ester;
4-{8-[6-(2-Methyl-pyrrolidin-1-yl)-pyridin-2-ylamino]-imidazo[1,2-b]pyridazin-6-yl}-benzoic acid;
4-{8-[6-(2-Methyl-pyrrolidin-1-yl)-pyridin-2-ylamino]-imidazo[1,2-b]pyridazin-6-yl}-N-(2-pyridin-4-yl-ethyl)-benzamide;
4-{8-[6-(2-Methyl-pyrrolidin-1-yl)-pyridin-2-ylamino]-imidazo[1,2-b]pyridazin-6-yl}-benzamide;
(6-Benzo[1,3]dioxol-5-yl-imidazo[1,2-b]pyridazin-8-yl)-[6-(2-methyl-pyrrolidin-1-yl)-pyridin-2-yl]-amine;
[6-(1H-Indazol-6-yl)-imidazo[1,2-b]pyridazin-8-yl]-[6-(2-methyl-pyrrolidin-1-yl)-pyridin-2-yl]-amine;
3-{8-[6-(2-Hydroxymethyl-pyrrolidin-1-yl)-pyridin-2-ylamino]-imidazo[1,2-b]pyridazin-6-yl}-benzoic acid;
[6-((R)-2-Methyl-pyrrolidin-1-yl)-pyridin-2-yl]-(6-phenyl-imidazo[1,2-b]pyridazin-8-yl)-amine;
3-[8-(6-Pyrrolidin-1-yl-pyridin-2-ylamino)-imidazo[1,2-b]pyridazin-6-yl]-benzoic acid;
3-{8-[6-(3-Aza-bicyclo[3.1.0]hex-3-yl)-pyridin-2-ylamino]-imidazo[1,2-b]pyridazin-6-yl}-benzoic acid;
2-Methyl-3-{8-[6-((S)-2-methyl-pyrrolidin-1-yl)-pyridin-2-ylamino]-imidazo[1,2-b]pyridazin-6-yl}-benzoic acid;
[6-(3-Methyl-pyrrolidin-1-yl)-pyridin-2-yl]-(6-phenyl-imidazo[1,2-b]pyridazin-8-yl)-amine;
4-[8-(5,6-Dimethoxy-pyridin-2-ylamino)-imidazo[1,2-b]pyridazin-6-yl]-benzoic acid;
4-[8-(5,6-Dimethoxy-pyridin-2-ylamino)-imidazo[1,2-b]pyridazin-6-yl]-N-(2-pyridin-4-yl-ethyl)-benzamide;
4-[8-(5,6-Dimethoxy-pyridin-2-ylamino)-imidazo[1,2-b]pyridazin-6-yl]-N-[2-(2-oxo-1,2-dihydro-pyridin-4-yl)-ethyl]-benzamide;
[6-(2,5-Dimethyl-pyrrolidin-1-yl)-pyridin-2-yl]-(6-phenyl-imidazo[1,2-b]pyridazin-8-yl)-amine;
[6-(2-Ethyl-pyrrolidin-1-yl)-pyridin-2-yl]-(6-phenyl-imidazo[1,2-b]pyridazin-8-yl)-amine;
{1-[6-(6-Phenyl-imidazo[1,2-b]pyridazin-8-ylamino)-pyridin-2-yl]-pyrrolidin-2-yl}-methanol;
[6-(2,2-Dimethyl-pyrrolidin-1-yl)-pyridin-2-yl]-(6-phenyl-imidazo[1,2-b]pyridazin-8-yl)-amine;
4-[8-(5,6-Dimethoxy-pyridin-2-ylamino)-imidazo[1,2-b]pyridazin-6-yl]-N-[2-(1-methyl-2-oxo-1,2-dihydro-pyridin-4-yl)-ethyl]-benzamide;
[6-(3,3-Dimethyl-pyrrolidin-1-yl)-pyridin-2-yl]-(6-phenyl-imidazo[1,2-b]pyridazin-8-yl)-amine;
[6-(2-Methoxymethyl-pyrrolidin-1-yl)-pyridin-2-yl]-(6-phenyl-imidazo[1,2-b]pyridazin-8-yl)-amine;
3-{8-[6-(2-Methoxymethyl-pyrrolidin-1-yl)-pyridin-2-ylamino]-imidazo[1,2-b]pyridazin-6-yl}-benzoic acid;
[6-(1H-Indazol-5-yl)-imidazo[1,2-b]pyridazin-8-yl]-[6-(2-methyl-pyrrolidin-1-yl)-pyridin-2-yl]-amine;
3-[8-(3,5-Dimethyl-3,4,5,6-tetrahydro-2H-[1,2']bipyridinyl-6'-ylamino)-imidazo[1,2-b]pyridazin-6-yl]-benzoic acid;
[6-(3-Methoxy-phenyl)-imidazo[1,2-b]pyridazin-8-yl]-[6-(2-methyl-pyrrolidin-1-yl)-pyridin-2-yl]-amine;
N-(2-Hydroxy-ethyl)-3-{8-[6-(2-methyl-pyrrolidin-1-yl)-pyridin-2-ylamino]-imidazo[1,2-b]pyridazin-6-yl}-benzamide;
N-(2-Hydroxy-1-methyl-ethyl)-3-{8-[6-(2-methyl-pyrrolidin-1-yl)-pyridin-2-ylamino]-imidazo[1,2-b]pyridazin-6-yl}-benzamide;

(3-{8-[6-(2-Methyl-pyrrolidin-1-yl)-pyridin-2-ylamino]-imidazo[1,2-b]pyridazin-6-yl}-phenyl)-morpholin-4-yl-methanone;
[6-((S)-2-Methyl-pyrrolidin-1-yl)-pyridin-2-yl]-(6-phenyl-imidazo[1,2-b]pyridazin-8-yl)-amine;
(5,6-Dimethoxy-pyridin-2-yl)-(6-phenyl-imidazo[1,2-b]pyridazin-8-yl)-amine;
[6-(2-Chloro-phenyl)-imidazo[1,2-b]pyridazin-8-yl]-[6-(2-methyl-pyrrolidin-1-yl)-pyridin-2-yl]-amine;
N-(2-Dimethylamino-ethyl)-3-{8-[6-(2-methyl-pyrrolidin-1-yl)-pyridin-2-ylamino]-imidazo[1,2-b]pyridazin-6-yl}-benzamide;
[6-(2-Methyl-pyrrolidin-1-yl)-pyridin-2-yl]-(6-o-tolyl-imidazo[1,2-b]pyridazin-8-yl)-amine;
[6-(2-Methyl-pyrrolidin-1-yl)-pyridin-2-yl]-[6-(2-trifluoromethyl-phenyl)-imidazo[1,2-b]pyridazin-8-yl]-amine;
3-{8-[6-((S)-2-Methyl-pyrrolidin-1-yl)-pyridin-2-ylamino]-imidazo[1,2-b]pyridazin-6-yl}-benzoic acid;
4-{8-[6-((S)-2-Methyl-pyrrolidin-1-yl)-pyridin-2-ylamino]-imidazo[1,2-b]pyridazin-6-yl}-benzamide;
3-{8-[6-((S)-2-Methyl-pyrrolidin-1-yl)-pyridin-2-ylamino]-imidazo[1,2-b]pyridazin-6-yl}-benzamide;
(6-Benzothiazol-6-yl-imidazo[1,2-b]pyridazin-8-yl)-[6-((S)-2-methyl-pyrrolidin-1-yl)-pyridin-2-yl]-amine;
[6-(2,5-Dimethyl-pyrrolidin-1-yl)-pyridin-2-yl]-(6-phenyl-imidazo[1,2-b]pyridazin-8-yl)-amine;
4-{3-[8-(5,6-Dimethoxy-pyridin-2-ylamino)-imidazo[1,2-b]pyridazin-6-yl]-benzoylamino}-benzoic acid;
3-[8-(5,6-Dimethoxy-pyridin-2-ylamino)-imidazo[1,2-b]pyridazin-6-yl]-N-(1H-indazol-5-yl)-benzamide;
3-[8-(5,6-Dimethoxy-pyridin-2-ylamino)-imidazo[1,2-b]pyridazin-6-yl]-N-(1-oxo-2,3-dihydro-1H-isoindol-5-yl)-benzamide;
4-{3-[8-(5,6-Dimethoxy-pyridin-2-ylamino)-imidazo[1,2-b]pyridazin-6-yl]-benzoylamino}-2-methoxy-benzoic acid;
3-[8-(5,6-Dimethoxy-pyridin-2-ylamino)-imidazo[1,2-b]pyridazin-6-yl]-N-(2-oxo-2,3-dihydro-1H-indol-5-yl)-benzamide;
3-{8-[6-(3,3-Dimethyl-pyrrolidin-1-yl)-pyridin-2-ylamino]-imidazo[1,2-b]pyridazin-6-yl}-benzoic acid;
3-{8-[6-(2,5-Dimethyl-pyrrolidin-1-yl)-pyridin-2-ylamino]-imidazo[1,2-b]pyridazin-6-yl}-benzoic acid;
3-[8-(4,4-Dimethyl-3,4,5,6-tetrahydro-2H-[1,2']bipyridinyl-6'-ylamino)-imidazo[1,2-b]pyridazin-6-yl]-benzoic acid;
[6-(3,4-Dimethoxy-phenyl)-imidazo[1,2-b]pyridazin-8-yl]-[6-(2-methyl-pyrrolidin-1-yl)-pyridin-2-yl]-amine;
[6-(2-Methyl-pyrrolidin-1-yl)-pyridin-2-yl]-[6-(1,2,3,4-tetrahydro-quinolin-7-yl)-imidazo[1,2-b]pyridazin-8-yl]-amine;
1-(7-{8-[6-(2-Methyl-pyrrolidin-1-yl)-pyridin-2-ylamino]-imidazo[1,2-b]pyridazin-6-yl}-3,4-dihydro-1H-isoquinolin-2-yl)-ethanone;
3-{8-[6-(3-tert-Butyl-pyrrolidin-1-yl)-pyridin-2-ylamino]-imidazo[1,2-b]pyridazin-6-yl}-benzoic acid methyl ester;
3-{8-[6-(3-tert-Butyl-pyrrolidin-1-yl)-pyridin-2-ylamino]-imidazo[1,2-b]pyridazin-6-yl}-benzoic acid;
3-{8-[6-(3-tert-Butyl-pyrrolidin-1-yl)-pyridin-2-ylamino]-imidazo[1,2-b]pyridazin-6-yl}-benzamide;
(3-{8-[6-(2-Methyl-pyrrolidin-1-yl)-pyridin-2-ylamino]-imidazo[1,2-b]pyridazin-6-yl}-phenyl)-methanol;
[6-(2-Methyl-pyrrolidin-1-yl)-pyridin-2-yl]-[6-(3-piperidin-1-ylmethyl-phenyl)-imidazo[1,2-b]pyridazin-8-yl]-amine;
[6-(2-Methyl-pyrrolidin-1-yl)-pyridin-2-yl]-[6-(3-pyrrolidin-1-ylmethyl-phenyl)-imidazo[1,2-b]pyridazin-8-yl]-amine;
[6-(3-Chloro-phenyl)-imidazo[1,2-b]pyridazin-8-yl]-[6-((S)-2-methyl-pyrrolidin-1-yl)-pyridin-2-yl]-amine;
N-{1-[8-(5,6-Dimethoxy-pyridin-2-ylamino)-imidazo[1,2-b]pyridazin-6-yl]-piperidin-3-yl}-terephthalamic acid;
1-[8-(5,6-Dimethoxy-pyridin-2-ylamino)-imidazo[1,2-b]pyridazin-6-yl]-piperidine-3-carboxylic acid (1,3-dioxo-2,3-dihydro-1H-isoindol-5-yl)-amide;
4-({1-[8-(5,6-Dimethoxy-pyridin-2-ylamino)-imidazo[1,2-b]pyridazin-6-yl]-piperidine-3-carbonyl}-amino)-benzoic acid;
4-({1-[8-(5,6-Dimethoxy-pyridin-2-ylamino)-imidazo[1,2-b]pyridazin-6-yl]-pyrrolidine-3-carbonyl}-amino)-benzoic acid;
N-{1-[8-(5,6-Dimethoxy-pyridin-2-ylamino)-imidazo[1,2-b]pyridazin-6-yl]-pyrrolidin-3-yl}-terephthalamic acid;
4-{8-[6-(2-Methyl-pyrrolidin-1-yl)-pyridin-2-ylamino]-imidazo[1,2-b]pyridazin-6-yl}-phenol;
[6-(2-Methyl-pyrrolidin-1-yl)-pyridin-2-yl]-(6-pyridin-3-yl-imidazo[1,2-b]pyridazin-8-yl)-amine;
[6-(4-Fluoro-phenyl)-imidazo[1,2-b]pyridazin-8-yl]-[6-(2-methyl-pyrrolidin-1-yl)-pyridin-2-yl]-amine;
3-{8-[6-(2-Methyl-pyrrolidin-1-yl)-pyridin-2-ylamino]-imidazo[1,2-b]pyridazin-6-yl}-benzonitrile;
[6-(2-Methyl-pyrrolidin-1-yl)-pyridin-2-yl]-(6-pyridin-4-yl-imidazo[1,2-b]pyridazin-8-yl)-amine;
[6-(5-Methoxy-pyridin-3-yl)-imidazo[1,2-b]pyridazin-8-yl]-[6-(2-methyl-pyrrolidin-1-yl)-pyridin-2-yl]-amine;
[6-(2-Methyl-pyrrolidin-1-yl)-pyridin-2-yl]-{6-[4-(2-pyrrolidin-1-yl-ethoxy)-phenyl]-imidazo[1,2-b]pyridazin-8-yl}-amine;
[6-(3-Aminomethyl-phenyl)-imidazo[1,2-b]pyridazin-8-yl]-[6-(2-methyl-pyrrolidin-1-yl)-pyridin-2-yl]-amine;
[6-(4-tert-Butyl-phenyl)-imidazo[1,2-b]pyridazin-8-yl]-[6-(2-methyl-pyrrolidin-1-yl)-pyridin-2-yl]-amine;
3-{8-[6-(2-Methyl-pyrrolidin-1-yl)-pyridin-2-ylamino]-imidazo[1,2-b]pyridazin-6-yl}-phenol;
[6-(2-Methyl-pyrrolidin-1-yl)-pyridin-2-yl]-{6-[3-(2-piperidin-1-yl-ethoxy)-phenyl]-imidazo[1,2-b]pyridazin-8-yl}-amine;
[6-(2-Methyl-pyrrolidin-1-yl)-pyridin-2-yl]-{6-[3-(2-morpholin-4-yl-ethoxy)-phenyl]-imidazo[1,2-b]pyridazin-8-yl}-amine
[6-(2-Methyl-pyrrolidin-1-yl)-pyridin-2-yl]-{6-[4-(2-piperidin-1-yl-ethoxy)-phenyl]-imidazo[1,2-b]pyridazin-8-yl}-amine;
[6-(2-Methyl-pyrrolidin-1-yl)-pyridin-2-yl]-{6-[4-(2-morpholin-4-yl-ethoxy)-phenyl]-imidazo[1,2-b]pyridazin-8-yl}-amine;
{6-[3-(2-Diethylamino-ethoxy)-phenyl]-imidazo[1,2-b]pyridazin-8-yl}-[6-(2-methyl-pyrrolidin-1-yl)-pyridin-2-yl]-amine;
{6-[4-(2-Diethylamino-ethoxy)-phenyl]-imidazo[1,2-b]pyridazin-8-yl}-[6-(2-methyl-pyrrolidin-1-yl)-pyridin-2-yl]-amine;
[6-(2-Methyl-pyrrolidin-1-yl)-pyridin-2-yl]-{6-[3-(piperidin-4-ylaminomethyl)-phenyl]-imidazo[1,2-b]pyridazin-8-yl}-amine;
[6-(2-Methyl-pyrrolidin-1-yl)-pyridin-2-yl]-{6-[3-(2-piperazin-1-yl-ethoxy)-phenyl]-imidazo[1,2-b]pyridazin-8-yl}-amine;
3-[8-(5,6-Dimethoxy-pyridin-2-ylamino)-imidazo[1,2-b]pyridazin-6-yl]-benzoic acid; and
3-(8-(5,6-Dimethoxypyridin-2-ylamino)imidazo[1,2-b]pyridazin-6-yl)-N-(4-(methylcarbamoyl)phenyl)benzamide.
(6-Phenyl-imidazo[1,2-b]pyridazin-8-yl)-(6-trifluoromethyl-pyridin-2-yl)-amine;

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with a therapeutically effective amount of the compound of Formula I.

The application provides a method for treating an immune disorder comprising co-administering to a patient in need thereof a therapeutically effective amount of an immunosuppressant compound in combination with a therapeutically effective amount of the compound of Formula I.

The application provides a pharmaceutical composition comprising a therapeutically effective amount of the compound of Formula I, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides the use of the compound of formula I for the manufacture of a medicament useful for the treatment of disorders associated with Syk.

The application provides the use of the compound of formula I for the manufacture of a medicament useful for the treatment of rheumatoid arthritis.

A compound, method, or composition as described herein.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system or Struct=Name, a CambridgeSoft® application, for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I.

TABLE I

| Compound | Nomenclature | Structure |
|---|---|---|
| I-1 | 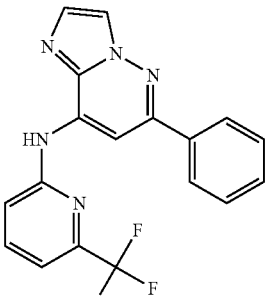 | (6-Phenyl-imidazo[1,2-b]pyridazin-8-yl)-(6-trifluoromethyl-pyridin-2-yl)-amine |
| I-2 | 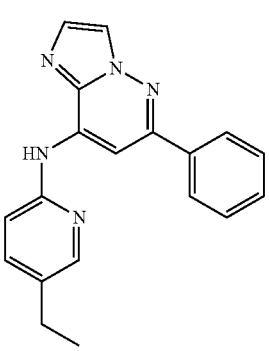 [SMILES: CCc1ccc(Nc2cc(-c3ccccc3)nn3ccnc23)nc1] | (5-Ethyl-pyridin-2-yl)-(6-phenyl-imidazo[1,2-b]pyridazin-8-yl)-amine |

TABLE I-continued

| Compound | Nomenclature | Structure |
| --- | --- | --- |
| I-3 | (6-Phenyl-imidazo[1,2-b]pyridazin-8-yl)-(3,4,5,6-tetrahydro-2H-[1,2']bipyridinyl-6'-yl)-amine hydrochloride | |
| I-4 | (6-Phenyl-imidazo[1,2-b]pyridazin-8-yl)-(6-pyrrolidin-1-yl-pyridin-2-yl)-amine | |
| I-5 | [6-(2-Methyl-pyrrolidin-1-yl)-pyridin-2-yl]-(6-phenyl-imidazo[1,2-b]pyridazin-8-yl)-amine hydrochloride | |
| I-6 | (1-tert-Butyl-1H-pyrazol-3-yl)-(6-phenyl-imidazo[1,2-b]pyridazin-8-yl)-amine hydrochloride | |
| I-7 | 8-(2,2-Dimethyl-pyrrolidin-1-yl)-6-phenyl-imidazo[1,2-b]pyridazine | |

TABLE I-continued

| Compound | Nomenclature | Structure |
|---|---|---|
| I-8 | 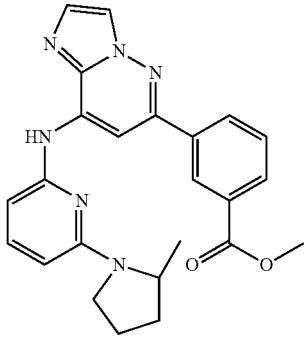 [SMILES: COC(=O)c1cccc(-c2cc(Nc3cccc(N4CCCC4C)n3)c3nccn3n2)c1] | 3-{8-[6-(2-Methyl-pyrrolidin-1-yl)-pyridin-2-ylamino]-imidazo[1,2-b]pyridazin-6-yl}-benzoic acid methyl ester |
| I-9 | 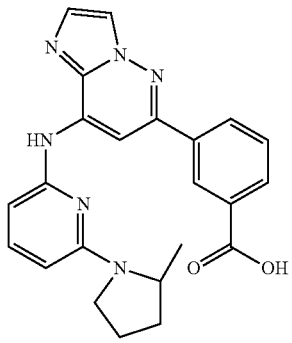 [SMILES: CC1CCCN1c1cccc(Nc2cc(-c3cccc(C(=O)O)c3)nn3ccnc23)n1] | 3-{8-[6-(2-Methyl-pyrrolidin-1-yl)-pyridin-2-ylamino]-imidazo[1,2-b]pyridazin-6-yl}-benzoic acid |
| I-10 | 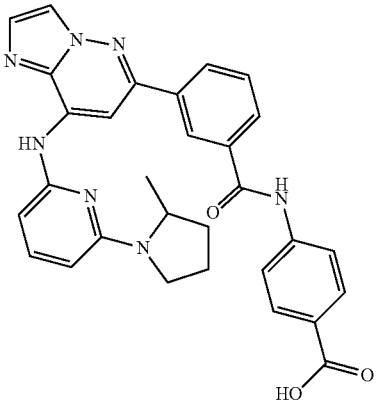 [SMILES: CC1CCCN1c1cccc(Nc2cc(-c3cccc(C(=O)Nc4ccc(C(=O)O)cc4)c3)nn3ccnc23)n1] | 4-(3-{8-[6-(2-Methyl-pyrrolidin-1-yl)-pyridin-2-ylamino]-imidazo[1,2-b]pyridazin-6-yl}-benzoylamino)-benzoic acid |
| I-11 | 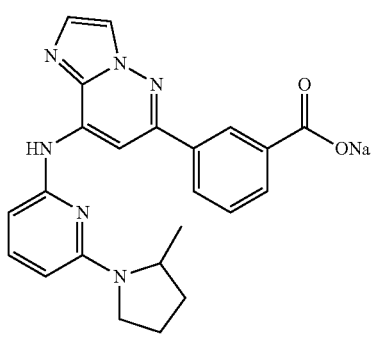 | Sodium 3-(8-(6-(2-methylpyrrolidin-1-yl)pyridin-2-ylamino)imidazo[1,2-b]pyridazin-6-yl)benzoate |

TABLE I-continued

| Compound | Nomenclature | Structure |
|---|---|---|
| I-12 | 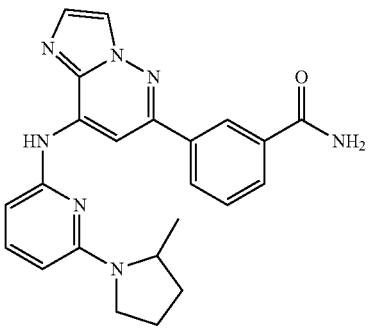 [SMILES: CC1CCCN1c1cccc(Nc2cc(-c3cccc(C(N)=O)c3)nn3ccnc23)n1] | 3-{8-[6-(2-Methyl-pyrrolidin-1-yl)-pyridin-2-ylamino]-imidazo[1,2-b]pyridazin-6-yl}-benzamide |
| I-13 | 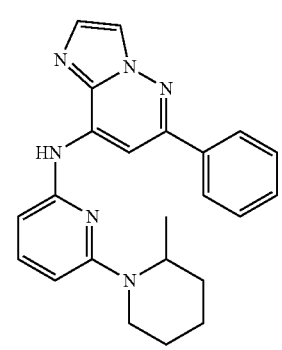 [SMILES: CC1CCCCN1c1cccc(Nc2cc(-c3ccccc3)nn3ccnc23)n1] | (2-Methyl-3,4,5,6-tetrahydro-2H-[1,2']bipyridinyl-6'-yl)-(6-phenyl-imidazo[1,2-b]pyridazin-8-yl)-amine hydrochloride |
| I-14 | 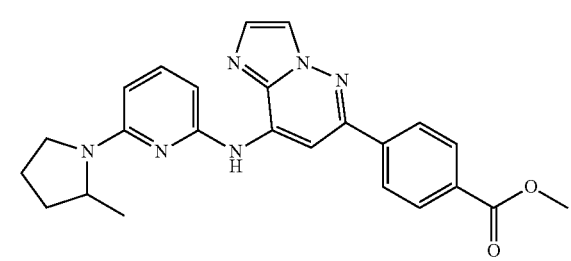 [SMILES: COC(=O)c1ccc(-c2cc(Nc3cccc(N4CCCC4C)n3)c3nccn3n2)cc1] | 4-{8-[6-(2-Methyl-pyrrolidin-1-yl)-pyridin-2-ylamino]-imidazo[1,2-b]pyridazin-6-yl}-benzoic acid methyl ester |
| I-15 | 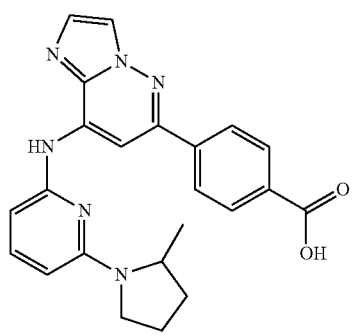 [SMILES: CC1CCCN1c1cccc(Nc2cc(-c3ccc(C(=O)O)cc3)nn3ccnc23)n1] | 4-{8-[6-(2-Methyl-pyrrolidin-1-yl)-pyridin-2-ylamino]-imidazo[1,2-b]pyridazin-6-yl}-benzoic acid |
| I-16 | 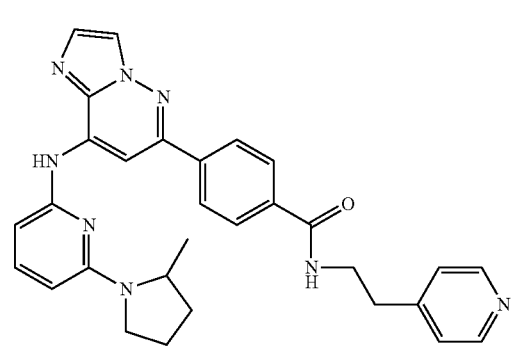 [SMILES: CC1CCCN1c1cccc(Nc2cc(-c3ccc(C(=O)NCCc4ccncc4)cc3)nn3ccnc23)n1] | 4-{8-[6-(2-Methyl-pyrrolidin-1-yl)-pyridin-2-ylamino]-imidazo[1,2-b]pyridazin-6-yl}-N-(2-pyridin-4-yl-ethyl)-benzamide |

TABLE I-continued

| Compound | Nomenclature | Structure |
|---|---|---|
| I-17 | 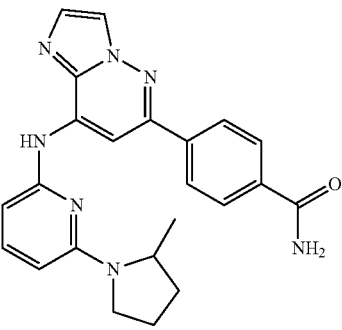 | 4-{8-[6-(2-Methyl-pyrrolidin-1-yl)-pyridin-2-ylamino]-imidazo[1,2-b]pyridazin-6-yl}-benzamide |
| I-18 | 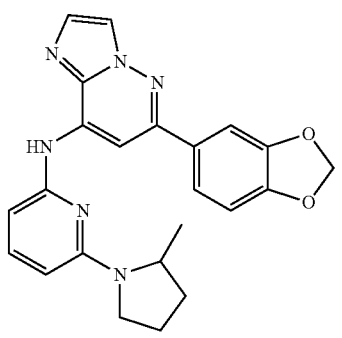 [SMILES: CC1CCCN1c1cccc(Nc2cc(-c3ccc4c(c3)OCO4)nn3ccnc23)n1] | (6-Benzo[1,3]dioxol-5-yl-imidazo[1,2-b]pyridazin-8-yl)-[6-(2-methyl-pyrrolidin-1-yl)-pyridin-2-yl]-amine |
| I-19 | 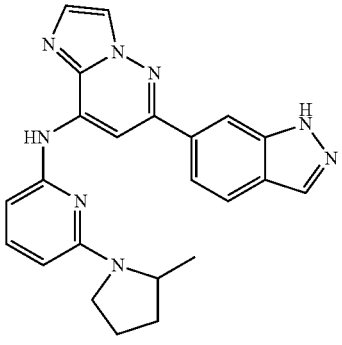 [SMILES: CC1CCCN1c1cccc(Nc2cc(-c3ccc4cn[nH]c4c3)nn3ccnc23)n1] | [6-(1H-Indazol-6-yl)-imidazo[1,2-b]pyridazin-8-yl]-[6-(2-methyl-pyrrolidin-1-yl)-pyridin-2-yl]-amine |
| I-20 | 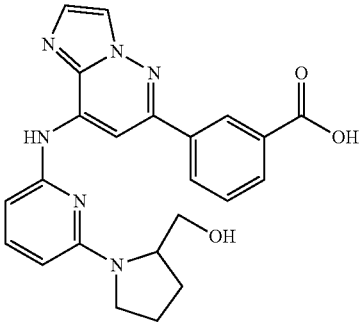 [SMILES: O=C(O)c1cccc(-c2cc(Nc3cccc(N4CCCC4CO)n3)c3nccn3n2)c1] | 3-{8-[6-(2-Hydroxymethyl-pyrrolidin-1-yl)-pyridin-2-ylamino]-imidazo[1,2-b]pyridazin-6-yl}-benzoic acid |

TABLE I-continued

| Compound | Nomenclature | Structure |
|---|---|---|
| I-21 | 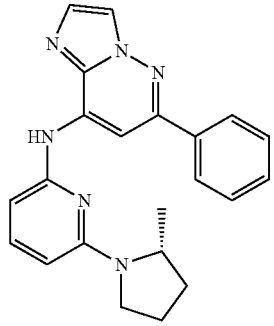 [SMILES: C[C@@H]1CCCN1c1cccc(Nc2cc(-c3ccccc3)nn3ccnc23)n1] | [6-((R)-2-Methyl-pyrrolidin-1-yl)-pyridin-2-yl]-(6-phenyl-imidazo[1,2-b]pyridazin-8-yl)-amine |
| I-22 | 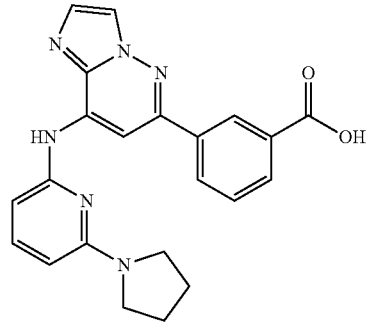 [SMILES: O=C(O)c1cccc(-c2cc(Nc3cccc(N4CCCC4)n3)c3nccn3n2)c1] | 3-[8-(6-Pyrrolidin-1-yl-pyridin-2-ylamino)-imidazo[1,2-b]pyridazin-6-yl]-benzoic acid hydrochloride |
| I-23 | 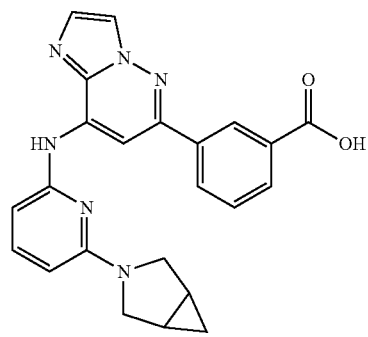 [SMILES: O=C(O)c1cccc(-c2cc(Nc3cccc(N4CC5CC5C4)n3)c3nccn3n2)c1] | 3-{8-[6-(3-Aza-bicyclo[3.1.0]hex-3-yl)-pyridin-2-ylamino]-imidazo[1,2-b]pyridazin-6-yl}-benzoic acid |
| I-24 | 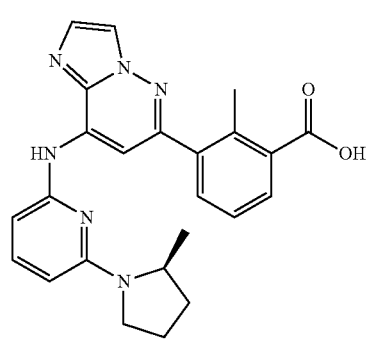 [SMILES: Cc1c(C(=O)O)cccc1-c1cc(Nc2cccc(N3CCC[C@@H]3C)n2)c2nccn2n1] | 2-Methyl-3-{8-[6-((S)-2-methyl-pyrrolidin-1-yl)-pyridin-2-ylamino]-imidazo[1,2-b]pyridazin-6-yl}-benzoic acid |

TABLE I-continued

| Compound | Nomenclature | Structure |
|---|---|---|
| I-25 | 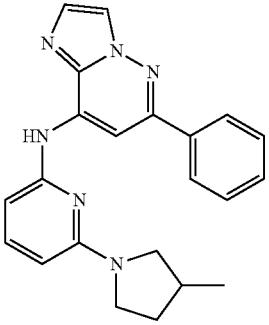 [SMILES: CC1CCN(c2cccc(Nc3cc(-c4ccccc4)nn4ccnc34)n2)C1] | [6-(3-Methyl-pyrrolidin-1-yl)-pyridin-2-yl]-(6-phenyl-imidazo[1,2-b]pyridazin-8-yl)-amine |
| I-26 | 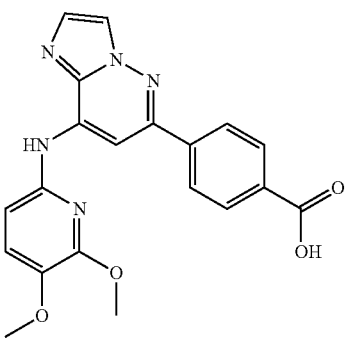 [SMILES: COc1ccc(Nc2cc(-c3ccc(C(=O)O)cc3)nn3ccnc23)nc1OC] | 4-[8-(5,6-Dimethoxy-pyridin-2-ylamino)-imidazo[1,2-b]pyridazin-6-yl]-benzoic acid |
| I-27 | 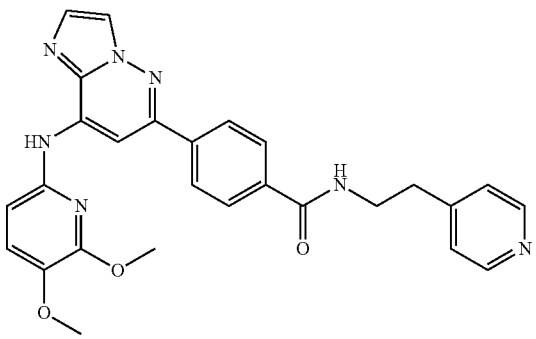 [SMILES: COc1ccc(Nc2cc(-c3ccc(C(=O)NCCc4ccncc4)cc3)nn3ccnc23)nc1OC] | 4-[8-(5,6-Dimethoxy-pyridin-2-ylamino)-imidazo[1,2-b]pyridazin-6-yl]-N-(2-pyridin-4-yl-ethyl)-benzamide |
| I-28 | 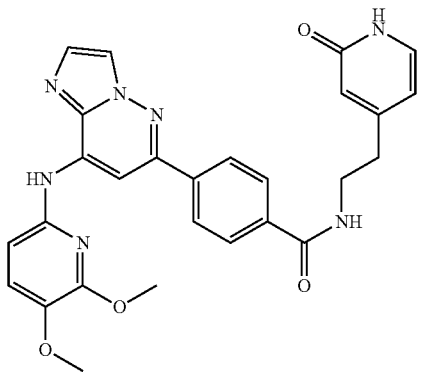 [SMILES: COc1ccc(Nc2cc(-c3ccc(C(=O)NCCc4cc[nH]c(=O)c4)cc3)nn3ccnc23)nc1OC] | 4-[8-(5,6-Dimethoxy-pyridin-2-ylamino)-imidazo[1,2-b]pyridazin-6-yl]-N-[2-(2-oxo-1,2-dihydro-pyridin-4-yl)-ethyl]-benzamide |
| I-29 | 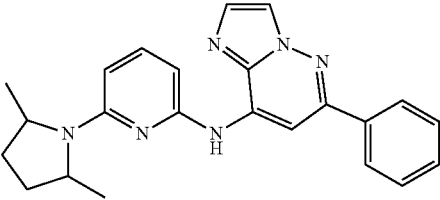 [SMILES: CC1CCC(C)N1c1cccc(Nc2cc(-c3ccccc3)nn3ccnc23)n1] | [6-(2,5-Dimethyl-pyrrolidin-1-yl)-pyridin-2-yl]-(6-phenyl-imidazo[1,2-b]pyridazin-8-yl)-amine hydrochloride |

TABLE I-continued

| Compound | Nomenclature | Structure |
| --- | --- | --- |
| I-30 | | [6-(2-Ethyl-pyrrolidin-1-yl)-pyridin-2-yl]-(6-phenyl-imidazo[1,2-b]pyridazin-8-yl)-amine hydrochloride |
| I-31 | | {1-[6-(6-Phenyl-imidazo[1,2-b]pyridazin-8-ylamino)-pyridin-2-yl]-pyrrolidin-2-yl}-methanol hydrochloride |
| I-32 | | [6-(2,2-Dimethyl-pyrrolidin-1-yl)-pyridin-2-yl]-(6-phenyl-imidazo[1,2-b]pyridazin-8-yl)-amine hydrochloride |
| I-33 | | 4-[8-(5,6-Dimethoxy-pyridin-2-ylamino)-imidazo[1,2-b]pyridazin-6-yl]-N-[2-(1-methyl-2-oxo-1,2-dihydro-pyridin-4-yl)-ethyl]-benzamide |

TABLE I-continued

| Compound | Nomenclature | Structure |
|---|---|---|
| I-34 | 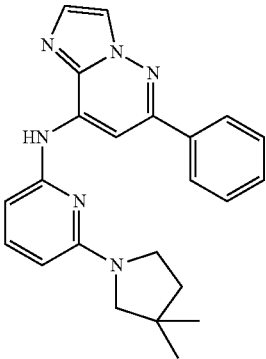 [SMILES: CC1(C)CCN(c2cccc(Nc3cc(-c4ccccc4)nn4ccnc34)n2)C1] | [6-(3,3-Dimethyl-pyrrolidin-1-yl)-pyridin-2-yl]-(6-phenyl-imidazo[1,2-b]pyridazin-8-yl)-amine |
| I-35 | 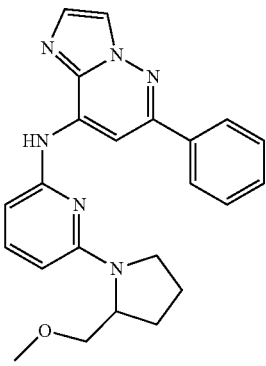 [SMILES: COCC1CCCN1c1cccc(Nc2cc(-c3ccccc3)nn3ccnc23)n1] | [6-(2-Methoxymethyl-pyrrolidin-1-yl)-pyridin-2-yl]-(6-phenyl-imidazo[1,2-b]pyridazin-8-yl)-amine hydrochloride |
| I-36 | 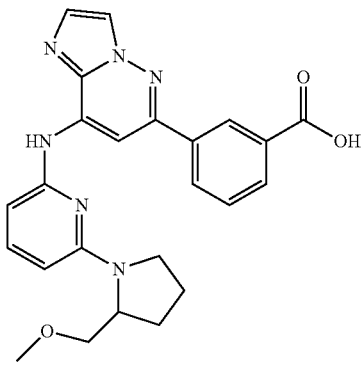 [SMILES: COCC1CCCN1c1cccc(Nc2cc(-c3cccc(C(=O)O)c3)nn3ccnc23)n1] | 3-{8-[6-(2-Methoxymethyl-pyrrolidin-1-yl)-pyridin-2-ylamino]-imidazo[1,2-b]pyridazin-6-yl}-benzoic acid |
| I-37 | 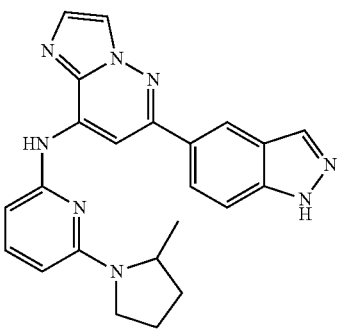 [SMILES: CC1CCCN1c1cccc(Nc2cc(-c3ccc4[nH]ncc4c3)nn3ccnc23)n1] | [6-(1H-Indazol-5-yl)-imidazo[1,2-b]pyridazin-8-yl]-[6-(2-methyl-pyrrolidin-1-yl)-pyridin-2-yl]-amine |

TABLE I-continued

| Compound | Nomenclature | Structure |
| --- | --- | --- |
| I-38 | 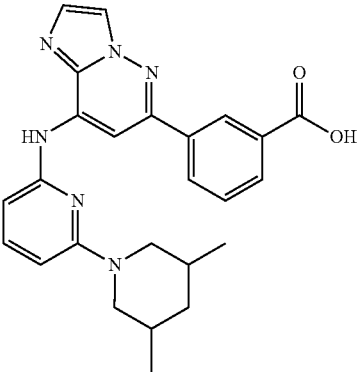 [SMILES: CC1CC(C)CN(c2cccc(Nc3cc(-c4cccc(C(=O)O)c4)nn4ccnc34)n2)C1] | 3-[8-(3,5-Dimethyl-3,4,5,6-tetrahydro-2H-[1,2']bipyridinyl-6'-ylamino)-imidazo[1,2-b]pyridazin-6-yl]-benzoic acid |
| I-39 | 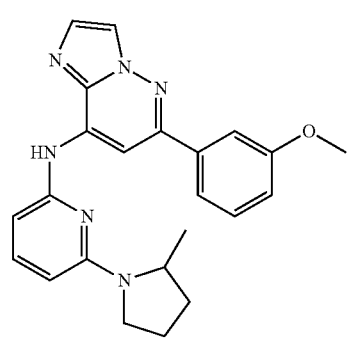 [SMILES: COc1cccc(-c2cc(Nc3cccc(N4CCCC4C)n3)c3nccn3n2)c1] | [6-(3-Methoxy-phenyl)-imidazo[1,2-b]pyridazin-8-yl]-[6-(2-methyl-pyrrolidin-1-yl)-pyridin-2-yl]-amine |
| I-40 | 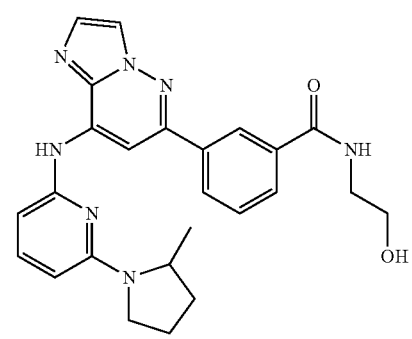 [SMILES: CC1CCCN1c1cccc(Nc2cc(-c3cccc(C(=O)NCCO)c3)nn3ccnc23)n1] | N-(2-Hydroxy-ethyl)-3-{8-[6-(2-methyl-pyrrolidin-1-yl)-pyridin-2-ylamino]-imidazo[1,2-b]pyridazin-6-yl}-benzamide |
| I-41 | 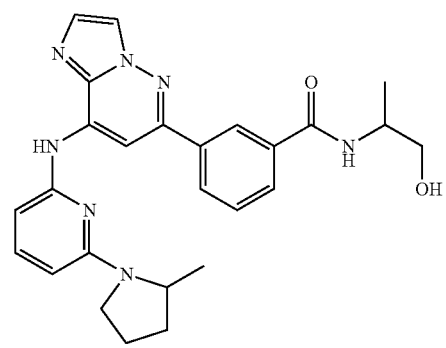 [SMILES: CC(CO)NC(=O)c1cccc(-c2cc(Nc3cccc(N4CCCC4C)n3)c3nccn3n2)c1] | N-(2-Hydroxy-1-methyl-ethyl)-3-{8-[6-(2-methyl-pyrrolidin-1-yl)-pyridin-2-ylamino]-imidazo[1,2-b]pyridazin-6-yl}-benzamide |

| Compound | Nomenclature | Structure |
|---|---|---|
| I-42 | 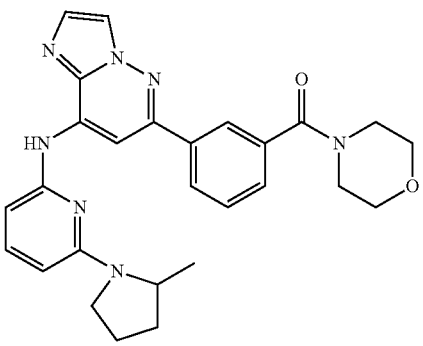 [SMILES: CC1CCCN1c1cccc(Nc2cc(-c3cccc(C(=O)N4CCOCC4)c3)nn3ccnc23)n1] | (3-{8-[6-(2-Methyl-pyrrolidin-1-yl)-pyridin-2-ylamino]-imidazo[1,2-b]pyridazin-6-yl}-phenyl)-morpholin-4-yl-methanone |
| I-43 | 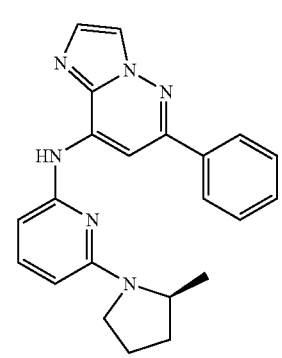 [SMILES: C[C@H]1CCCN1c1cccc(Nc2cc(-c3ccccc3)nn3ccnc23)n1] | [6-((S)-2-Methyl-pyrrolidin-1-yl)-pyridin-2-yl]-(6-phenyl-imidazo[1,2-b]pyridazin-8-yl)-amine |
| I-44 | 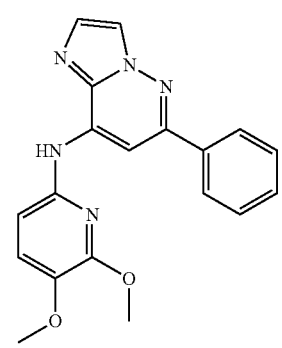 [SMILES: COc1ccc(Nc2cc(-c3ccccc3)nn3ccnc23)nc1OC] | (5,6-Dimethoxy-pyridin-2-yl)-(6-phenyl-imidazo[1,2-b]pyridazin-8-yl)-amine |
| I-45 | 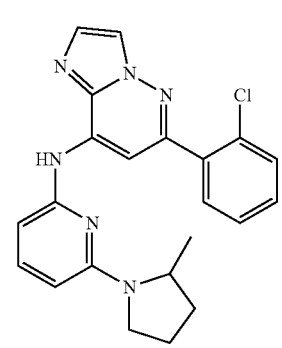 [SMILES: CC1CCCN1c1cccc(Nc2cc(-c3ccccc3Cl)nn3ccnc23)n1] | [6-(2-Chloro-phenyl)-imidazo[1,2-b]pyridazin-8-yl]-[6-(2-methyl-pyrrolidin-1-yl)-pyridin-2-yl]-amine hydrochloride |

TABLE I-continued

| Compound | Structure | Nomenclature |
|---|---|---|
| I-46 | 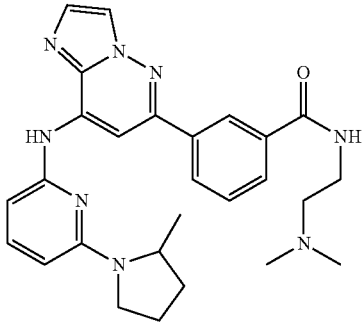 [SMILES: CC1CCCN1c1cccc(Nc2cc(-c3cccc(C(=O)NCCN(C)C)c3)nn3ccnc23)n1] | N-(2-Dimethylamino-ethyl)-3-{8-[6-(2-methyl-pyrrolidin-1-yl)-pyridin-2-ylamino]-imidazo[1,2-b]pyridazin-6-yl}-benzamide |
| I-47 | 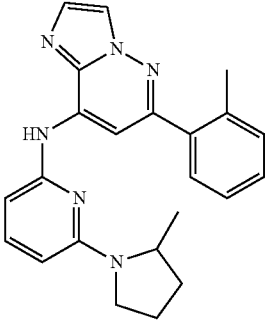 [SMILES: Cc1ccccc1-c1cc(Nc2cccc(N3CCCC3C)n2)c2nccn2n1] | [6-(2-Methyl-pyrrolidin-1-yl)-pyridin-2-yl]-(6-o-tolyl-imidazo[1,2-b]pyridazin-8-yl)-amine |
| I-48 | 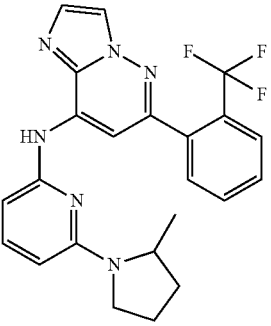 [SMILES: CC1CCCN1c1cccc(Nc2cc(-c3ccccc3C(F)(F)F)nn3ccnc23)n1] | [6-(2-Methyl-pyrrolidin-1-yl)-pyridin-2-yl]-[6-(2-trifluoromethyl-phenyl)-imidazo[1,2-b]pyridazin-8-yl]-amine hydrochloride |
| I-49 | 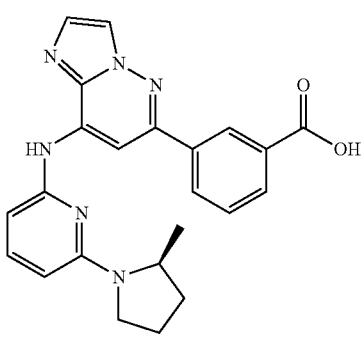 [SMILES: C[C@H]1CCCN1c1cccc(Nc2cc(-c3cccc(C(=O)O)c3)nn3ccnc23)n1] | 3-{8-[6-((S)-2-Methyl-pyrrolidin-1-yl)-pyridin-2-ylamino]-imidazo[1,2-b]pyridazin-6-yl}-benzoic acid |

TABLE I-continued

| Compound | Nomenclature | Structure |
|---|---|---|
| I-50 | 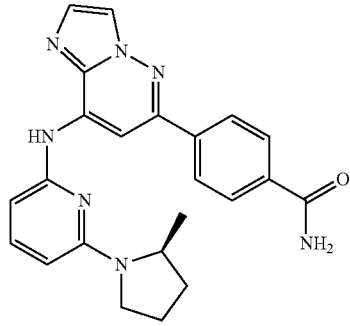 [SMILES: C[C@H]1CCCN1c1cccc(Nc2cc(-c3ccc(C(N)=O)cc3)nn3ccnc23)n1] | 4-{8-[6-((S)-2-Methyl-pyrrolidin-1-yl)-pyridin-2-ylamino]-imidazo[1,2-b]pyridazin-6-yl}-benzamide |
| I-51 | 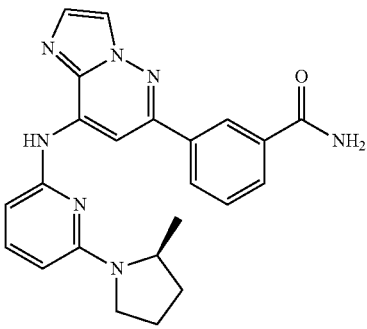 [SMILES: C[C@H]1CCCN1c1cccc(Nc2cc(-c3cccc(C(N)=O)c3)nn3ccnc23)n1] | 3-{8-[6-((S)-2-Methyl-pyrrolidin-1-yl)-pyridin-2-ylamino]-imidazo[1,2-b]pyridazin-6-yl}-benzamide |
| I-52 | 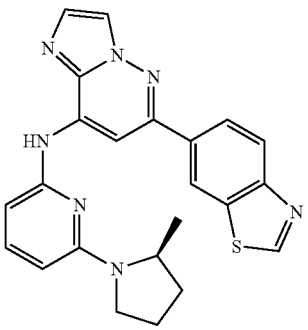 [SMILES: C[C@H]1CCCN1c1cccc(Nc2cc(-c3ccc4ncsc4c3)nn3ccnc23)n1] | (6-Benzothiazol-6-yl-imidazo[1,2-b]pyridazin-8-yl)-[6-((S)-2-methyl-pyrrolidin-1-yl)-pyridin-2-yl]-amine |
| I-53 | 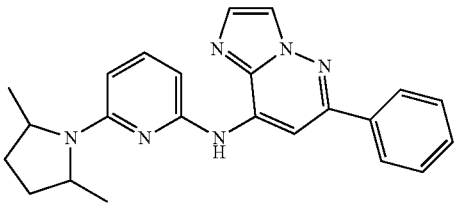 [SMILES: CC1CCC(C)N1c1cccc(Nc2cc(-c3ccccc3)nn3ccnc23)n1] | [6-(2,5-Dimethyl-pyrrolidin-1-yl)-pyridin-2-yl]-(6-phenyl-imidazo[1,2-b]pyridazin-8-yl)-amine hydrochloride |
| I-54 | 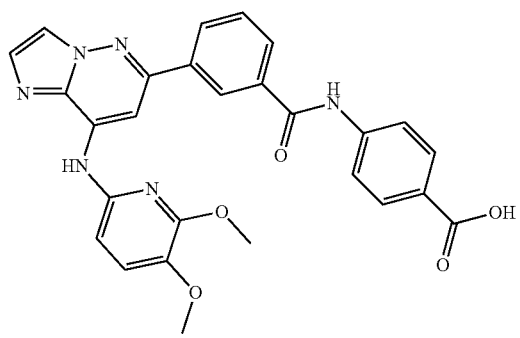 [SMILES: COc1ccc(Nc2cc(-c3cccc(C(=O)Nc4ccc(C(=O)O)cc4)c3)nn3ccnc23)nc1OC] | 4-{3-[8-(5,6-Dimethoxy-pyridin-2-ylamino)-imidazo[1,2-b]pyridazin-6-yl]-benzoylamino}-benzoic acid |

| Compound | Nomenclature | Structure |
|---|---|---|
| I-55 | 3-[8-(5,6-Dimethoxy-pyridin-2-ylamino)-imidazo[1,2-b]pyridazin-6-yl]-N-(1H-indazol-5-yl)-benzamide hydrochloride | 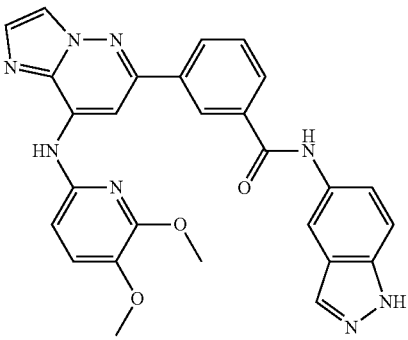 [SMILES: COc1ccc(Nc2cc(-c3cccc(C(=O)Nc4ccc5[nH]ncc5c4)c3)nn3ccnc23)nc1OC] |
| I-56 | 3-[8-(5,6-Dimethoxy-pyridin-2-ylamino)-imidazo[1,2-b]pyridazin-6-yl]-N-(1-oxo-2,3-dihydro-1H-isoindol-5-yl)-benzamide | 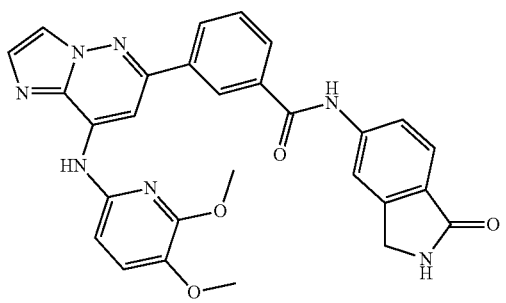 [SMILES: COc1ccc(Nc2cc(-c3cccc(C(=O)Nc4ccc5c(c4)CNC5=O)c3)nn3ccnc23)nc1OC] |
| I-57 | 4-{3-[8-(5,6-Dimethoxy-pyridin-2-ylamino)-imidazo[1,2-b]pyridazin-6-yl]-benzoylamino}-2-methoxy-benzoic acid | 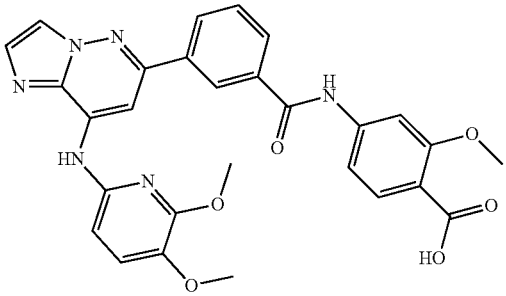 [SMILES: COc1cc(NC(=O)c2cccc(-c3cc(Nc4ccc(OC)c(OC)n4)c4nccn4n3)c2)ccc1C(=O)O] |
| I-58 | 3-[8-(5,6-Dimethoxy-pyridin-2-ylamino)-imidazo[1,2-b]pyridazin-6-yl]-N-(2-oxo-2,3-dihydro-1H-indol-5-yl)-benzamide hydrochloride | 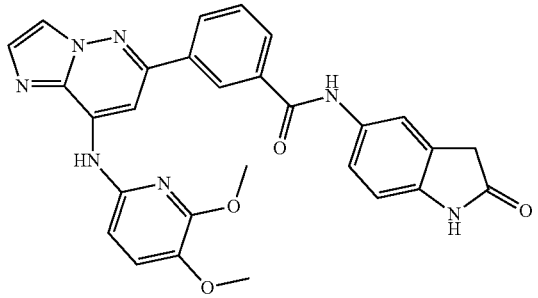 [SMILES: COc1ccc(Nc2cc(-c3cccc(C(=O)Nc4ccc5c(c4)CC(=O)N5)c3)nn3ccnc23)nc1OC] |
| I-59 | 3-{8-[6-(3,3-Dimethyl-pyrrolidin-1-yl)-pyridin-2-ylamino]-imidazo[1,2-b]pyridazin-6-yl}-benzoic acid | 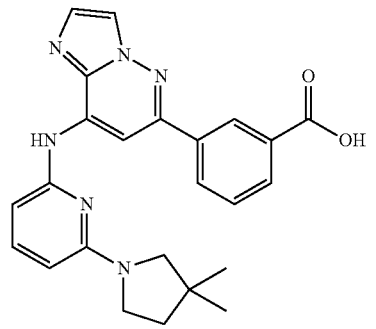 [SMILES: CC1(C)CCN(c2cccc(Nc3cc(-c4cccc(C(=O)O)c4)nn4ccnc34)n2)C1] |

TABLE I-continued

| Compound | Structure | Nomenclature |
|---|---|---|
| I-60 | 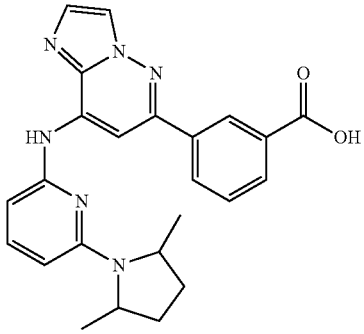 [SMILES: CC1CCC(C)N1c1cccc(Nc2cc(-c3cccc(C(=O)O)c3)nn3ccnc23)n1] | 3-{8-[6-(2,5-Dimethyl-pyrrolidin-1-yl)-pyridin-2-ylamino]-imidazo[1,2-b]pyridazin-6-yl}-benzoic acid |
| I-61 | 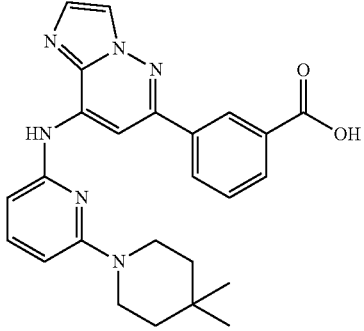 [SMILES: CC1(C)CCN(c2cccc(Nc3cc(-c4cccc(C(=O)O)c4)nn4ccnc34)n2)CC1] | 3-[8-(4,4-Dimethyl-3,4,5,6-tetrahydro-2H-[1,2']bipyridinyl-6'-ylamino)-imidazo[1,2-b]pyridazin-6-yl]-benzoic acid |
| I-62 | 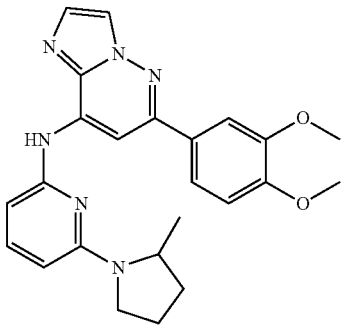 [SMILES: COc1ccc(-c2cc(Nc3cccc(N4CCCC4C)n3)c3nccn3n2)cc1OC] | [6-(3,4-Dimethoxy-phenyl)-imidazo[1,2-b]pyridazin-8-yl]-[6-(2-methyl-pyrrolidin-1-yl)-pyridin-2-yl]-amine |
| I-63 | 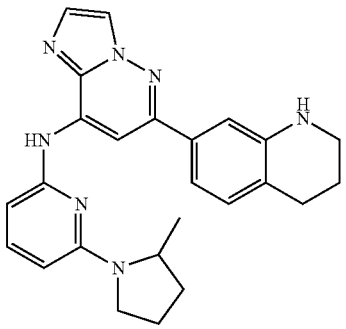 [SMILES: CC1CCCN1c1cccc(Nc2cc(-c3ccc4c(c3)NCCC4)nn3ccnc23)n1] | [6-(2-Methyl-pyrrolidin-1-yl)-pyridin-2-yl]-[6-(1,2,3,4-tetrahydro-quinolin-7-yl)-imidazo[1,2-b]pyridazin-8-yl]-amine hydrochloride |

TABLE I-continued

| Compound | Nomenclature | Structure |
|---|---|---|
| I-64 | 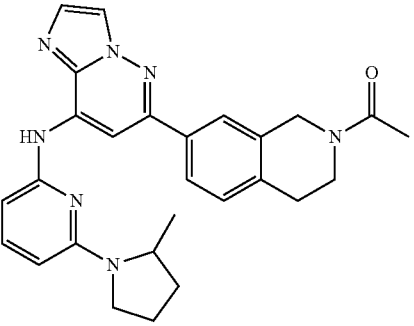 [SMILES: CC(=O)N1CCc2ccc(-c3cc(Nc4cccc(N5CCCC5C)n4)c4nccn4n3)cc2C1] | 1-(7-{8-[6-(2-Methyl-pyrrolidin-1-yl)-pyridin-2-ylamino]-imidazo[1,2-b]pyridazin-6-yl}-3,4-dihydro-1H-isoquinolin-2-yl)-ethanone |
| I-65 | 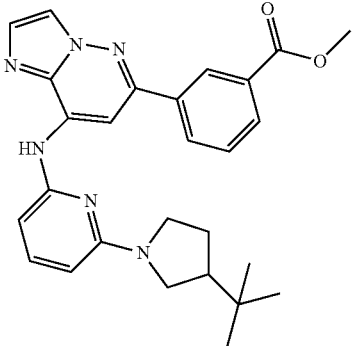 [SMILES: COC(=O)c1cccc(-c2cc(Nc3cccc(N4CCC(C(C)(C)C)C4)n3)c3nccn3n2)c1] | 3-{8-[6-(3-tert-Butyl-pyrrolidin-1-yl)-pyridin-2-ylamino]-imidazo[1,2-b]pyridazin-6-yl}-benzoic acid methyl ester |
| I-66 | 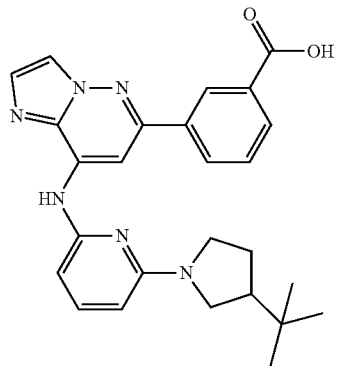 [SMILES: CC(C)(C)C1CCN(c2cccc(Nc3cc(-c4cccc(C(=O)O)c4)nn4ccnc34)n2)C1] | 3-{8-[6-(3-tert-Butyl-pyrrolidin-1-yl)-pyridin-2-ylamino]-imidazo[1,2-b]pyridazin-6-yl}-benzoic acid |
| I-67 | 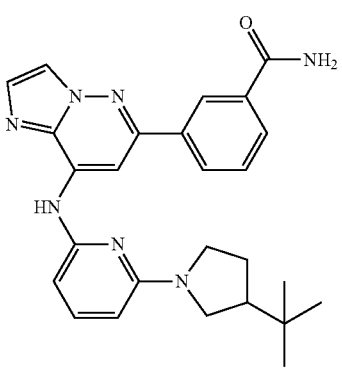 [SMILES: CC(C)(C)C1CCN(c2cccc(Nc3cc(-c4cccc(C(N)=O)c4)nn4ccnc34)n2)C1] | 3-{8-[6-(3-tert-Butyl-pyrrolidin-1-yl)-pyridin-2-ylamino]-imidazo[1,2-b]pyridazin-6-yl}-benzamide |

TABLE I-continued

| Compound | Nomenclature | Structure |
|---|---|---|
| I-68 | | (3-{8-[6-(2-Methyl-pyrrolidin-1-yl)-pyridin-2-ylamino]-imidazo[1,2-b]pyridazin-6-yl}-phenyl)-methanol |
| I-69 | | [6-(2-Methyl-pyrrolidin-1-yl)-pyridin-2-yl]-[6-(3-piperidin-1-ylmethyl-phenyl)-imidazo[1,2-b]pyridazin-8-yl]-amine |
| I-70 | | [6-(2-Methyl-pyrrolidin-1-yl)-pyridin-2-yl]-[6-(3-pyrrolidin-1-ylmethyl-phenyl)-imidazo[1,2-b]pyridazin-8-yl]-amine |
| I-71 | | [6-(3-Chloro-phenyl)-imidazo[1,2-b]pyridazin-8-yl]-[6-((S)-2-methyl-pyrrolidin-1-yl)-pyridin-2-yl]-amine hydrochloride |

TABLE I-continued

| Compound | Nomenclature | Structure |
|---|---|---|
| I-72 | 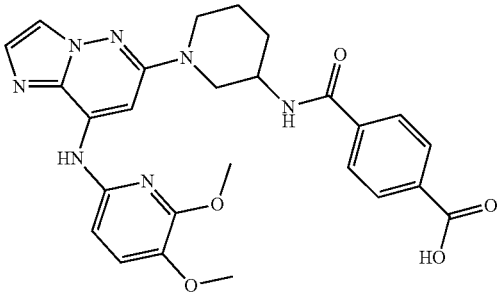 [SMILES: COc1ccc(Nc2cc(N3CCCC(NC(=O)c4ccc(C(=O)O)cc4)C3)nn3ccnc23)nc1OC] | N-{1-[8-(5,6-Dimethoxy-pyridin-2-ylamino)-imidazo[1,2-b]pyridazin-6-yl]-piperidin-3-yl}-terephthalamic acid |
| I-73 | 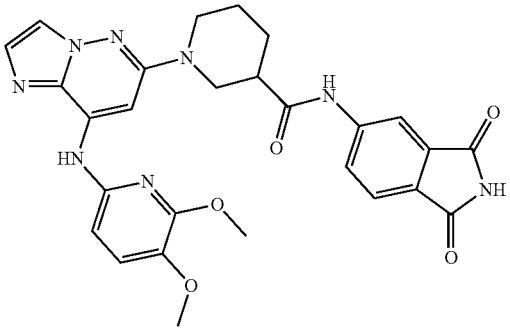 [SMILES: COc1ccc(Nc2cc(N3CCCC(C(=O)Nc4ccc5c(c4)C(=O)NC5=O)C3)nn3ccnc23)nc1OC] | 1-[8-(5,6-Dimethoxy-pyridin-2-ylamino)-imidazo[1,2-b]pyridazin-6-yl]-piperidine-3-carboxylic acid (1,3-dioxo-2,3-dihydro-1H-isoindol-5-yl)-amide hydrochloride |
| I-74 | 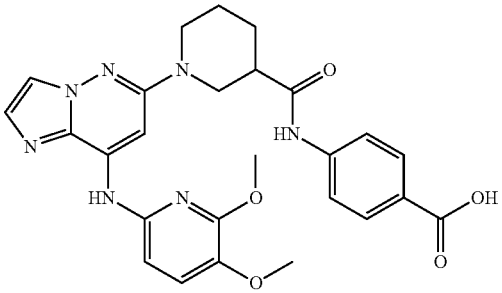 [SMILES: COc1ccc(Nc2cc(N3CCCC(C(=O)Nc4ccc(C(=O)O)cc4)C3)nn3ccnc23)nc1OC] | 4-({1-[8-(5,6-Dimethoxy-pyridin-2-ylamino)-imidazo[1,2-b]pyridazin-6-yl]-piperidine-3-carbonyl}-amino)-benzoic acid |
| I-75 | 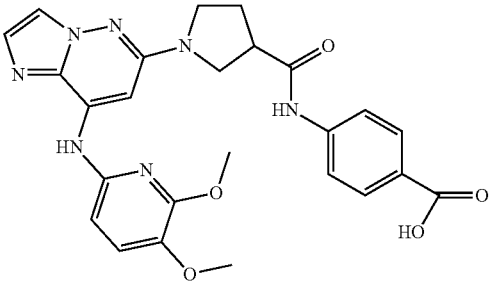 [SMILES: COc1ccc(Nc2cc(N3CCC(C(=O)Nc4ccc(C(=O)O)cc4)C3)nn3ccnc23)nc1OC] | 4-({1-[8-(5,6-Dimethoxy-pyridin-2-ylamino)-imidazo[1,2-b]pyridazin-6-yl]-pyrrolidine-3-carbonyl}-amino)-benzoic acid |
| I-76 | 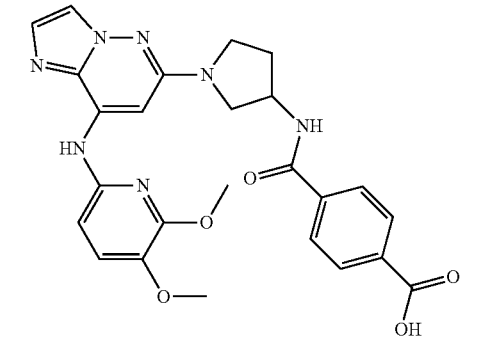 [SMILES: COc1ccc(Nc2cc(N3CCC(NC(=O)c4ccc(C(=O)O)cc4)C3)nn3ccnc23)nc1OC] | N-{1-[8-(5,6-Dimethoxy-pyridin-2-ylamino)-imidazo[1,2-b]pyridazin-6-yl]-pyrrolidin-3-yl}-terephthalamic acid |

TABLE I-continued
| Compound | Nomenclature | Structure |
|---|---|---|
| I-77 | 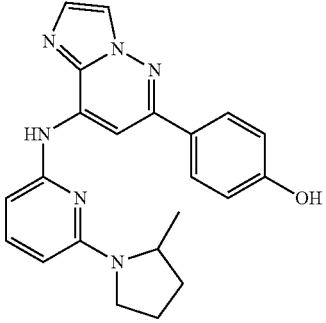 [SMILES: CC1CCCN1c1cccc(Nc2cc(-c3ccc(O)cc3)nn3ccnc23)n1] | 4-{8-[6-(2-Methyl-pyrrolidin-1-yl)-pyridin-2-ylamino]-imidazo[1,2-b]pyridazin-6-yl}-phenol |
| I-78 | 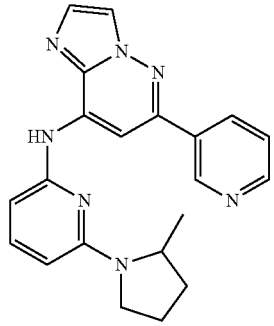 [SMILES: CC1CCCN1c1cccc(Nc2cc(-c3cccnc3)nn3ccnc23)n1] | [6-(2-Methyl-pyrrolidin-1-yl)-pyridin-2-yl]-(6-pyridin-3-yl-imidazo[1,2-b]pyridazin-8-yl)-amine |
| I-79 | 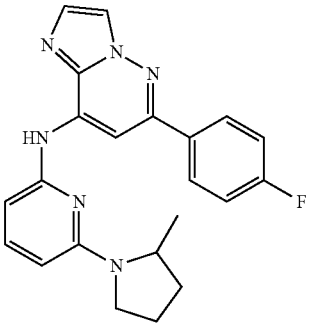 [SMILES: CC1CCCN1c1cccc(Nc2cc(-c3ccc(F)cc3)nn3ccnc23)n1] | [6-(4-Fluoro-phenyl)-imidazo[1,2-b]pyridazin-8-yl]-[6-(2-methyl-pyrrolidin-1-yl)-pyridin-2-yl]-amine |
| I-80 | 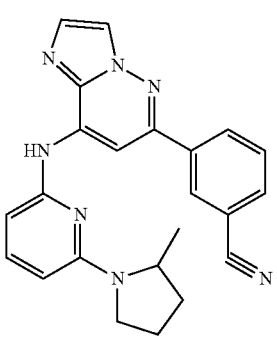 [SMILES: CC1CCCN1c1cccc(Nc2cc(-c3cccc(C#N)c3)nn3ccnc23)n1] | 3-{8-[6-(2-Methyl-pyrrolidin-1-yl)-pyridin-2-ylamino]-imidazo[1,2-b]pyridazin-6-yl}-benzonitrile |

TABLE I-continued

| Compound | Nomenclature | Structure |
|---|---|---|
| I-81 | 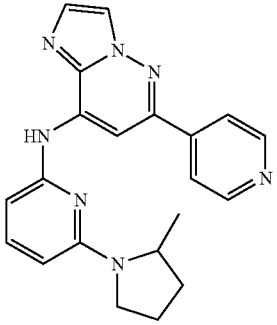 [SMILES: CC1CCCN1c1cccc(Nc2cc(-c3ccncc3)nn3ccnc23)n1] | [6-(2-Methyl-pyrrolidin-1-yl)-pyridin-2-yl]-(6-pyridin-4-yl-imidazo[1,2-b]pyridazin-8-yl)-amine |
| I-82 | 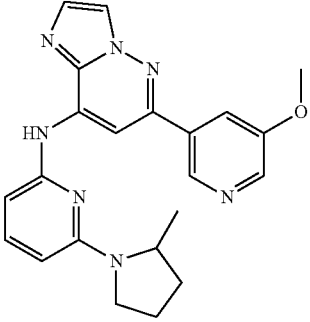 [SMILES: COc1cncc(-c2cc(Nc3cccc(N4CCCC4C)n3)c3nccn3n2)c1] | [6-(5-Methoxy-pyridin-3-yl)-imidazo[1,2-b]pyridazin-8-yl]-[6-(2-methyl-pyrrolidin-1-yl)-pyridin-2-yl]-amine |
| I-83 | 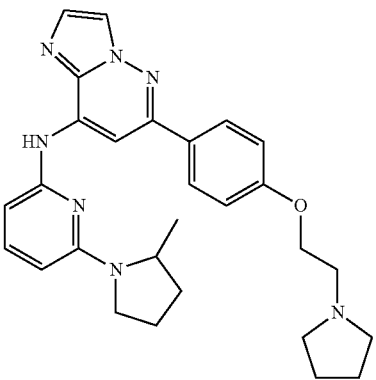 [SMILES: CC1CCCN1c1cccc(Nc2cc(-c3ccc(OCCN4CCCC4)cc3)nn3ccnc23)n1] | [6-(2-Methyl-pyrrolidin-1-yl)-pyridin-2-yl]-{6-[4-(2-pyrrolidin-1-yl-ethoxy)-phenyl]-imidazo[1,2-b]pyridazin-8-yl}-amine hydrochloride |
| I-84 | 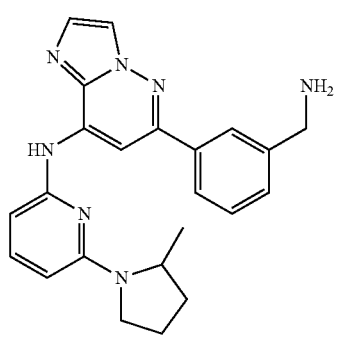 [SMILES: CC1CCCN1c1cccc(Nc2cc(-c3cccc(CN)c3)nn3ccnc23)n1] | [6-(3-Aminomethyl-phenyl)-imidazo[1,2-b]pyridazin-8-yl]-[6-(2-methyl-pyrrolidin-1-yl)-pyridin-2-yl]-amine hydrochloride |

TABLE I-continued

| Compound | Nomenclature | Structure |
|---|---|---|
| I-85 | 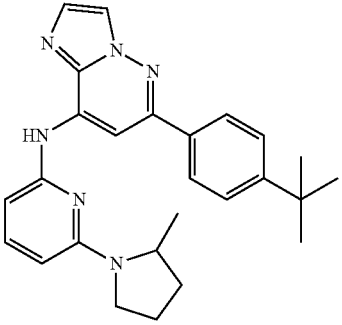 [SMILES: CC1CCCN1c1cccc(Nc2cc(-c3ccc(C(C)(C)C)cc3)nn3ccnc23)n1] | [6-(4-tert-Butyl-phenyl)-imidazo[1,2-b]pyridazin-8-yl]-[6-(2-methyl-pyrrolidin-1-yl)-pyridin-2-yl]-amine |
| I-86 | 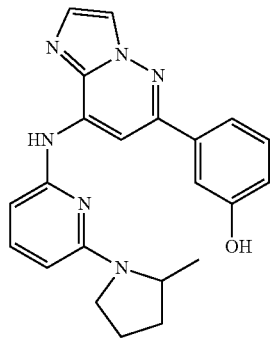 [SMILES: CC1CCCN1c1cccc(Nc2cc(-c3cccc(O)c3)nn3ccnc23)n1] | 3-{8-[6-(2-Methyl-pyrrolidin-1-yl)-pyridin-2-ylamino]-imidazo[1,2-b]pyridazin-6-yl}-phenol |
| I-87 | 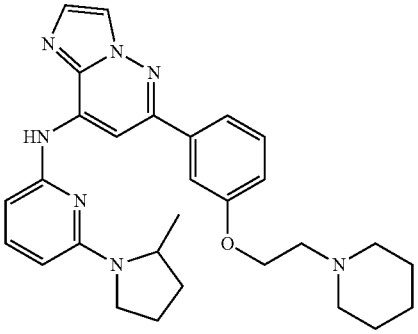 [SMILES: CC1CCCN1c1cccc(Nc2cc(-c3cccc(OCCN4CCCCC4)c3)nn3ccnc23)n1] | [6-(2-Methyl-pyrrolidin-1-yl)-pyridin-2-yl]-{6-[3-(2-piperidin-1-yl-ethoxy)-phenyl]-imidazo[1,2-b]pyridazin-8-yl}-amine |
| I-88 | 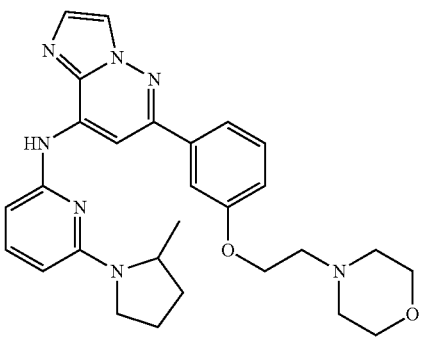 [SMILES: CC1CCCN1c1cccc(Nc2cc(-c3cccc(OCCN4CCOCC4)c3)nn3ccnc23)n1] | [6-(2-Methyl-pyrrolidin-1-yl)-pyridin-2-yl]-{6-[3-(2-morpholin-4-yl-ethoxy)-phenyl]-imidazo[1,2-b]pyridazin-8-yl}-amine |

TABLE I-continued

| Compound | Nomenclature | Structure |
|---|---|---|
| I-89 | [6-(2-Methyl-pyrrolidin-1-yl)-pyridin-2-yl]-{6-[4-(2-piperidin-1-yl-ethoxy)-phenyl]-imidazo[1,2-b]pyridazin-8-yl}-amine | |
| I-90 | [6-(2-Methyl-pyrrolidin-1-yl)-pyridin-2-yl]-{6-[4-(2-morpholin-4-yl-ethoxy)-phenyl]-imidazo[1,2-b]pyridazin-8-yl}-amine | |
| I-91 | {6-[3-(2-Diethylamino-ethoxy)-phenyl]-imidazo[1,2-b]pyridazin-8-yl}-[6-(2-methyl-pyrrolidin-1-yl)-pyridin-2-yl]-amine | |
| I-92 | (6-[4-(2-Diethylamino-ethoxy)-phenyl]-imidazo[1,2-b]pyridazin-8-yl}-[6-(2-methyl-pyrrolidin-1-yl)-pyridin-2-yl]-amine | |

TABLE I-continued

| Compound | Nomenclature | Structure |
|---|---|---|
| I-93 | [6-(2-Methyl-pyrrolidin-1-yl)-pyridin-2-yl]-{6-[3-(piperidin-4-ylaminomethyl)-phenyl]-imidazo[1,2-b]pyridazin-8-yl}-amine hydrochloride | 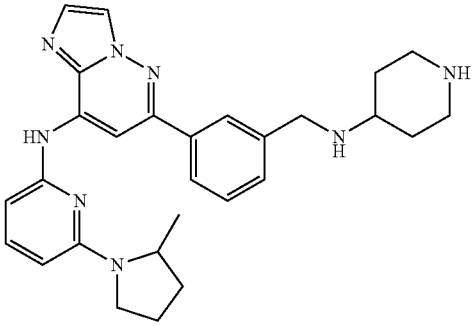 [SMILES: CC1CCCN1c1cccc(Nc2cc(-c3cccc(CNC4CCNCC4)c3)nn3ccnc23)n1] |
| I-94 | [6-(2-Methyl-pyrrolidin-1-yl)-pyridin-2-yl]-{6-[3-(2-piperazin-1-yl-ethoxy)-phenyl]-imidazo[1,2-b]pyridazin-8-yl}-amine hydrochloride | 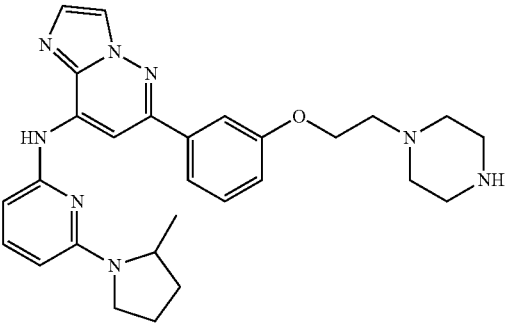 [SMILES: CC1CCCN1c1cccc(Nc2cc(-c3cccc(OCCN4CCNCC4)c3)nn3ccnc23)n1] |
| I-95 | 3-[8-(5,6-Dimethoxy-pyridin-2-ylamino)-imidazo[1,2-b]pyridazin-6-yl]-benzoic acid | 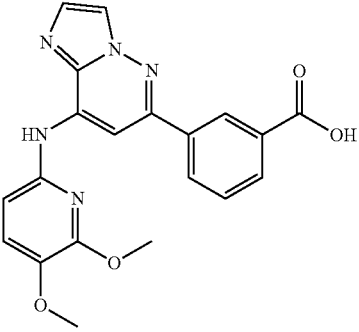 [SMILES: COc1ccc(Nc2cc(-c3cccc(C(=O)O)c3)nn3ccnc23)nc1OC] |
| I-96 | 3-(8-(5,6-Dimethoxypyridin-2-ylamino)imidazo[1,2-b]pyridazin-6-yl)-N-(4-(methylcarbamoyl)phenyl)benzamide | 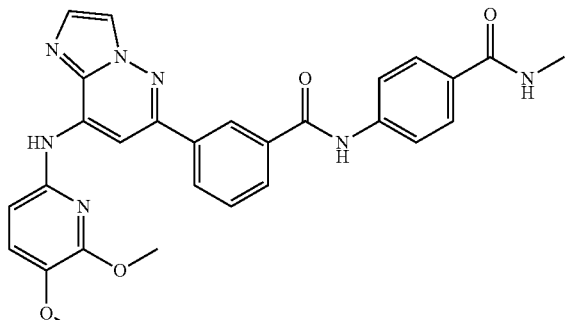 |

Synthesis
General Schemes
Representative General Schemes in the synthesis of the imidazopyridazine core:
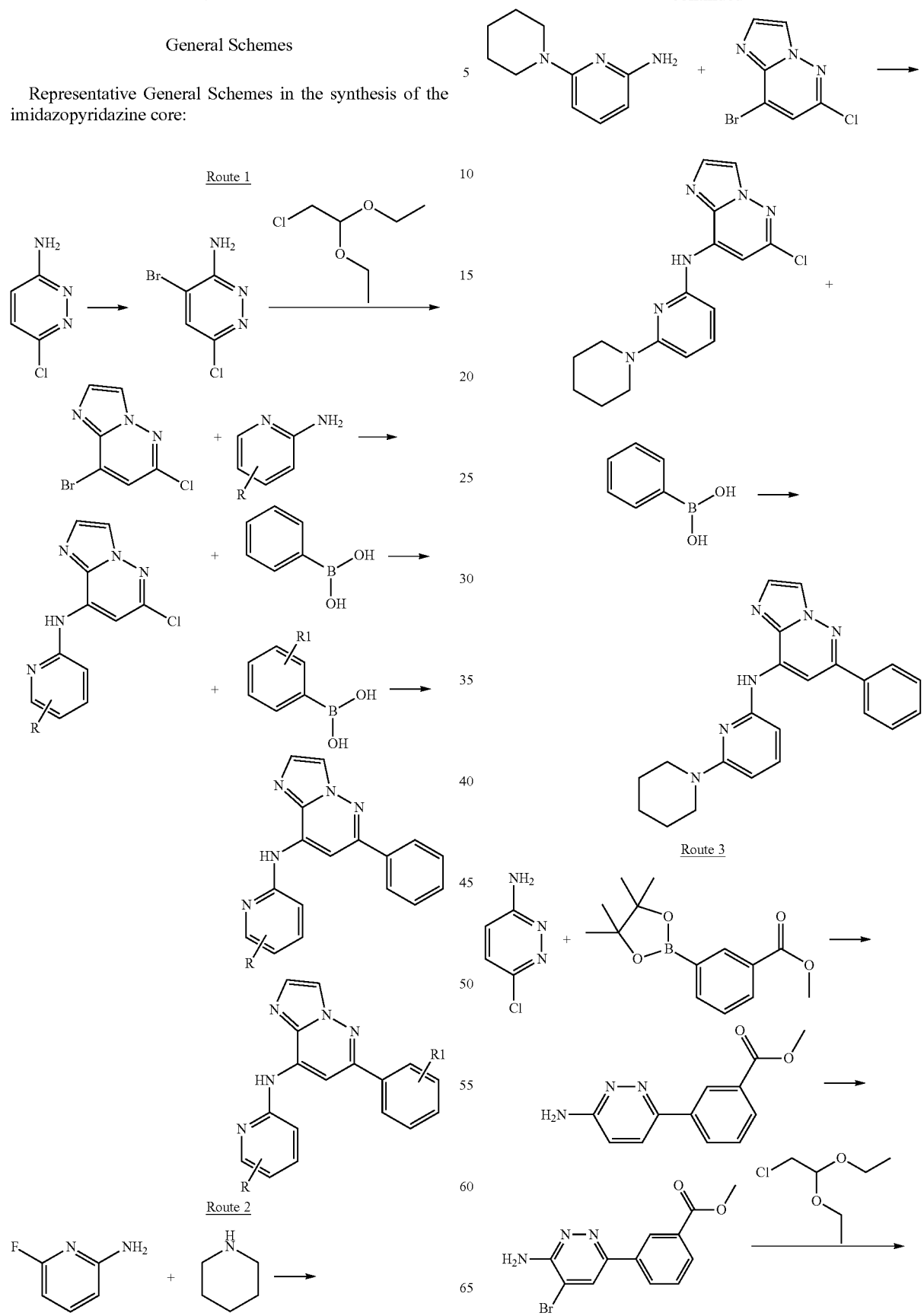

-continued

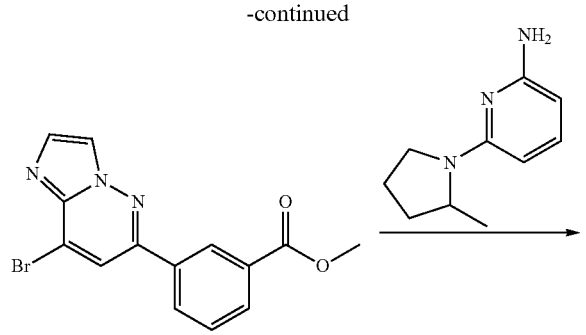

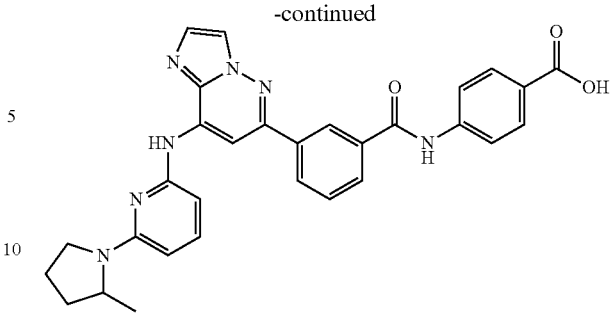

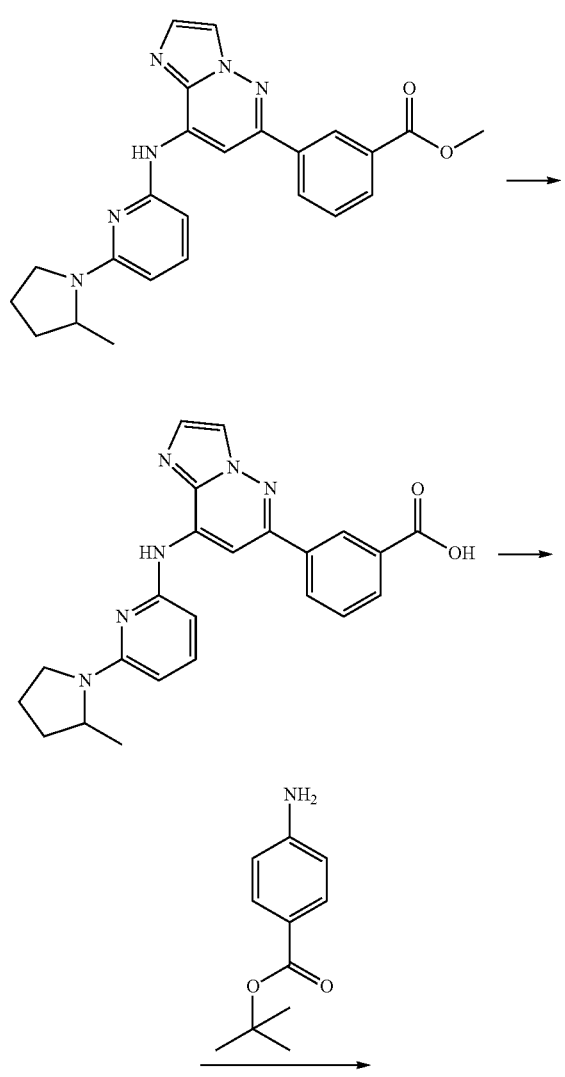

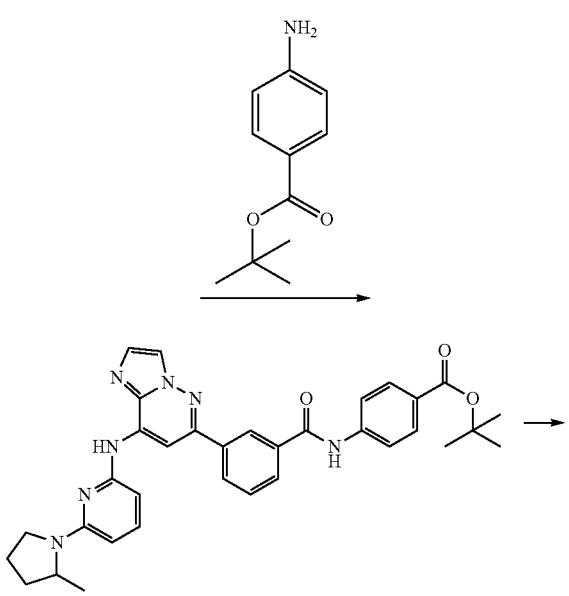

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 h.

Indications and Methods of Treatment

The compounds described herein are kinase inhibitors, in particular SYK inhibitors. These inhibitors can be useful for treating one or more diseases responsive to kinase inhibition, including diseases responsive to SYK inhibition and/or inhibition of B-cell proliferation, in mammals. Without wishing to be bound to any particular theory, it is believed that the interaction of the compounds of the invention with SYK results in the inhibition of SYK activity and thus in the pharmaceutical utility of these compounds. Accordingly, the invention includes a method of treating a mammal, for instance a human, having a disease responsive to inhibition of SYK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to SYK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

Abbreviations

Commonly used abbreviations include: acetyl (Ac), azo-bis-isobutyrylnitrile (AIBN), atmospheres (Atm), 9-borabi-cyclo[3.3.1]nonane (9-BBN or BBN), 2,2'-bis(diphenylphos-phino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propyl-ethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl)palladium(II) (Pd(dppf)Cl$_2$), palladium(II) acetate (Pd(OAc)$_2$), tris(dibenzylideneacetone)dipalladium(0) (Pd$_2$(dba)$_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The preceding abbreviations may be used in the Preparations and Examples. All names were generated using Autonom or ChemDraw.

The following preparations and examples are given to enable those skilled in the art to more clearly understand and to practice the present invention. They should not be considered as limiting the scope of the invention, but merely as being illustrative and representative thereof.

PREPARATIVE EXAMPLES

Example 1

Synthesis of 6-Phenyl-N-(6-(trifluoromethyl)pyridin-2-yl)imidazo[1,2-b]pyridazin-8-amine hydrochloride

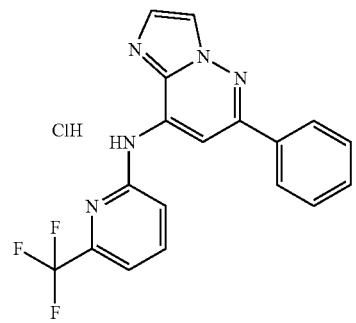 [SMILES: FC(F)(F)c1cccc(Nc2cc(-c3ccccc3)nn3ccnc23)n1 ; Cl]

Step 1

4-Bromo-6-chloropyridazin-3-amine

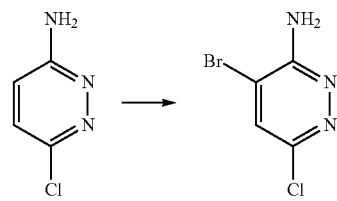 [SMILES: Nc1ccc(Cl)nn1 ; Nc1nnc(Cl)cc1Br]

To a suspension of 6-chloropyridazin-3-amine (30 g, 232 mmol), NaHCO$_3$ (39 g, 464 mmol) and methanol (576 mL) was added Br$_2$ (11.9 mL, 232 mmol) drop wise over 30 minutes at room temperature. The mixture was stirred for 16 h then filtered and concentrated in vacuo. The residue was purified by chromatography (silica gel, 200-300 mesh, petroleum ether:ethyl acetate=3:1) to give 4-bromo-6-chloropyridazin-3-amine (31.5 g, 65%) as a light orange solid. LC-MS: [M+H]+, 207.9, 209.9, $t_R$=1.189 min.

Step 2

8-Bromo-6-chloroimidazo[1,2-b]pyridazine

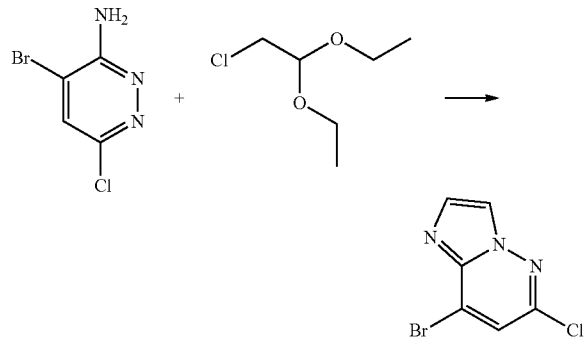

A solution of 4-bromo-6-chloropyridazin-3-amine (15.7 g, 75.3 mmol), 2-chloro-1,1-diethoxyethane (13.9 g, 90.3 mmol) and PTSA (17.2 g, 90.3 mmol) in isopropanol (150 mL) was heated to 80° C. for 20 h. After cooling to room temperature, the solution was concentrated in vacuo. The resulting mixture was treated with a saturated NaHCO₃ solution (300 mL), extracted with dichloromethane (200 mL×3), dried over Na₂SO₄, filtered and concentrated. The residue was purified by chromatography (silica gel, 200-300 mesh, petroleum ether:ethyl acetate=3:1) to give 8-bromo-6-chloroimidazo[1,2-b]pyridazine (17.2 g, 98%) as an orange solid. LC-MS: [M+H]+, 231.9, 233.9, $t_R$=1.46 min.

Step 3

6-Chloro-N-(6-(trifluoromethyl)pyridin-2-yl)imidazo[1,2-b]pyridazin-8-amine

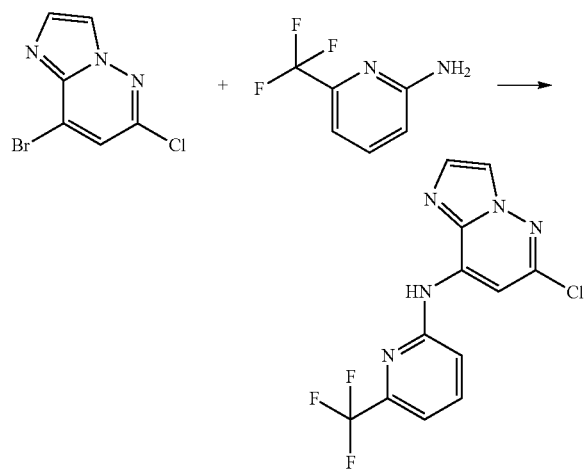

A solution of 6-(trifluoromethyl)pyridin-2-amine (0.668 g, 4.12 mmol) in DMF (5 mL) was added NaH (0.10 g, 4.18 mmol) and stirred for 0.5 h. To the mixture was added 8-bromo-6-chloroimidazo[1,2-b]pyridazine (0.38 g, 1.65 mmol) under N₂. The mixture was stirred at room temperature for 16 h then 100 mL of water was added and the precipitate collected by filtration and washed with water to give 6-chloro-N-(6-(trifluoromethyl)pyridin-2-yl)imidazo[1,2-b]pyridazin-8-amine (0.513 g, 99%) as a light brown solid. LC-MS: [M+H]+, 314.1, $t_R$=1.738 min.

Step 4

6-Phenyl-N-(6-(trifluoromethyl)pyridin-2-yl)imidazo[1,2-b]pyridazin-8-amine hydrochloride

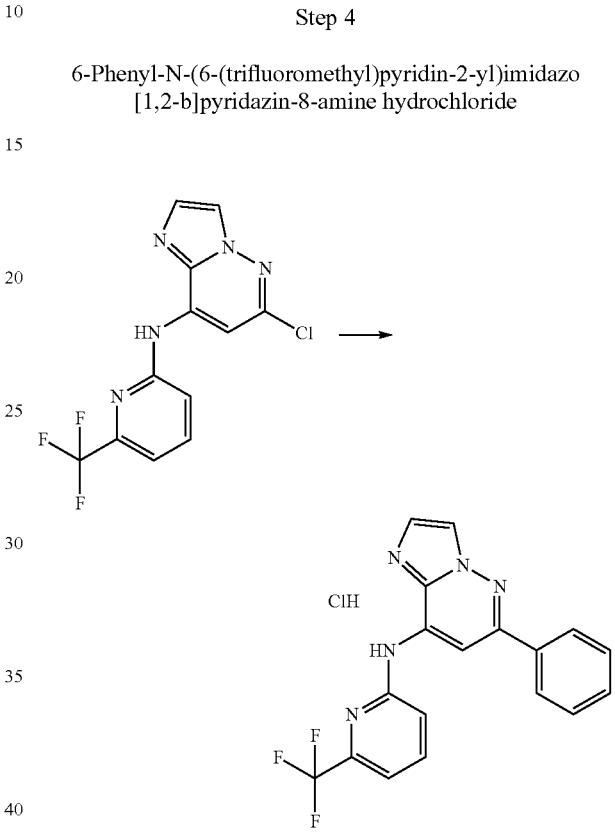

A mixture of 6-chloro-N-(6-(trifluoromethyl)pyridin-2-yl)imidazo[1,2-b]pyridazin-8-amine (157 mg, 0.5 mmol), phenylboronic acid (92 mg, 0.75 mmol), Pd₂(dba)₃ (29 mg, 0.05 mmol), X-phos (96 mg, 0.2 mmol) and K₂CO₃ (208 mg, 1.5 mmol) in dioxane (10 mL) and water (1 mL) was heated to 100° C. with stirring for 4 h under N₂. The solvent was removed in vacuo and the resulting mixture was purified by chromatography (silica gel, 200-300 mesh, petroleum ether:ethyl acetate=3:1) to give crude product (135 mg) which was further purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to give a light yellow solid. The mixture was dissolved in methanol then three drops of concentrated HCl were added and the mixture was stirred for 5 minutes, then concentrated in vacuo to give the final product 6-phenyl-N-(6-(trifluoromethyl)pyridin-2-yl)imidazo[1,2-b]pyridazin-8-amine hydrochloride (65 mg, 37%) as a HCl salt. ¹H NMR (300 MHz, CD₃OD): δ 9.40 (s, 1H), 8.48 (d, 1H, J=2.1 Hz), 8.21 (d, 1H, J=2.4 Hz), 8.12-8.06 (m, 3H), 7.61-7.56 (m, 4 h), 7.48 (d, 1H, J=8.4 Hz). LC-MS: 356, [M+H]+, $t_R$=1.822 min, HPLC: 100% at 214 nm, 99.96% at 254 nm, $t_R$=7.247 min.

Example 2

Synthesis of N-(5-Ethylpyridin-2-yl)-6-phenylimidazo[1,2-b]pyridazin-8-amine

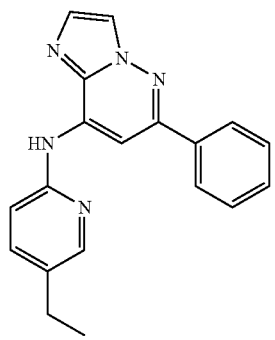 [SMILES: CCc1ccc(Nc2cc(-c3ccccc3)nn3ccnc23)nc1]

Step 1

6-Chloro-N-(5-ethylpyridin-2-yl) imidazo[1,2-b]pyridazin-8-amine

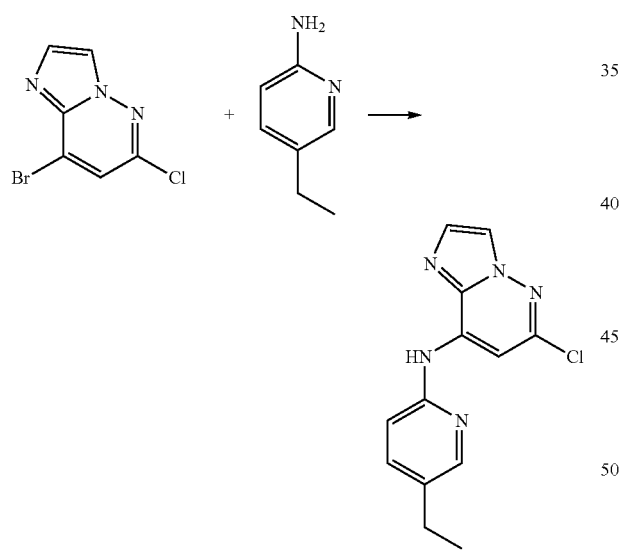

To a solution of 5-ethylpyridin-2-amine (394 mg, 3.23 mmol) in DMF (8 mL) was added NaH (129 mg, 60% dispersion in mineral oil, 3.23 mmol) under $N_2$ atmosphere at room temperature and stirred for another 0.5 h. To this mixture was added 8-bromo-6-chloroimidazo[1,2-b]pyridazine (0.3 g, 1.3 mmol). After 20 h stirring at room temperature, saturated $NH_4Cl$ solution was added and the reaction mixture was extracted with ether (200 mL) and washed with water (2×50 mL), then brine (2×50 mL). After drying and filtration, it was concentrated to afford 6-chloro-N-(5-ethylpyridin-2-yl)imidazo[1,2-b]pyridazin-8-amine (785 mg, crude) as a yellow solid that was used directly without further purification. LC-MS: $[M+1]^+$=274, $t_R$=1.726 min.

Step 2

N-(5-Ethylpyridin-2-yl)-6-phenylimidazo[1,2-b]pyridazin-8-amine

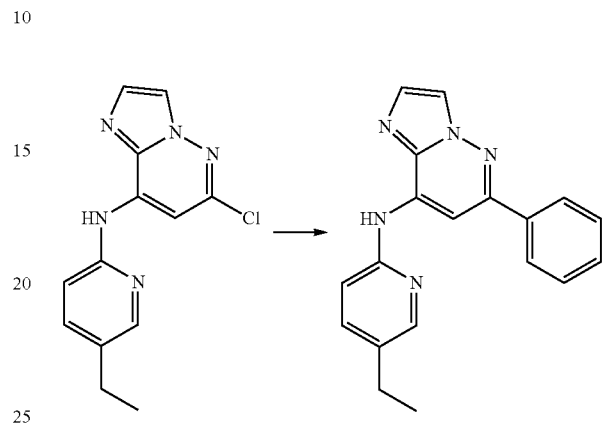

A mixture of 6-chloro-N-(5-ethylpyridin-2-yl)imidazo[1,2-b]pyridazin-8-amine (329 mg, 1.21 mmol), 4,4,5,5-tetramethyl-2-phenyl-1,3,2-dioxaborolane (221 mg, 1.81 mmol), $Pd_2(dba)_3$ (70 mg, 0.121 mmol), X-Phos (231 mg, 0.484 mmol) and $K_2CO_3$ (499 mg, 3.62 mmol) in dioxane (40 mL) and $H_2O$ (10 mL) was heated to 110° C. for 20 h under $N_2$. The mixture was cooled and concentrated in vacuo. The residue was purified by chromatography (silica gel, 10 g, 200~300 mesh, ethyl acetate:petroleum ether=1:5) to afford N-(5-ethylpyridin-2-yl)-6-phenylimidazo[1,2-b]pyridazin-8-amine (84 mg, 22%) as a yellow solid. $^1$H NMR (300 MHz, $CDCl_3$): δ 8.69 (s, 1H), 8.37 (d, 1H, J=1.8 Hz), 8.24 (s, 1H), 8.09-8.01 (m, 3H), 7.68-7.55 (m, 5H), 7.02 (d, 1H, J=8.4 Hz), 2.75 (q, 2H, J=7.8 Hz), 1.37 (t, 3H, J=7.8 Hz). LC-MS: 316, [M+H]+, $t_R$=1.827 min, HPLC: 99.73% at 214 nm, 99.88% at 254 nm, $t_R$=3.262 min.

Example 3

Synthesis of 6-Phenyl-N-(6-(piperidin-1-yl)pyridin-2-yl)imidazo[1,2-b]pyridazin-8-amine hydrochloride

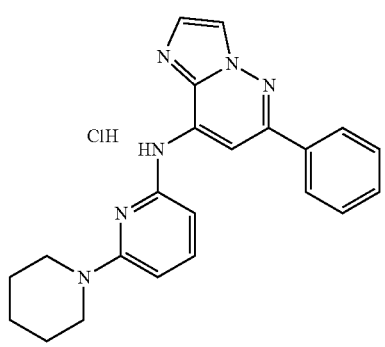 [SMILES: c1ccc(-c2cc(Nc3cccc(N4CCCCC4)n3)c3nccn3n2)cc1 ; Cl]

Step 1

6-(Piperidin-1-yl)pyridin-2-amine

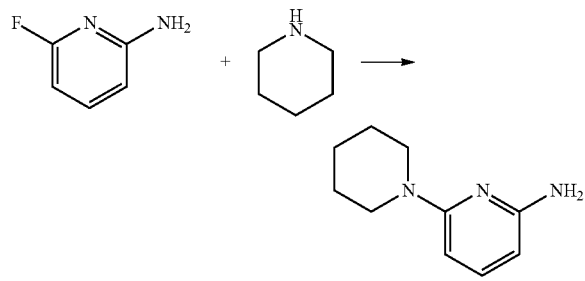

A suspension of 6-fluoropyridin-2-amine (500 mg, 4.4 mmol), piperidine (1.4 mL, 14.1 mmol) in water (0.5 mL) was heated to 205° C. in a microwave oven for 30 minutes. The reaction mixture was purified by chromatography (silica gel, 200-300 mesh, petroleum ether:ethyl acetate=3:1) to give 6-(piperidin-1-yl)pyridin-2-amine (740 mg, 94%) as a light yellow oil. LC-MS: [M+H]$^+$, 178.1, $t_R$=0.974 min.

Step 2

6-Chloro-N-(6-(piperidin-1-yl)pyridin-2-yl)imidazo[1,2-b]pyridazin-8-amine

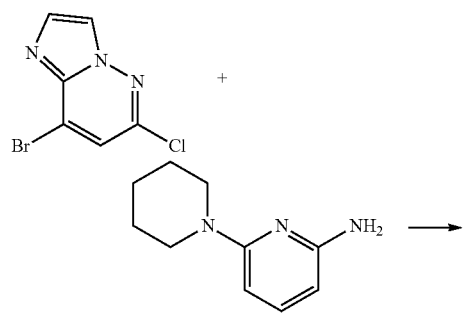

To a solution of 6-(piperidin-1-yl)pyridin-2-amine (0.725 g, 4.12 mmol) in DMF (8 mL) was added NaH (0.11 g, 60% dispersion in mineral oil, 4.18 mmol) and the mixture stirred for 0.5 h. To this mixture was added 8-bromo-6-chloroimidazo[1,2-b]pyridazine (0.384 g, 1.65 mmol) under N$_2$. The mixture was stirred at room temperature for 16 h. The resulting mixture was treated with a saturated NH$_4$Cl solution (50 mL), extracted with ether (80 mL), dried over Na$_2$SO$_4$, filtered and concentrated. The residue was purified by chromatography (silica gel, 200-300 mesh, petroleum ether:ethyl acetate=3:1) to give 6-chloro-N-(6-(piperidin-1-yl)pyridin-2-yl)imidazo[1,2-b]pyridazin-8-amine (0.13 g, 24.1%) as a yellow solid. LC-MS: [M+H]$^+$, 329.0, 331.0, $t_R$=1.912 min

Step 3

6-Phenyl-N-(6-(piperidin-1-yl)pyridin-2-yl)imidazo[1,2-b]pyridazin-8-amine hydrochloride

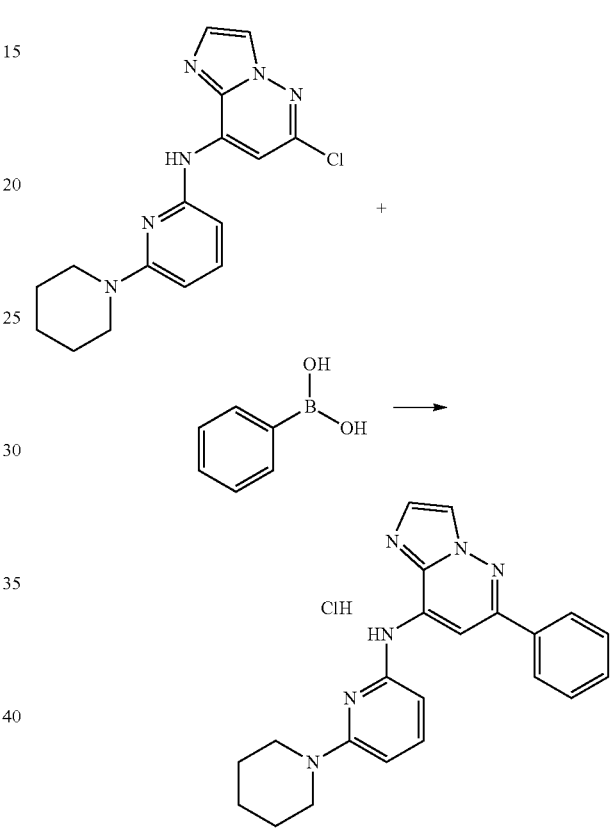

A mixture of 6-chloro-N-(6-(piperidin-1-yl)pyridin-2-yl)imidazo[1,2-b]pyridazin-8-amine (130 mg, 0.4 mmol), phenylboronic acid (74 mg, 0.6 mmol), Pd$_2$(dba)$_3$ (24 mg, 0.04 mmol), X-phos (76 mg, 0.16 mmol) and K$_2$CO$_3$ (166 mg, 1.2 mmol) in dioxane (10 mL) and water (1 mL) was heated to 100° C. with stirring for 4 h under N$_2$. The solvent was removed in vacuo and the resulting mixture was purified by chromatography (silica gel, 200-300 mesh, petroleum ether: ethyl acetate=3:1) to give crude product which was further purified by prep-HPLC (Gemini 5u C18 150×21.2 mm; inject volume: 3 mL/inj; flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to give a white solid. This was dissolved in methanol and three drops of concentrated HCl was added. After 5 minutes, the mixture was concentrated in vacuo to give the final product (135 mg, 58.3%) as an HCl salt. $^1$H NMR (300 MHz, CDCl$_3$): δ 9.07 (s, 1H), 8.50 (d, 1H, J=2.1 Hz), 8.25 (d, 1H, J=2.1 Hz), 8.14-8.10 (m, 2H), 7.97-7.94 (m, 1H), 7.65-7.61 (m, 3H), 7.29 (d, 1H, J=8.1 Hz), 7.20 (d, 1H, J=8.1 Hz), 3.78-3.74 (m, 4 h), 2.02-3.00 (m, 4 h), 1.85-1.83 (m, 2H). LC-MS: 371, [M+H]+, $t_R$=2.016 min, HPLC: 100% at 214 nm, 100% at 254 nm, $t_R$=7.5 min.

Example 4

Synthesis of 6-Phenyl-N-(6-(pyrrolidin-1-yl)pyridin-2-yl)imidazo[1,2-b]pyridazin-8-amine hydrochloride

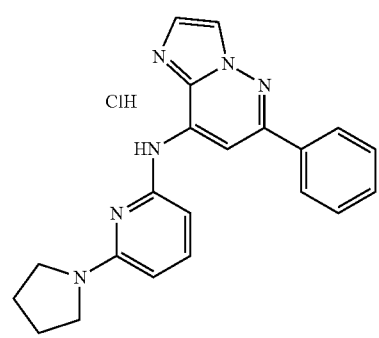 [SMILES: c1ccc(-c2cc(Nc3cccc(N4CCCC4)n3)c3nccn3n2)cc1 ; Cl]

Step 1

6-Chloro-N-(6-fluoropyridin-2-yl)imidazo[1,2-b]pyridazin-8-amine

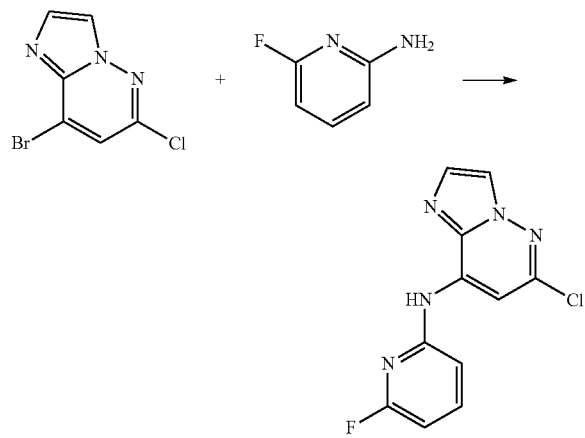

To a solution of 6-fluoropyridin-2-amine (1.12 g, 10 mmol) in DMF (16 mL) was added NaH (0.24 g, 60% dispersion in mineral oil, 10 mmol) and the mixture stirred for 0.5 h. To the mixture was added 6-chloro-N-(6-fluoropyridin-2-yl)imidazo[1,2-b]pyridazin-8-amine (0.93 g, 4 mmol) under $N_2$. The mixture was stirred at room temperature for 16 h, then partitioned between 45 mL of saturated $NH_4Cl$ solution and 45 mL of ether. The organic layer was washed with water (30 mL×3) and saturated NaCl solution (30 mL×3), dried over $Na_2SO_4$, concentrated in vacuo, and purified by chromatography (silica gel, 200-300 mesh, petroleum ether:ethyl acetate=3:1) to give 6-chloro-N-(6-fluoropyridin-2-yl)imidazo[1,2-b]pyridazin-8-amine (1.04 g, 99%) as a light brown solid. LC-MS: [M+H]+, 264.1, 266.2, $t_R$=1.601 min.

Step 2

6-Chloro-N-(6-(pyrrolidin-1-yl)pyridin-2-yl)imidazo[1,2-b]pyridazin-8-amine

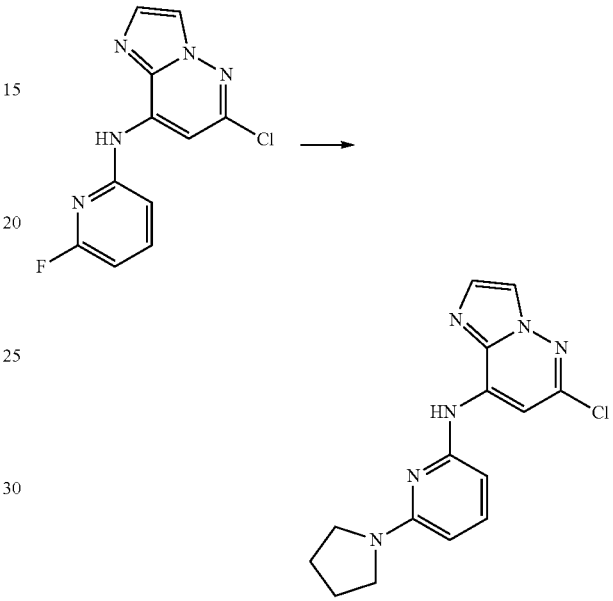

A suspension of 6-chloro-N-(6-fluoropyridin-2-yl)imidazo[1,2-b]pyridazin-8-amine (132 mg, 0.5 mmol) and pyrrolidine (54 mg, 0.75 mmol) in water (0.3 mL) was heated to 205° C. in a microwave oven for 30 minutes. The reaction mixture was purified by chromatography (silica gel, 200-300 mesh, $CH_2Cl_2$:MeOH=200:1) to give 6-chloro-N-(6-(pyrrolidin-1-yl)pyridin-2-yl)imidazo[1,2-b]pyridazin-8-amine (29 mg, 18%) as a light yellow solid. LC-MS: [M+H]+, 315.0, $t_R$=1.837 min.

Step 3

6-Phenyl-N-(6-(pyrrolidin-1-yl)pyridin-2-yl)imidazo[1,2-b]pyridazin-8-amine hydrochloride

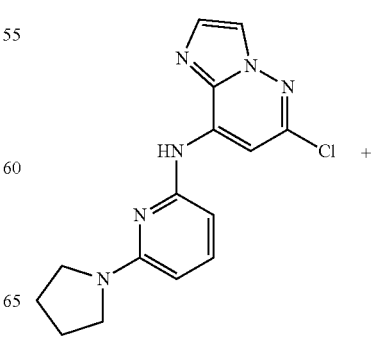

77

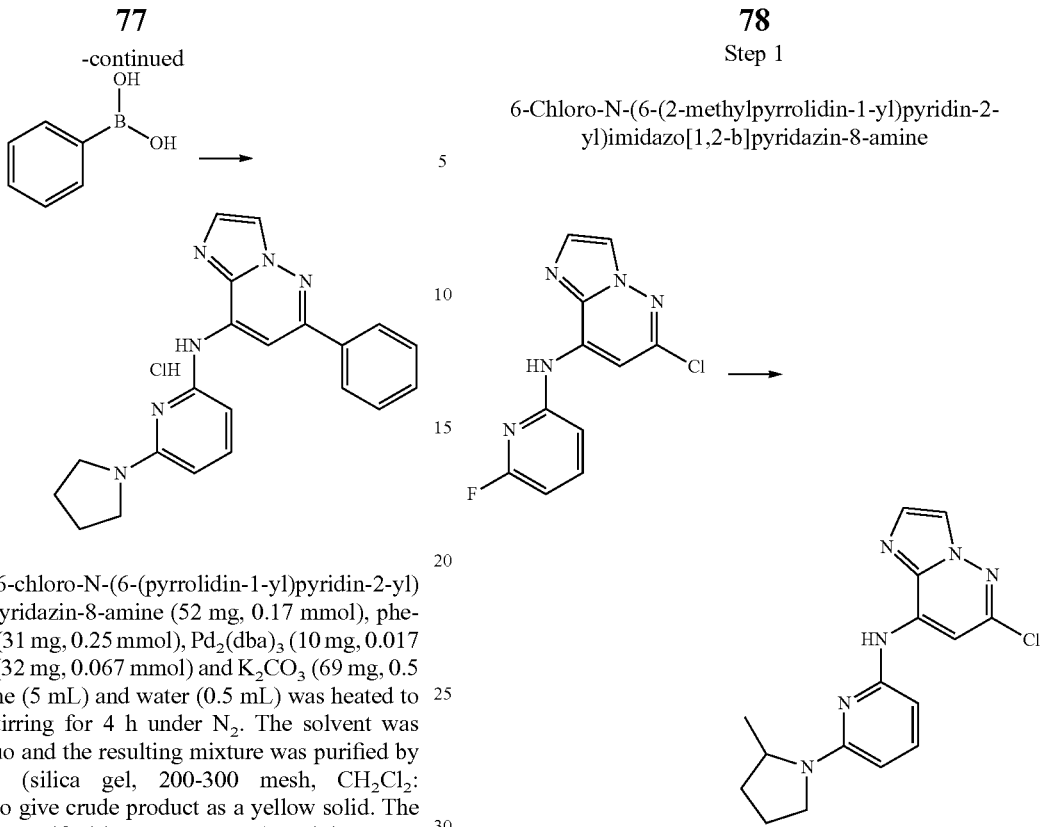

A mixture of 6-chloro-N-(6-(pyrrolidin-1-yl)pyridin-2-yl)imidazo[1,2-b]pyridazin-8-amine (52 mg, 0.17 mmol), phenylboronic acid (31 mg, 0.25 mmol), Pd₂(dba)₃ (10 mg, 0.017 mmol), X-phos (32 mg, 0.067 mmol) and K₂CO₃ (69 mg, 0.5 mmol) in dioxane (5 mL) and water (0.5 mL) was heated to 100° C. with stirring for 4 h under N₂. The solvent was removed in vacuo and the resulting mixture was purified by chromatography (silica gel, 200-300 mesh, CH₂Cl₂: MeOH=180:1) to give crude product as a yellow solid. The solid was further purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to give a light yellow solid. This was dissolved in methanol and three drops of concentrated HCl added. The mixture was stirred for 5 minutes, then concentrated in vacuo to give the final product 6-phenyl-N-(6-(pyrrolidin-1-yl)pyridin-2-yl)imidazo[1,2-b]pyridazin-8-amine hydrochloride (46 mg, 78%) as an HCl salt. ¹H NMR (300 MHz, CD₃OD): δ 8.81 (s, 1H), 8.31 (s, 1H), 8.04-7.96 (m, 3H), 7.56-7.50 (m, 4 h), 6.38 (d, 1H, J=7.8 Hz), 6.20 (d, 1H, J=8.4 Hz), 3.54-3.49 (m, 4 h), 2.08-2.03 (m, 4 h). LC-MS: [M+H]⁺, 357.1, t$_R$=1.912 min, HPLC: 95.34% at 214 nm, 99.67% at 254 nm, t$_R$=7.083 min.

Example 5

Synthesis of N-(6-(2-Methylpyrrolidin-1-yl)pyridin-2-yl)-6-phenylimidazo[1,2-b]pyridazin-8-amine

78

Step 1

6-Chloro-N-(6-(2-methylpyrrolidin-1-yl)pyridin-2-yl)imidazo[1,2-b]pyridazin-8-amine A suspension of 6-chloro-N-(6-fluoropyridin-2-yl)imidazo[1,2-b]pyridazin-8-amine (132 mg, 0.5 mmol) and 2-methylpyrrolidine (64 mg, 0.75 mmol) in water (0.3 mL) was heated to 205° C. in a microwave oven for 30 minutes. The reaction mixture was purified by chromatography (silica gel, 200-300 mesh, CH₂Cl₂:MeOH=200:1) to give 6-chloro-N-(6-(2-methylpyrrolidin-1-yl)pyridin-2-yl)imidazo[1,2-b]pyridazin-8-amine (105 mg, 63.8%) as a yellow solid. LC-MS: [M+H]⁺, 329.1, t$_R$=2.019 min.

Step 2

N-(6-(2-Methylpyrrolidin-1-yl)pyridin-2-yl)-6-phenylimidazo[1,2-b]pyridazin-8-amine

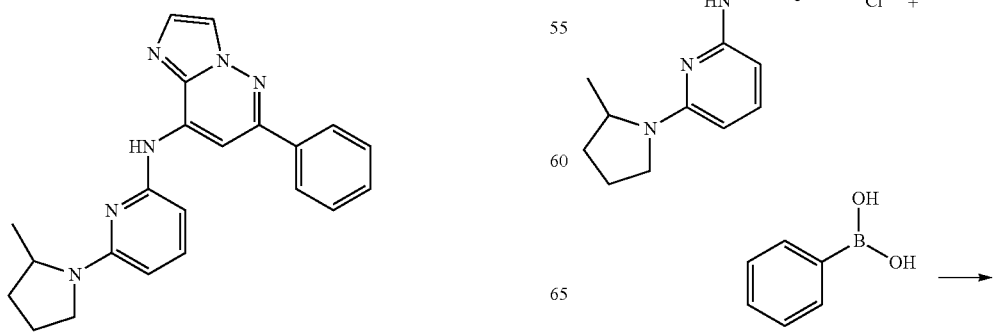

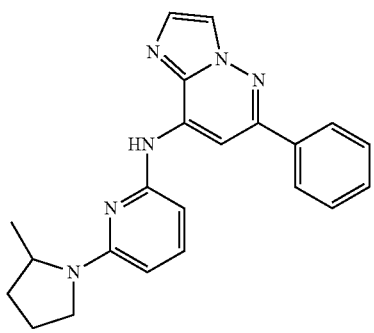 [SMILES: CC1CCCN1c1cccc(Nc2cc(-c3ccccc3)nn3ccnc23)n1]

A mixture of 6-chloro-N-(6-(2-methylpyrrolidin-1-yl)pyridin-2-yl)imidazo[1,2-b]pyridazin-8-amine (180 mg, 0.55 mmol), phenylboronic acid (102 mg, 0.83 mmol), Pd$_2$(dba)$_3$ (33 mg, 0.056 mmol), X-phos (105 mg, 0.22 mmol) and K$_2$CO$_3$ (226 mg, 1.63 mmol) in dioxane (10 mL) and water (1 mL) was heated to 100° C. with stirring for 4 h under N$_2$. The reaction mixture was purified by chromatography (silica gel, 200-300 mesh, CH$_2$Cl$_2$:MeOH=180:1) to give crude product. This was further purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to give a light yellow solid. This was dissolved in methanol and three drops of concentrated HCl added. The mixture was stirred for 5 minutes, then concentrated in vacuo to give a light yellow solid (80 mg, 40%) as an HCl salt. $^1$H NMR (300 MHz, CD$_3$OD): δ 8.87 (s, 1H), 8.37 (d, 1H, J=2.4 Hz), 8.10 (d, 1H, J=1.8 Hz), 8.01-7.98 (m, 2H), 7.60-7.53 (m, 4 h), 6.45 (d, 1H, J=7.8 Hz), 6.30 (d, 1H, J=8.4 Hz), 4.28-4.24 (m, 1H), 3.67-3.47 (m, 2H), 2.20-1.80 (m, 4 h), 1.20 (d, 1H, J=6.3 Hz). LC-MS: [M+H]$^+$, 371, t$_R$=1.97 min, HPLC: 97.57% at 214 nm, 99.43% at 254 nm, t$_R$=7.473 min.

Example 6

Synthesis of N-(6-(1-tert-Butyl-1H-pyrazol-3-yl)pyridin-2-yl)-6-phenylimidazo[1,2-b]pyridazin-8-amine hydrochloride

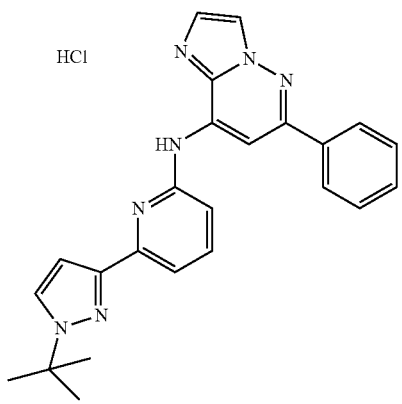 [SMILES: CC(C)(C)n1ccc(-c2cccc(Nc3cc(-c4ccccc4)nn4ccnc34)n2)n1 ; Cl]

Step 1

1-tert-Butyl-1H-pyrazol-3-amine

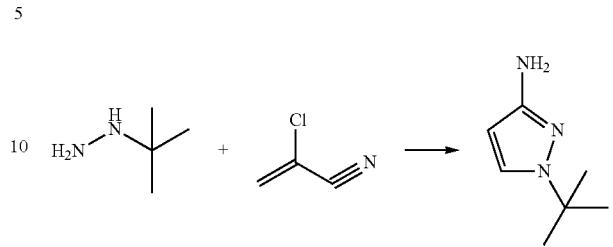

A mixture of tert-butylhydrazine (2.4 g, 27 mmol), 2-chloroacrylonitrile (2.9 g, 33 mmol), NaOAc (3.17 g, 38 mmol) and ethanol (30 mL) was heated to 80° C. with stirring for 12 h. The solvent was removed in vacuo and the resulting mixture was treated with saturated NaHCO$_3$ solution (200 mL) and extracted with ethyl acetate (200 mL×3). The organic layers were dried over NaSO$_4$, concentrated in vacuo, purified by chromatography (silica gel, 200-300 mesh, petroleum ether:ethyl acetate=2:1 to 1:2) to give 1-tert-butyl-1H-pyrazol-3-amine (1.39 g, 37%) as a brown oil. LC-MS: [M+H]$^+$, 140.2, t$_R$=0.696 min.

Step 2

N-(6-(1-tert-Butyl-1H-pyrazol-3-yl)pyridin-2-yl)-6-chloroimidazo[1,2-b]pyridazin-8-amine

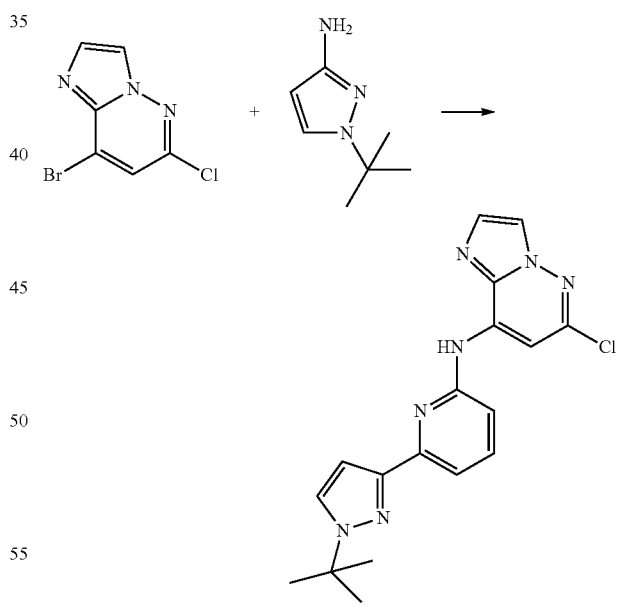

To a solution of 1-tert-Butyl-1H-pyrazol-3-amine (0.348 g, 2.5 mmol) in DMF (8 mL) was added NaH (0.060 g, 60% dispersion in mineral oil, 2.5 mmol) and the mixture stirred for 0.5 h. To this mixture was added 8-bromo-6-chloroimidazo[1,2-b]pyridazine (0.233 g, 1 mmol) under N$_2$. The mixture was stirred at room temperature for 16 h then partitioned between 15 mL of saturated aq. MH$_4$Cl and 15 mL of ether. The organic layer was washed with water (10 mL×3) and saturated aq. NaCl (10 mL×3), dried over NaSO$_4$, concentrated in vacuo, purified by chromatography (silica gel, 200-300 mesh, petroleum ether:ethyl acetate=3:1) to give N-(6-(1-tert-butyl-1H-pyrazol-3-yl)pyridin-2-yl)-6-chloroimidazo[1,2-b]pyridazin-8-amine (0.168 g, 23%) as a light brown solid. LC-MS: [M+H]⁺, 291.1, $t_R$=1.648 min.

Step 3

N-(6-(1-tert-Butyl-1H-pyrazol-3-yl)pyridin-2-yl)-6-phenylimidazo[1,2-b]pyridazin-8-amine hydrochloride

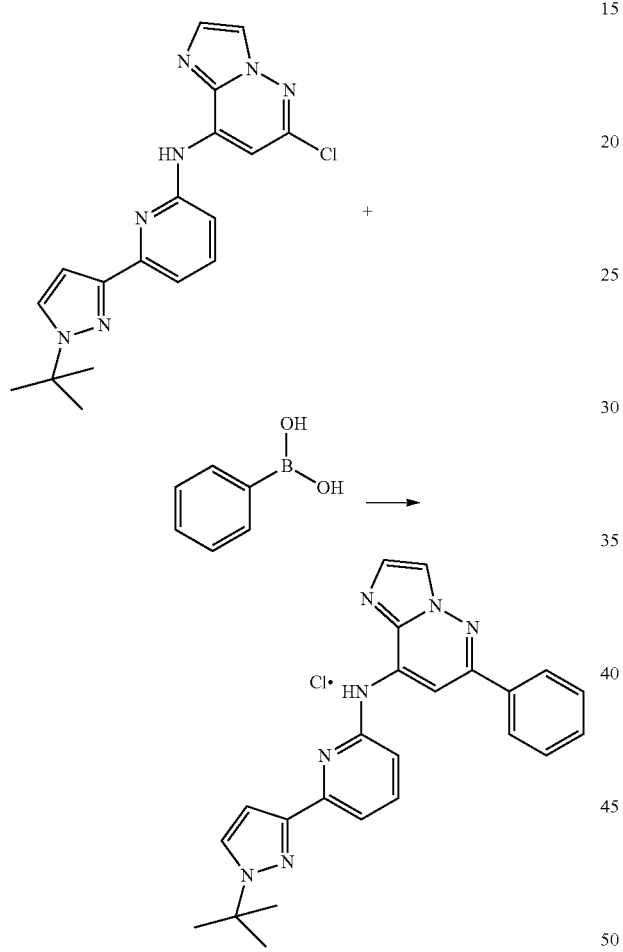

A mixture of N-(6-(1-tert-butyl-1H-pyrazol-3-yl)pyridin-2-yl)-6-chloroimidazo[1,2-b]pyridazin-8-amine (168 mg, 0.58 mmol), phenylboronic acid (105 mg, 0.86 mmol), Pd₂(dba)₃ (34 mg, 0.06 mmol), X-phos (114 mg, 0.24 mmol) and K₂CO₃ (240 mg, 1.74 mmol) in dioxane (10 mL) and water (1 mL) was heated to 100° C. with stirring for 4 h under N₂. The solvent was removed in vacuo and the resulting mixture was purified by chromatography (silica gel, 200-300 mesh, CH₂Cl₂:MeOH=180:1) to give crude product. This solid was further purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to give a white solid. This was dissolved in methanol and three drops of concentrated HCl added. The mixture was stirred for 5 minutes, then concentrated in vacuo to give the final product N-(6-(1-tert-butyl-1H-pyrazol-3-yl)pyridin-2-yl)-6-phenylimidazo[1,2-b]pyridazin-8-amine hydrochloride (72 mg, 39%) as an HCl salt. ¹H NMR (300 MHz, DMSO): δ 10.26 (s, 1H), 8.58 (d, 1H, J=1.8 Hz), 8.32 (s, 1H), 7.83-7.79 (m, 2H), 7.56-7.51 (m, 4 h), 6.62 (s, 1H), 6.39 (d, 1H, J=1.5 Hz), 1.61 (s, 9H). LC-MS: [M+H]⁺, 333, $t_R$=1.648 min, HPLC: 98.3% at 214 nm, 99.29% at 254 nm, $t_R$=6.1 min.

Example 7

Synthesis of 8-(2,2-Dimethylpyrrolidin-1-yl)-6-phenylimidazo[1,2-b]pyridazine

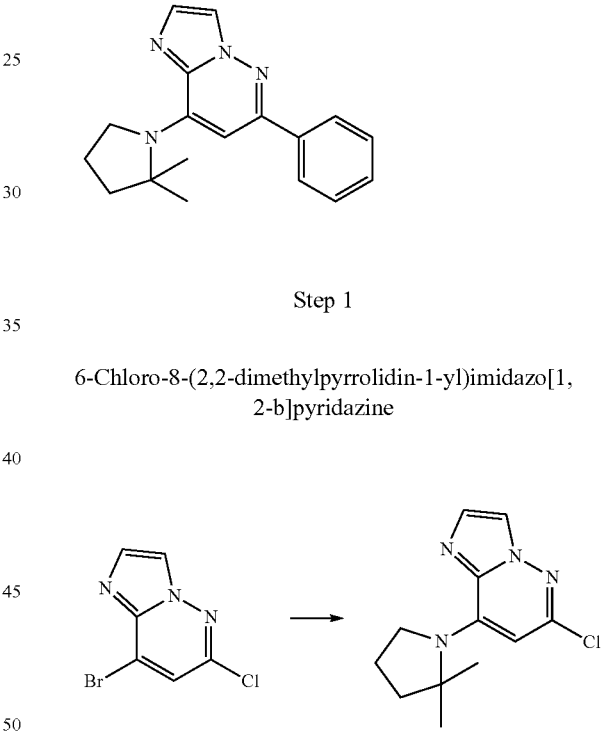

Step 1

6-Chloro-8-(2,2-dimethylpyrrolidin-1-yl)imidazo[1,2-b]pyridazine

To a solution of 2,2-dimethylpyrrolidine (0.248 g, 2.5 mmol) in DMF (8 mL) was added NaH (0.060 g, 60% dispersion in mineral oil, 2.5 mmol) and stirred for 0.5 h. To this mixture was added 8-bromo-6-chloroimidazo[1,2-b]pyridazine (0.233 g, 1 mmol) under N₂. The mixture was stirred at room temperature for 16 h. Then it was partitioned between 15 mL of saturated NH₄Cl solution and 15 mL of ether. The organic layer was washed with water (10 mL×3) and saturated NaCl solution (10 mL×3), dried over NaSO₄, concentrated in vacuo, and purified by chromatography (silica gel, 200-300 mesh, petroleum ether:ethyl acetate=3:1) to give 6-chloro-8-(2,2-dimethylpyrrolidin-1-yl)imidazo[1,2-b]pyridazine (0.140 g, 22%) as a light brown solid. LC-MS: [M+H]⁺, 251.1, $t_R$=1.698 min.

83
Step 2

8-(2,2-Dimethylpyrrolidin-1-yl)-6-phenylimidazo[1,2-b]pyridazine

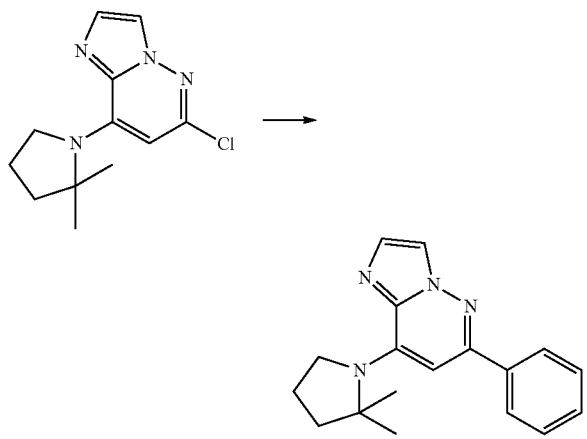

A mixture of 6-chloro-8-(2,2-dimethylpyrrolidin-1-yl)imidazo[1,2-b]pyridazine (140 mg, 0.56 mmol), phenylboronic acid (103 mg, 0.84 mmol), Pd$_2$(dba)$_3$ (34 mg, 0.06 mmol), X-phos (114 mg, 0.24 mmol) and K$_2$CO$_3$ (235 mg, 1.70 mmol) in dioxane (10 mL) and water (1 mL) was heated to 100° C. with stirring for 4 h under N$_2$. The solvent was removed in vacuo and the resulting mixture was purified by chromatography (silica gel, 200-300 mesh, CH$_2$Cl$_2$:MeOH=200:1) to give 8-(2,2-dimethylpyrrolidin-1-yl)-6-phenylimidazo[1,2-b]pyridazine (65 mg, 40%) as a light yellow solid. $^1$H NMR (300 MHz, DMSO): δ 7.91-7.87 (m, 3H), 7.53-7.49 (m, 4 h), 6.54 (s, 1H), 4.43-4.40 (m, 1H), 2.08-2.06 (m, 4 h), 1.70 (s, 6H). LC-MS: [M+H]$^+$, 293, t$_R$=1.76 min, HPLC: 95% at 214 nm, 95.55% at 254 nm, t$_R$=3.943 min.

Example 8

Synthesis of Methyl 3-(8-(6-(2-methylpyrrolidin-1-yl)pyridin-2-ylamino)imidazo[1,2-b]pyridazin-6-yl)benzoate

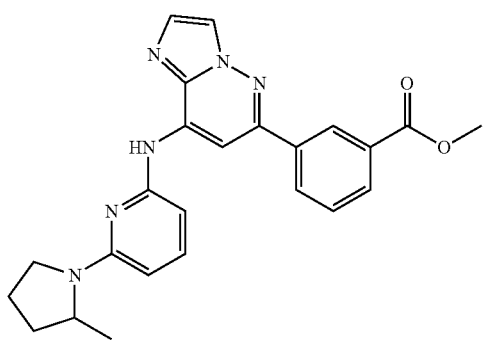 [SMILES: COC(=O)c1cccc(-c2cc(Nc3cccc(N4CCCC4C)n3)c3nccn3n2)c1]

84
Step 1

Methyl 3-(6-aminopyridazin-3-yl)benzoate

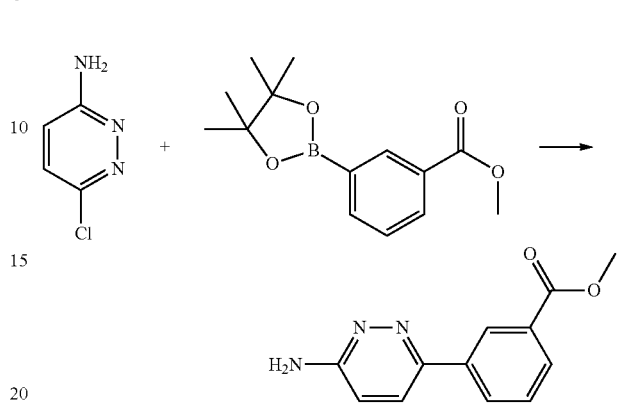

To a mixture of 6-chloropyridazin-3-amine (5 g, 38.6 mmol), methyl 3-(4,4,5,5-tetramethyl-1,3,2-dioxaborolan-2-yl)benzoate (15.2 g, 58 mmol), Pd$_2$(dba)$_3$ (2.22 g, 3.86 mmol), X-phos (7.35 g, 15.44 mmol) and Na$_2$CO$_3$ (12.3 g, 115.8 mmol) in dioxane (150 mL) and water (15 mL) was heated to 100° C. with stirring for 6 h under N$_2$. The solvent was removed in vacuo and the resulting residue was purified by chromatography (silica gel, 200-300 mesh, CH$_2$Cl$_2$:MeOH=20:1) to give methyl 3-(6-aminopyridazin-3-yl)benzoate (7.4 g, 84%) as a white solid. LC-MS: [M+H]$^+$, 230.1, t$_R$=1.111 min.

Step 2

Methyl 3-(6-amino-5-bromopyridazin-3-yl)benzoate

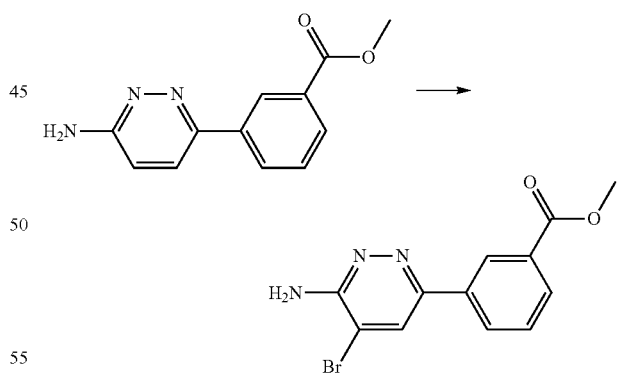

In a 150 mL round bottom flask was placed methyl 3-(6-aminopyridazin-3-yl)benzoate (2.29 g, 10 mmol), NaHCO$_3$ (1.68 g, 20 mmol) and methanol (40 mL). To this suspension was added Br$_2$ (1.6 g, 10 mmol) drop wise over about 30 minutes at room temperature. The mixture was stirred for 16 h, then filtered and concentrated in vacuo. The residue was purified by chromatography (silica gel, 200-300 mesh, petroleum ether:ethyl acetate=2:1) to give methyl 3-(6-amino-5-bromopyridazin-3-yl)benzoate (1.2 g, 39%) as a light orange solid. LC-MS: [M+H]$^+$, 308.0, t$_R$=1.377 min.

Step 3

Methyl 3-(8-bromoimidazo[1,2-b]pyridazin-6-yl)benzoate

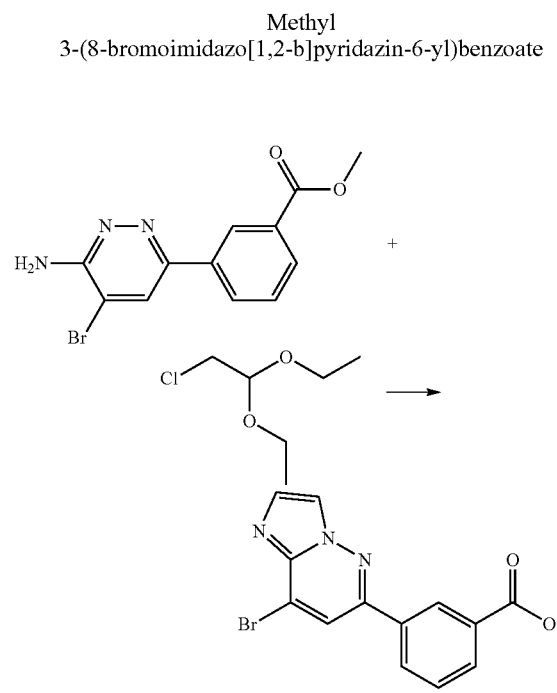

A solution of methyl 3-(6-amino-5-bromopyridazin-3-yl)benzoate (1 g, 3.25 mmol), 2-chloro-1,1-diethoxyethane (0.6 g, 3.9 mmol), PTSA (0.62 g, 3.9 mmol) in isopropanol (10 mL) was heated to 80° C. for 40 h. After cooling to room temperature, the solution was concentrated in vacuo. The resulting mixture was treated with a saturated NaHCO₃ solution (50 mL), extracted with dichloromethane (50 mL×3), dried over Na₂SO₄, filtered and concentrated. The residue was purified by chromatography (silica gel, 200-300 mesh, petroleum ether:ethyl acetate=3:1) to give methyl 3-(8-bromoimidazo[1,2-b]pyridazin-6-yl)benzoate (0.6 g, 56%) as a white solid. LC-MS: [M+H]⁺, 332.0, 333.9, $t_R$=1.520 min.

Step 4

Methyl 3-(8-(6-(2-methylpyrrolidin-1-yl)pyridin-2-ylamino)imidazo[1,2-b]pyridazin-6-yl)benzoate

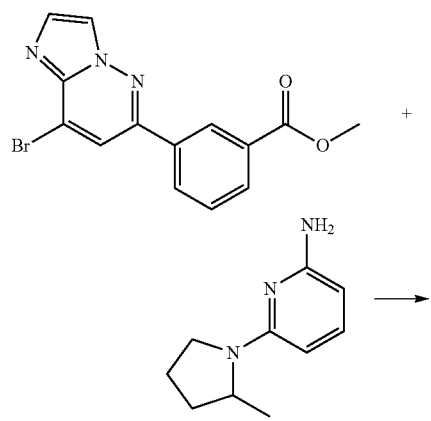

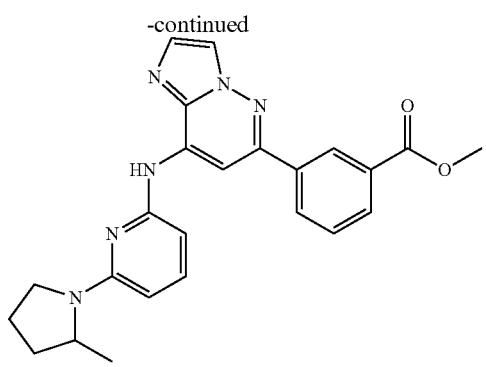

A mixture of methyl 3-(8-bromoimidazo[1,2-b]pyridazin-6-yl)benzoate (288 mg, 0.87 mmol), 6-(2-methylpyrrolidin-1-yl)pyridin-2-amine (230 mg, 1.3 mmol), Pd₂(dba)₃ (50 mg, 0.087 mmol), BINAP (217 mg, 0.348 mmol), Cs₂CO₃ (851 mg, 2.61 mmol) and dioxane (20 mL) was heated to 100° C. with stirring for 16 h under N₂. The solvent was removed in vacuo and the resulting mixture was purified by chromatography (silica gel, 200-300 mesh, CH₂Cl₂:MeOH=100:1) to give methyl 3-(8-(6-(2-methylpyrrolidin-1-yl)pyridine-2-ylamino)imidazo[1,2-b]pyridazin-6-yl)benzoate (240 mg, 64%) as a yellow solid. ¹H NMR (300 MHz, CDCl₃): δ 8.72 (s, 1H), 8.60 (s, 1H), 8.19-8.08 (m, 3H), 7.92 (s, 1H), 7.59-7.54 (m, 2H), 7.41 (t, 1H, J=8.1 Hz), 6.20 (d, 1H, J=7.5 Hz), 6.03 (d, 1H, J=8.1 Hz), 4.27-4.23 (m, 1H), 3.99 (s, 3H), 3.69-3.63 (m, 1H), 3.53-3.43 (m, 1H), 2.15-1.99 (m, 3H), 1.99 (brs, 1H), 1.21 (d, 3H, J=6.3 Hz). LC-MS: [M+H]⁺, 429, $t_R$=2.055 min, HPLC: 96.86% at 214 nm, 96.95% at 254 nm, $t_R$=3.763 min.

Example 9

Synthesis of 3-(8-(6-(2-Methylpyrrolidin-1-yl)pyridin-2-ylamino)imidazo[1,2-b]pyridazin-6-yl)benzoic acid

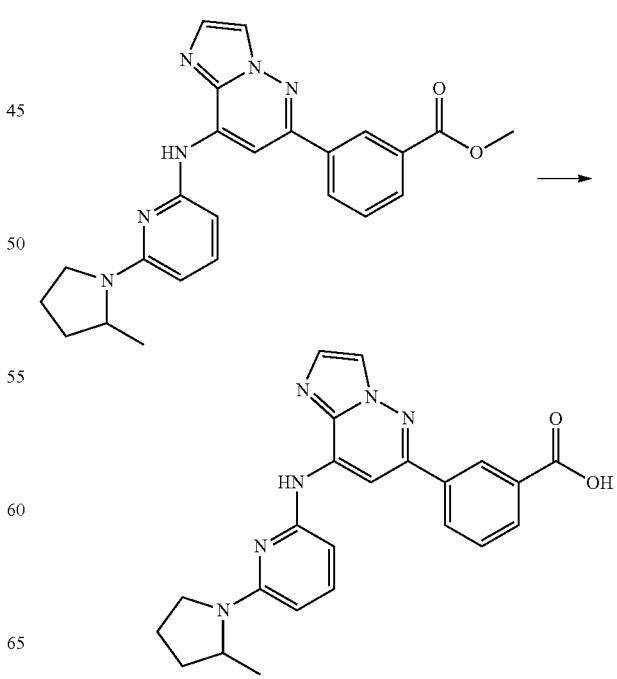

To a solution of methyl 3-(8-(6-(2-methylpyrrolidin-1-yl)pyridin-2-ylamino)imidazo[1,2-b]pyridazin-6-yl)benzoate (210 mg, 0.49 mmol) in dioxane (10 mL) and water (10 mL) was added NaOH (150 mg, 3.75 mmol), The mixture was heated to 40° C. with stirring for 2 h. The solution was concentrated in vacuo, washed with dichloromethane (10 mL×3), then additional water (10 mL) was added and this solution was adjusted to pH=4 by addition of concentrated HCl. The solid formed was filtered to give 3-(8-(6-(2-methylpyrrolidin-1-yl)pyridin-2-ylamino)imidazo[1,2-b]pyridazin-6-yl)benzoic acid (0.160 g, 78%) as a light yellow solid. $^1$H NMR (300 MHz, DMSO): δ 13.25 (s, 1H), 9.74 (s, 1H), 8.85 (s, 1H), 8.50 (s, 1H), 8.26-8.08 (m, 3H), 7.72-7.67 (m, 2H), 7.53-7.44 (m, 1H), 6.75 (d, 1H, J=7.8 Hz), 6.09 (d, 1H, J=8.1 Hz), 4.25-4.21 (m, 1H), 3.62-3.57 (m, 1H), 2.13-1.98 (m, 3H), 1.70-1.68 (m, 2H), 1.12 (d, 3H, J=6.0 Hz). LC-MS: [M+H]$^+$, 415, $t_R$=1.68 min, HPLC: 98.2% at 214 nm, 98.37% at 254 nm, $t_R$=6.21 min.

Example 10

Synthesis of 4-(3-(8-(6-(2-Methylpyrrolidin-1-yl)pyridin-2-ylamino)imidazo[1,2-b]pyridazin-6-yl)benzamido)benzoic acid

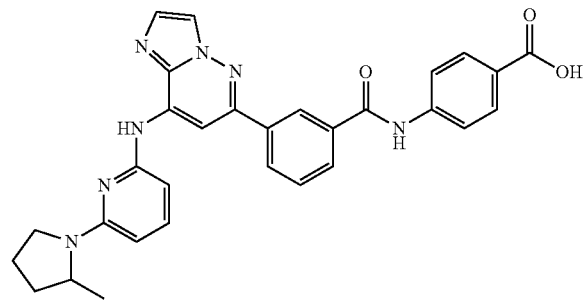 [SMILES: CC1CCCN1c1cccc(Nc2cc(-c3cccc(C(=O)Nc4ccc(C(=O)O)cc4)c3)nn3ccnc23)n1]

Step 1 tert-Butyl 4-(3-(8-(6-(2-methylpyrrolidin-1-yl)pyridin-2-ylamino)imidazo[1,2-b]pyridazin-6-yl)benzamido)benzoate

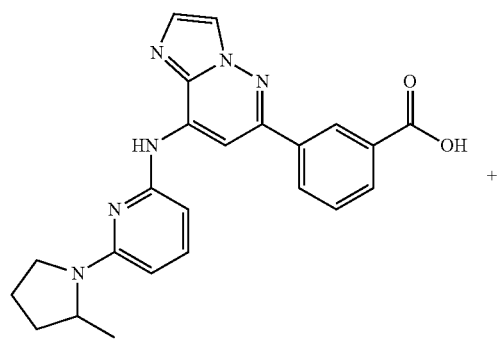

+

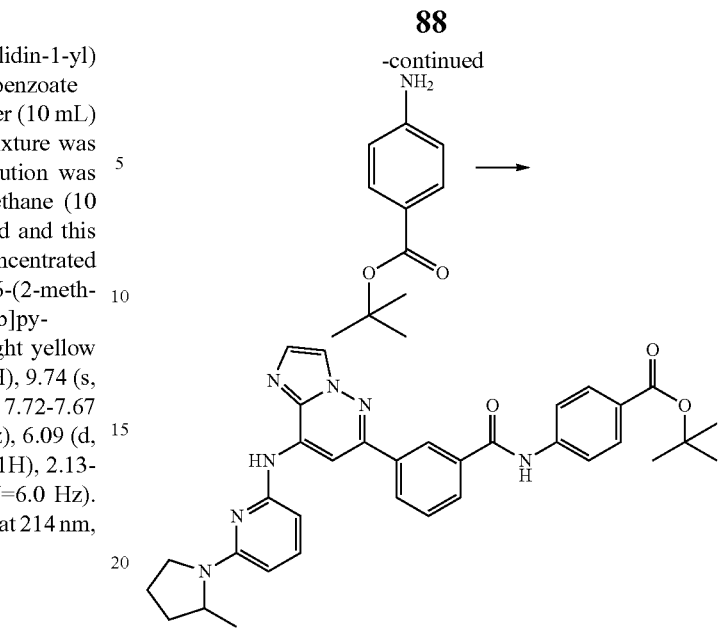

A mixture of 3-(8-(6-(2-Methylpyrrolidin-1-yl)pyridin-2-ylamino)imidazo[1,2-b]pyridazin-6-yl)benzoic acid (49 mg, 0.12 mmol), tert-butyl 4-aminobenzoate (23 mg, 0.12 mmol), EDCI (92 mg, 0.48 mmol), N-methyl-imidazole (40 mg, 0.48 mmol) and dichloromethane (3 mL) was stirred at room temperature for 16 h. The solution was concentrated in vacuo and the residue was purified by chromatography (silica gel, 200-300 mesh, CH$_2$Cl$_2$:MeOH=40:1~100:1) to give tert-butyl 4-(3-(8-(6-(2-methylpyrrolidin-1-yl)pyridin-2-ylamino)imidazo[1,2-b]pyridazin-6-yl)benzamido)benzoate (43 mg, 61%) as a yellow oil. [M+H]$^+$, 590.2, $t_R$=2.283 min.

Step 2

4-(3-(8-(6-(2-Methylpyrrolidin-1-yl)pyridin-2-ylamino)imidazo[1,2-b]pyridazin-6-yl)benzamido) benzoic acid

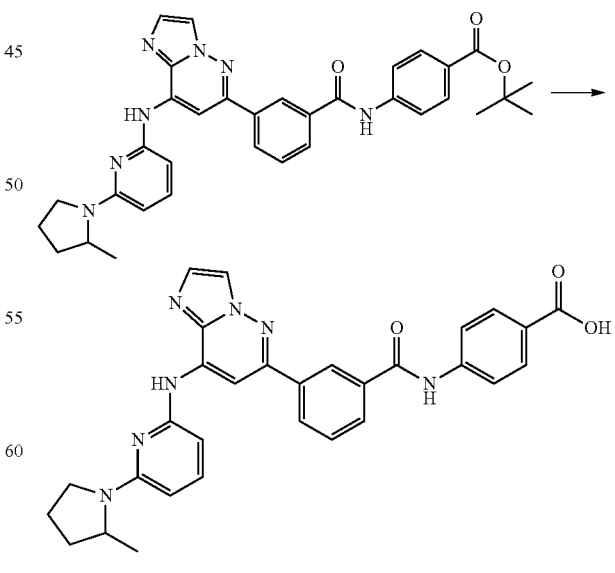

To a solution of tert-butyl 4-(3-(8-(6-(2-methylpyrrolidin-1-yl)pyridin-2-ylamino)imidazo[1,2-b]pyridazin-6-yl)benzamido)benzoate (39 mg, 0.12 mmol) in dichloromethane (3 mL) was added TFA (3 mL). The solution was stirred at room temperature for 16 h. The solution was concentrated in vacuo The residue was purified by chromatography (silica gel, 200-300 mesh, petroleum ether:ethyl acetate=1:1) to give 4-(3-(8-(6-(2-methylpyrrolidin-1-yl)pyridin-2-ylamino)imidazo[1,2-b]pyridazin-yl)benzamido)benzoic acid (30 mg, 85%) as a yellow solid. $^1$H NMR (300 MHz, DMSO): δ 8.95 (s, 1H), 8.32 (s, 1H), 8.29 (s, 1H), 8.02-7.99 (m, 3H), 7.90-7.80 (m, 4H), 7.59 (t, 1H, J=7.5 Hz), 7.38 (t, 1H, J=7.5 Hz), 6.18 (d, 1H, J=7.8 Hz), 6.03 (d, 1H, J=8.1 Hz), 4.05-3.97 (m, 1H), 3.37 (s, 1H), 3.19-3.17 (m, 1H), 1.80-1.71 (m, 3H), 1.44 (brs, 1H), 0.92 (d, 3H, J=6.0 Hz). LC-MS: [M+H]$^+$, 534, $t_R$=1.660 min, HPLC: 96.17% at 214 nm, 96.09% at 254 nm, $t_R$=4.541 min.

Example 11

Synthesis of Sodium 3-(8-(6-(2-methylpyrrolidin-1-yl)pyridin-2-ylamino)imidazo[1,2-b]pyridazin-6-yl)benzoate

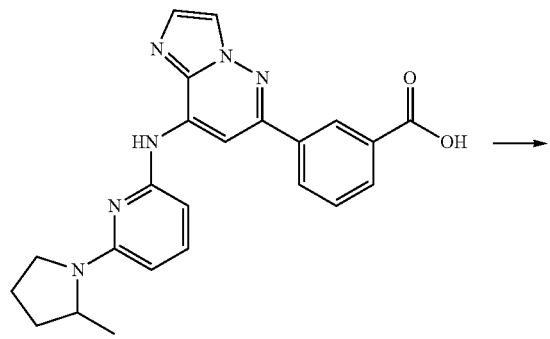

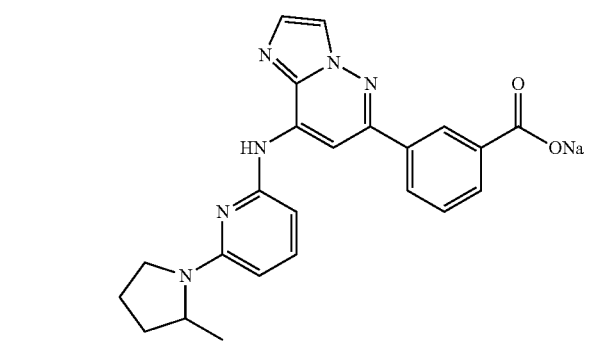

A solution of NaOH in water (0.05 mol/L, 1.2 mL) was added to 3-(8-(6-(2-methylpyrrolidin-1-yl)pyridin-2-ylamino)imidazo[1,2-b]pyridazin-6-yl)benzoic acid (25 mg, 0.06 mmol) and the mixture stirred until the solid was completely dissolved. The solution was concentrated in vacuo to give sodium 3-(8-(6-(2-methylpyrrolidin-1-yl)pyridin-2-ylamino)imidazo[1,2-b]pyridazin-6-yl)benzoate (20 mg, 76%) as a white solid. $^1$H NMR (300 MHz, D$_2$O): δ 7.98-7.77 (m, 2H), 7.55-7.38 (m, 2H), 7.26-7.05 (m, 3H), 6.80 (brs, 1H), 5.50 (brs, 1H), 5.41-5.33 (m, 1H), 3.39 (brs, 1H), 2.91 (brs, 1H), 2.63 (brs, 1H), 1.58-1.30 (m, 4 h), 0.60 (s, 3H).

Example 12

Synthesis of 3-(8-(6-(2-Methylpyrrolidin-1-yl)pyridin-2-ylamino)imidazo[1,2-b]pyridazin-6-yl)benzamide

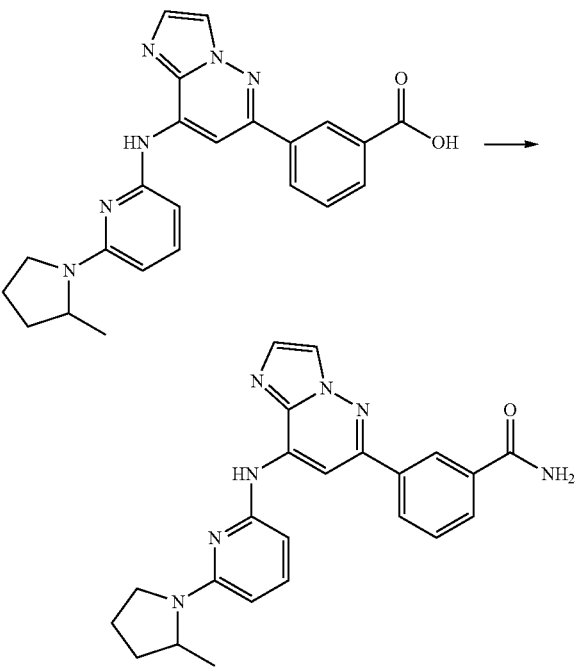

A mixture of 3-(8-(6-(2-methylpyrrolidin-1-yl)pyridin-2-ylamino)imidazo[1,2-b]pyridazin-6-yl)benzoic acid (50 mg, 0.12 mmol), ammonium chloride (25 mg, 1.44 mmol), EDCI (36 mg, 0.18 mmol), HOBT (24 mg, 0.18 mmol) in dichloromethane (3 mL), DMF (0.5 mL) and Et$_3$N (27 mg, 0.24 mmol) was stirred at room temperature for 16 h. The solution was concentrated in vacuo, washed with water (10 mL×3), purified by chromatography (silica gel, 200-300 mesh, CH$_2$Cl$_2$:MeOH=20:1) to give 3-(8-(6-(2-methylpyrrolidin-1-yl)pyridin-2-ylamino)imidazo[1,2-b]pyridazin-6-yl)benzamide (24 mg, 48%) as a yellow oil. $^1$H NMR (300 MHz, DMSO): δ 9.67 (s, 1H), 8.85 (s, 1H), 8.45 (s, 1H), 8.23 (s, 1H), 8.13-7.99 (m, 3H), 7.68-7.59 (m, 2H), 7.49-7.42 (m, 2H), 6.73 (d, 1H, J=7.8 Hz), 6.08 (d, 1H, J=8.1 Hz), 4.25-4.21 (m, 1H), 3.60-3.57 (m, 1H), 3.44-3.38 (m, 1H), 2.06-1.95 (m, 3H), 1.67 (s, 1H), 1.08 (d, 3H, J=6.0 Hz). LC-MS: [M+H]$^+$, 414, $t_R$=1.633 min, HPLC: 98.33% at 214 nm, 97.74% at 254 nm, $t_R$=5.64 min.

Example 13

Synthesis of N-(6-(2-Methylpiperidin-1-yl)pyridin-2-yl)-6-phenylimidazo[1,2-b]pyridazin-8-amine

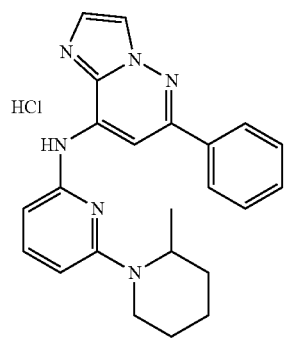 [SMILES: Cl ; CC1CCCCN1c1cccc(Nc2cc(-c3ccccc3)nn3ccnc23)n1]

Step 1

6-Phenylpyridazin-3-amine

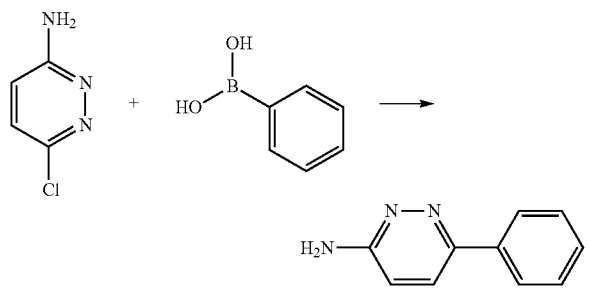

A mixture of 6-chloropyridazin-3-amine (2 g, 15.4 mmol), phenylboronic acid (2.83 g, 23.2 mmol), Pd$_2$(dba)$_3$ (0.89 g, 1.6 mmol), X-phos (2.94 g, 6.2 mmol) and Na$_2$CO$_3$ (4.91 g, 46.3 mmol) in dioxane (50 mL) and water (5 mL) was heated to 100° C. with stirring for 6 h under N$_2$. The solvent was removed in vacuo and the resulting mixture was purified by chromatography (silica gel, 200-300 mesh, CH$_2$Cl$_2$:MeOH=20:1) to give 6-phenylpyridazin-3-amine (2.06 g, 78%) as a white solid. LC-MS: [M+H]$^+$, 172.1, $t_R$=1.04 min.

Step 2

4-Bromo-6-phenylpyridazin-3-amine

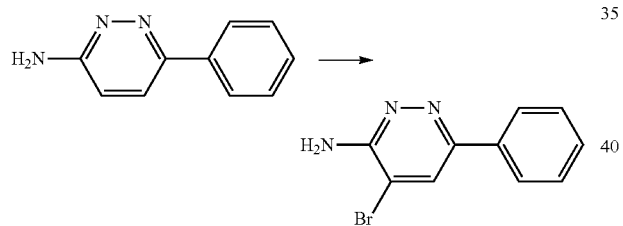

In a 150 mL round bottom flask was placed 6-phenylpyridazin-3-amine (2.5 g, 14.5 mmol), NaHCO$_3$ (2.44 g, 29 mmol) and methanol (50 mL) then to this suspension was added Br$_2$ (2.317 g, 14.5 mmol) drop wise over about 30 minutes at room temperature. The mixture was stirred for 16 h, then filtered and concentrated in vacuo. The residue was purified by chromatography (silica gel, 200-300 mesh, petroleum ether:ethyl acetate=2:1) to give 4-bromo-6-phenylpyridazin-3-amine (1.2 g, 33%) as a light orange solid. LC-MS: [M+H]$^+$, 250.0, $t_R$=1.487 min.

Step 3

8-Bromo-6-phenylimidazo[1,2-b]pyridazine

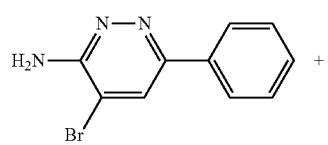

+

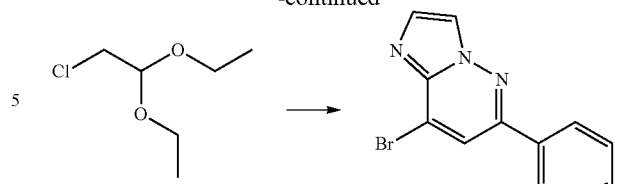

A solution of 4-bromo-6-phenylpyridazin-3-amine (1.2 g, 4.8 mmol), 2-chloro-1,1-diethoxyethane (0.884 g, 5.74 mmol), PTSA (1.09 g, 5.74 mmol) in isopropanol (25 mL) was heated to 80° C. for 40 h. After cooling to room temperature, the solution was concentrated in vacuo. The resulting mixture was treated with a saturated aq. NaHCO$_3$ solution (50 mL), extracted with dichloromethane (50 mL×3), dried over Na$_2$SO$_4$, filtered and concentrated. The residue was purified by chromatography (silica gel, 200-300 mesh, petroleum ether:ethyl acetate=3:1) to give 8-bromo-6-phenylimidazo[1,2-b]pyridazine (0.6 g, 46%) as a white solid. LC-MS: [M+H]$^+$, 274.0, $t_R$=1.541 min.

Step 4

6-(2-Methylpiperidin-1-yl)pyridin-2-amine

A suspension of 6-fluoropyridin-2-amine (448 mg, 4 mmol) and 2-methylpiperidine (596 mg, 6 mmol) in water (0.5 mL) was heated to 205° C. in a microwave oven for 30 minutes. The reaction mixture was purified by chromatography (silica gel, 200-300 mesh, petroleum ether:ethyl acetate=10:1) to give 6-(2-methylpiperidin-1-yl)pyridin-2-amine (376 mg, 49%) as a brown oil. LC-MS: [M+H]$^+$, 192.2, $t_R$=1.266 min.

Step 5

N-(6-(2-Methylpiperidin-1-yl)pyridin-2-yl)-6-phenylimidazo[1,2-b]pyridazin-8-amine

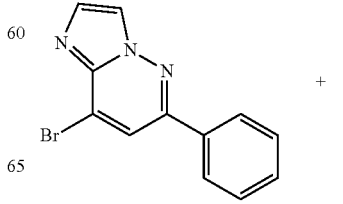

+

-continued

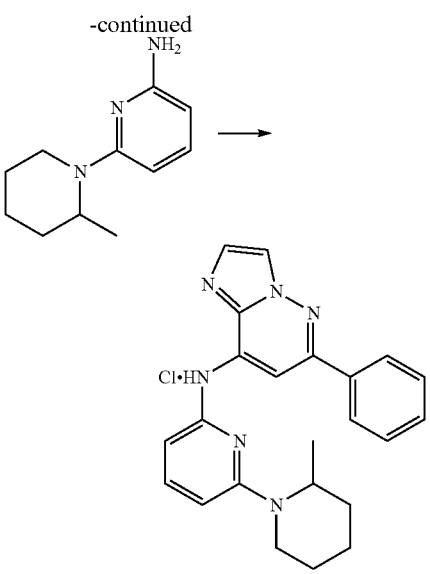

A mixture of 8-bromo-6-phenylimidazo[1,2-b]pyridazine (125 mg, 0.46 mmol), 6-(2-methylpiperidin-1-yl)pyridin-2-amine (144 mg, 0.75 mmol), Pd$_2$(dba)$_3$ (29 mg, 0.05 mmol), BINAP (125 mg, 0.2 mmol), Cs$_2$CO$_3$ (489 mg, 1.5 mmol) and dioxane (10 mL) was heated to 100° C. with stirring for 16 h under N$_2$. The solution was removed in vacuo and the resulting mixture was purified by chromatography (silica gel, 200-300 mesh, petroleum ether:ethyl acetate=3:1) to give crude product which was further purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to give a light yellow solid. This was dissolved in methanol, three drops of concentrated HCl was added, and the mixture was stirred for 5 minutes, then concentrated in vacuo to give N-(6-(2-methylpiperidin-1-yl)pyridin-2-yl)-6-phenylimidazo[1,2-b]pyridazin-8-amine (18 mg, 10%) as an HCl salt. $^1$H NMR (300 MHz, CD3OD): δ 8.99 (s, 1H), 8.44 (s, 1H), 8.20 (s, 1H), 8.05-7.98 (m, 3H), 7.60 (brs, 3H), 7.46-7.28 (m, 2H), 4.12 (brs, 1H), 3.92-3.81 (m, 1H), 3.65-3.56 (m, 1H), 2.07-1.66 (m, 6H), 1.17 (d, 3H, J=5.7 Hz). LC-MS: [M+H]$^+$, 385, t$_R$=2.081 min, HPLC: 99.49% at 214 nm, 99.48% at 254 nm, t$_R$=3.588 min.

Example 14

Synthesis of Methyl 4-(8-(6-(2-methylpyrrolidin-1-yl)pyridin-2-ylamino)imidazo[1,2-b]pyridazin-6-yl)benzoate

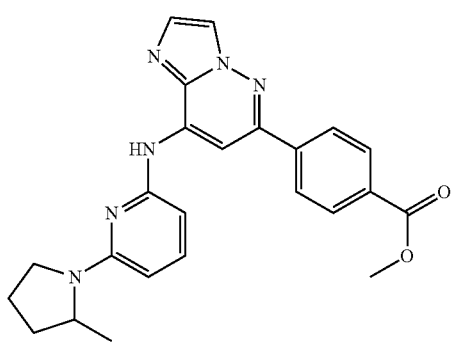 [SMILES: COC(=O)c1ccc(-c2cc(Nc3cccc(N4CCCC4C)n3)c3nccn3n2)cc1]

Step 1

Methyl 4-(6-aminopyridazin-3-yl)benzoate

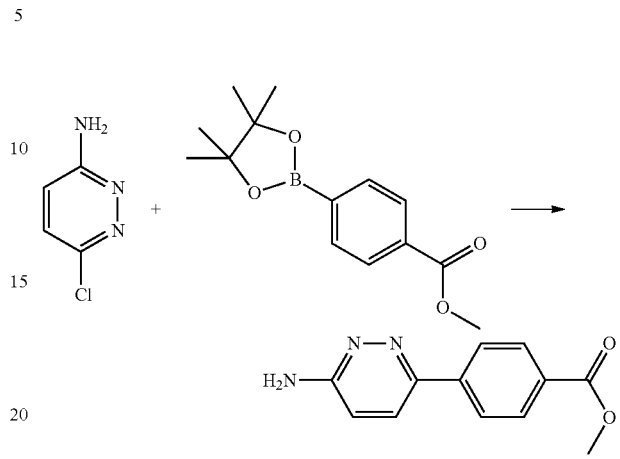

A mixture of 6-chloropyridazin-3-amine (3.24 g, 25 mmol), methyl 4-(4,4,5,5-tetramethyl-1,3,2-dioxaborolan-2-yl)benzoate (9.8 g, 37.4 mmol), Pd$_2$(dba)$_3$ (0.72 g, 1.25 mmol), X-phos (1.19 g, 2.5 mmol) and Na$_2$CO$_3$ (7.95 g, 75 mmol) in dioxane (150 mL) and water (15 mL) was heated to 100° C. with stirring for 4 h under N$_2$. The solvent was removed in vacuo and the resulting mixture was purified by chromatography (silica gel, 200-300 mesh, CH$_2$Cl$_2$:MeOH=20:1) to give methyl 4-(6-aminopyridazin-3-yl)benzoate (2.8 g, 48%) as a white solid. LC-MS: [M+H]$^+$, 230.1, t$_R$=1.213 min.

Step 2

Methyl 4-(6-amino-5-bromopyridazin-3-yl)benzoate

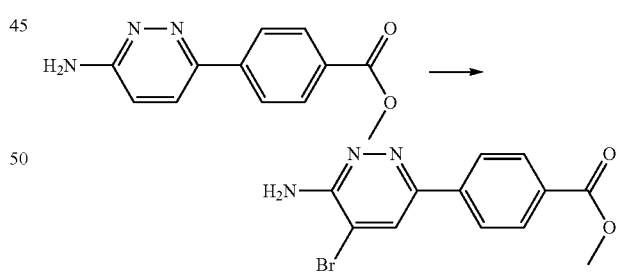

In a 250 mL round bottom flask was placed methyl 4-(6-aminopyridazin-3-yl)benzoate (2.8 g, 12.2 mmol), NaHCO$_3$ (2.05 g, 22.4 mmol) and methanol (100 mL) and to this suspension was added Br$_2$ (1.95 g, 12.2 mmol) drop wise over about 30 minutes at room temperature. The mixture was stirred for 16 h, then filtered and concentrated in vacuo. The residue was purified by chromatography (silica gel, 200-300 mesh, petroleum ether:ethyl acetate=2:1) to give methyl 4-(6-amino-5-bromopyridazin-3-yl)benzoate (1.64 g, 43.6%) as a light orange solid. LC-MS: [M+H]$^+$, 309.9, t$_R$=1.397 min.

Step 3

Methyl 4-(8-bromoimidazo[1,2-b]pyridazin-6-yl)benzoate

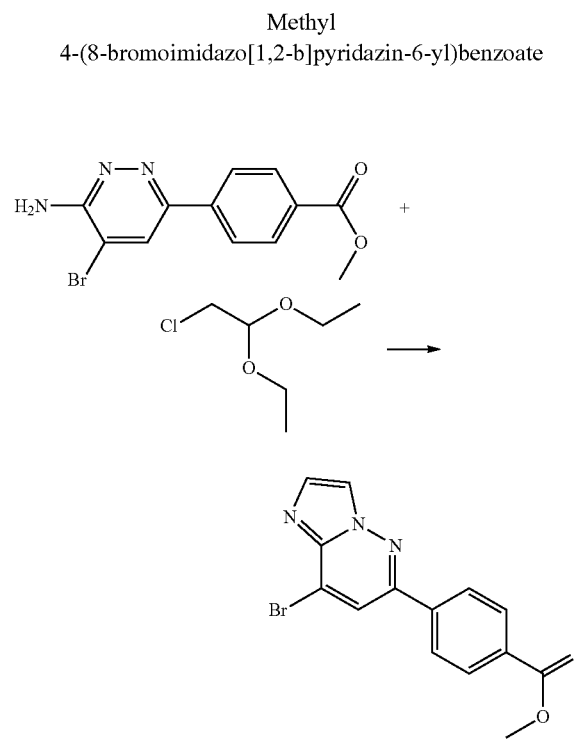

A solution of methyl 4-(6-amino-5-bromopyridazin-3-yl)benzoate (1.64 g, 5.32 mmol), 2-chloro-1,1-diethoxyethane (0.984 g, 6.39 mmol) and PTSA (1.215 g, 6.39 mmol) in isopropanol (50 mL) was heated to 80° C. for 40 h. After cooling to room temperature, the solution was concentrated in vacuo. The resulting mixture was treated with a saturated NaHCO$_3$ solution (50 mL), extracted with dichloromethane (50 mL×3), dried over Na$_2$SO$_4$, filtered and concentrated. The residue was purified by chromatography (silica gel, 200-300 mesh, petroleum ether:ethyl acetate=3:1) to give methyl 4-(8-bromoimidazo[1,2-b]pyridazin-6-yl)benzoate (640 mg, 36%) as a white solid. LC-MS: [M+H]$^+$, 333.9, $t_R$=1.637 min.

Step 4

Methyl 4-(8-(6-(2-methylpyrrolidin-1-yl)pyridin-2-ylamino)imidazo[1,2-b]pyridazin-6-yl)benzoate

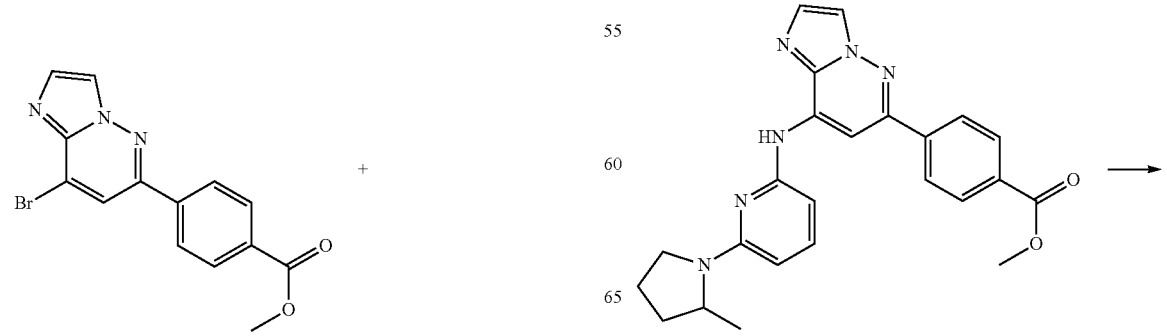

A mixture of methyl 4-(8-bromoimidazo[1,2-b]pyridazin-6-yl)benzoate (208 mg, 0.63 mmol), 6-(2-methylpyrrolidin-1-yl)pyridin-2-amine (168 mg, 0.95 mmol), Pd$_2$(dba)$_3$ (37 mg, 0.063 mmol), BINAP (157 mg, 0.252 mmol), Cs$_2$CO$_3$ (616 mg, 1.89 mmol) and dioxane (10 mL) was heated to 100° C. with stirring for 16 h under N$_2$. The solvent was removed in vacuo and the resulting mixture was purified by chromatography (silica gel, 200-300 mesh, CH$_2$Cl$_2$:MeOH=30:1) to give methyl 4-(8-(6-(2-methylpyrrolidin-1-yl)pyridin-2-ylamino)imidazo [1,2-b]pyridazin-6-yl)benzoate (120 mg, 45%) as a yellow solid. $^1$H NMR (300 MHz, CD3OD): δ 8.81 (s, 1H), 8.09-7.98 (m, 5H), 7.59 (d, 1H, J=1.5 Hz), 7.42 (t, 1H, J=8.4 Hz), 6.27 (d, 1H, J=7.5 Hz), 6.08 (d, 1H, J=8.1 Hz), 4.29-4.21 (m, 1H), 3.96 (s, 3H), 3.62-3.58 (m, 1H), 3.43-3.40 (m, 1H), 2.16-2.12 (m, 3H), 1.78-75 (m, 1H), 1.19 (d, 3H, J=6.3 Hz). LC-MS: [M+H]$^+$, 429, $t_R$=1.989 min, HPLC: 94.6% at 214 nm, 96.8% at 254 nm, $t_R$=5.255 min.

Example 15

Synthesis of 4-(8-(6-(2-Methylpyrrolidin-1-yl)pyridin-2-ylamino)imidazo[1,2-b]pyridazin-6-yl)benzoic acid -continued

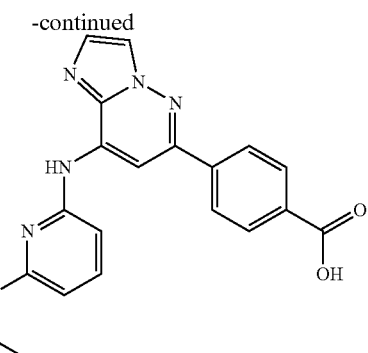

To a solution of methyl 4-(8-(6-(2-methylpyrrolidin-1-yl)pyridin-2-ylamino)imidazo[1,2-b]pyridazin-6-yl)benzoate (220 mg, 0.51 mmol) in dioxane (10 mL) and water (9 mL) was added NaOH (200 mg, 5 mmol), then the mixture was heated to 40° C. with stirring for 4 h. The solution was concentrated to approximately 10 mL in vacuo and washed with dichloromethane (10 mL×3). Water (10 mL) was added and the solution was adjusted to pH=4 by the addition of concentrated HCl. The solid formed was filtered to give 4-(8-(6-(2-methylpyrrolidin-1-yl)pyridin-2-ylamino)imidazo[1,2-b]pyridazin-6-yl)benzoic acid (0.185 g, 87%) as a light yellow solid. $^1$H NMR (300 MHz, DMSO): δ 9.72 (s, 1H), 8.82 (s, 1H), 8.23 (s, 1H), 8.09-8.02 (m, 3H), 7.69 (s, 1H), 7.44 (t, 1H, J=7.5 Hz), 6.73 (d, 1H, J=7.5 Hz), 6.08 (d, 1H, J=8.4 Hz), 4.23-4.20 (m, 1H), 3.58-3.56 (m, 2H), 2.08-1.97 (m, 3H), 1.68 (s, 1H), 1.12 (d, 1H, J=6.3 Hz). LC-MS: [M+H]$^+$, 415, $t_R$=1.652 min, HPLC: 98.19% at 214 nm, 97.87% at 254 nm, $t_R$=5.967 min.

Example 16

Synthesis of 4-(8-(6-(2-Methylpyrrolidin-1-yl)pyridin-2-ylamino)imidazo[1,2-b]pyridazin-6-yl)-N-(2-(pyridin-4-yl)ethyl)benzamide

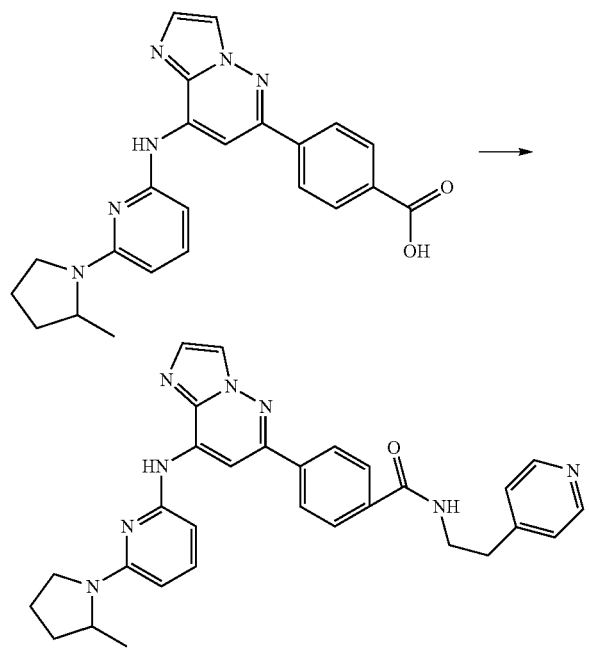

A mixture of 4-(8-(6-(2-methylpyrrolidin-1-yl)pyridin-2-ylamino)imidazo[1,2-b]pyridazin-6-yl)benzoic acid (41 mg, 0.1 mmol), 2-(pyridin-4-yl)ethanamine (15 mg, 0.12 mmol), EDCI (77 mg, 0.4 mmol), N-methyl-imidazole (33 mg, 0.4 mmol), dichloromethane (3 mL) and DMF (0.5 mL) was stirred at room temperature for 16 h. The solution was concentrated in vacuo, triturated with water (10 mL×3), and the residue purified by chromatography (silica gel, 200-300 mesh, CH$_2$Cl$_2$:MeOH=30:1) to give 4-(8-(6-(2-methylpyrrolidin-1-yl)pyridin-2-ylamino)imidazo[1,2-b]pyridazin-6-yl)-N-(2-(pyridin-4-yl)ethyl)benzamide (12 mg, 24%) as a yellow oil. $^1$H NMR (300 MHz, DMSO): δ 9.68 (s, 1H), 8.81 (s, 1H), 8.74-8.70 (m, 1H), 8.49-8.47 (m, 2H), 8.23 (s, 1H), 8.03-7.95 (m, 4 h), 7.68 (s, 1H), 7.46 (t, 1H, J=8.4 Hz), 7.30 (s, 1H), 7.29 (s, 1H), 6.75 (d, 1H, J=7.5 Hz), 6.09 (d, 1H, J=8.1 Hz), 4.25-4.21 (m, 1H), 3.61-3.56 (m, 2H), 3.47-3.40 (m, 2H), 2.92 (t, 2H, J=6.6 Hz), 2.11-1.99 (m, 3H), 1.71 (s, 1H), 0.85 (d, 3H, J=6.6 Hz). LC-MS: [M+H]$^+$, 519, $t_R$=1.333 min, HPLC: 100% at 214 nm, 100% at 254 nm, $t_R$=5.008 min.

Example 17

Synthesis of 4-(8-(6-(2-Methylpyrrolidin-1-yl)pyridin-2-ylamino)imidazo[1,2-b]pyridazin-6-yl)benzamide

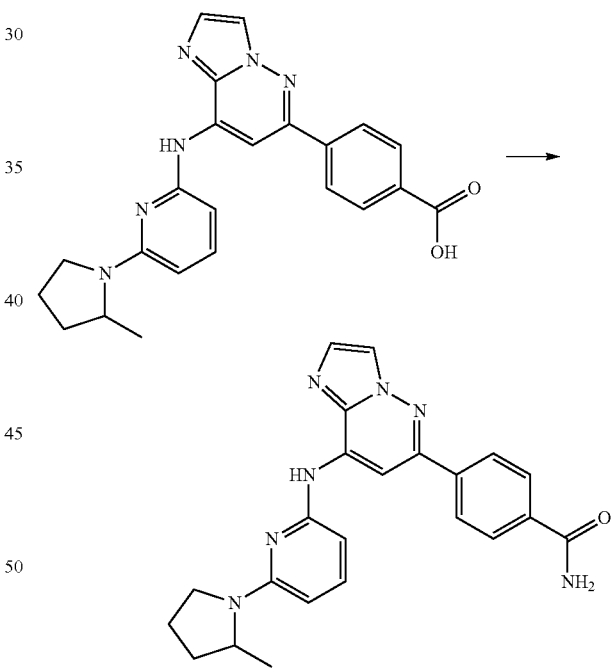

A mixture of 4-(8-(6-(2-methylpyrrolidin-1-yl)pyridin-2-ylamino)imidazo[1,2-b]pyridazin-6-yl)benzoic acid (45 mg, 0.11 mmol), 0.5 M ammonia in dioxane solution (23 mg, 1.3 mmol), EDCI (32 mg, 0.163 mmol) and HOBt (22 mg, 0.163 mmol) in dichloromethane (3 mL), DMF (0.5 mL) and Et$_3$N (22 mg, 0.22 mmol) was stirred at room temperature for 16 h. The solution was concentrated in vacuo, washed with water (10 mL×3), and purified by chromatography (silica gel, 200-300 mesh, CH$_2$Cl$_2$:MeOH=30:1) to give 4-(8-(6-(2-methylpyrrolidin-1-yl)pyridin-2-ylamino)imidazo[1,2-b]pyridazin-6-yl)benzamide (13 mg, 29%) as a yellow oil. $^1$H NMR (300 MHz, DMSO): δ 9.68 (s, 1H), 8.82 (s, 1H), 8.44 (s, 1H), 8.23 (s, 1H), 8.12-7.99 (m, 5H), 7.68 (s, 1H), 7.48-7.43 (m, 2H), 6.74 (d, 1H, J=7.8 Hz), 6.09 (d, 1H, J=8.1 Hz), 4.26-4.21 (m, 1H), 3.58-3.40 (m, 2H), 2.09-2.00 (m, 3H), 1.74-1.70 (m, 1H), 1.15 (d, 3H, J=6.0 Hz). LC-MS: [M+H]$^+$, 414, $t_R$=1.547 min, HPLC: 99.34% at 214 nm, 99.33% at 254 nm, $t_R$=5.357 min.

Example 18

Synthesis of 6-(Benzo[d][1,3]dioxol-5-yl)-N-(6-(2-methylpyrrolidin-1-yl)pyridin-2-yl)imidazo[1,2-b]pyridazin-8-amine

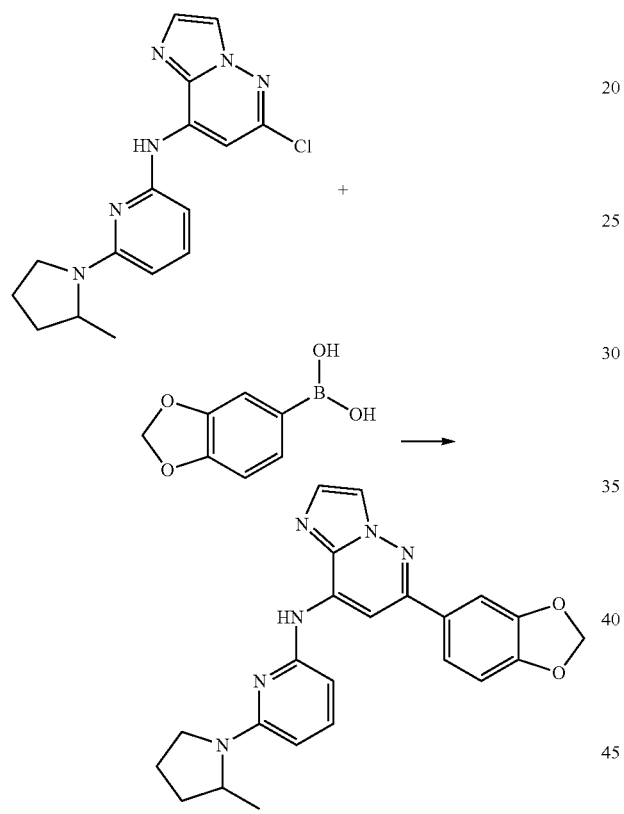

A mixture of 6-chloro-N-(6-(2-methylpyrrolidin-1-yl)pyridin-2-yl)imidazo[1,2-b]pyridazin-8-amine (66 mg, 0.2 mmol), benzo[d][1,3]dioxol-5-ylboronic acid (60 mg, 0.24 mmol), Pd$_2$(dba)$_3$ (12 mg, 0.02 mmol), X-phos (39 mg, 0.08 mmol) and Na$_2$CO$_3$ (64 mg, 0.6 mmol) in dioxane (5 mL) and water (0.5 mL) was heated to 100° C. with stirring for 16 h under N$_2$. The solvent was removed in vacuo and the resulting mixture was purified by chromatography (silica gel, 200-300 mesh, CH$_2$Cl$_2$:MeOH=20:1) to give crude product as a yellow oil, which was then purified by chromatography (silica gel, 200-300 mesh, petroleum ether:ethyl acetate=3:1) to give 6-(benzo[d][1,3]dioxol-5-yl)-N-(6-(2-methylpyrrolidin-1-yl)pyridin-2-yl)imidazo[1,2-b]pyridazin-8-amine (62 mg, 75%) as a yellow solid. $^1$H NMR (300 MHz, DMSO): δ 9.58 (s, 1H), 8.69 (s, 1H), 8.14 (s, 1H), 7.61 (s, 1H), 7.44-7.39 (m, 3H), 7.06-7.04 (m, 1H), 6.70 (d, 1H, J=7.5 Hz), 6.11 (s, 2H), 6.05 (d, 1H, J=8.1 Hz), 4.27-4.20 (m, 1H), 3.58-3.53 (m, 1H), 3.41-3.36 (m, 1H), 2.07-1.99 (m, 3H), 1.71-1.68 (m, 2H), 1.14 (d, 1H, J=6.0 Hz). LC-MS: [M+H]$^+$, 415, $t_R$=1.965 min, HPLC: 99.31% at 214 nm, 99.64% at 254 nm, $t_R$=6.821 min.

Example 19

Synthesis of 6-(1H-Indazol-6-yl)-N-(6-(2-methylpyrrolidin-1-yl)pyridin-2-yl)imidazo[1,2-b]pyridazin-8-amine A mixture of 6-chloro-N-(6-(2-methylpyrrolidin-1-yl)pyridin-2-yl)imidazo[1,2-b]pyridazin-8-amine (120 mg, 0.365 mmol), 6-(4,4,5,5-tetramethyl-1,3,2-dioxaborolan-2-yl)-1H-indazole (134 mg, 0.547 mmol), Pd$_2$(dba)$_3$ (21 mg, 0.037 mmol), X-phos (70 mg, 0.146 mmol) and Na$_2$CO$_3$ (117 mg, 1.1 mmol) in dioxane (5 mL) and water (0.5 mL) was heated to 100° C. with stirring for 16 h under N$_2$. The solvent was removed in vacuo and the resulting mixture was first purified by chromatography (silica gel, 200-300 mesh, CH$_2$Cl$_2$:MeOH=20:1), and then again (silica gel, 200-300 mesh, petroleum ether:ethyl acetate=3:1) to give 6-(1H-indazol-6-yl)-N-(6-(2-methylpyrrolidin-1-yl)pyridin-2-yl)imidazo[1,2-b]pyridazin-8-amine (37 mg, 25%) as a yellow solid. $^1$H NMR (300 MHz, DMSO): δ 13.31 (s, 1H), 9.69 (s, 1H), 8.87 (s, 1H), 8.23 (s, 1H), 8.17 (s, 1H), 8.03 (s, 1H), 7.91 (d, 1H, J=8.4 Hz), 7.69-7.67 (m, 2H), 7.45 (t, 1H, J=7.8 Hz), 6.75 (d, 1H, J=7.8 Hz), 6.08 (d, 1H, J=8.1 Hz), 4.21 (brs, 1H), 3.58 (brs, 1H), 3.45-3.38 (m, 1H), 2.06-1.97 (m, 3H), 1.69 (brs, 1H), 1.11 (d, 3H, J=6.0 Hz). LC-MS: [M+H]$^+$, 411, $t_R$=1.672 min, HPLC: 95.88% at 214 nm, 98.36% at 254 nm, $t_R$=5.913 min.

Example 20

Synthesis of 3-(8-(6-(2-(Hydroxymethyl)pyrrolidin-1-yl)pyridin-2-ylamino)imidazo[1,2-b]pyridazin-6-yl)benzoic acid

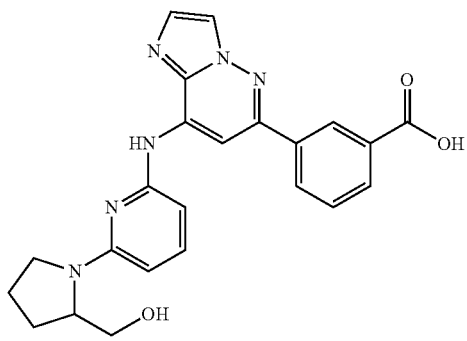 [SMILES: O=C(O)c1cccc(-c2cc(Nc3cccc(N4CCCC4CO)n3)c3nccn3n2)c1]

Step 1

Methyl 3-(8-(6-(2-(hydroxymethyl)pyrrolidin-1-yl)pyridin-2-ylamino)imidazo[1,2-b]pyridazin-6-yl)benzoate

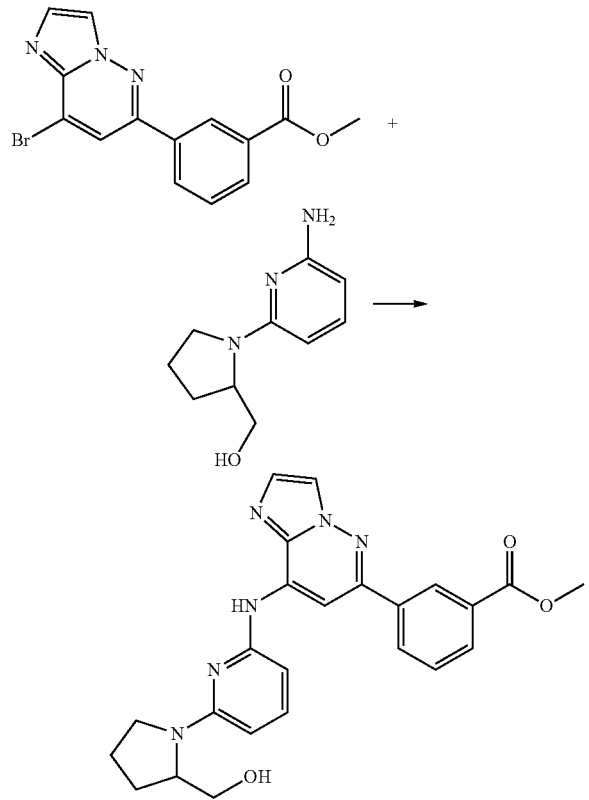

A mixture of methyl 3-(8-bromoimidazo[1,2-b]pyridazin-6-yl)benzoate (200 mg, 0.6 mmol), (1-(6-aminopyridin-2-yl)pyrrolidin-2-yl)methanol (176 mg, 0.9 mmol), Pd$_2$(dba)$_3$ (36 mg, 0.06 mmol), BINAP (152 mg, 0.24 mmol), Cs$_2$CO$_3$ (592 mg, 1.8 mmol) and dioxane (10 mL) was heated to 100° C. with stirring for 16 h under N$_2$. The solvent was removed in vacuo and the resulting mixture was purified by chromatography (silica gel, 200-300 mesh, CH$_2$Cl$_2$:MeOH=20:1) to give methyl 3-(8-(6-(2-(hydroxymethyl)pyrrolidin-1-yl)pyridin-2-ylamino)imidazo[1,2-b]pyridazin-6-yl)benzoate (185 mg, 69%) as a yellow solid. LC-MS: [M+H]$^+$, 223.2, [2M+H]$^+$, 445.2, t$_R$=1.737 min.

Step 2

3-(8-(6-(2-(Hydroxymethyl)pyrrolidin-1-yl)pyridin-2-ylamino)imidazo[1,2-b]pyridazin-6-yl)benzoic acid

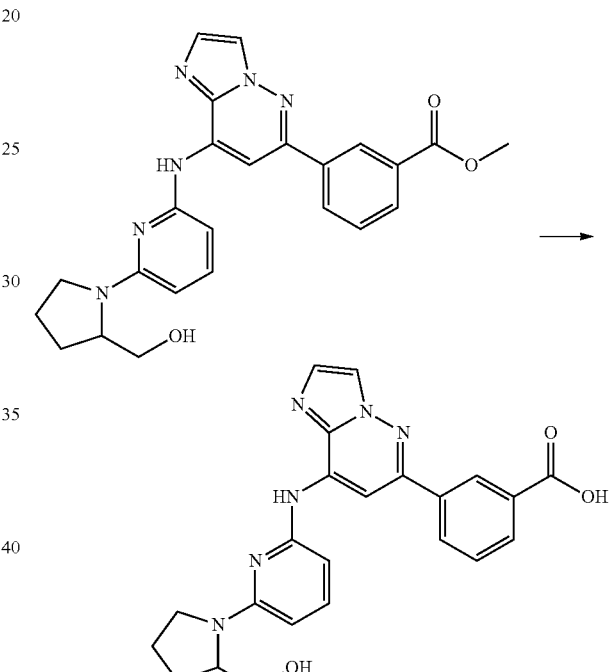

To a solution of methyl 3-(8-(6-(2-(hydroxymethyl)pyrrolidin-1-yl)pyridin-2-ylamino)imidazo[1,2-b]pyridazin-6-yl)benzoate (185 mg, 0.416 mmol) in dioxane (5 mL) and water (4.5 mL) was added NaOH (167 mg, 4.16 mmol), then the mixture was heated to 40° C. with stirring for 4 h. The solution was concentrated in vacuo then water (10 mL) was added and the solution was washed with dichloromethane (10 mL×3). The aqueous layer was adjusted to pH=4 by addition of concentrated HCl. The solid formed was filtered to give 3-(8-(6-(2-(hydroxymethyl)pyrrolidin-1-yl)pyridin-2-ylamino)imidazo[1,2-b]pyridazin-6-yl)benzoic acid (0.096 g, 54%) as a yellow solid. $^1$H NMR (300 MHz, DMSO): δ 10.84 (s, 1H), 9.19 (s, 1H), 8.60 (s, 1H), 8.51 (s, 1H), 8.31 (s, 1H), 8.23 (d, 1H, J=7.5 Hz), 8.13 (d, 1H, J=7.5 Hz), 7.71 (t, 1H, J=7.8 Hz), 7.53 (t, 1H, J=7.8 Hz), 6.72 (d, 1H, J=7.5 Hz), 6.27 (d, 1H, J=8.1 Hz), 3.96 (brs, 2H), 3.61 (brs, 1H), 3.46-3.37 (m, 2H), 2.07-1.95 (m, 4 h). LC-MS: [M+H]$^+$, 431, t$_R$=1.459 min, HPLC: 99.27% at 214 nm, 99.49% at 254 nm, t$_R$=5.08 min.

Example 21

Synthesis of (R)—N-(6-(2-Methylpyrrolidin-1-yl)pyridin-2-yl)-6-phenylimidazo[1,2-b]pyridazin-8-amine

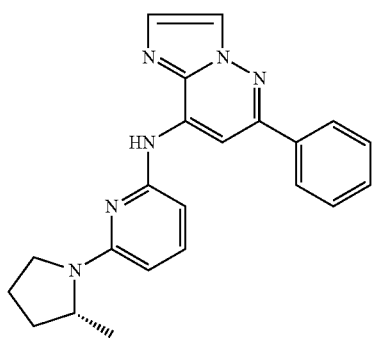 [SMILES: C[C@@H]1CCCN1c1cccc(Nc2cc(-c3ccccc3)nn3ccnc23)n1]

Step 1

(R)-6-(2-Methylpyrrolidin-1-yl)pyridin-2-amine

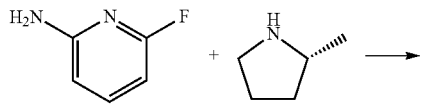

A suspension of 6-fluoropyridin-2-amine (448 mg, 4 mmol) and (R)-2-methylpyrrolidine (511 mg, 6 mmol) in water (0.5 mL) was heated to 205° C. in a microwave oven for 30 minutes. The reaction mixture was purified by chromatography (silica gel, 200-300 mesh, petroleum ether:ethyl acetate=3:1) to give (R)-6-(2-methylpyrrolidin-1-yl)pyridin-2-amine (581 mg, 82%) as a light yellow oil. LC-MS: [M+H]$^+$, 178.2, $t_R$=1.049 min.

Step 2

(R)—N-(6-(2-methylpyrrolidin-1-yl)pyridin-2-yl)-6-phenylimidazo[1,2-b]pyridazin-8-amine

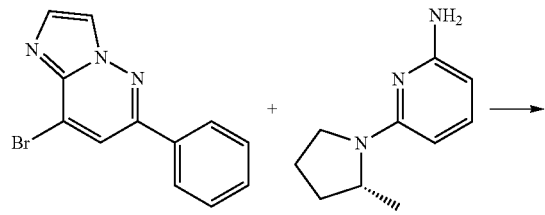

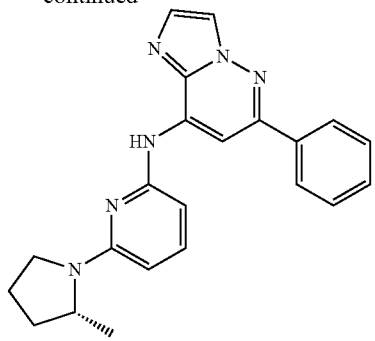

A mixture of 8-bromo-6-phenylimidazo[1,2-b]pyridazine (166 mg, 0.6 mmol), (R)-6-(2-methylpyrrolidin-1-yl)pyridin-2-amine (160 mg, 0.9 mmol), Pd$_2$(dba)$_3$ (36 mg, 0.06 mmol), BINAP (152 mg, 0.24 mmol), Cs$_2$CO$_3$ (593 mg, 1.8 mmol) and dioxane (10 mL) was heated to 100° C. with stirring for 16 h under N$_2$. The solvent was removed in vacuo and the resulting mixture was purified by chromatography (silica gel, 200-300 mesh, petroleum ether:ethyl acetate=3:1) to give (R)—N-(6-(2-methylpyrrolidin-1-yl)pyridine-2-yl)-6-phenylimidazo[1,2-b]pyridazin-8-amine (78 mg, 35%) as a white solid. $^1$H NMR (300 MHz, DMSO): δ 8.76 (s, 1H), 7.95-7.87 (m, 3H), 7.55-7.35 (m, 5H), 6.23 (d, 1H, J=7.5 Hz), 6.02 (d, 1H, J=8.1 Hz), 4.22-4.18 (m, 1H), 3.57-3.53 (m, 1H), 3.41-3.36 (m, 1H), 2.09-1.98 (m, 3H), 1.72 (brs, 1H), 1.16 (d, 3H, J=6.0 Hz). LC-MS: [M+H]$^+$, 371, $t_R$=1.994 min, HPLC: 99.27% at 214 nm, 99.26% at 254 nm, $t_R$=4.72 min.

Example 22

Synthesis of (R)-3-(8-(6-(2-methylpyrrolidin-1-yl)pyridin-2-ylamino)imidazo[1,2-b]pyridazin-6-yl)benzoic acid hydrochloride

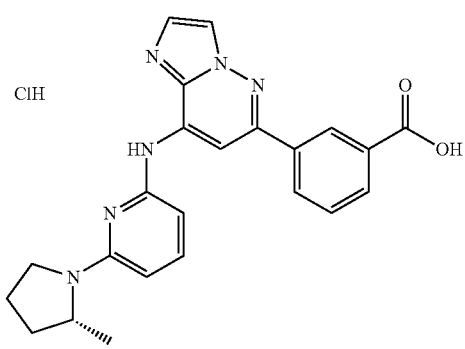 [SMILES: C[C@@H]1CCCN1c1cccc(Nc2cc(-c3cccc(C(=O)O)c3)nn3ccnc23)n1 ; Cl]

Step 1

(R)-Methyl 3-(8-(6-(2-methylpyrrolidin-1-yl)pyridin-2-ylamino)imidazo[1,2-b]pyridazin-6-yl)benzoate

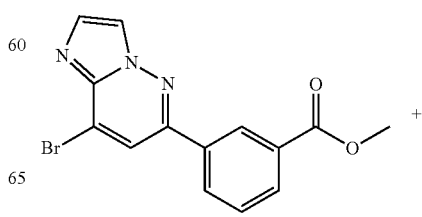

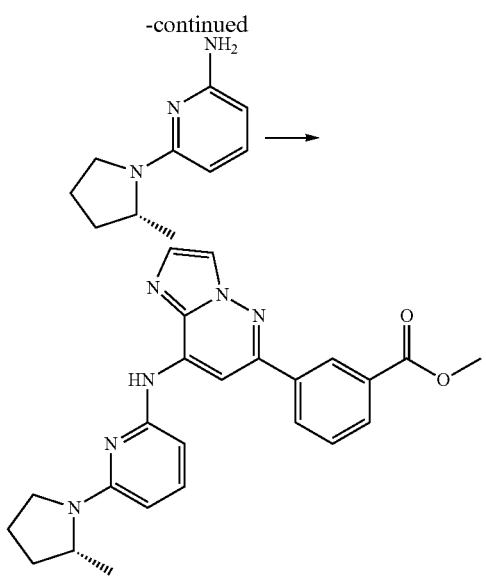

A mixture of methyl 3-(8-bromoimidazo[1,2-b]pyridazin-6-yl)benzoate (200 mg, 0.6 mmol), (R)-6-(2-methylpyrrolidin-1-yl)pyridin-2-amine (160 mg, 0.9 mmol), Pd$_2$(dba)$_3$ (36 mg, 0.06 mmol), BINAP (152 mg, 0.24 mmol), Cs$_2$CO$_3$ (592 mg, 1.8 mmol) and dioxane (10 mL) was heated to 100° C. with stirring for 16 h under N$_2$. The solvent was removed in vacuo and the resulting mixture was purified by chromatography (silica gel, 200-300 mesh, petroleum ether:ethyl acetate=3:1) to give (R)-methyl 3-(8-(6-(2-methylpyrrolidin-1-yl)pyridine-2-ylamino)imidazo[1,2-b]pyridazin-6-yl)benzoate (110 mg, 43%) as a yellow solid. LC-MS: [M+H]$^+$, 429.1, t$_R$=2.064 min.

Step 2

(R)-3-(8-(6-(2-methylpyrrolidin-1-yl)pyridin-2-ylamino)imidazo[1,2-b]pyridazin-6-yl)benzoic acid hydrochloride

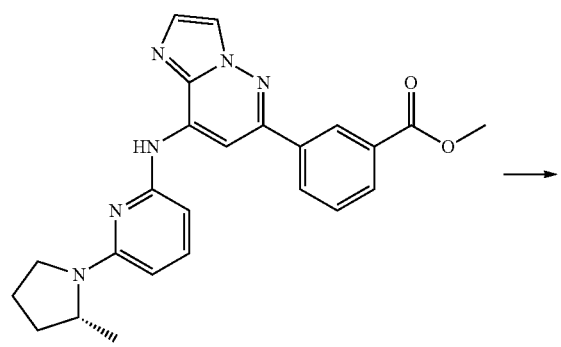

To a stirred solution of (R)-methyl 3-(8-(6-(2-methylpyrrolidin-1-yl)pyridine-2-ylamino)imidazo[1,2-b]pyridazin-6-yl)benzoate (78 mg, 0.18 mmol) in dioxane (5 mL) and water (5 mL) was added NaOH (72 mg, 1.8 mmol), then the mixture was heated to 40° C. After 4 h the solution was concentrated in vacuo. Water (5 mL) was added to the residue and the mixture washed with dichloromethane (5 mL×3). The aqueous layer was adjusted to pH=4 by the addition of concentrated HCl. The solid formed was collected with filtration. The solid was further purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to give a light yellow solid. This was dissolved in methanol and three drops of concentrated HCl added. The mixture was stirred for 5 minutes, then concentrated in vacuo to give the final product (R)-3-(8-(6-(2-methylpyrrolidin-1-yl)pyridin-2-ylamino)imidazo[1,2-b]pyridazin-6-yl)benzoic acid hydrochloride (0.035 g, 46%) as a yellow solid. $^1$H NMR (300 MHz, CD3OD): δ 8.81 (d, 1H, J=2.7 Hz), 8.58 (s, 1H), 8.42 (d, 1H, J=1.8 Hz), 8.25-8.16 (m, 3H), 7.67-7.58 (m, 2H), 6.55 (d, 1H, J=7.5 Hz), 6.41 (d, 1H, J=8.4 Hz), 4.26-4.24 (m, 1H), 3.68-3.63 (m, 1H), 3.57-3.48 (m, 1H), 2.21-2.07 (m, 3H), 1.83-1.79 (m, 1H), 1.20 (d, 3H, J=6.3 Hz). LC-MS: [M+H]$^+$, 415, t$_R$=1.625 min, HPLC: 100% at 214 nm, 100% at 254 nm, t$_R$=6.27 min.

Example 23

Synthesis of 3-(8-(6-(3-Aza-bicyclo[3.1.0]hexan-3-yl)pyridin-2-ylamino)imidazo[1,2-b]pyridazin-6-yl)benzoic acid Step 1

3-Benzyl-3-aza-bicyclo[3.1.0]hexane-2,4-dione

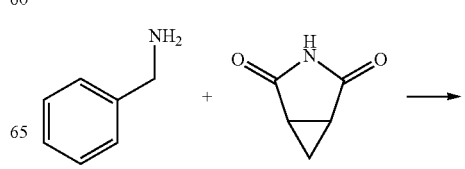

-continued

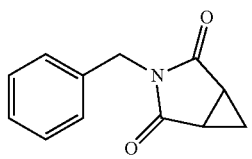

Benzylamine (2.5 mL, 22.3 mmol) was added drop wise to ice cooled 3-aza-bicyclo[3.1.0]hexane-2,4-dione (2.5 g, 22.3 mmol) then the mixture was heated to 170° C. with stirring for 1.5 h. After cooling to room temperature, the resulting mixture was crystallized from isopropanol to give 3-benzyl-3-aza-bicyclo[3.1.0]hexane-2,4-dione (3.72 g, 83%) as a white solid. LC-MS: [M+H]$^+$, 202.1, $t_R$=1.478 min.

Step 2

3-Benzyl-3-aza-bicyclo[3.1.0]hexane

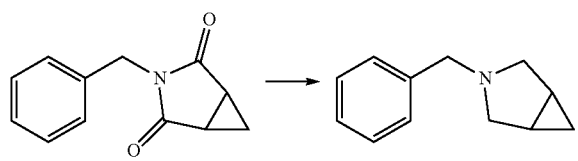 [SMILES: O=C1C2CC2C(=O)N1Cc1ccccc1 ; c1ccc(CN2CC3CC3C2)cc1]

Red-Al (70% in toluene) (24 g, 83.2 mmol) was dissolved in absolute ether (100 mL) and cooled to 0° C. under N$_2$, then 3-benzyl-3-aza-bicyclo[3.1.0]hexane-2,4-dione (3.72 g, 18.5 mmol) was added. The mixture was stirred at 0° C. for 30 mins then stirred under reflux for 4 h. Water (50 mL) was added to the cooled solution and the mixture filtered through celite. The organic phase was dried over Na$_2$SO$_4$, concentrated in vacuo to give 3-benzyl-3-aza-bicyclo[3.1.0]hexane (3.0 g, 94%) as a light red oil. LC-MS: [M+H]$^+$, 174.2, $t_R$=0.546 min.

Step 3

3-Aza-bicyclo[3.1.0]hexane hydrochloride

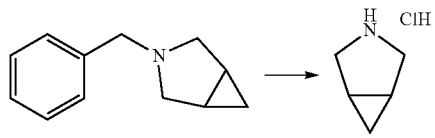 [SMILES: Cl ; c1ccc(CN2CC3CC3C2)cc1 ; C1NCC2CC12]

A mixture of 3-benzyl-3-aza-bicyclo[3.1.0]hexane (3.0 g, 17.3 mmol), Pd(OH)$_2$ (150 mg, 1.1 mmol) and methanol (25 mL) was stirred at room temperature under 4 atmospheres pressure of H$_2$ for 24 h. The solution was filtered and into the organic layer was bubbled HCl gas until pH=4 was reached. The solution was concentrated in vacuo, the resulting residue was washed with dichloromethane (10 mL×2) and dried to give 3-aza-bicyclo[3.1.0]hexane hydrochloride (1.83 g, 88%) as a white solid. LC-MS: [M+H]$^+$, 84.2, $t_R$=0.313 min.

Step 4

6-(3-Aza-bicyclo[3.1.0]hexan-3-yl)pyridin-2-amine

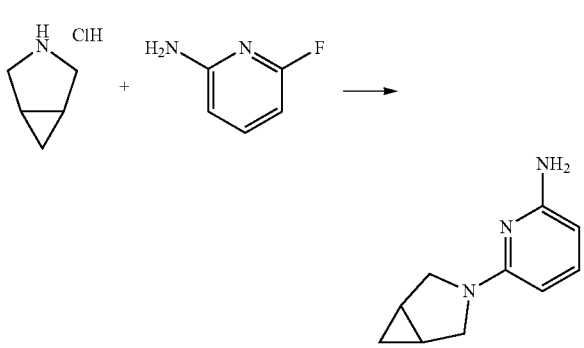

A suspension of 6-fluoropyridin-2-amine (448 mg, 4 mmol), 3-aza-bicyclo[3.1.0]hexane hydrochloride (576 mg, 4.8 mmol) and Et$_3$N (808 mg, 8 mmol) in water (0.5 mL) was heated to 205° C. in a microwave oven for 30 minutes. The reaction mixture was purified by chromatography (silica gel, 200-300 mesh, petroleum ether:ethyl acetate=10:1) to give 6-(3-aza-bicyclo[3.1.0]hexan-3-yl)pyridin-2-amine (535 mg, 76%) as a colorless oil. LC-MS: [M+H]$^+$, 176.2, $t_R$=1.042 min.

Step 5

Methyl 3-(8-(6-(3-aza-bicyclo[3.1.0]hexan-3-yl)pyridin-2-ylamino)imidazo[1,2-b]pyridazin-6-yl)benzoate

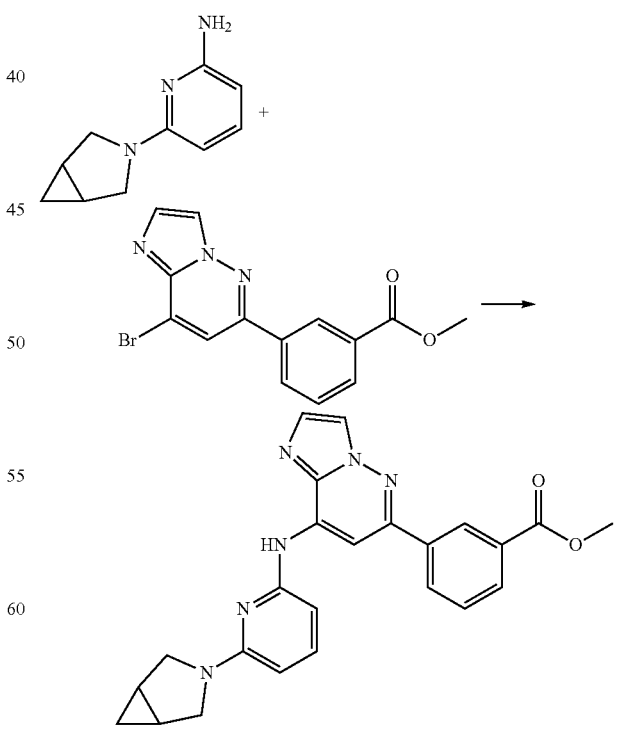

A mixture of methyl 3-(8-bromoimidazo[1,2-b]pyridazin-6-yl)benzoate (250 mg, 0.75 mmol), 6-(3-aza-bicyclo[3.1.0]

hexan-3-yl)pyridin-2-amine (198 mg, 1.13 mmol), Pd$_2$(dba)$_3$ (43 mg, 0.075 mmol), BINAP (187 mg, 0.3 mmol), Cs$_2$CO$_3$ (734 mg, 2.25 mmol) and dioxane (10 mL) was heated to 100° C. with stirring for 16 h under N$_2$. The solvent was removed in vacuo and the resulting mixture was purified by chromatography (silica gel, 200-300 mesh, petroleum ether:ethyl acetate=3:1) to give crude product which was further purified by prep-HPLC (Gemini 5u C18 150×21.2 mm; inject volume: 3 mL/inj, flow rate: 20 mL/min; wavelength: 214 nm and 254 nm; gradient conditions: 30% acetonitrile/70% water (0.1% TFA, v/v) initially, proceeding to 50% acetonitrile/50% water (0.1% TFA, v/v) in a linear fashion over 9 min) to give methyl 3-(8-(6-(3-aza-bicyclo[3.1.0]hexan-3-yl)pyridine-2-ylamino)imidazo[1,2-b]pyridazin-6-yl)benzoate (70 mg, 22%) as a light yellow solid. [M+H]$^+$, 427.1, $t_R$=1.926 min.

Step 6

3-(8-(6-(3-Aza-bicyclo[3.1.0]hexan-3-yl)pyridin-2-ylamino)imidazo[1,2-b]pyridazin-6-yl)benzoic acid

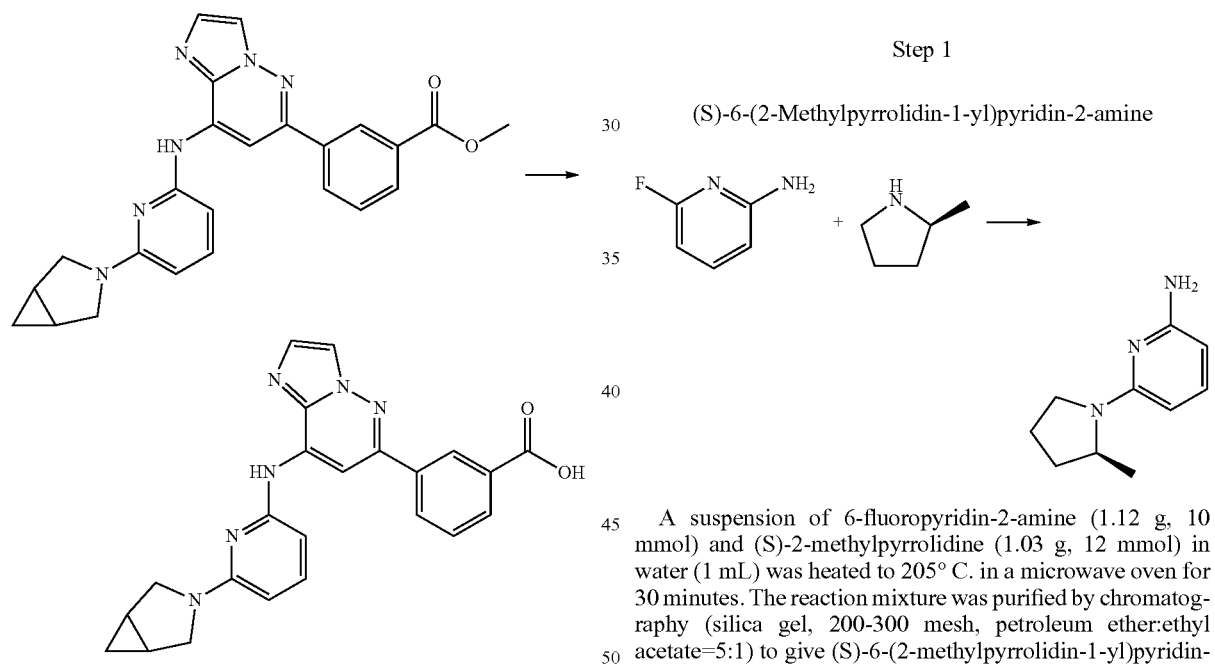

To a solution of methyl 3-(8-(6-(3-aza-bicyclo[3.1.0] hexan-3-yl)pyridin-2-ylamino)imidazo[1,2-b]pyridazin-6-yl)benzoate (70 mg, 0.16 mmol) in dioxane (5 mL) and water (4 mL) was added NaOH (63 mg, 1.6 mmol), then the mixture was heated to 40° C. with stirring for 4 h. The solution was concentrated in vacuo. Water (10 mL) was added to the residue and was washed with dichloromethane (15 mL×3). The aqueous layer was adjusted to pH=4 by the addition of concentrated HCl. The solid formed was collected by filtration to give 3-(8-(6-(3-aza-bicyclo[3.1.0]hexan-3-yl)pyridin-2-ylamino)imidazo[1,2-b]pyridazin-6-yl)benzoic acid (0.045 g, 67%) as a yellow solid. $^1$H NMR (300 MHz, DMSO): δ 9.88 (s, 1H), 8.92 (s, 1H), 8.54 (s, 1H), 8.31-8.10 (m, 3H), 7.80-7.72 (m, 2H), 7.47 (s, 1H), 6.76 (s, 1H), 6.11 (s, 1H), 3.71-3.54 (m, 4 h), 1.72 (s, 2H), 0.78 (s, 1H), 0.22 (s, 1H).

LC-MS: [M+H]$^+$, 413, $t_R$=1.665 min, HPLC: 95.09% at 214 nm, 95% at 254 nm, $t_R$=5.831 min.

Example 24

Synthesis of (S)-2-methyl-3-(8-(6-(2-methylpyrrolidin-1-yl)pyridin-2-ylamino)imidazo[1,2-b]pyridazin-6-yl)benzoic acid

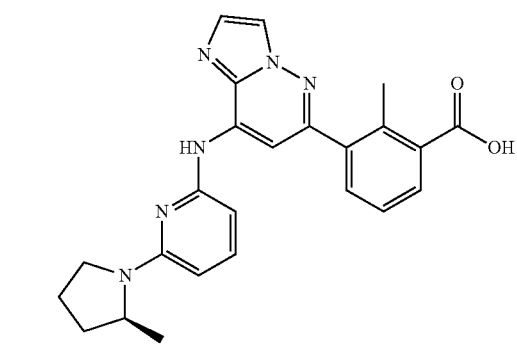 [SMILES: Cc1c(C(=O)O)cccc1-c1cc(Nc2cccc(N3CCC[C@@H]3C)n2)c2nccn2n1]

Step 1

(S)-6-(2-Methylpyrrolidin-1-yl)pyridin-2-amine

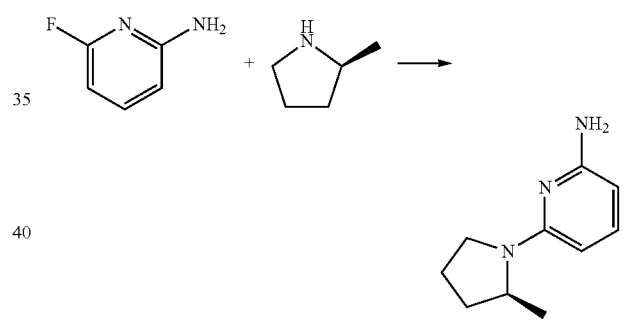

A suspension of 6-fluoropyridin-2-amine (1.12 g, 10 mmol) and (S)-2-methylpyrrolidine (1.03 g, 12 mmol) in water (1 mL) was heated to 205° C. in a microwave oven for 30 minutes. The reaction mixture was purified by chromatography (silica gel, 200-300 mesh, petroleum ether:ethyl acetate=5:1) to give (S)-6-(2-methylpyrrolidin-1-yl)pyridin-2-amine (1.5 g, 83%) as a colorless oil. LC-MS: [M+H]$^+$, 178.2, $t_R$=1.066 min.

Step 2

(S)-6-Chloro-N-(6-(2-methylpyrrolidin-1-yl)pyridin-2-yl)imidazo[1,2-b]pyridazin-8-amine

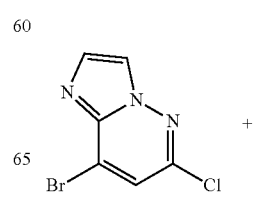

111
-continued

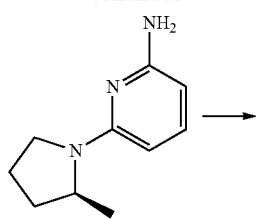

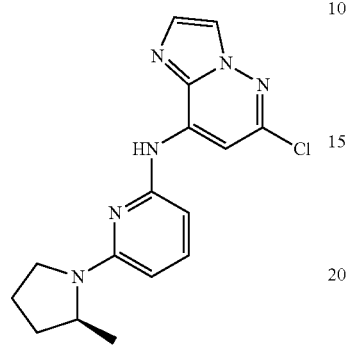

A mixture of 8-bromo-6-chloroimidazo[1,2-b]pyridazine (300 mg, 1.3 mmol), (S)-6-(2-methylpyrrolidin-1-yl)pyridin-2-amine (252 mg, 1.42 mmol), Pd$_2$(dba)$_3$ (75 mg, 0.13 mmol), BINAP (324 mg, 0.52 mmol), Cs$_2$CO$_3$ (1272 mg, 3.9 mmol) and dioxane (20 mL) was heated to 100° C. with stirring for 16 h under N$_2$. The solvent was removed in vacuo and the resulting mixture was purified by chromatography (silica gel, 200-300 mesh, petroleum ether:ethyl acetate=3:1) to give (S)-6-chloro-N-(6-(2-methylpyrrolidin-1-yl)pyridin-2-yl)imidazo[1,2-b]pyridazin-8-amine (124 mg, 29%) as a yellow solid. LC-MS: [M+H]$^+$, 329.0, $t_R$=1.951 min.

Step 3

(S)-Methyl 2-methyl-3-(8-(6-(2-methylpyrrolidin-1-yl)pyridin-2-ylamino)imidazo[1,2-b]pyridazin-6-yl)benzoate

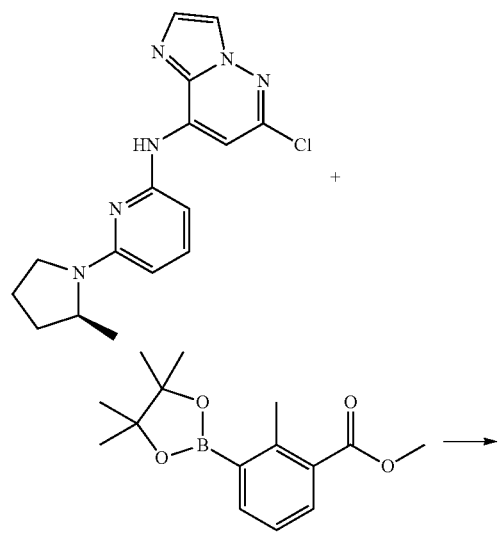

112
-continued

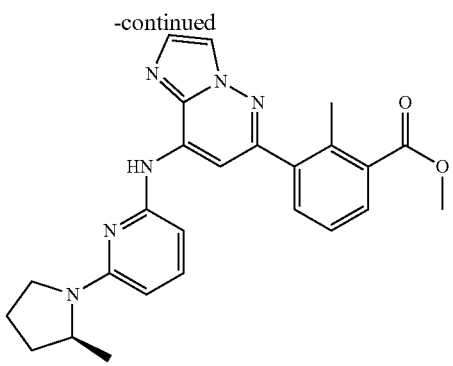

A mixture of (S)-6-chloro-N-(6-(2-methylpyrrolidin-1-yl)pyridin-2-yl)imidazo[1,2-b]pyridazin-8-amine (124 mg, 0.38 mmol), methyl 2-methyl-3-(4,4,5,5-tetramethyl-1,3,2-dioxaborolan-2-yl)benzoate (124 mg, 0.45 mmol), Pd$_2$(dba)$_3$ (22 mg, 0.038 mmol), X-phos (73 mg, 0.152 mmol) and Na$_2$CO$_3$ (121 mg, 1.14 mmol) in dioxane (10 mL) and water (1 mL) was heated to 100° C. with stirring for 16 h under N$_2$. The solvent was removed in vacuo and the resulting mixture was purified by chromatography (silica gel, 200-300 mesh, CH$_2$Cl$_2$:MeOH=20:1) to give (S)-methyl 2-methyl-3-(8-(6-(2-methylpyrrolidin-1-yl)pyridin-2-ylamino)imidazo[1,2-b]pyridazin-6-yl)benzoate (72 mg, 43%) as a yellow solid. LC-MS: [M+H]$^+$, 443.2, $t_R$=1.880 min.

Step 4

(S)-2-Methyl-3-(8-(6-(2-methylpyrrolidin-1-yl)pyridin-2-ylamino)imidazo[1,2-b]pyridazin-6-yl)benzoic acid

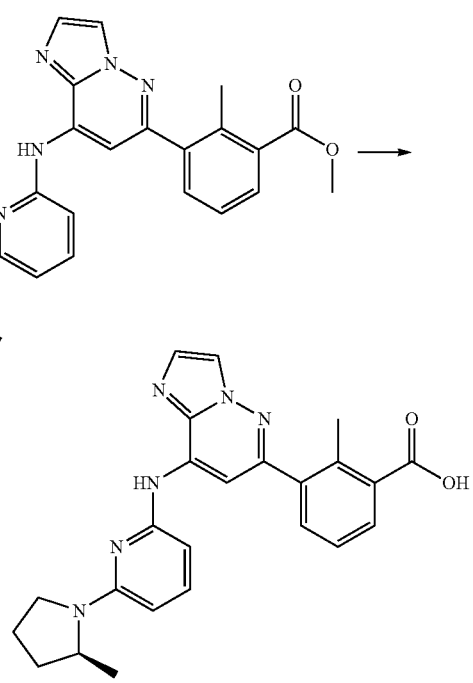

To a solution of (S)-2-methyl-3-(8-(6-(2-methylpyrrolidin-1-yl)pyridin-2-ylamino)imidazo[1,2-b]pyridazin-6-yl)benzoate (72 mg, 0.16 mmol) in dioxane (5 mL) and water (4 mL) was added NaOH (64 mg, 1.6 mmol), then the mixture was heated to 40° C. with stirring for 4 h. The solution was concentrated in vacuo, water (10 mL) was added and the solution was washed with dichloromethane (10 mL×3). The aqueous layer was adjusted to pH=4 by the addition of concentrated HCl. The solid formed was collected by filtration and was purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to give the final product (S)-2-methyl-3-(8-(6-(2-methylpyrrolidin-1-yl)pyridin-2-ylamino)imidazo[1,2-b]pyridazin-6-yl)benzoic acid (41 mg, 59%). $^1$H NMR (300 MHz, DMSO): δ 10.43 (s, 1H), 8.72 (s, 1H), 8.45 (s, 1H), 8.12 (s, 1H), 7.90 (d, 1H, J=7.5 Hz), 7.62-7.42 (m, 3H), 6.68 (d, 1H, J=7.8 Hz), 6.10 (d, 1H, J=8.1 Hz), 4.04-4.00 (m, 2H), 3.40-3.35 (m, 1H), 3.18-3.15 (m, 1H), 2.47 (s, 3H), 1.96-1.88 (m, 2H), 1.55-1.51 (m, 1H), 0.86 (d, 3H, J=6.0 Hz). LC-MS: [M+H]$^+$, 429, $t_R$=1.619 min, HPLC: 100% at 214 nm, 99.42% at 254 nm, $t_R$=5.838 min.

Example 25

Synthesis of N-(6-(3-Methylpyrrolidin-1-yl)pyridin-2-yl)-6-phenylimidazo[1,2-b]pyridazin-8-amine

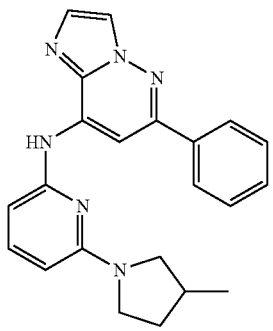

Step 1

6-(3-Methylcyclopentyl)pyridin-2-amine

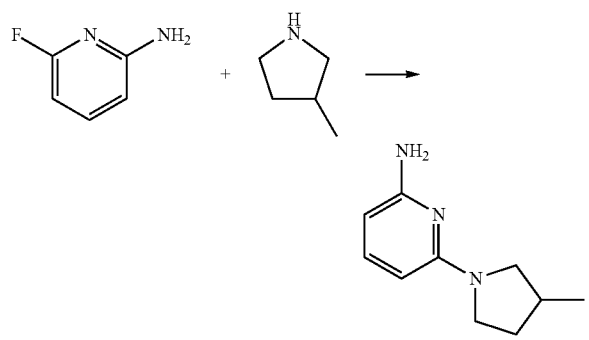

A suspension of 6-fluoropyridin-2-amine (448 mg, 4 mmol) and 3-methylpyrrolidine (408 mg, 4.8 mmol) in water (0.5 mL) was heated to 205° C. in a microwave oven for 30 minutes. The reaction mixture was purified by chromatography (silica gel, 200-300 mesh, petroleum ether:ethyl acetate=5:1) to give 6-(3-methylcyclopentyl)pyridin-2-amine (630 mg, 89%) as a colorless oil. LC-MS: [M+H]$^+$, 178.2, $t_R$=1.080 min.

Step 2

6-Chloro-N-(6-(3-methylpyrrolidin-1-yl)pyridin-2-yl)imidazo[1,2-b]pyridazin-8-amine

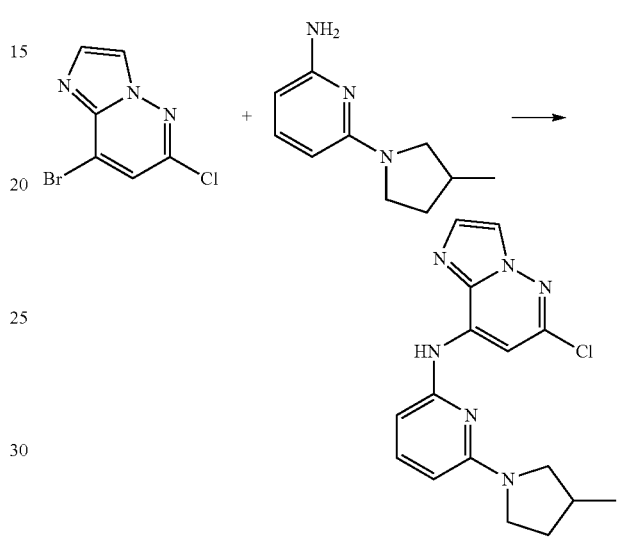

A mixture of 8-bromo-6-chloroimidazo[1,2-b]pyridazine (300 mg, 1.3 mmol), 6-(3-methylcyclopentyl)pyridin-2-amine (277 mg, 1.56 mmol), Pd$_2$(dba)$_3$ (75 mg, 0.13 mmol), BINAP (324 mg, 0.52 mmol), Cs$_2$CO$_3$ (1272 mg, 3.9 mmol) and dioxane (20 mL) was heated to 100° C. with stirring for 16 h under N$_2$. The solvent was removed in vacuo and the resulting mixture was purified by chromatography (silica gel, 200-300 mesh, petroleum ether:ethyl acetate=5:1) to give 6-chloro-N-(6-(3-methylpyrrolidin-1-yl)pyridin-2-yl)imidazo[1,2-b]pyridazin-8-amine (301 mg, 70%) as a yellow solid. LC-MS: [M+H]$^+$, 329.1, $t_R$=1.949 min.

Step 3

N-(6-(3-Methylpyrrolidin-1-yl)pyridin-2-yl)-6-phenylimidazo[1,2-b]pyridazin-8-amine

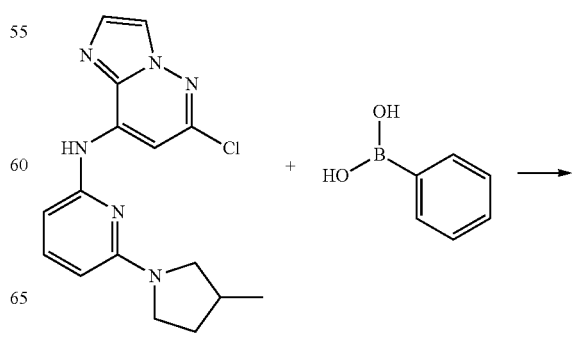

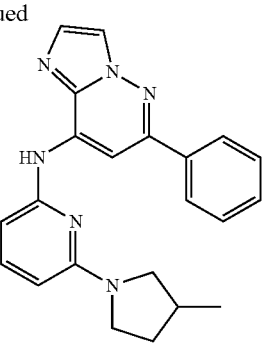

A mixture of 6-chloro-N-(6-(3-methylpyrrolidin-1-yl)pyridin-2-yl)imidazo[1,2-b]pyridazin-8-amine (296 mg, 0.9 mmol), phenylboronic acid (165 mg, 1.35 mmol), Pd$_2$(dba)$_3$ (52 mg, 0.09 mmol), X-phos (172 mg, 0.36 mmol) and Na$_2$CO$_3$ (287 mg, 2.7 mmol) in dioxane (10 mL) and water (1 mL) was heated to 100° C. with stirring for 16 h under N$_2$. The solution was removed in vacuo and the resulting mixture was purified by chromatography (silica gel, 200-300 mesh, petroleum ether:ethyl acetate=5:1) to give N-(6-(3-methylpyrrolidin-1-yl)pyridin-2-yl)-6-phenylimidazo[1,2-b]pyridazin-8-amine (134 mg, 40%) as a yellow solid. $^1$H NMR (300 MHz, CDCl$_3$): δ 8.82 (s, 1H), 8.06-7.93 (m, 3H), 7.93-7.39 (m, 5H), 6.20 (d, 1H, J=7.8 Hz), 5.98 (d, 1H, J=8.1 Hz), 3.86-3.80 (m, 1H), 3.67-3.62 (m, 1H), 3.55-3.46 (m, 1H), 3.14 (t, 1H, J=9.3 Hz), 2.47-2.37 (m, 1H), 2.23-2.14 (m, 1H), 1.75-1.62 (m, 1H), 1.19 (d, 3H, J=6.6 Hz). LC-MS: [M+H]$^+$, 371, t$_R$=2.057 min, HPLC: 100% at 214 nm, 100% at 254 nm, t$_R$=4.787 min.

Example 26

Synthesis of 4-(8-(5,6-Dimethoxypyridin-2-ylamino)imidazo[1,2-b]pyridazin-6-yl)benzoic acid

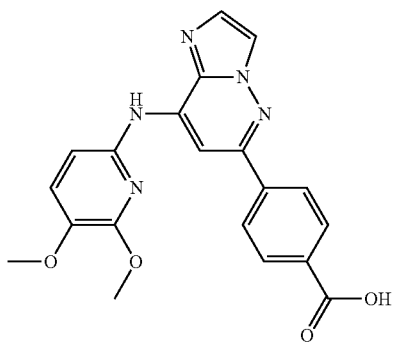 [SMILES: COc1ccc(Nc2cc(-c3ccc(C(=O)O)cc3)nn3ccnc23)nc1OC]

Step 1

Methyl 4-(8-(5,6-dimethoxypyridin-2-ylamino) imidazo[1,2-h]pyridazin-6-yl)benzoate

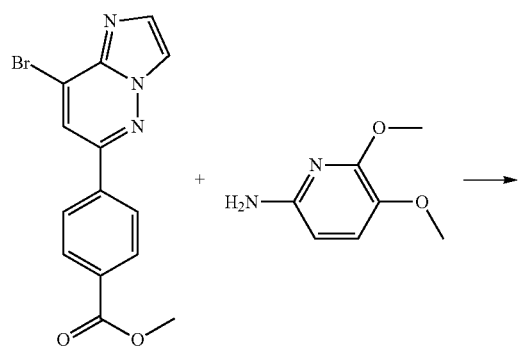

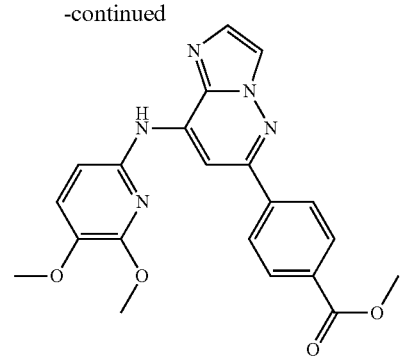

A mixture of methyl 4-(8-bromoimidazo[1,2-b]pyridazin-6-yl)benzoate (0.3 g, 0.904 mmol), 5,6-dimethoxypyridin-2-amine (0.167 g, 1.084 mmol), Pd$_2$(dba)$_3$ (52 mg, 0.09 mmol), BINAP (225 mg, 0.362 mmol) and Cs$_2$CO$_3$ (0.884 g, 2.712 mmol) in dioxane (20 mL) was heated to 100° C. for 16 h in a sealed tube under N$_2$ atmosphere. The mixture was cooled and concentrated in vacuo. The residue was purified by chromatography (silica, 10 g, 200-300 mesh, ethyl acetate:petroleum ether=1:3) to afford methyl 4-(8-(5,6-dimethoxypyridin-2-ylamino)imidazo[1,2-b]pyridazin-6-yl)benzoate (0.518 g) as a yellow solid containing unidentified impurities. LC-MS: [M+H]$^+$=406, t$_R$=1.766 min.

Step 2

4-(8-(5,6-Dimethoxypyridin-2-ylamino) imidazo[1,2-b]pyridazin-6-yl)benzoic acid

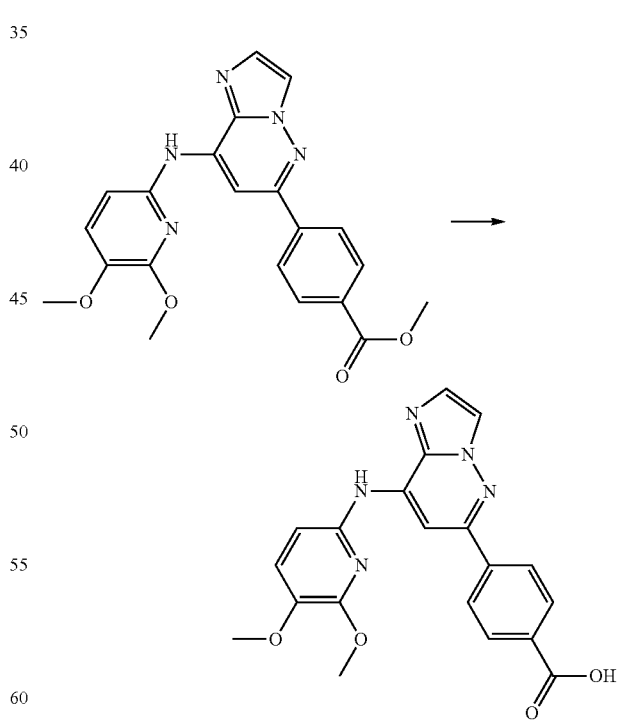

To a stirred solution of methyl 4-(8-(5,6-dimethoxypyridin-2-ylamino)imidazo[1,2-b]pyridazin-6-yl)benzoate (0.135 g, 0.333 mmol) in dioxane (20 mL) and H$_2$O (10 mL) was added NaOH (133 mg, 3.33 mmol) at 25° C. After 2 h the mixture was washed with ether (10 mL) and the aqueous layer was adjusted to pH=4 with concentrated HCl, then it was concentrated and filtered. The solid was washed with ether and dried to afford 4-(8-(5,6-dimethoxypyridin-2-ylamino) imidazo[1,2-b]pyridazin-6-yl)benzoic acid (0.101 g, 77%) as a yellow solid. $^1$H NMR (300 MHz, DMSO): δ 9.98 (s, 1H), 8.57 (s, 1H), 8.24 (s, 1H), 8.11-8.03 (m, 4 h), 7.69 (s, 1H), 7.43 (d, 1H, J=8.4 Hz), 7.13 (d, 1H, J=8.7 Hz), 4.04 (s, 3H), 3.79 (s, 3H). LC-MS: [M+H]$^+$, 391.9, $t_R$=1.454 min, HPLC: 98.08% at 214 nm, 95.71% at 254 nm, $t_R$=3.628 min.

Example 27

Synthesis of 4-(8-(5,6-Dimethoxypyrin-2-ylamino) imidazo[1,2-b]pyridazin-6-yl)-N-(2-(pyridin-4-yl) ethyl)benzamide

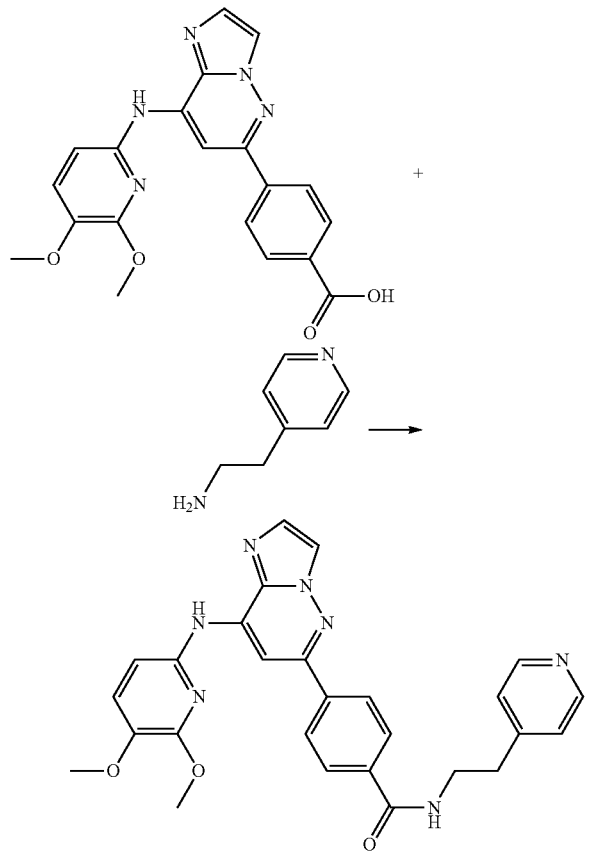

A mixture of 4-(8-(5,6-dimethoxypyridin-2-ylamino)imidazo[1,2-b]pyridazin-6-yl)benzoic acid (47 mg, 0.12 mmol), 2-(pyridin-4-yl)ethanamine (16 mg, 0.132 mmol), HATU (50 mg, 0.132 mmol), DIPEA (18 mg, 0.144 mmol), DMAP (18 mg, 0.144 mmol) and EDCI (28 mg, 0.144 mmol) in DMF (3 mL) was stirred at room temperature for 16 h. Ethyl acetate (50 mL) was added then the mixture was washed with water (2×2 mL) and brine (2×2 mL), then dried over anhydrous sodium sulfate and concentrated in vacuo. The residue was washed with ether and filtered to afford 4-(8-(5,6-dimethoxypyridin-2-ylamino)imidazo[1,2-b]pyridazin-6-yl)-N-(2-(pyridin-4-yl)ethyl)benzamide (43 mg, 72%) as a yellow solid. $^1$H NMR (300 MHz, DMSO): δ 9.96 (s, 1H), 8.71 (t, 1H, J=5.4 Hz), 8.53-8.46 (m, 3H), 8.21 (s, 1H), 8.03-7.94 (m, 4 h), 7.67 (s, 1H), 7.42 (d, 1H, J=8.4 Hz), 7.29-7.27 (m, 2H), 7.11 (d, 1H, J=8.4 Hz), 4.01 (s, 3H), 3.78 (s, 3H), 3.60-3.54 (m, 2H), 2.90 (t, 2H, J=7.2 Hz). LC-MS: [M+H]$^+$, 496, $t_R$=1.226 min, HPLC: 98.86% at 214 nm, 98.46% at 254 nm, $t_R$=3.144 min.

Example 28

Synthesis of 4-(8-(5,6-Dimethoxypyridin-2-ylamino) imidazo[1,2-b]pyridazin-6-yl)-N-(2-(2-oxo-1,2-dihydropyridin-4-yl)ethyl)benzamide

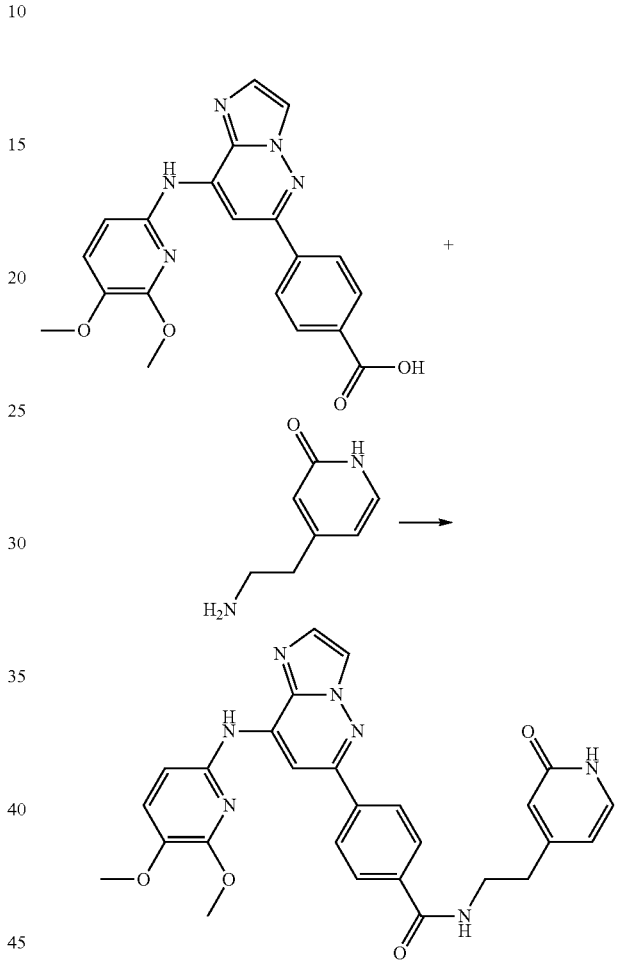

A mixture of 4-(8-(5,6-dimethoxypyridin-2-ylamino)imidazo[1,2-b]pyridazin-6-yl)benzoic acid (76 mg, 0.195 mmol), 4-(2-aminoethyl)pyridin-2(1H)-one (64 mg, 0.215 mmol), 1-methyl-1H-imidazole (96 mg, 1.17 mmol) and EDCI (223 mg, 1.17 mmol) in dichloromethane (10 mL) and DMF (0.5 mL) was stirred at room temperature for 16 h then dichloromethane (20 mL) was added. The mixture was washed with water (2×2 mL) and brine (2×2 mL) then dried over anhydrous sodium sulfate and concentrated in vacuo. The residue was purified by chromatography (silica gel, 10 g, 200~300 mesh, MeOH:dichloromethane=1:10) to afford 4-(8-(5,6-dimethoxypyridin-2-ylamino)imidazo[1,2-b]pyridazin-6-yl)-N-(2-(2-oxo-1,2-dihydropyridin-4-yl)ethyl)benzamide (44 mg, 44%) as a yellow solid. $^1$H NMR (300 MHz, DMSO): δ 11.35 (s, 1H), 9.94 (s, 1H), 8.67 (s, 1H), 8.52 (s, 1H), 8.19 (s, 1H), 8.02-7.93 (m, 4 h), 7.66 (s, 1H), 7.40 (d, 1H, J=8.4 Hz), 7.26 (d, 1H, J=6.6 Hz), 7.10 (d, 1H, J=8.1 Hz), 6.16 (s, 1H), 6.08 (d, 1H, J=6.3 Hz), 4.00 (s, 3H), 3.76 (s, 3H), 3.50-3.40 (m, 2H), 2.69-2.67 (m, 2H). LC-MS: [M+H]$^+$, 512, $t_R$=1.412 min, HPLC: 98.19% at 214 nm, 97.49% at 254 nm, $t_R$=7.244 min.

Example 29

Synthesis of N-(5-(2,5-dimethylpyrrolidin-1-yl)pyridin-2-yl)-6-phenylimidazo[1,2-b]pyridazin-8-amine hydrochloride

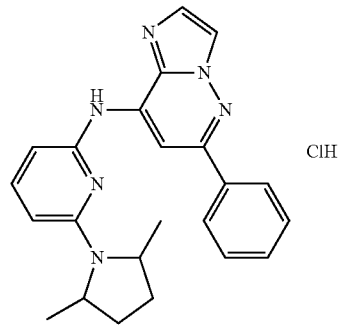 [SMILES: CC1CCC(C)N1c1cccc(Nc2cc(-c3ccccc3)nn3ccnc23)n1 ; Cl]

Step 1

6-(2,5-Dimethylpyrrolidin-1-yl)pyridin-2-amine

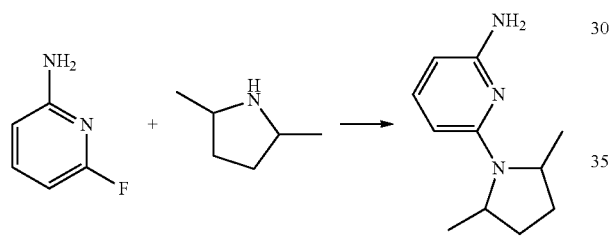

A mixture of 6-fluoropyridin-2-amine (0.5 g, 4.46 mmol) and 2,5-dimethylpyrrolidine (0.664 g, 6.7 mmol) in water (0.3 mL) was heated to 205° C. for 0.5 h in a microwave oven then concentrated in vacuo. The residue was purified by chromatography (silica gel, 10 g, 200~300 mesh, ethyl acetate: petroleum ether=1:30) to afford 6-(2,5-dimethylpyrrolidin-1-yl)pyridin-2-amine (0.383 g, 45%) as a yellow oil. LC-MS: [M+1]$^+$=192, $t_R$=1.048 min.

Step 2

N-(5-(2,5-Dimethylpyrrolidin-1-yl)pyridin-2-yl)-6-phenylimidazo[1,2-b]pyridazin-8-amine hydrochloride

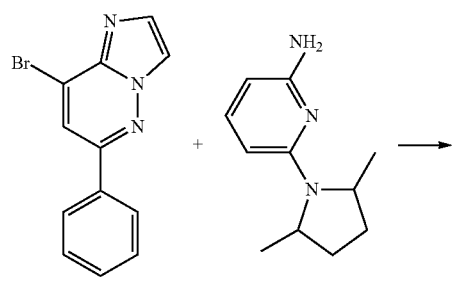

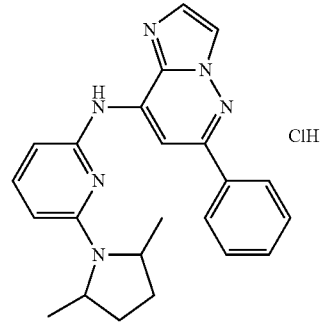

A mixture of 8-bromo-6-phenylimidazo[1,2-b]pyridazine (0.10 g, 0.37 mmol), 6-(2,5-dimethylpyrrolidin-1-yl)pyridin-2-amine (0.084 g, 0.44 mmol), Pd$_2$(dba)$_3$ (21 mg, 0.037 mmol), BINAP (92 mg, 0.148 mmol) and Cs$_2$CO$_3$ (0.362 g, 1.11 mmol) in dioxane (10 mL) was heated to 100° C. for 16 h in a sealed tube under N$_2$ atmosphere. After being concentrated in vacuo the residue was purified by Prep-HPLC (Gemini 5u C18 150×21.2 mm; inject volume: 3 mL/inj, flow rate: 20 mL/min; wavelength: 214 nm and 254 nm; gradient conditions: 30% acetonitrile/70% water (0.1% TFA V/V) initially, proceeding to 50% acetonitrile/50% water (0.1% TFA V/V) in a linear fashion over 9 min) and the fractions containing the desired product were acidified by the addition of concentrated HCl to afford N-(5-(2,5-dimethylpyrrolidin-1-yl)pyridin-2-yl)-6-phenylimidazo[1,2-b]pyridazin-8-amine hydrochloride (40 mg, 26%) as a yellow solid. $^1$H NMR (300 MHz, DMSO): δ 10.71 (s, 1H), 9.06 (s, 1H), 8.55 (s, 1H), 8.28 (s, 1H), 7.95-7.92 (m, 2H), 7.59-7.48 (m, 4 h), 6.69 (d, 1H, J=7.5 Hz), 6.19 (d, 1H, J=8.1 Hz), 4.12 (brs, 2H), 2.10-2.06 (m, 2H), 1.75-1.68 (m, 2H), 1.19 (s, 3H), 1.17 (s, 3H). LC-MS: [M+H]$^+$, 385, $t_R$=2.162 min, HPLC: 96.33% at 214 nm, 98.73% at 254 nm, $t_R$=5.154 min.

Example 30

Synthesis of N-(6-(2-Ethylpyrrolidin-1-yl)pyridin-2-yl)-6-phenylimidazo[1,2-b]pyridazin-8-amine hydrochloride

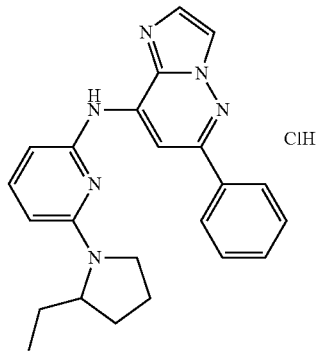 [SMILES: CCC1CCCN1c1cccc(Nc2cc(-c3ccccc3)nn3ccnc23)n1 ; Cl]

Step 1

6-(2-Ethylpyrrolidin-1-yl)pyridin-2-amine

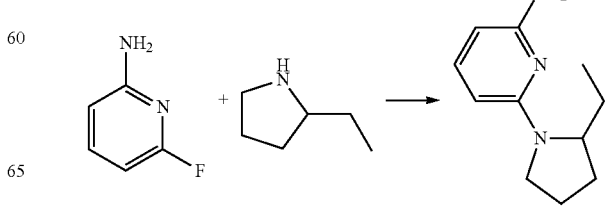

A mixture of 6-fluoropyridin-2-amine (0.5 g, 4.46 mmol) and 2-ethylpyrrolidine (0.664 g, 6.7 mmol) in water (0.3 mL) was heated to 205° C. for 0.5 h in a microwave oven then concentrated in vacuo. The residue was purified by chromatography (silica gel, 10 g, 200~300 mesh, ethyl acetate:petroleum ether=1:30) to afford 6-(2-ethylpyrrolidin-1-yl)pyridin-2-amine (0.57 g, 67%) as a yellow oil. LC-MS: [M+1]⁺=192, $t_R$=1.100 min.

Step 2

N-(6-(2-Ethylpyrrolidin-1-yl)pyridin-2-yl)-6-phenylimidazo[1,2-b]pyridazin-8-amine hydrochloride

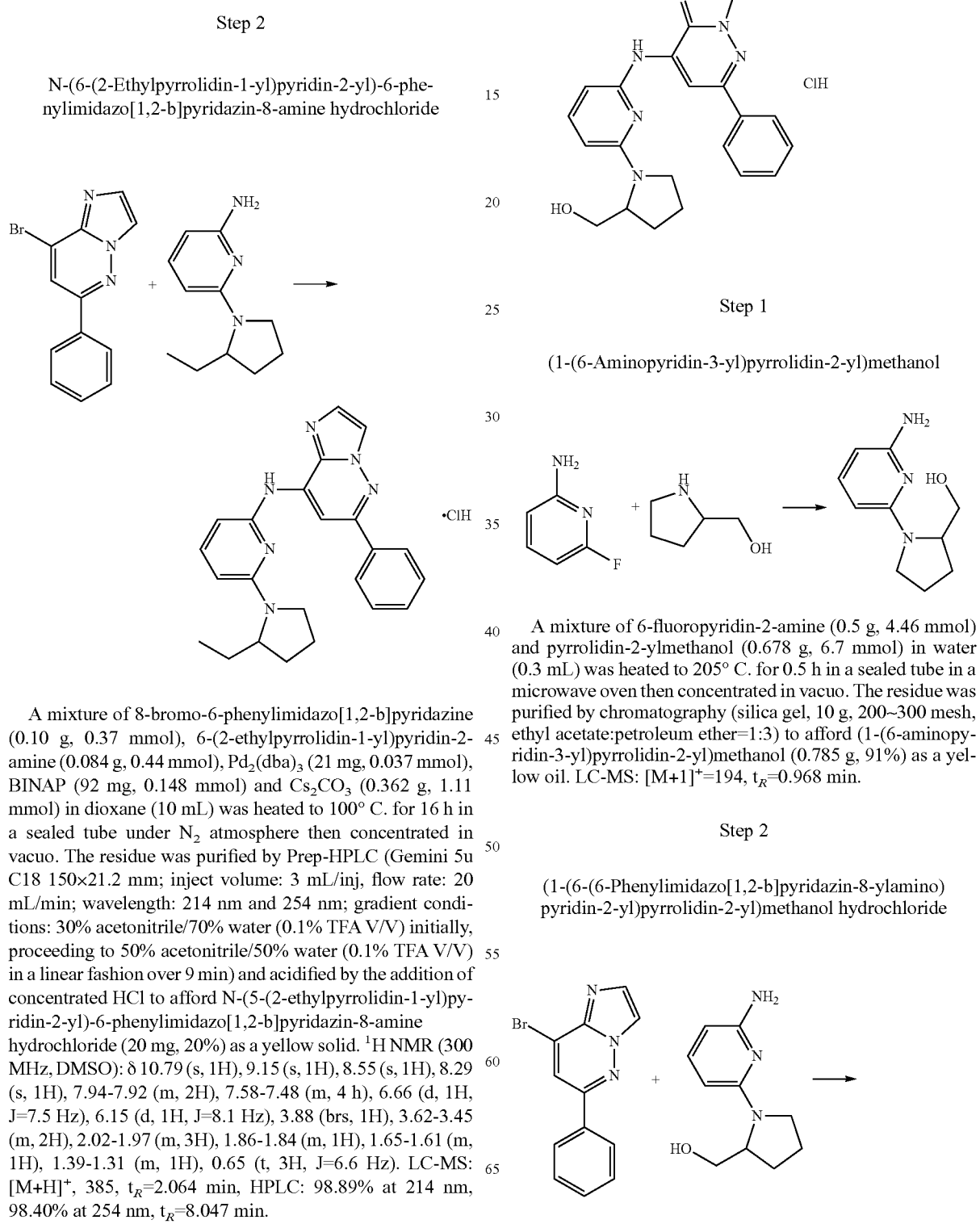

A mixture of 8-bromo-6-phenylimidazo[1,2-b]pyridazine (0.10 g, 0.37 mmol), 6-(2-ethylpyrrolidin-1-yl)pyridin-2-amine (0.084 g, 0.44 mmol), Pd₂(dba)₃ (21 mg, 0.037 mmol), BINAP (92 mg, 0.148 mmol) and Cs₂CO₃ (0.362 g, 1.11 mmol) in dioxane (10 mL) was heated to 100° C. for 16 h in a sealed tube under N₂ atmosphere then concentrated in vacuo. The residue was purified by Prep-HPLC (Gemini 5u C18 150×21.2 mm; inject volume: 3 mL/inj, flow rate: 20 mL/min; wavelength: 214 nm and 254 nm; gradient conditions: 30% acetonitrile/70% water (0.1% TFA V/V) initially, proceeding to 50% acetonitrile/50% water (0.1% TFA V/V) in a linear fashion over 9 min) and acidified by the addition of concentrated HCl to afford N-(5-(2-ethylpyrrolidin-1-yl)pyridin-2-yl)-6-phenylimidazo[1,2-b]pyridazin-8-amine hydrochloride (20 mg, 20%) as a yellow solid. ¹H NMR (300 MHz, DMSO): δ 10.79 (s, 1H), 9.15 (s, 1H), 8.55 (s, 1H), 8.29 (s, 1H), 7.94-7.92 (m, 2H), 7.58-7.48 (m, 4 h), 6.66 (d, 1H, J=7.5 Hz), 6.15 (d, 1H, J=8.1 Hz), 3.88 (brs, 1H), 3.62-3.45 (m, 2H), 2.02-1.97 (m, 3H), 1.86-1.84 (m, 1H), 1.65-1.61 (m, 1H), 1.39-1.31 (m, 1H), 0.65 (t, 3H, J=6.6 Hz). LC-MS: [M+H]⁺, 385, $t_R$=2.064 min, HPLC: 98.89% at 214 nm, 98.40% at 254 nm, $t_R$=8.047 min.

Example 31

Synthesis of (1-(6-(6-Phenylimidazo[1,2-b]pyridazin-8-ylamino)pyridin-2-yl)pyrrolidin-2-yl) methanol hydrochloride Step 1

(1-(6-Aminopyridin-3-yl)pyrrolidin-2-yl)methanol

A mixture of 6-fluoropyridin-2-amine (0.5 g, 4.46 mmol) and pyrrolidin-2-ylmethanol (0.678 g, 6.7 mmol) in water (0.3 mL) was heated to 205° C. for 0.5 h in a sealed tube in a microwave oven then concentrated in vacuo. The residue was purified by chromatography (silica gel, 10 g, 200~300 mesh, ethyl acetate:petroleum ether=1:3) to afford (1-(6-aminopyridin-3-yl)pyrrolidin-2-yl)methanol (0.785 g, 91%) as a yellow oil. LC-MS: [M+1]⁺=194, $t_R$=0.968 min.

Step 2

(1-(6-(6-Phenylimidazo[1,2-b]pyridazin-8-ylamino) pyridin-2-yl)pyrrolidin-2-yl)methanol hydrochloride

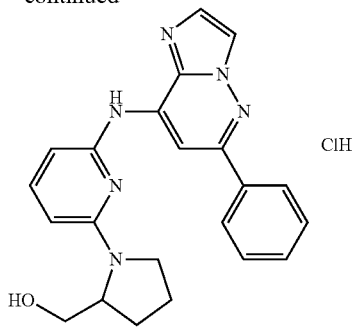

A mixture of 8-bromo-6-phenylimidazo[1,2-b]pyridazine (0.10 g, 0.37 mmol), (1-(6-aminopyridin-3-yl)pyrrolidin-2-yl)methanol (0.085 g, 0.44 mmol), Pd$_2$(dba)$_3$ (21 mg, 0.037 mmol), BINAP (92 mg, 0.148 mmol) and Cs$_2$CO$_3$ (0.362 g, 1.11 mmol) in dioxane (20 mL) was heated to 100° C. for 16 h in a sealed tube under N$_2$ atmosphere then concentrated in vacuo. The residue was purified by Prep-HPLC (Gemini 5u C18 150×21.2 mm; inject volume: 3 mL/inj, flow rate: 20 mL/min; wavelength: 214 nm and 254 nm; gradient conditions: 30% acetonitrile/70% water (0.1% TFA V/V) initially, proceeding to 60% acetonitrile/40% water (0.1% TFA V/V) in a linear fashion over 9 min) then the fractions containing product were acidified by the addition of concentrated HCl to afford (1-(6-(6-phenylimidazo[1,2-b]pyridazin-8-ylamino)pyridin-2-yl)pyrrolidin-2-yl)methanol hydrochloride (68 mg, 44%) as a yellow solid. $^1$H NMR (300 MHz, DMSO): δ 11.06 (s, 1H), 9.19 (s, 1H), 8.58 (d, 1H, J=2.1 Hz), 8.38 (d, 1H, J=2.1 Hz), 7.94-7.91 (m, 2H), 7.57-7.44 (m, 4 h), 6.68 (d, 1H, J=7.5 Hz), 6.22 (d, 1H, J=8.4 Hz), 3.94 (brs, 1H), 3.55-3.32 (m, 4 h), 2.06-1.91 (m, 4 h). LC-MS: [M+H]$^+$, 387, t$_R$=1.646 min, HPLC: 100% at 214 nm, 100% at 254 nm, t$_R$=3.695 min.

Example 32

Synthesis of N-(6-(2,2-dimethylpyrrolidin-1-yl)pyridin-2-yl)-6-phenylimidazo[1,2-b]pyridazin-8-amine hydrochloride

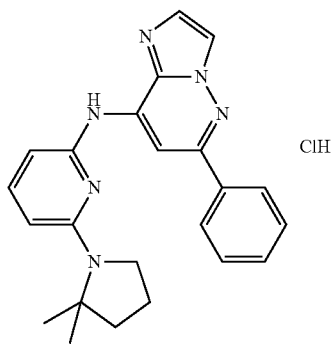 [SMILES: CC1(C)CCCN1c1cccc(Nc2cc(-c3ccccc3)nn3ccnc23)n1 ; Cl]

Step 1

6-(2,2-Dimethylpyrrolidin-1-yl)pyridin-2-amine

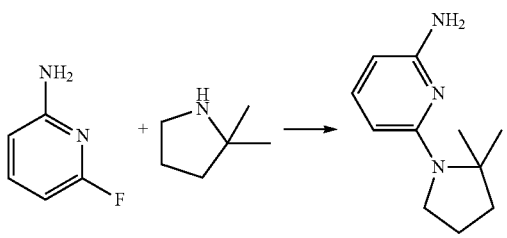

A mixture of 6-fluoropyridin-2-amine (0.5 g, 4.46 mmol) and 2,2-dimethylpyrrolidine (0.67 g, 6.75 mmol) in water (0.3 mL) was heated to 205° C. for 0.5 h in a sealed tube in a microwave oven then concentrated in vacuo. The residue was purified by chromatography (silica gel, 10 g, 200~300 mesh, ethyl acetate:petroleum ether=1:15) to afford 6-(2,2-dimethylpyrrolidin-1-yl)pyridin-2-amine (0.035 g, 4%) as a yellow oil. LC-MS: [M+1]$^+$=192, t$_R$=1.048 min.

Step 2

N-(6-(2,2-Dimethylpyrrolidin-1-yl)pyridin-2-yl)-6-phenylimidazo[1,2-b]pyridazin-8-amine hydrochloride

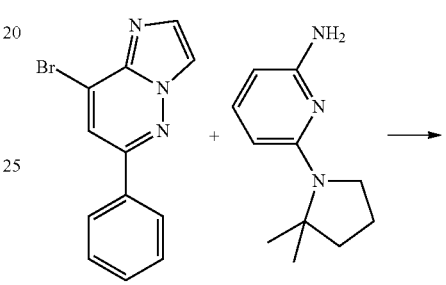

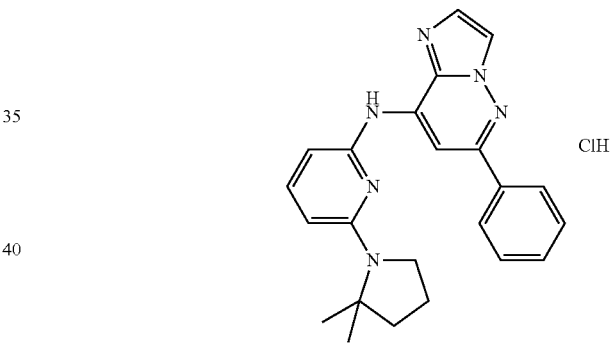

A mixture of 8-bromo-6-phenylimidazo[1,2-b]pyridazine (0.042 g, 0.152 mmol), 6-(2,2-dimethylpyrrolidin-1-yl)pyridin-2-amine (0.035 g, 0.183 mmol), Pd$_2$(dba)$_3$ (9 mg, 0.015 mmol), BINAP (37 mg, 0.06 mmol) and Cs$_2$CO$_3$ (0.15 g, 0.46 mmol) in dioxane (20 mL) was heated to 100° C. for 16 h in a sealed tube under N$_2$ atmosphere then concentrated in vacuo. The residue was purified by Prep-HPLC (Gemini 5u C18 150×21.2 mm; inject volume: 3 mL/inj, flow rate: 20 mL/min; wavelength: 214 nm and 254 nm; gradient conditions: 30% acetonitrile/70% water (0.1% TFA V/V) initially, proceeding to 50% acetonitrile/50% water (0.1% TFA V/V) in a linear fashion over 9 min) then the fractions containing product were acidified by the addition of concentrated HCl to afford N-(6-(2,2-dimethylpyrrolidin-1-yl)pyridin-2-yl)-6-p-tolylimidazo[1,2-b]pyridazin-8-amine hydrochloride (21 mg, 32%) as a yellow solid. $^1$H NMR (300 MHz, DMSO): δ 10.45 (s, 1H), 8.89 (s, 1H), 8.52 (s, 1H), 8.22 (s, 1H), 7.93-7.89 (m, 2H), 7.58-7.45 (m, 4 h), 6.67 (d, 1H, J=7.5 Hz), 6.02 (d, 1H, J=8.4 Hz), 3.62 (t, 1H, J=6.9 Hz). 1.92-1.90 (m, 4 h), 1.23 (s, 6H). LC-MS: [M+H]$^+$, 385, t$_R$=2.057 min, HPLC: 96.85% at 214 nm, 97.34% at 254 nm, t$_R$=8.063 min.

Example 33

Synthesis of 4-(8-(5,6-Dimethoxypyridin-2-ylamino)imidazo[1,2-b]pyridazin-6-yl)-N-(2-(1-methyl-2-oxo-1,2-dihydropyridin-4-yl)ethyl)benzamide

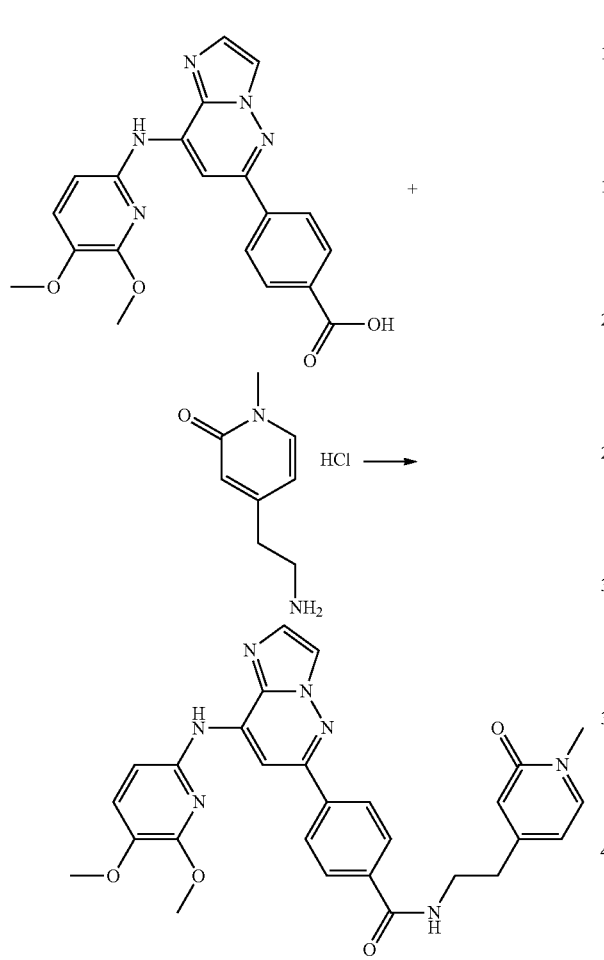

A mixture of 4-(8-(5,6-dimethoxypyridin-2-ylamino)imidazo[1,2-b]pyridazin-6-yl)benzoic acid (50 mg, 0.265 mmol), 4-(2-aminoethyl)-1-methylpyridin-2(1H)-one hydrochloride (16 mg, 0.132 mmol), 1-methyl-1H-imidazole (118 mg, 1.45 mmol) and EDCI (276 mg, 1.45 mmol) in dichloromethane (10 mL) and DMF (3 mL) was stirred at room temperature for 16 h then extracted with ethyl acetate (50 mL). The combined extracts were washed with water (5 mL×2), then brine (5 mL×2). After drying and concentration, the residue was purified by chromatography (silica gel, 5 g, 200–300 mesh, methanol:dichloromethane=1:30) to afford 4-(8-(5,6-dimethoxypyridin-2-ylamino)imidazo[1,2-b]pyridazin-6-yl)-N-(2-(1-methyl-2-oxo-1,2-dihydropyridin-4-yl)ethyl)benzamide (27 mg, 21%) as a yellow solid. $^1$H NMR (300 MHz, DMSO): δ 9.94 (s, 1H), 8.67 (s, 1H), 8.53 (s, 1H), 8.20 (s, 1H), 8.03-7.94 (m, 4 h), 7.66 (s, 1H), 7.58 (d, 1H, J=6.6 Hz), 7.41 (d, 1H, J=8.4 Hz), 7.11 (d, 1H, J=8.4 Hz), 6.23 (s, 1H), 6.13 (d, 1H, J=7.2 Hz), 4.01 (s, 3H), 3.77 (s, 3H), 3.53-3.47 (m, 2H), 3.36 (s, 3H), 2.69 (t, 2H, J=6.6 Hz). LC-MS: [M+H]$^+$, 526, $t_R$=1.367 min, HPLC: 98.9% at 214 nm, 99.36% at 254 nm, $t_R$=4.615 min.

Example 34

Synthesis of N-(6-(3,3-Dimethylpyrrolidin-1-yl)pyridin-2-yl)-6-phenylimidazo[1,2-b]pyridazin-8-amine

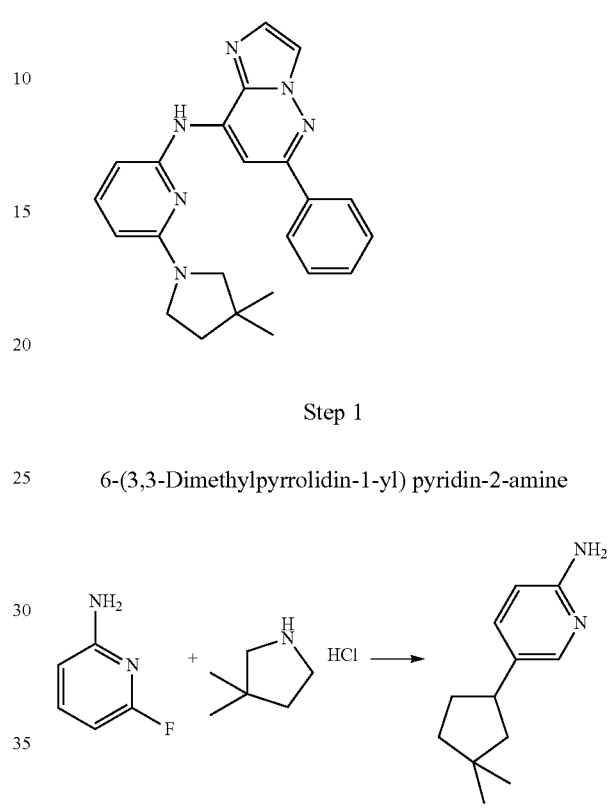

Step 1

6-(3,3-Dimethylpyrrolidin-1-yl) pyridin-2-amine

A mixture of 6-fluoropyridin-2-amine (0.5 g, 4.46 mmol), 3,3-dimethylpyrrolidine hydrochloride (0.73 g, 5.35 mmol) and Et$_3$N (1.08 g, 10.7 mmol) in water (0.2 mL) was heated to 205° C. for 0.5 h in a sealed tube in a microwave oven then concentrated in vacuo. The residue was purified by chromatography (silica gel, 10 g, 200-300 mesh, ethyl acetate:petroleum ether=1:15) to afford 6-(3,3-dimethylpyrrolidin-1-yl) pyridin-2-amine (0.67 g, 78%) as a yellow oil. LC-MS: [M+1]$^+$=192, $t_R$=1.187 min.

Step 2

N-(6-(3,3-Dimethylpyrrolidin-1-yl)pyridin-2-yl)-6-phenylimidazo[1,2-b]pyridazin-8-amine

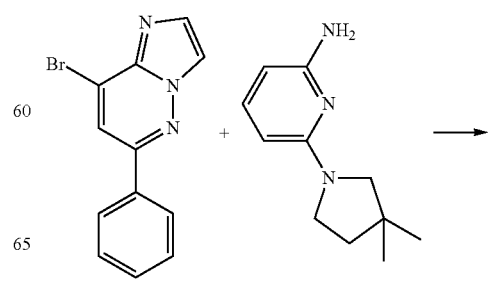

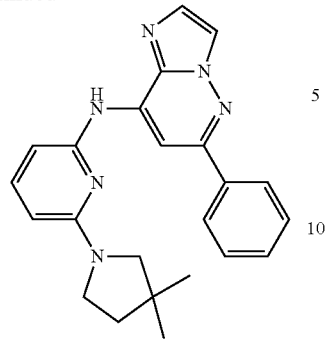

A mixture of 8-bromo-6-phenylimidazo[1,2-b]pyridazine (0.10 g, 0.37 mmol), 6-(3,3-dimethyl pyrrolidin-1-yl)pyridin-2-amine (0.084 g, 0.44 mmol), Pd$_2$(dba)$_3$ (21 mg, 0.037 mmol), BINAP (92 mg, 0.148 mmol) and Cs$_2$CO$_3$ (0.362 g, 1.11 mmol) in dioxane (10 mL) was heated to 100° C. for 16 h in a sealed tube under N$_2$ atmosphere then concentrated and the residue was purified by chromatography (silica gel, 10 g, 200~300 mesh, ethyl acetate:petroleum ether=1:10) to afford N-(6-(3,3-dimethylpyrrolidin-1-yl)pyridin-2-yl)-6-phenylimidazo[1,2-b]pyridazin-8-amine (36 mg, 26%) as a yellow solid. $^1$H NMR (300 MHz, DMSO): δ 9.68 (s, 1H), 8.87 (s, 1H), 8.19 (d, 1H, J=1.2 Hz), 7.95-7.92 (m, 2H), 7.64 (s, 1H), 7.53-7.40 (m, 4H), 6.72 (d, 1H, J=7.8 Hz), 6.02 (d, 1H, J=8.1 Hz), 3.51 (t, 1H, J=6.9 Hz). 3.30 (s, 2H), 1.81 (t, 2H, J=6.9 Hz), 1.13 (s, 6H). LC-MS: [M+H]$^+$, 385, t$_R$=2.099 min, HPLC: 96.88% at 214 nm, 97.82% at 254 nm, t$_R$=8.077 min.

Example 35

Synthesis of N-(6-(2-(Methoxymethyl)pyrrolidin-1-yl)pyridin-2-yl)-6-phenylimidazo[1,2-b]pyridazin-8-amine hydrochloride

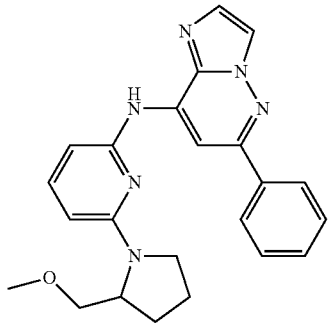 [SMILES: COCC1CCCN1c1cccc(Nc2cc(-c3ccccc3)nn3ccnc23)n1]

Step 1

6-(2-(Methoxymethyl)pyrrolidin-1-yl)pyridin-2-amine

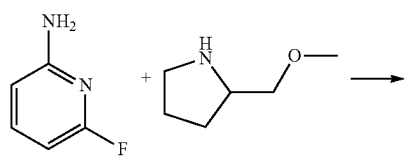

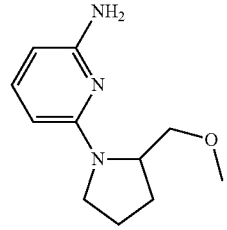

A mixture of 6-fluoropyridin-2-amine (0.5 g, 4.46 mmol) and 2-(methoxymethyl)pyrrolidine (0.617 g, 5.35 mmol) in water (0.2 mL) was heated to 205° C. for 0.5 h in a sealed tube in a microwave oven then concentrated in vacuo. The residue was purified by chromatography (silica gel, 10 g, 200~300 mesh, ethyl acetate:petroleum ether=1:15) to afford 6-(2-(methoxymethyl)pyrrolidin-1-yl)pyridin-2-amine (0.68 g, 74%) as a yellow oil. LC-MS: [M+1]$^+$=208, t$_R$=1.052 min.

Step 2

N-(6-(2-(Methoxymethyl)pyrrolidin-1-yl)pyridin-2-yl)-6-phenylimidazo[1,2-b]pyridazin-8-amine hydrochloride

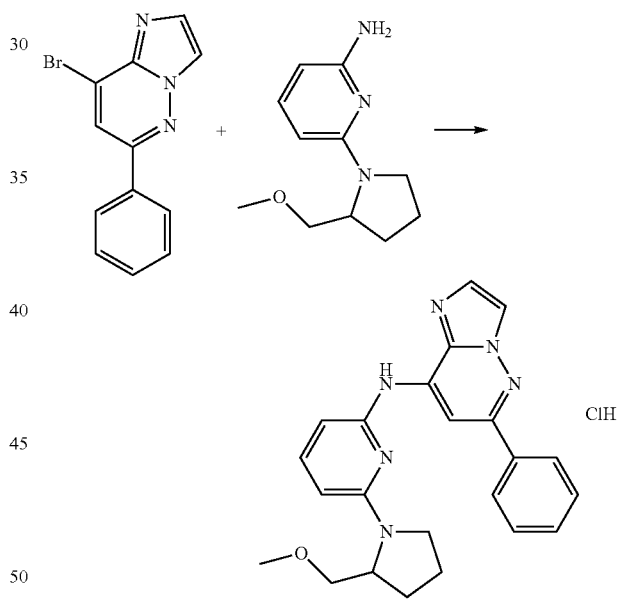

A mixture of 8-bromo-6-phenylimidazo[1,2-b]pyridazine (0.10 g, 0.37 mmol), 6-(2-(methoxymethyl)pyrrolidin-1-yl)pyridin-2-amine (0.091 g, 0.44 mmol), Pd$_2$(dba)$_3$ (21 mg, 0.037 mmol), BINAP (92 mg, 0.148 mmol) and Cs$_2$CO$_3$ (0.362 g, 1.11 mmol) in dioxane (10 mL) was heated to 100° C. for 16 h in a sealed tube under N$_2$ atmosphere then concentrated in vacuo. The residue was purified by Prep-HPLC (Gemini 5u C18 150×21.2 mm; inject volume: 3 mL/inj, flow rate: 20 mL/min; wavelength: 214 nm and 254 nm; gradient conditions: 35% acetonitrile/65% water (0.1% TFA V/V) initially, proceeding to 50% acetonitrile/50% water (0.1% TFA V/V) in a linear fashion over 9 min) then the fractions containing product were acidified by the addition of concentrated HCl to afford N-(5-(2-(methoxymethyl)pyrrolidin-1-yl)pyridin-2-yl)-6-p-tolylimidazo[1,2-b]pyridazin-8-amine hydrochloride (41 mg, 26%) as a yellow solid. ¹H NMR (300 MHz, CD3OD): δ 8.92 (s, 1H), 8.36 (d, 1H, J=2.1 Hz), 8.11 (d, 1H, J=2.1 Hz), 8.01-7.98 (m, 2H), 7.58-7.50 (m, 4 h), 6.45 (d, 1H, J=7.5 Hz), 6.32 (d, 1H, J=8.1 Hz), 4.24 (brs, 1H), 3.61-3.58 (m, 1H), 3.52-3.43 (m, 2H), 3.38-3.35 (m, 1H), 3.18 (s, 3H), 2.12-2.00 (m, 4 h). LC-MS: [M+H]⁺, 401, $t_R$=1.974 min, HPLC: 99.50% at 214 nm, 99.43% at 254 nm, $t_R$=6.735 min.

Example 36

Synthesis of 3-(8-(6-(2-(Methoxymethyl)pyrrolidin-1-yl) pyridin-2-ylamino) imidazo[1,2-b]pyridazin-6-yl)benzoic acid

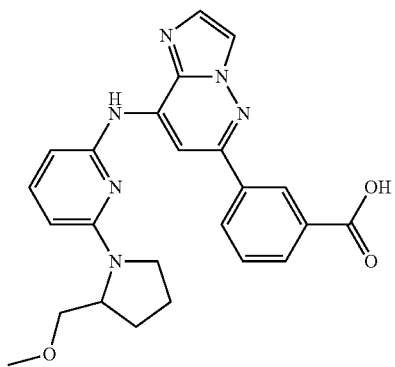 [SMILES: COCC1CCCN1c1cccc(Nc2cc(-c3cccc(C(=O)O)c3)nn3ccnc23)n1]

Step 1

Methyl 3-(8-(6-(2-(methoxymethyl)pyrrolidin-1-yl) pyridin-2-ylamino) imidazo[1,2-b]pyridazin-6-yl) benzoate

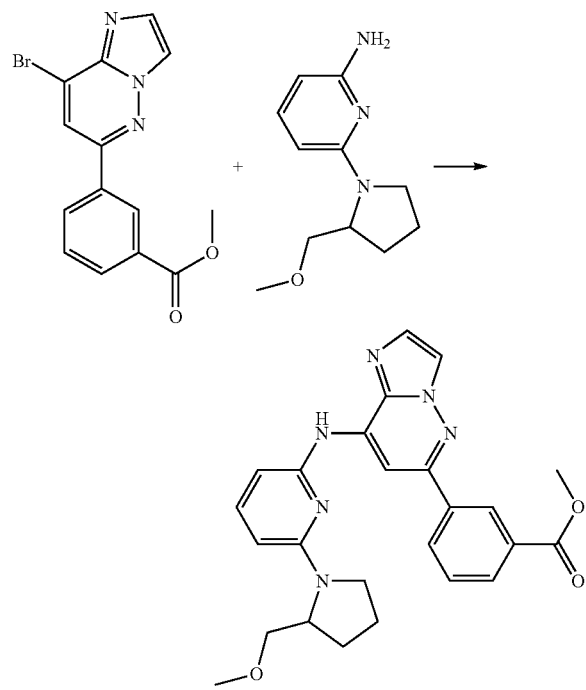

A mixture of methyl 3-(8-bromoimidazo[1,2-b]pyridazin-6-yl)benzoate (0.10 g, 0.3 mmol), 6-(2-(methoxymethyl)pyrrolidin-1-yl)pyridin-2-amine (0.083 g, 0.4 mmol), Pd₂(dba)₃ (0.019 g, 0.033 mmol), BINAP (0.083 g, 0.134 mmol) and Cs₂CO₃ (0.326 g, 1.0 mmol) in dioxane (20 mL) was heated to 100° C. for 16 h in a sealed tube under N₂ atmosphere then concentrated in vacuo. The residue was purified by chromatography (silica gel, 10 g, 200~300 mesh, ethyl acetate:petroleum ether=1:15) to afford methyl 3-(8-(6-(2-(methoxymethyl)pyrrolidin-1-yl)pyridin-2-ylamino)imidazo[1,2-b]pyridazin-6-yl)benzoate (0.050 g) as a yellow solid. LC-MS: [M+1]⁺=459, $t_R$=1.985 min. This contained some unidentified impurities and was used directly without further purification.

Step 2

3-(8-(6-(2-(Methoxymethyl)pyrrolidin-1-yl)pyridin-2-ylamino) imidazo[1,2-b]pyridazin-6-yl)benzoic acid

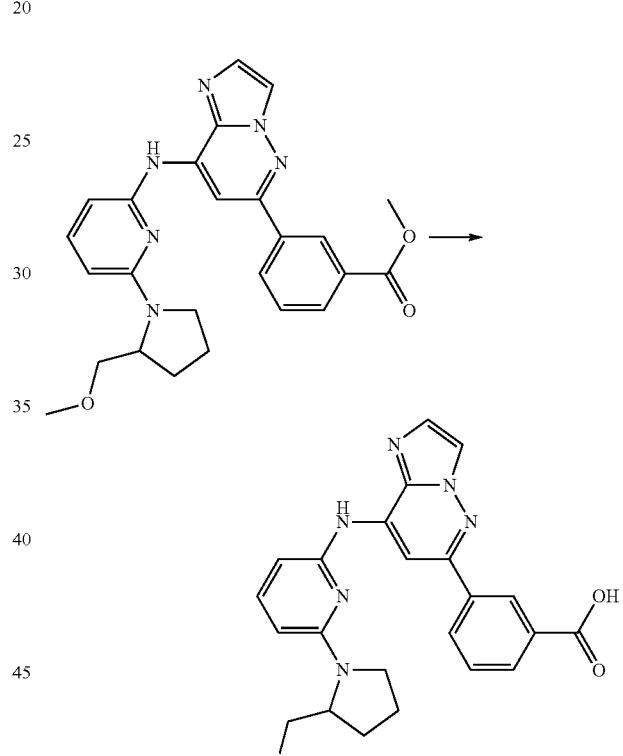

To a stirred solution of methyl 3-(8-(6-(2-(methoxymethyl)pyrrolidin-1-yl)pyridin-2-ylamino)imidazo[1,2-b]pyridazin-6-yl)benzoate (0.155 g, 0.34 mmol) in dioxane (10 mL) and H₂O (4 mL) was added NaOH (135 mg, 3.4 mmol) at 40° C. After 4 h the mixture was washed with ether (10 mL), the aqueous layer adjusted to pH=4 with concentrated HCl, then was concentrated and filtered. The collected solid was washed with ether and dried to afford 3-(8-(6-(2-(methoxymethyl)pyrrolidin-1-yl)pyridin-2-ylamino)imidazo[1,2-b]pyridazin-6-yl)benzoic acid (0.037 g, 28% over two steps) as a yellow solid. ¹H NMR (300 MHz, CD3OD): δ 8.80 (s, 1H), 8.54 (s, 1H), 8.20-8.08 (m, 3H), 7.72 (d, 1H, J=1.5 Hz), 7.59 (t, 1H, J=7.8 Hz), 7.45 (t, 1H, J=7.8 Hz), 6.31 (d, 1H, J=7.5 Hz), 6.17 (d, 1H, J=8.4 Hz), 4.21 (brs, 1H), 3.62-3.58 (m, 1H), 3.51-3.42 (m, 2H), 3.34-3.32 (m, 1H), 3.11 (s, 3H), 2.10-2.00 (m, 4 h). LC-MS: [M+H]⁺, 445, $t_R$=1.714 min, HPLC: 95.14% at 214 nm, 95.00% at 254 nm, $t_R$=5.9 min.

Example 37

Synthesis of 6-(1H-indazol-5-yl)-N-(6-(2-methylpyrrolidin-1-yl)pyridin-2-yl)imidazo[1,2-b]pyridazin-8-amine

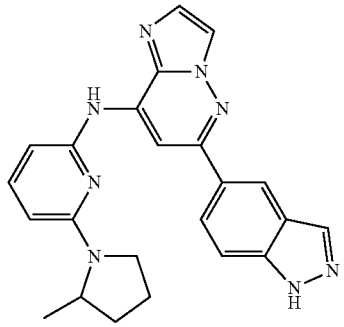 [SMILES: CC1CCCN1c1cccc(Nc2cc(-c3ccc4[nH]ncc4c3)nn3ccnc23)n1]

Step 1

6-Chloro-N-(6-(2-methylpyrrolidin-1-yl) pyridin-2-yl) imidazo[1,2-b]pyridazin-8-amine

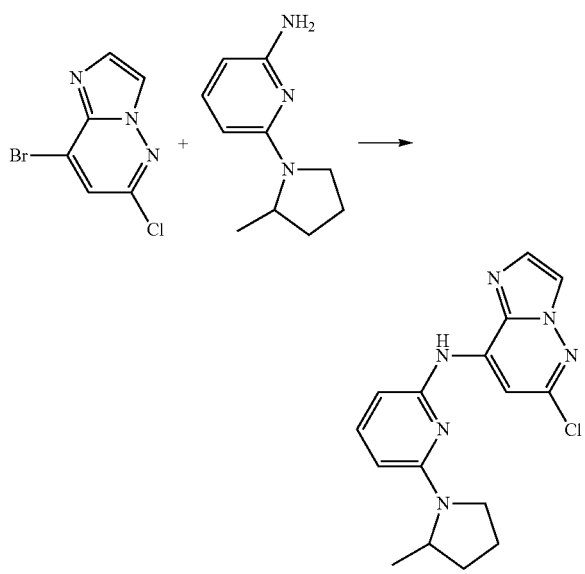

A mixture of 8-bromo-6-chloroimidazo[1,2-b]pyridazine (1.0 g, 4.3 mmol), 6-(2-methylpyrrolidin-1-yl)pyridin-2-amine (0.84 g, 4.73 mmol), Pd$_2$(dba)$_3$ (0.247 g, 0.43 mmol), BINAP (0.536 g, 0.86 mmol) and Cs$_2$CO$_3$ (4.21 g, 12.9 mmol) in dioxane (30 mL) was heated to 100° C. for 16 h in a sealed tube under N$_2$ atmosphere then concentrated in vacuo. The residue was purified by chromatography (silica gel, 10 g, 200~300 mesh, ethyl acetate:petroleum ether=1:15) to afford 6-chloro-N-(6-(2-methylpyrrolidin-1-yl)pyridin-2-yl)imidazo[1,2-b]pyridazin-8-amine (1.2 g, 85%) as a yellow solid. LC-MS: [M+1]$^+$=329, t$_R$=1.930 min.

Step 2

6-(1H-Indazol-5-yl)-N-(6-(2-methylpyrrolidin-1-yl)pyridin-2-yl)imidazo[1,2-b]pyridazin-8-amine

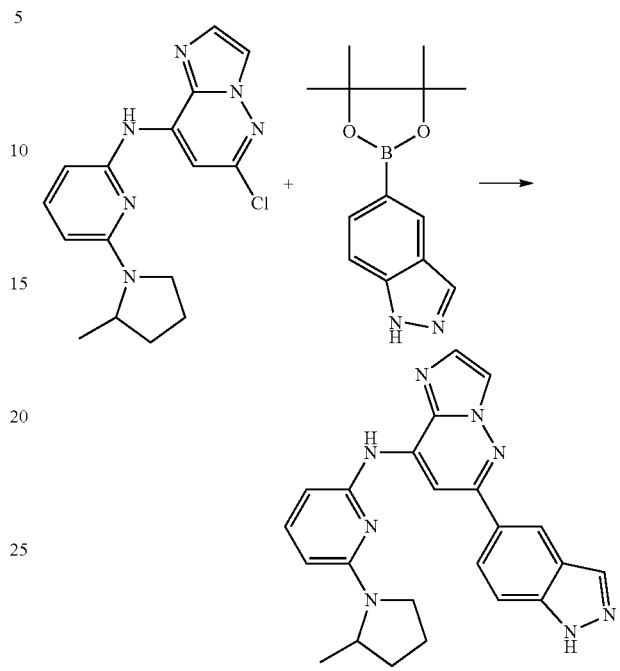

A mixture of 6-chloro-N-(6-(2-methylpyrrolidin-1-yl)pyridin-2-yl)imidazo[1,2-b]pyridazin-8-amine (0.1 g, 0.304 mmol), 5-(4,4,5,5-tetramethyl-1,3,2-dioxaborolan-2-yl)-1H-indazole (0.082 g, 0.33 mmol), Pd$_2$(dba)$_3$ (0.035 g, 0.061 mmol), X-phos (0.058 g, 0.122 mmol) and Na$_2$CO$_3$ (0.097 g, 0.912 mmol) in dioxane (20 mL) and water (10 mL) was heated to 100° C. for 16 h in a sealed tube under N$_2$ atmosphere then concentrated in vacuo. The residue was purified by chromatography (silica gel, 10 g, 200~300 mesh, methanol:dichloromethane=1:30) to afford 6-(1H-indazol-5-yl)-N-(6-(2-methylpyrrolidin-1-yl)pyridin-2-yl)imidazo[1,2-b]pyridazin-8-amine (48 mg, 38%) as a yellow solid. $^1$H NMR (300 MHz, DMSO): δ 13.25 (s, 1H), 9.59 (s, 1H), 8.87 (s, 1H), 8.29-8.17 (m, 3H), 7.96 (dd, 1H, J1=8.7 Hz, J2=1.8 Hz), 7.67-7.62 (m, 2H), 7.43 (t, 1H, J=7.8 Hz), 6.73 (d, 1H, J=7.5 Hz), 6.06 (d, 1H, J=8.1 Hz), 4.25-4.21 (m, 1H), 3.63-3.58 (m, 1H), 3.44-3.39 (m, 1H), 2.10-2.05 (m, 3H), 1.70 (s, 1H), 1.12 (d, 3H, J=6.0 Hz). LC-MS: [M+H]$^+$, 411, t$_R$=1.619 min, HPLC: 98.4% at 214 nm, 97.91% at 254 nm, t$_R$=5.848 min.

Example 38

Synthesis of 3-(8-(6-(3,5-Dimethylpiperidin-1-yl)pyridin-2-ylamino) imidazo[1,2-b]pyridazin-6-yl-benzoic acid

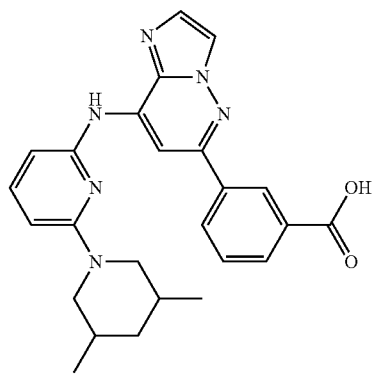 [SMILES: CC1CC(C)CN(c2cccc(Nc3cc(-c4cccc(C(=O)O)c4)nn4ccnc34)n2)C1]

Step 1

6-(3,5-Dimethylpiperidin-1-yl) pyridin-2-amine

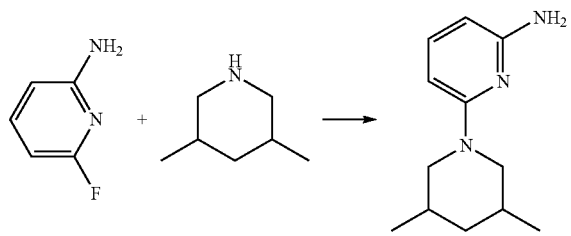

A mixture of 6-fluoropyridin-2-amine (0.5 g, 4.46 mmol) and 3,5-dimethylpiperidine (0.61 g, 5.35 mmol) in water (0.2 mL) was heated to 205° C. for 0.5 h in a sealed tube in a microwave oven then concentrated in vacuo. The residue was purified by chromatography (silica gel, 10 g, 200-300 mesh, ethyl acetate:petroleum ether=1:8) to afford 6-(3,5-dimethylpiperidin-1-yl)pyridin-2-amine (0.76 g, 83%) as a yellow oil. LC-MS: [M+1]$^+$=206, $t_R$=1.240 min.

Step 2

Methyl 3-(8-(6-(3,5-Dimethylpiperidin-1-yl) pyridin-2-ylamino) imidazo[1,2-b]pyridazin-6-yl)benzoate hydrochloride

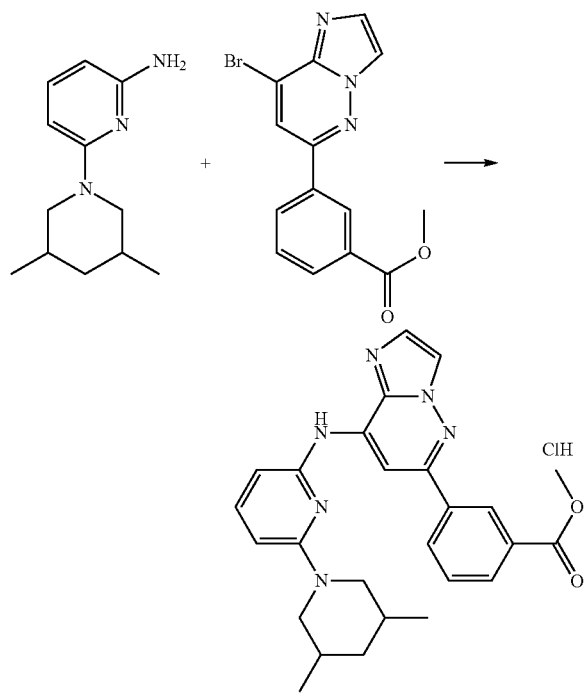

A mixture of methyl 3-(8-bromoimidazo[1,2-b]pyridazin-6-yl)benzoate (0.10 g, 0.3 mmol), 6-(3,5-dimethylpiperidin-1-yl)pyridin-2-amine (0.068 g, 0.33 mmol), Pd$_2$(dba)$_3$ (0.017 g, 0.03 mmol), BINAP (0.037 g, 0.06 mmol) and Cs$_2$CO$_3$ (0.293 g, 0.9 mmol) in dioxane (20 mL) was heated to 100° C. for 16 h in a sealed tube under N$_2$ atmosphere then concentrated in vacuo. The residue was purified by chromatography (silica gel, 10 g, 200~300 mesh, ethyl acetate:petroleum ether=1:20) and then further purified by Prep-HPLC (Gemini 5u C18 150×21.2 mm; inject volume: 3 mL/inj, flow rate: 20 mL/min; wavelength: 214 nm and 254 nm; gradient conditions: 25% acetonitrile/75% water (0.1% TFA, v/v) initially, proceeding to 50% acetonitrile/50% water (0.1% TFA, v/v) in a linear fashion over 9 min). The fractions containing product were acidified by the addition of concentrated HCl then concentration to afford methyl 3-(8-(6-(3,5-dimethylpiperidin-1-yl)pyridin-2-ylamino)imidazo[1,2-b]pyridazin-6-yl)benzoate hydrochloride (0.025 g, 18%) as a yellow solid. LC-MS: [M+1]$^+$=457, $t_R$=2.284 min.

Step 3

3-(8-(6-(3,5-Dimethylpiperidin-1-yl) pyridin-2-ylamino) imidazo[1,2-b]pyridazin-6-ylbenzoic acid

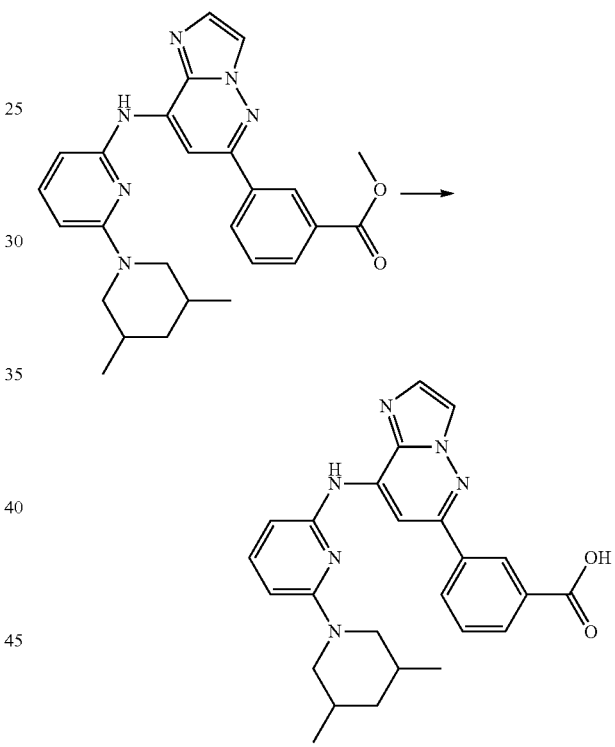

To a stirred solution of methyl 3-(8-(6-(3,5-dimethylpiperidin-1-yl)pyridin-2-ylamino)imidazo[1,2-b]pyridazin-6-yl)benzoate hydrochloride (0.025 g, 0.055 mmol) in dioxane (10 mL) and H$_2$O (5 mL) was added NaOH (22 mg, 0.55 mmol) at 40° C. After 2 h the mixture was washed with ether (10 mL) and the aqueous layer was adjusted to pH=4, then filtered. The solid was washed with ether and dried to afford 3-(8-(6-(3,5-dimethylpiperidin-1-yl)pyridin-2-ylamino)imidazo[1,2-b]pyridazin-6-yl)benzoic acid (0.017 g, 70%) as a yellow solid. $^1$H NMR (300 MHz, DMSO): δ 9.99 (s, 1H), 8.67 (s, 1H), 8.52 (s, 1H), 8.35 (s, 1H), 8.19 (d, 1H, J=7.8 Hz), 8.09 (d, 1H, J=7.8 Hz), 7.84 (s, 1H), 7.71-7.49 (m, 2H), 6.76-6.72 (m, 1H), 6.52-6.48 (m, 1H), 4.22 (d, 1H, J=12.6 Hz), 3.65-3.59 (m, 1H), 3.28-3.21 (m, 1H), 2.33 (t, 1H, J=12.0 Hz), 1.92-1.41 (m, 4 h), 0.80-0.69 (m, 6H). LC-MS: [M+H]$^+$, 443, $t_R$=1.825 min, HPLC: 98.43% at 214 nm, 99.05% at 254 nm, $t_R$=6.85 min.

Example 39

Synthesis of 6-(3-Methoxyphenyl)-N-(6-(2-methylpyrrolidin-1-yl) pyridin-2-yl) imidazo[1,2-b]pyridazin-8-amine

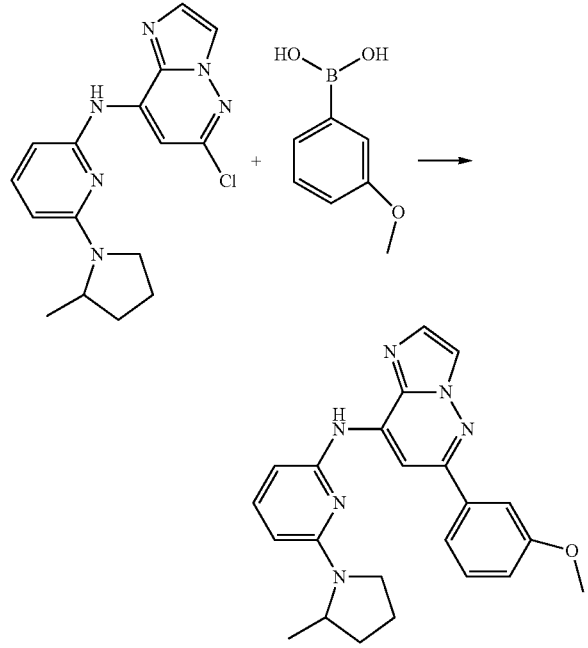

A mixture of 6-chloro-N-(6-(2-methylpyrrolidin-1-yl)pyridin-2-yl)imidazo[1,2-b]pyridazin-8-amine (0.05 g, 0.152 mmol), 3-methoxyphenylboronic acid (0.025 g, 0.167 mmol), Pd$_2$(dba)$_3$ (0.017 g, 0.03 mmol), X-phos (0.029 g, 0.06 mmol) and Na$_2$CO$_3$ (0.048 g, 0.456 mmol) in dioxane (20 mL) and water (5 mL) was heated to 100° C. for 16 h in a sealed tube under N$_2$ atmosphere then concentrated in vacuo. The residue was purified by chromatography (silica gel, 10 g, 200~300 mesh, ethyl acetate:petroleum ether=1:10) to afford 6-(3-methoxyphenyl)-N-(6-(2-methylpyrrolidin-1-yl)pyridin-2-yl)imidazo[1,2-b]pyridazin-8-amine (25 mg, 41%) as a yellow solid. $^1$H NMR (300 MHz, CD3OD): δ 8.76 (s, 1H), 7.95 (s, 1H), 7.56 (s, 1H), 7.47-7.32 (m, 4 h), 7.03-6.99 (m, 1H), 6.23 (d, 1H, J=7.5 Hz), 6.03 (d, 1H, J=8.4 Hz), 4.25-4.21 (m, 1H), 3.86 (s, 3H), 3.62-3.56 (m, 1H), 3.44-3.35 (m, 1H), 2.17-1.99 (m, 3H), 1.74-1.71 (m, 1H), 1.17 (d, 3H, J=6.3 Hz). LC-MS: [M+H]$^+$, 401, t$_R$=1.961 min, HPLC: 95.06% at 214 nm, 98.71% at 254 nm, t$_R$=7.643 min.

Example 40

Synthesis of N-(2-Hydroxyethyl)-3-(8-(6-(2-methylpyrrolidin-1-yl) pyridin-2-ylamino) imidazo[1,2-b]pyridazin-6-yl)benzamide

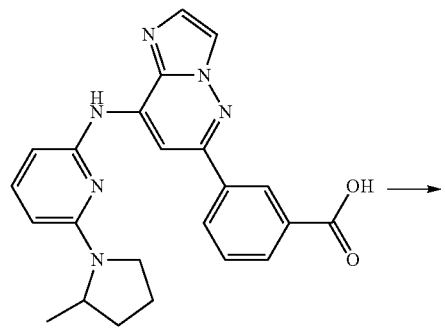

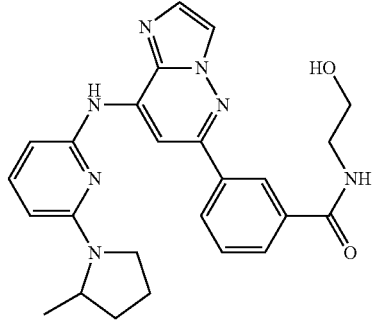

A mixture of 3-(8-(6-(2-methylpyrrolidin-1-yl)pyridin-2-ylamino)imidazo[1,2-b]pyridazin-6-yl)benzoic acid (50 mg, 0.121 mmol), 2-aminoethanol (8 mg, 0.133 mmol), 1-methyl-1H-imidazole (40 mg, 0.484 mmol) and EDCI (92 mg, 0.484 mmol) in dichloromethane (10 mL) and DMF (0.2 mL) was stirred at room temperature for 16 h then extracted with ethyl acetate (50 mL). The combined extracts were washed with water (2×2 mL), then brine (2×2 mL). After drying and concentration in vacuo, the residue was purified by chromatography (silica gel, 10 g, 200~300 mesh, methanol:dichloromethane=1:50) and further purified by Prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to afford N-(2-hydroxyethyl)-3-(8-(6-(2-methylpyrrolidin-1-yl)pyridin-2-ylamino)imidazo[1,2-b]pyridazin-6-yl)benzamide (6 mg, 10%) as a yellow solid. $^1$H NMR (300 MHz, CD3OD): δ 8.93 (s, 1H), 8.49 (s, 1H), 8.37 (s, 1H), 8.18 (dd, 1H, J1=6.6 Hz, J2=1.8 Hz), 8.08 (d, 1H, J=2.1 Hz), 8.04-8.01 (m, 1H), 7.67 (t, 1H, J=7.8 Hz), 7.60-7.55 (m, 1H), 6.39 (d, 1H, J=7.5 Hz), 6.29 (d, 1H, J=8.7 Hz), 4.30-4.26 (m, 1H), 3.78-3.69 (m, 3H), 3.58-3.49 (m, 3H), 2.21-2.08 (m, 3H), 1.81-1.78 (m, 1H), 1.19 (d, 3H, J=5.1 Hz). LC-MS: [M+H]$^+$, 458, t$_R$=1.52 min, HPLC: 96.29% at 214 nm, 96.47% at 254 nm, t$_R$=5.332 min.

Example 41

Synthesis of N-(1-Hydroxypropan-2-yl)-3-(8-(6-(2-methylpyrrolidin-1-yl)pyridin-2-ylamino) imidazo[1,2-b]pyridazin-6-yl)benzamide

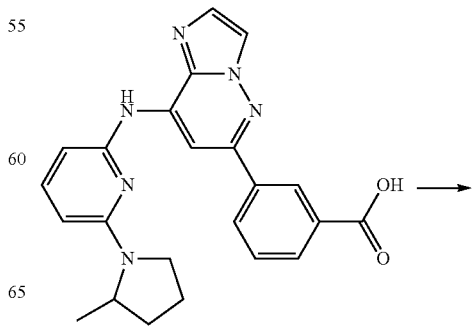

137

-continued

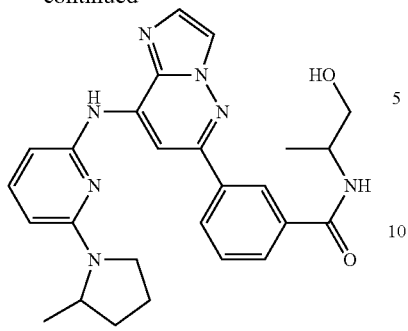

138

-continued

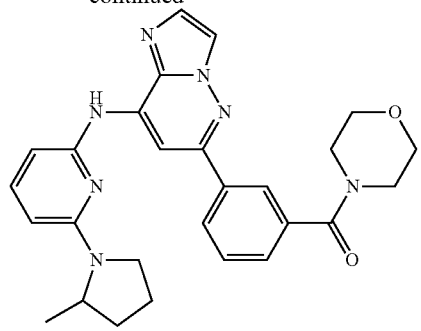

A mixture of 3-(8-(6-(2-methylpyrrolidin-1-yl)pyridin-2-ylamino)imidazo[1,2-b]pyridazin-6-yl)benzoic acid (50 mg, 0.121 mmol), 2-aminopropan-1-ol (10 mg, 0.133 mmol), 1-methyl-1H-imidazole (40 mg, 0.484 mmol) and EDCI (92 mg, 0.484 mmol) in dichloromethane (10 mL) and DMF (0.2 mL) was stirred at room temperature for 20 h then extracted with ethyl acetate (50 mL) and washed with water (2×2 mL), then brine (2×2 mL). After drying and concentration, the residue was purified by chromatography (silica gel, 10 g, 200–300 mesh, methanol:dichloromethane=1:50) and further purified by Prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 45% acetonitrile/55% water (0.1% TFA, v/v) in a linear fashion over 9 min) to afford N-(1-hydroxypropan-2-yl)-3-(8-(6-(2-methylpyrrolidin-1-yl)pyridin-2-ylamino)imidazo[1,2-b]pyridazin-6-yl)benzamide (8.7 mg, 14%) as a yellow solid. $^1$H NMR (300 MHz, CD3OD): δ 8.91 (s, 1H), 8.46 (s, 1H), 8.37 (s, 1H), 8.17-8.00 (m, 4 h), 7.65 (t, 1H, J=7.8 Hz), 7.58-7.55 (m, 1H), 6.40 (d, 1H, J=7.5 Hz), 6.28 (d, 1H, J=8.4 Hz), 4.25-4.21 (m, 2H), 3.71-3.58 (m, 3H), 3.54-3.48 (m, 1H), 2.19-2.07 (m, 3H), 1.81 (brs, 1H), 1.29 (d, 3H, J=6.3 Hz), 1.19 (d, 3H, J=6.0 Hz). LC-MS: [M+H]$^+$, 472, $t_R$=1.654 min, HPLC: 99.36% at 214 nm, 98.85% at 254 nm, $t_R$=5.697 min.

Example 42

Synthesis of (3-(8-(6-(2-Methylpyrrolidin-1-yl) pyridin-2-ylamino) imidazo[1,2-b]pyridazin-6-yl)phenyl)(morpholino)methanone

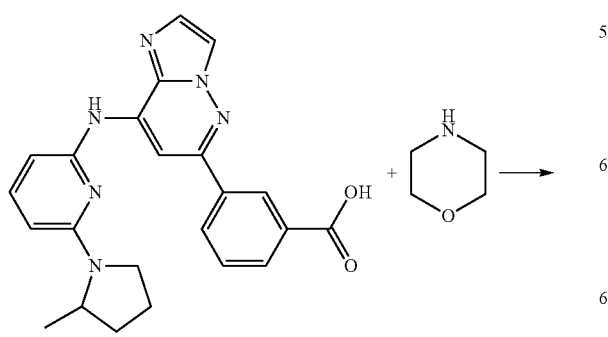

A mixture of 3-(8-(6-(2-methylpyrrolidin-1-yl)pyridin-2-ylamino)imidazo[1,2-b]pyridazin-6-yl)benzoic acid (50 mg, 0.121 mmol), 2-aminopropan-1-ol (12 mg, 0.133 mmol), 1-methyl-1H-imidazole (40 mg, 0.484 mmol) and EDCI (92 mg, 0.484 mmol) in dichloromethane (10 mL) was stirred at room temperature for 20 h then concentrated. The residue was purified by Prep-TLC (silica gel, 200-300 mesh, methanol: dichloromethane=1:30) to afford (3-(8-(6-(2-methylpyrrolidin-1-yl)pyridin-2-ylamino)imidazo[1,2-b]pyridazin-6-yl) phenyl)(morpholino)methanone (30 mg, 51%) as a yellow solid. $^1$H NMR (300 MHz, CD3OD): δ 8.84 (s, 1H), 8.11-8.01 (m, 3H), 7.61-7.54 (m, 3H), 7.44 (t, 1H, J=8.1 Hz), 6.30 (d, 1H, J=7.8 Hz), 6.09 (d, 1H, J=8.4 Hz), 4.27-4.21 (m, 1H), 3.79-3.44 (m, 10H), 2.18-2.04 (m, 3H), 1.79 (brs, 1H), 1.19 (d, 3H, J=6.3 Hz). LC-MS: [M+H]$^+$, 484, $t_R$=1.738 min, HPLC: 99.76% at 214 nm, 99.56% at 254 nm, $t_R$=5.698 min.

Example 43

Synthesis of (S)—N-(6-(2-Methylpyrrolidin-1-yl) pyridin-2-yl)-6-phenylimidazo[1,2-b]pyridazin-8-amine

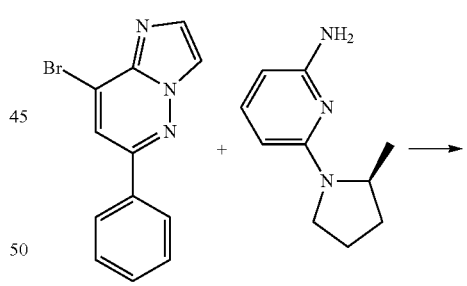

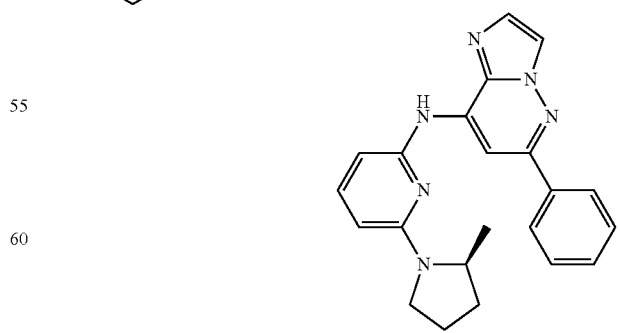

A mixture of 8-bromo-6-phenylimidazo[1,2-b]pyridazine (0.15 g, 0.55 mmol), (S)-6-(2-methylpyrrolidin-1-yl)pyridin- 2-amine (0.107 g, 0.61 mmol), Pd$_2$(dba)$_3$ (32 mg, 0.055 mmol), BINAP (68 mg, 0.11 mmol) and Cs$_2$CO$_3$ (0.54 g, 1.65 mmol) in dioxane (20 mL) was heated to 100° C. for 16 h in a sealed tube under N$_2$ atmosphere then concentrated and the residue purified by chromatography (silica gel, 20 g, 200~300 mesh, ethyl acetate:petroleum ether=1:15) to afford (S)—N-(6-(2-methylpyrrolidin-1-yl)pyridin-2-yl)-6-phenylimidazo[1,2-b]pyridazin-8-amine (51 mg, 25%) as a yellow solid. $^1$H NMR (300 MHz, CD3OD): δ 8.83 (s, 1H), 7.99 (s, 1H), 7.95-7.91 (m, 2H), 7.59 (s, 1H), 7.51-7.40 (m, 4 h), 6.29 (d, 1H, J=7.5 Hz), 6.08 (d, 1H, J=8.1 Hz), 4.28-4.24 (m, 1H), 3.64-3.60 (m, 1H), 3.48-3.40 (m, 1H), 2.18-2.10 (m, 3H), 1.78-1.75 (m, 1H), 1.19 (d, 3H, J=6.3 Hz). LC-MS: [M+H]$^+$, 371, $t_R$=2.015 min, HPLC: 99.09% at 214 nm, 99.69% at 254 nm, $t_R$=4.691 min.

Example 44

Synthesis of N-(5,6-Dimethoxypyridin-2-yl)-6-phenylimidazo[1,2-b]pyridazin-8-amine

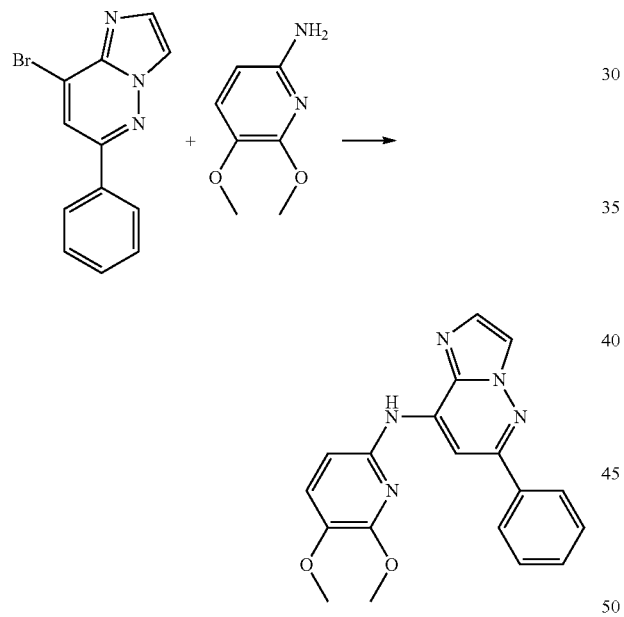

A mixture of 8-bromo-6-phenylimidazo[1,2-b]pyridazine (0.15 g, 0.55 mmol), 5,6-dimethoxypyridin-2-amine (0.092 g, 0.61 mmol), Pd$_2$(dba)$_3$ (32 mg, 0.055 mmol), BINAP (68 mg, 0.11 mmol) and Cs$_2$CO$_3$ (0.54 g, 1.65 mmol) in dioxane (20 mL) was heated to 100° C. for 16 h in a sealed tube under N$_2$ atmosphere then concentrated and the residue purified by chromatography (silica gel, 10 g, 200~300 mesh, ethyl acetate:petroleum ether=1:6) to afford N-(5,6-dimethoxypyridin-2-yl)-6-phenylimidazo[1,2-b]pyridazin-8-amine (49 mg, 26%) as a yellow solid. $^1$H NMR (300 MHz, CD3OD): δ 8.56 (s, 1H), 8.01-7.92 (m, 3H), 7.60 (s, 1H), 7.51-7.48 (m, 3H), 7.35 (d, 1H, J=8.4 Hz), 6.73 (d, 1H, J=8.4 Hz), 4.09 (s, 3H), 3.85 (s, 3H). LC-MS: [M+H]$^+$, 348, $t_R$=1.735 min, HPLC: 98.28% at 214 nm, 98.33% at 254 nm, $t_R$=5.85 min.

Example 45

Synthesis of 6-(2-Chlorophenyl)-N-(6-(2-methylpyrrolidin-1-yl) pyridin-2-yl) imidazo[1,2-b]pyridazin-8-amine hydrochloride

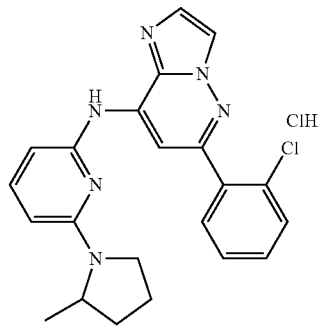 [SMILES: CC1CCCN1c1cccc(Nc2cc(-c3ccccc3Cl)nn3ccnc23)n1 ; Cl]

Step 1

6-Chloro-N-(6-(2-methylpyrrolidin-1-yl)pyridin-2-yl)imidazo[1,2-b]pyridazin-8-amine

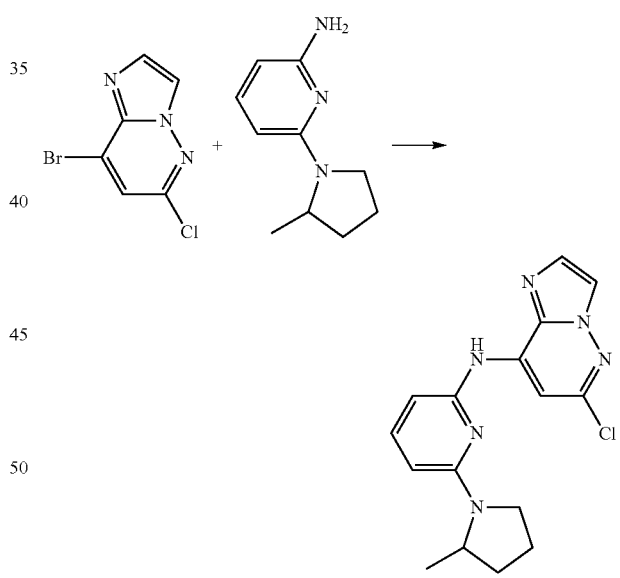

A mixture of 8-bromo-6-chloroimidazo[1,2-b]pyridazine (1.0 g, 4.3 mmol), 6-(2-methylpyrrolidin-1-yl)pyridin-2-amine (0.84 g, 4.73 mmol), Pd$_2$(dba)$_3$ (0.247 g, 0.43 mmol), BINAP (0.536 g, 0.86 mmol) and Cs$_2$CO$_3$ (4.21 g, 12.9 mmol) in dioxane (30 mL) was heated to 100° C. for 16 h in a sealed tube under N$_2$ atmosphere then concentrated in vacuo. The residue was purified by chromatography (silica gel, 10 g, 200~300 mesh, ethyl acetate:petroleum ether=1:15) to afford 6-chloro-N-(6-(2-methylpyrrolidin-1-yl)pyridin-2-yl)imidazo[1,2-b]pyridazin-8-amine (1.2 g, 85%) as a yellow solid. LC-MS: [M+1]$^+$=329, $t_R$=1.930 min.

Step 2

6-(2-Chlorophenyl)-N-(6-(2-methylpyrrolidin-1-yl)pyridin-2-yl)imidazo[1,2-b]pyridazin-8-amine hydrochloride

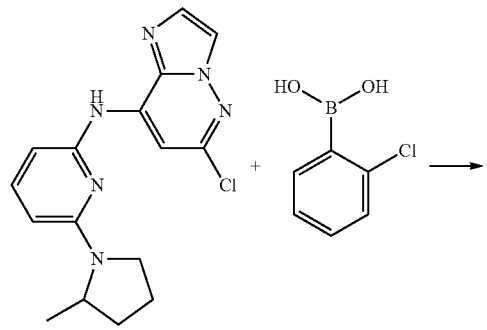

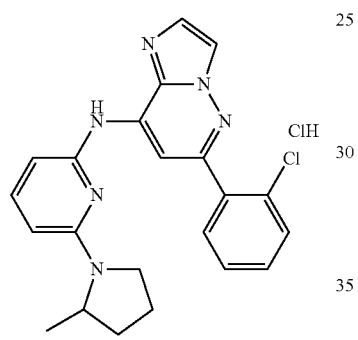

A mixture of 6-chloro-N-(6-(2-methylpyrrolidin-1-yl)pyridin-2-yl)imidazo[1,2-b]pyridazin-8-amine (0.15 g, 0.456 mmol), 2-chlorophenylboronic acid (0.078 g, 0.5 mmol), $Pd_2(dba)_3$ (0.058 g, 0.1 mmol), X-phos (0.095 g, 0.2 mmol) and $Na_2CO_3$ (0.145 g, 1.368 mmol) in dioxane (20 mL) and water (5 mL) was heated to 100° C. for 16 h in a sealed tube under $N_2$ atmosphere then concentrated in vacuo. The residue was purified by chromatography (silica gel, 10 g, 200~300 mesh, ethyl acetate petroleum ether=1:20) and then further purified by Prep-HPLC (Gemini 5u C18 150×21.2 mm; inject volume: 3 mL/inj, flow rate: 20 mL/min; wavelength: 214 nm and 254 nm; gradient conditions: 35% acetonitrile/65% water (0.1% TFA VAT) initially, proceeding to 50% acetonitrile/50% water (0.1% TFA VAT) in a linear fashion over 9 min). The fractions containing product were acidified by the addition of concentrated HCl and concentrated to afford 6-(2-chlorophenyl)-N-(6-(2-methylpyrrolidin-1-yl)pyridin-2-yl)imidazo[1,2-b]pyridazin-8-amine hydrochloride (81 mg, 40%) as a yellow solid. $^1$H NMR (300 MHz, CD3OD): δ 8.67 (s, 1H), 8.42 (d, 1H, J=1.8 Hz), 8.17 (d, 1H, J=1.8 Hz), 7.66-7.48 (m, 5H), 6.48 (d, 1H, J=7.5 Hz), 6.34 (d, 1H, J=8.4 Hz), 4.26-4.22 (m, 1H), 3.63-3.57 (m, 1H), 3.44-3.38 (m, 1H), 2.17-2.04 (m, 3H), 1.76-1.38 (m, 1H), 1.09 (d, 3H, J=6.3 Hz) LC-MS: $[M+H]^+$, 405, $t_R$=1.971 min, HPLC: 98.88% at 214 nm, 98.93% at 254 nm, $t_R$=7.63 min.

Example 46

Synthesis of N-(2-(Dimethylamino)ethyl)-3-(8-(6-(2-methylpyrrolidin-1-yl) pyridin-2-ylamino) imidazo[1,2-b]pyridazin-6-yl)benzamide

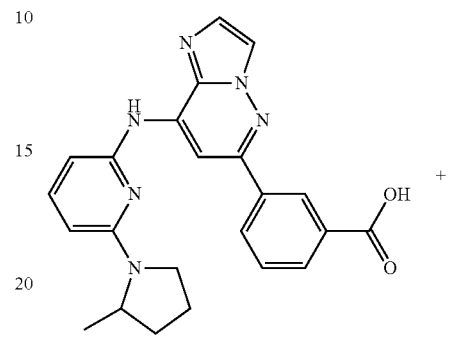

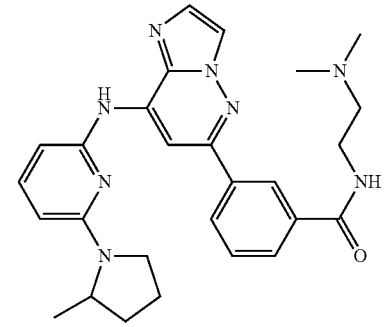

A mixture of 3-(8-(6-(2-methylpyrrolidin-1-yl)pyridin-2-ylamino)imidazo[1,2-b]pyridazin-6-yl)benzoic acid (83 mg, 0.2 mmol), N1,N1-dimethylethane-1,2-diamine (19 mg, 0.22 mmol), 1-methyl-1H-imidazole (66 mg, 0.8 mmol) and EDCI (153 mg, 0.8 mmol) in dichloromethane (10 mL) was stirred at room temperature for 16 h then concentrated. The residue was purified by chromatography (silica gel, 10 g, 200~300 mesh, methanol:dichloromethane=1:20) and further purified by Prep-TLC (silica gel, methanol:dichloromethane=1:10) to afford N-(2-(dimethylamino)ethyl)-3-(8-(6-(2-methylpyrrolidin-1-yl)pyridine-2-ylamino)imidazo[1,2-b]pyridazin-6-yl)benzamide (41 mg, 42%) as a yellow solid. $^1$H NMR (300 MHz, CD3OD): δ 8.89 (s, 1H), 8.48 (s, 1H), 8.13 (dd, 1H, J1=6.9 Hz, J2=1.8 Hz), 8.02-7.97 (m, 2H), 7.65-7.60 (m, 2H), 7.45 (t, 1H, J=8.1 Hz), 6.31 (d, 1H, J=7.5 Hz), 6.10 (d, 1H, J=8.1 Hz), 4.29-4.25 (m, 1H), 3.76-3.72 (m, 2H), 3.66-3.60 (m, 1H), 3.54-3.40 (m, 1H), 3.19-3.15 (m, 2H), 2.81 (s, 6H), 2.25-2.00 (m, 3H), 1.75-1.73 (m, 1H), 1.17 (d, 3H, J=6.0 Hz). LC-MS: $[M+H]^+$, 485, $t_R$=1.062 min, HPLC: 99.08% at 214 nm, 99.16% at 254 nm, $t_R$=4.868 min.

Example 47

Synthesis of N-(6-(2-Methylpyrrolidin-1-yl)pyridin-2-yl)-6-o-tolylimidazo[1,2-b]pyridazin-8-amine

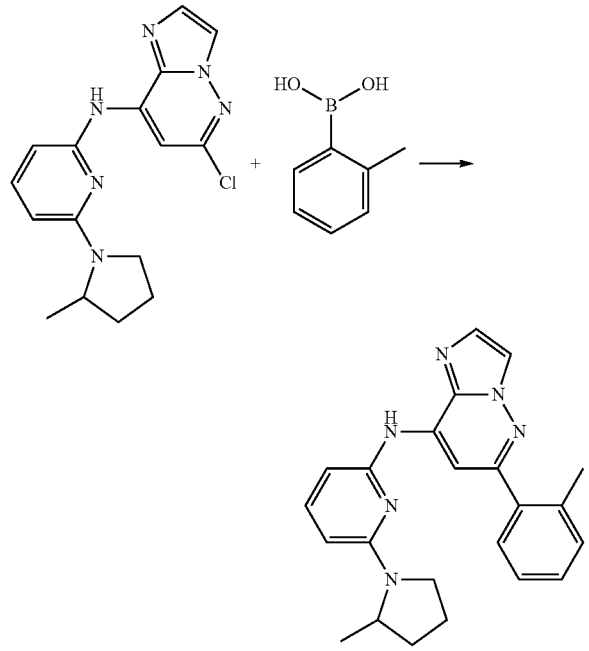

A mixture of 6-chloro-N-(6-(2-methylpyrrolidin-1-yl)pyridin-2-yl)imidazo[1,2-b]pyridazin-8-amine (0.10 g, 0.304 mmol), o-tolylboronic acid (0.045 g, 0.335 mmol), $Pd_2(dba)_3$ (0.017 g, 0.03 mmol), X-phos (0.029 g, 0.06 mmol) and $Na_2CO_3$ (0.097 g, 0.912 mmol) in dioxane (20 mL) and water (5 mL) was heated to 100° C. for 16 h in a sealed tube under $N_2$ atmosphere then concentrated in vacuo. The residue was purified by chromatography (silica gel, 10 g, 200~300 mesh, ethyl acetate:petroleum ether=1:15) to afford N-(6-(2-methylpyrrolidin-1-yl)pyridin-2-yl)-6-o-tolylimidazo[1,2-b]pyridazin-8-amine (51 mg, 44%) as a yellow solid. $^1$H NMR (300 MHz, CD3OD): δ 8.53 (s, 1H), 7.95 (s, 1H), 7.61 (s, 1H), 7.43-7.25 (m, 5H), 6.28 (d, 1H, J=7.5 Hz), 6.02 (d, 1H, J=8.1 Hz), 4.10-4.06 (m, 1H), 3.55 (s, 1H), 3.45-3.39 (m, 1H), 3.24-3.21 (m, 1H), 2.37 (s, 3H), 2.03-1.89 (m, 3H), 1.61-1.58 (m, 1H), 0.97 (d, 3H, J=6.3 Hz). LC-MS: [M+H]$^+$, 385, $t_R$=1.95 min, HPLC: 99.76% at 214 nm, 100% at 254 nm, $t_R$=4.68 min.

Example 48

Synthesis of N-(6-(2-Methylpyrrolidin-1-yl)pyridin-2-yl)-6-(2-(trifluoromethyl)phenyl)imidazo[1,2-b]pyridazin-8-amine hydrochloride

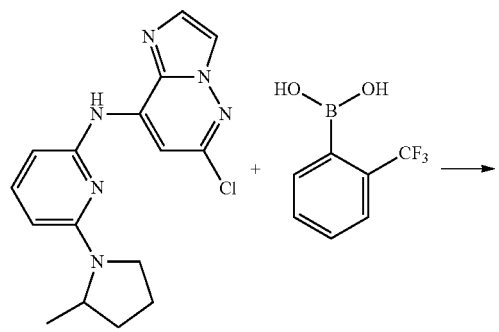

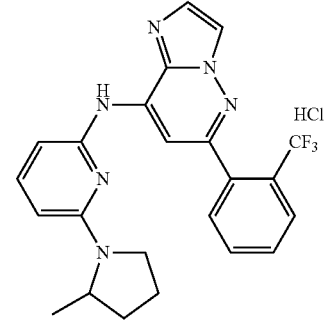

A mixture of 6-chloro-N-(6-(2-methylpyrrolidin-1-yl)pyridin-2-yl)imidazo[1,2-b]pyridazin-8-amine (0.10 g, 0.305 mmol), 2-(trifluoromethyl)phenylboronic acid (64 mg, 0.335 mmol), $Pd_2(dba)_3$ (0.035 g, 0.061 mmol), X-phos (0.058 g, 0.122 mmol) and $Na_2CO_3$ (0.097 g, 0.915 mmol) in dioxane (20 mL) and water (5 mL) was heated to 100° C. for 16 h in a sealed tube under $N_2$ atmosphere then concentrated in vacuo. The residue was purified by chromatography (silica gel, 10 g, 200~300 mesh, ethyl acetate:petroleum ether=1:10) and the residue was further purified by Prep-HPLC (Gemini 5u C18 150×21.2 mm; inject volume: 3 mL/inj, flow rate: 20 mL/min; wavelength: 214 nm and 254 nm; gradient conditions: 30% acetonitrile/70% water (0.1% TFA V/V) initially, proceeding to 50% acetonitrile/50% water (0.1% TFA V/V) in a linear fashion over 9 min). The fractions containing product were acidified by the addition of concentrated HCl then concentrated to afford N-(6-(2-methylpyrrolidin-1-yl)pyridin-2-yl)-6-(2-(trifluoromethyl)phenyl)imidazo[1,2-b]pyridazin-8-amine hydrochloride (38 mg, 26%) as a yellow solid. $^1$H NMR (300 MHz, DMSO): δ 10.88 (s, 1H), 8.84 (s, 1H), 8.52 (s, 1H), 8.27 (s, 1H), 7.94-7.66 (m, 4 h), 7.48 (t, 1H, J=7.5 Hz), 6.67 (d, 1H, J=7.5 Hz), 6.08 (d, 1H, J=8.1 Hz), 3.95-3.91 (m, 1H), 3.37-3.28 (m, 1H), 3.09-3.02 (m, 1H), 1.92-1.83 (m, 3H), 1.49-1.41 (m, 1H), 0.78 (d, 3H, J=6.0 Hz). LC-MS: [M+H]$^+$, 439, $t_R$=1.91 min, HPLC: 98.98% at 214 nm, 99.36% at 254 nm, $t_R$=6.99 min.

Example 49

Synthesis of (S)-3-(8-(6-(2-Methylpyrrolidin-1-yl)pyridin-2-ylamino)imidazo[1,2-h]pyridazin-6-yl)benzoic acid

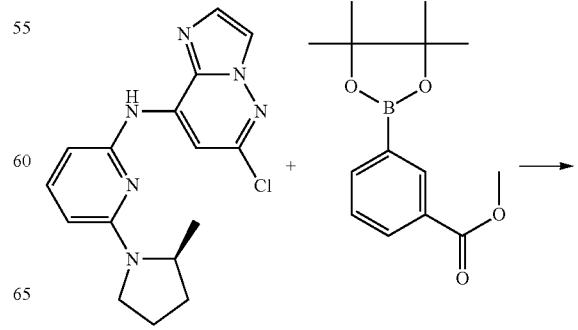

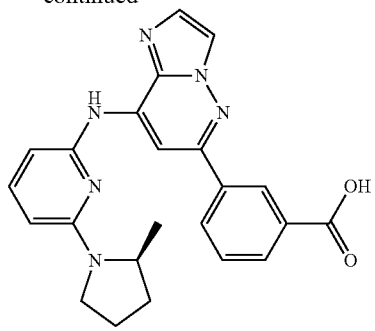

A mixture of (S)-6-chloro-N-(6-(2-methylpyrrolidin-1-yl)pyridin-2-yl)imidazo[1,2-b]pyridazin-8-amine (0.10 g, 0.30 mmol), methyl 3-(4,4,5,5-tetramethyl-1,3,2-dioxaborolan-2-yl)benzoate (0.096 g, 0.36 mmol), Pd$_2$(dba)$_3$ (0.035 g, 0.061 mmol), X-phos (0.057 g, 0.122 mmol) and Na$_2$CO$_3$ (0.095 g, 0.912 mmol) in dioxane (20 mL) and water (5 mL) was heated to 100° C. for 16 h in a sealed tube under N$_2$ atmosphere then concentrated in vacuo. The residue was purified by chromatography (silica gel, 10 g, 200~300 mesh, ethyl acetate:petroleum ether=1:10) and further purified by Prep-HPLC (Gemini 5u C18 150×21.2 mm; inject volume: 3 mL/inj, flow rate: 20 mL/min; wavelength: 214 nm and 254 nm; gradient conditions: 30% acetonitrile/70% water (0.1% TFA V/V) initially, proceeding to 60% acetonitrile/40% water (0.1% TFA V/V) in a linear fashion over 9 min) to afford (S)-3-(8-(6-(2-methylpyrrolidin-1-yl)pyridine-2-ylamino)imidazo[1,2-b]pyridazin-6-yl)benzoic acid (32 mg, 25%) as a yellow solid. $^1$H NMR (300 MHz, DMSO): δ 10.97 (s, 1H), 9.26 (s, 1H), 8.63 (s, 1H), 8.48 (s, 1H), 8.37 (s, 1H), 8.20 (d, 1H, J=7.8 Hz), 8.13-8.11 (m, 1H), 7.71 (t, 1H, J=7.8 Hz), 7.51 (t, 1H, J=7.8 Hz), 6.69 (d, 1H, J=7.5 Hz), 6.16 (d, 1H, J=8.1 Hz), 4.22-4.17 (m, 1H), 3.63-3.54 (m, 1H), 3.44-3.39 (m, 1H), 2.06-1.95 (m, 3H), 1.67-1.61 (m, 1H), 1.07 (d, 3H, J=6.3 Hz). LC-MS: [M+H]$^+$, 415, t$_R$=1.669 min, HPLC: 100% at 214 nm, 100% at 254 nm, t$_R$=6.01 min.

Example 50

Synthesis of (S)-4-(8-(6-(2-Methylpyrrolidin-1-yl)pyridin-2-ylamino) imidazo[1,2-b]pyridazin-6-yl)benzamide Step 1

(S)-4-(8-(6-(2-Methylpyrrolidin-1-yl) pyridin-2-ylamino) imidazo[1,2-b]pyridazin-6-yl)benzoic acid

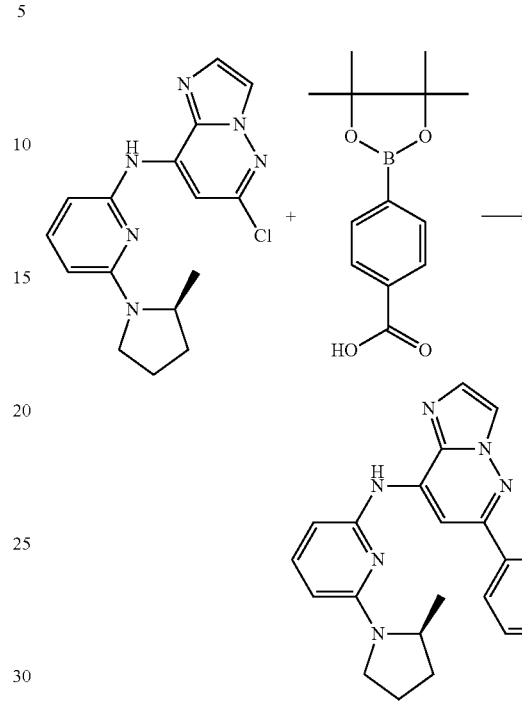

A mixture of (S)-6-chloro-N-(6-(2-methylpyrrolidin-1-yl)pyridin-2-yl)imidazo[1,2-b]pyridazin-8-amine (0.08 g, 0.243 mmol), 4-(4,4,5,5-tetramethyl-1,3,2-dioxaborolan-2-yl)benzoic acid (0.066 g, 0.268 mmol), Pd$_2$(dba)$_3$ (0.028 g, 0.049 mmol), X-phos (0.046 g, 0.097 mmol) and Na$_2$CO$_3$ (0.103 g, 0.992 mmol) in dioxane (20 mL) and water (5 mL) was heated to 100° C. for 16 h in a sealed tube under N$_2$ atmosphere then concentrated in vacuo. The residue was purified by chromatography (silica gel, 15 g, 200-300 mesh, MeOH:dichloromethane=1:10) to afford (S)-4-(8-(6-(2-methylpyrrolidin-1-yl)pyridin-2-ylamino)imidazo[1,2-b]pyridazin-6-yl)benzoic acid (90 mg) as a yellow solid. LC-MS: [M+1]$^+$=415, t$_R$=1.660 min. This contained unidentified impurities and was used directly without further purification.

Step 2

(S)-4-(8-(6-(2-Methylpyrrolidin-1-yl) pyridin-2-ylamino) imidazo[1,2-b]pyridazin-6-yl)benzamide

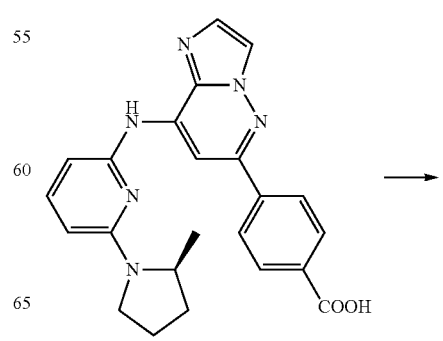

-continued

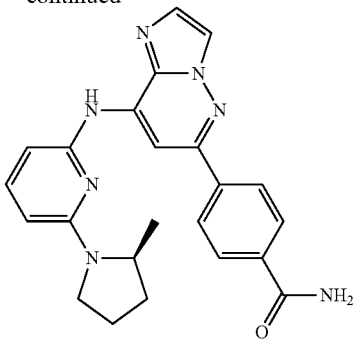

To a stirred solution of (S)-4-(8-(6-(2-methylpyrrolidin-1-yl)pyridin-2-ylamino)imidazo[1,2-b]pyridazin-6-yl)benzoic acid (90 mg), HOBT (49 mg, 0.365 mmol), Et$_3$N (49 mg, 0.486 mmol) and EDCI (70 mg, 0.365 mmol) in dichloromethane (20 mL) and dioxane (100 mL) was bubbled NH$_3$ gas until saturation and the mixture stirred for 16 h at room temperature. The mixture was filtered and the filtrate concentrated in vacuo. The residue was purified by chromatography (silica gel, 10 g, 200-300 mesh, MeOH:dichloromethane=1:50) to afford (S)-4-(8-(6-(2-methylpyrrolidin-1-yl)pyridin-2-ylamino)imidazo[1,2-b]pyridazin-6-yl)benzamide (38 mg, 47%) as a yellow solid. $^1$H NMR (300 MHz, CD3OD): δ 8.74 (s, 1H), 7.94-7.86 (m, 5H), 7.49 (s, 1H), 7.32 (t, 1H, J=8.1 Hz), 6.18 (d, 1H, J=6.0 Hz), 5.98 (d, 1H, J=8.4 Hz), 4.17-4.14 (m, 1H), 3.55-3.49 (m, 1H), 3.38-3.32 (m, 1H), 2.07-1.93 (m, 3H), 1.68 (s, 1H), 1.10 (d, 3H, J=6.0 Hz). LC-MS: [M+H]$^+$, 414, t$_R$=1.505 min, HPLC: 97.48% at 214 nm, 97.67% at 254 nm, t$_R$=6.027 min.

Example 51

Synthesis of (S)-3-(8-(6-(2-Methylpyrrolidin-1-yl)pyridin-2-ylamino) imidazo[1,2-b]pyridazin-6-yl)benzamide

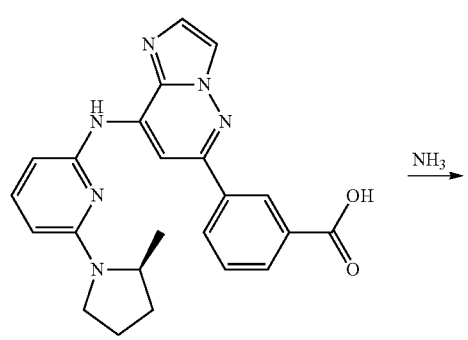

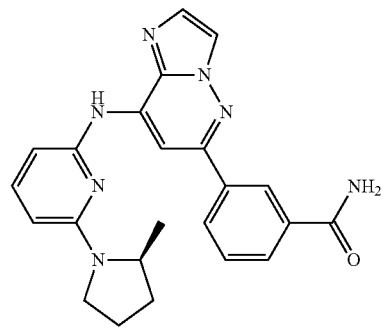

To a stirred solution of (S)-3-(8-(6-(2-methylpyrrolidin-1-yl)pyridin-2-ylamino)imidazo[1,2-b]pyridazin-6-yl)benzoic acid (76 mg, 0.195 mmol), HOBT (39 mg, 0.289 mmol), Et$_3$N (39 mg, 0.786 mmol) and EDCI (55 mg, 0.289 mmol) in dichloromethane (20 mL) and dioxane (10 mL) was bubbled NH$_3$ gas until saturation and the mixture stirred for 16 h at room temperature. The reaction mixture was filtered then the filtrate concentrated in vacuo. The residue was purified by chromatography (silica gel, 10 g, 200-300 mesh, MeOH:dichloromethane=1:50) to afford (S)-3-(8-(6-(2-methylpyrrolidin-1-yl)pyridin-2-ylamino)imidazo[1,2-b]pyridazin-6-yl)benzamide (38 mg, 47%) as a yellow solid. $^1$H NMR (300 MHz, CD3OD): δ 8.93 (s, 1H), 8.47 (s, 1H), 8.14 (d, 1H, J=8.1 Hz), 8.03-7.97 (m, 2H), 7.63-7.58 (m, 2H), 7.44 (t, 1H, J=8.1 Hz), 6.30 (d, 1H, J=7.8 Hz), 6.09 (d, 1H, J=8.1 Hz), 4.32-4.22 (m, 1H), 3.69-3.61 (m, 1H), 3.48-3.42 (m, 1H), 2.17-2.01 (m, 3H), 1.68 (s, 1H), 1.17 (d, 3H, J=6.3 Hz). LC-MS: [M+H]$^+$, 414, t$_R$=1.594 min, HPLC: 100% at 214 nm, 100% at 254 nm, t$_R$=4.417 min.

Example 52

Synthesis of (S)-6-(Benzo[d]thiazol-6-yl)-N-(6-(2-methylpyrrolidin-1-yl)pyridin-2-yl)imidazo[1,2-b]pyridazin-8-amine

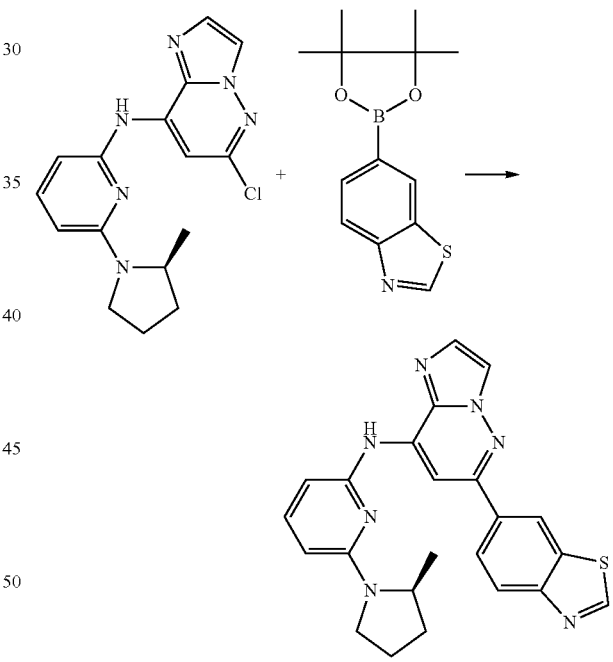

A mixture of (S)-6-chloro-N-(6-(2-methylpyrrolidin-1-yl)pyridin-2-yl)imidazo[1,2-b]pyridazin-8-amine (0.15 g, 0.456 mmol), 6-(4,4,5,5-tetramethyl-1,3,2-dioxaborolan-2-yl)benzo[d]thiazole (0.119 g, 0.456 mmol), Pd$_2$(dba)$_3$ (0.052 g, 0.09 mmol), X-phos (0.087 g, 0.18 mmol) and Na$_2$CO$_3$ (0.145 g, 1.368 mmol) in dioxane (20 mL) and water (5 mL) was heated to 100° C. for 16 h in a sealed tube under N$_2$ atmosphere then concentrated in vacuo. The residue was purified by chromatography (silica gel, 15 g, 200-300 mesh, ethyl acetate:petroleum ether=1:5) to afford (S)-6-(benzo[d]thiazol-6-yl)-N-(6-(2-methylpyrrolidin-1-yl)pyridin-2-yl)imidazo[1,2-b]pyridazin-8-amine (58 mg, 51%) as a yellow solid. $^1$H NMR (300 MHz, DMSO): δ 9.71 (s, 1H), 9.49 (s, 1H), 8.91 (s, 1H), 8.69 (s, 1H), 8.23-8.08 (m, 3H), 7.66 (s, 1H), 7.43 (t, 1H, J=7.8 Hz), 6.74 (d, 1H, J=7.8 Hz), 6.06 (d, 1H, J=7.8 Hz), 4.26-4.23 (m, 1H), 3.59-3.55 (m, 1H), 3.44-3.40 (m, 1H), 2.08-1.98 (m, 3H), 1.69-1.66 (m, 1H), 1.09 (d, 3H, J=6.3 Hz). LC-MS: [M+H]$^+$, 428, $t_R$=1.997 min, HPLC: 95.07% at 214 nm, 98.34% at 254 nm, $t_R$=4.349 min.

Example 53

Synthesis of N-(6-((2S,5S)-2,5-Dimethylpyrrolidin-1-yl) pyridin-2-yl)-6-phenylimidazo[1,2-b]pyridazin-8-amine hydrochloride

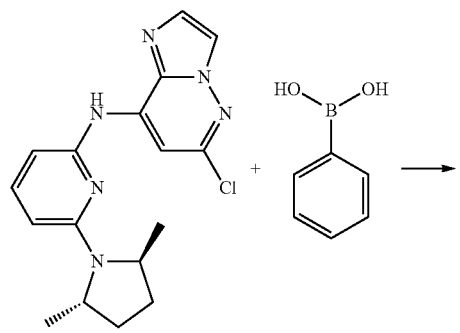

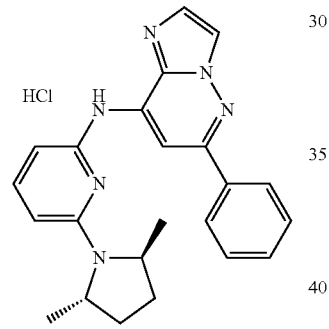

A mixture of 6-chloro-N-(6-((2S,5S)-2,5-dimethylpyrrolidin-1-yl)pyridin-2-yl)imidazo[1,2-b]pyridazin-8-amine (0.668 g, 1.95 mmol), phenylboronic acid (0.261 g, 2.14 mmol), Pd$_2$(dba)$_3$ (0.224 g, 0.39 mmol), X-phos (0.372 g, 0.78 mmol) and Na$_2$CO$_3$ (0.62 g, 5.85 mmol) in dioxane (30 mL) and water (10 mL) was heated to 90° C. for 16 h in a sealed tube under N$_2$ atmosphere then concentrated in vacuo. The residue was purified by Prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min). The fractions containing product were acidified by the addition of concentrated HCl and concentrated in vacuo to afford N-(6-((2S,5S)-2,5-dimethylpyrrolidin-1-yl)pyridin-2-yl)-6-phenylimidazo[1,2-b]pyridazin-8-amine (57 mg, 9% over two steps) as a yellow solid. $^1$H NMR (300 MHz, DMSO): δ 8.87 (s, 1H), 8.35 (s, 1H), 7.95-7.92 (m, 3H), 7.59-7.47 (m, 4 h), 6.48 (d, 1H, J=7.8 Hz), 6.17 (d, 1H, J=8.1 Hz), 4.23 (s, 2H), 2.25 (s, 2H), 1.64-1.62 (m, 2H), 1.09 (s, 3H), 1.07 (s, 3H). LC-MS: [M+H]$^+$, 385, $t_R$=2.023 min, HPLC: 96.85% at 214 nm, 96.97% at 254 nm, $t_R$=8.147 min.

Example 54

Synthesis of 4-(3-(8-(5,6-Dimethoxypyridin-2-ylamino)imidazo[1,2-b]pyridazin-6-yl)benzamido) benzoic acid

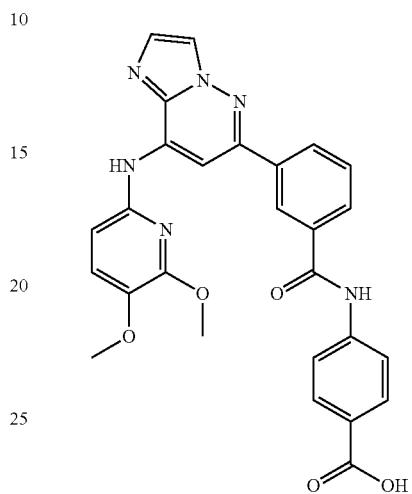

Step 1 tert-Butyl 4-(3-(8-(5,6-dimethoxypyridin-2-ylamino) imidazo[1,2-b]pyridazin-6-yl)benzamido)benzoate

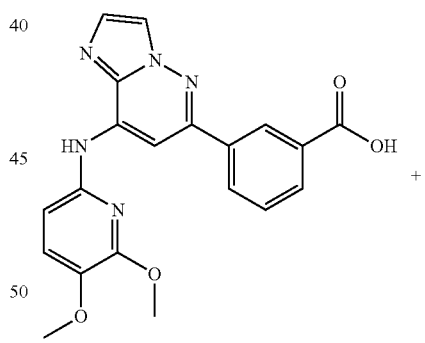

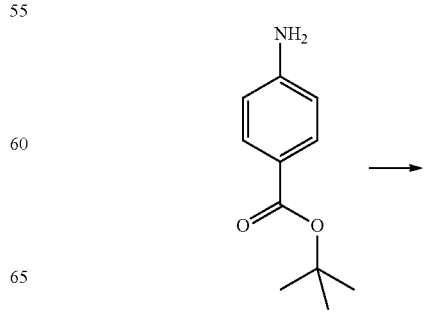

151

-continued

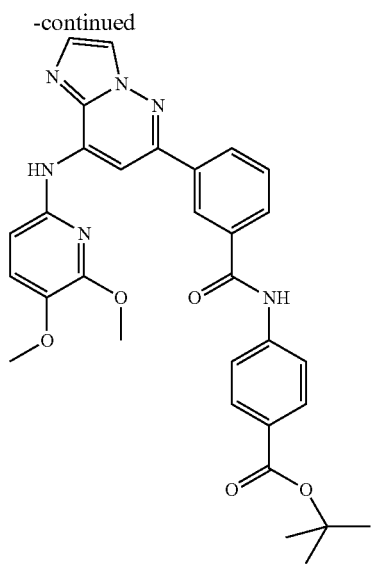

A mixture of 3-(8-(5,6-dimethoxypyridin-2-ylamino)imidazo[1,2-b]pyridazin-6-yl)benzoic acid (100 mg, 0.26 mmol), tert-butyl 4-aminobenzoate (50 mg, 0.26 mmol), 1-methyl-1H-imidazole (85 mg, 1.02 mmol) and EDCI (200 mg, 1.02 mmol) in DMF (3 mL) was stirred for 16 h at room temperature. Ethyl acetate (10 mL) and water (10 mL) were added to the mixture and the organic layer was washed with brine (10 mL×2) then dried over Na$_2$SO$_4$. The residue was concentrated and purified by chromatography (dichloromethane:MeOH=50:1) to give tert-butyl 4-(3-(8-(5,6-dimethoxypyridin-2-ylamino)imidazo[1,2-b]pyridazin-6-yl)benzamido)benzoate (80 mg, 55%) as a yellow solid. LC-MS: [M+H]$^+$, 567, t$_R$=1.820 min Step 2

4-(3-(8-(5,6-Dimethoxypyridin-2-ylamino)imidazo[1,2-b]pyridazin-6-yl)benzamido)benzoic acid

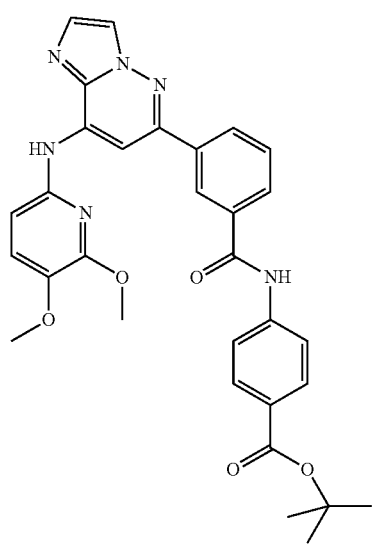

152

-continued

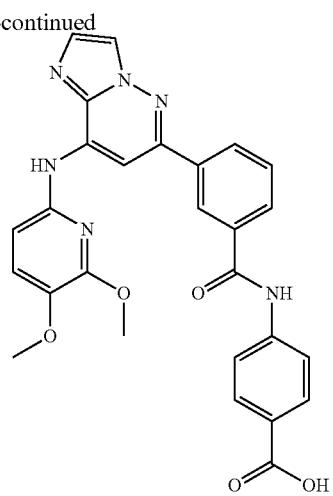

A mixture of tert-Butyl 4-(3-(8-(5,6-dimethoxypyridin-2-ylamino)imidazo[1,2-b]pyridazin-6-yl)benzamido)benzoate (80 mg, 0.14 mmol) and TFA (3 mL) in dichloromethane (3 mL) was stirred for 2 h at room temperature. The mixture was concentrated and then triturated with MeOH (2 mL) to give the product 4-(3-(8-(5,6-dimethoxypyridin-2-ylamino)imidazo[1,2-b]pyridazin-6-yl)benzamido)benzoic acid (28 mg, 39%) as a yellow solid. $^1$H NMR (300 MHz, DMSO): δ 10.71 (s, 1H), 10.02 (s, 1H), 8.66 (s, 1H), 8.55 (s, 1H), 8.29 (s, 1H), 8.24 (d, 1H, J=7.8 Hz), 8.12 (d, 1H, J=7.5 Hz), 7.97-7.93 (m, 2H), 7.76-7.71 (m, 3H), 7.44 (d, 1H, J=8.1 Hz), 7.13 (d, 1H, J=8.4 Hz), 4.05 (s, 3H), 3.88 (s, 3H). LC-MS: [M+H]$^+$, 510.9, t$_R$=1.505 min, HPLC: 97.21% at 214 nm, 99.12% at 254 nm, t$_R$=6.006 min.

Example 55

Synthesis of 3-(8-(5,6-Dimethoxypyridin-2-ylamino)imidazo[1,2-b]pyridazin-6-yl)-N-(1H-indazol-5-yl)benzamide hydrochloride

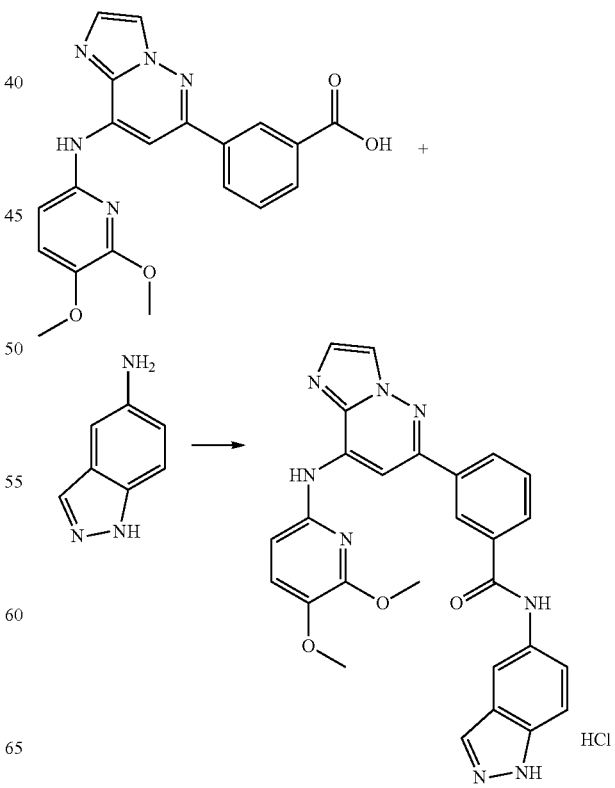

A mixture of 3-(8-(5,6-dimethoxypyridin-2-ylamino)imidazo[1,2-b]pyridazin-6-yl)benzoic acid (80 mg, 0.2 mmol), 1H-indazol-5-amine (27 mg, 0.2 mmol), 1-methyl-1H-imidazole (67 mg, 0.82 mmol) and EDCI (156 mg, 0.82 mmol) in DMF (3 mL) was stirred for 16 h at room temperature. Ethyl acetate (5 mL) and water (5 mL) were added. The organic layer was separated and the aqueous phase was extracted with ethyl acetate (20 mL). The organic phases were combined and washed with brine (10 mL) then dried over Na$_2$SO$_4$. The residue was concentrated and purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min). The fractions containing product were acidified with concentrated HCl and then concentrated in vacuo to give 3-(8-(5,6-dimethoxypyridin-2-ylamino)imidazo[1,2-b]pyridazin-6-yl)-N-(1H-indazol-5-yl)benzamide hydrochloride (11 mg, 11%) as a yellow solid. $^1$H NMR (300 MHz, DMSO): δ 10.59 (s, 1H), 10.44 (s, 1H), 8.86 (s, 1H), 8.56 (s, 1H), 8.46 (s, 1H), 8.25-8.06 (m, 5H), 7.75-7.63 (m, 2H), 7.54 (d, 1H, J=9.0 Hz), 7.45 (d, 1H, J=8.4 Hz), 7.08 (d, 1H, J=8.4 Hz), 4.04 (s, 2H), 3.77 (s, 3H). LC-MS: [M+H]$^+$, 506.9, $t_R$=1.478 min, HPLC: 100% at 214 nm, 100% at 254 nm, $t_R$=3.792 min.

Example 56

Synthesis of 3-(8-(5,6-Dimethoxypyridin-2-ylamino)imidazo[1,2-b]pyridazin-6-yl)-N-(1-oxoisoindolin-5-yl)benzamide

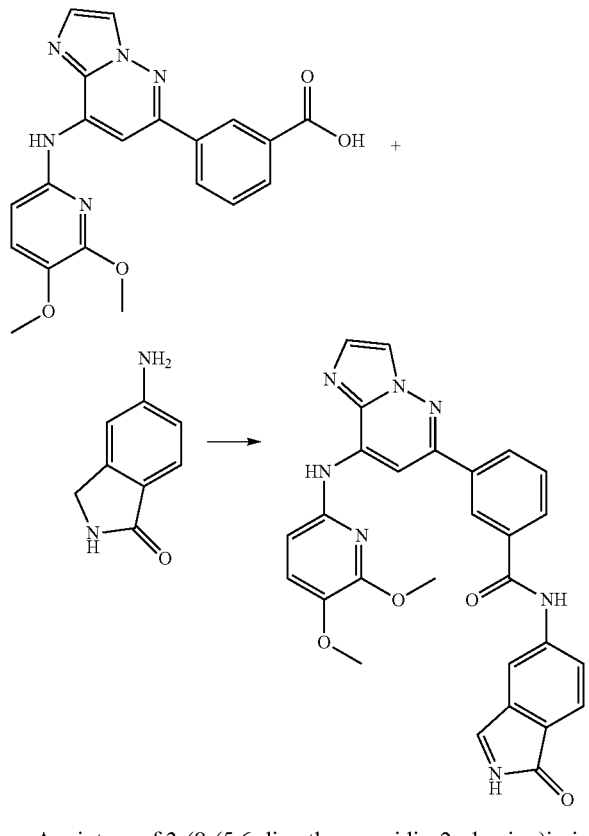

A mixture of 3-(8-(5,6-dimethoxypyridin-2-ylamino)imidazo[1,2-b]pyridazin-6-yl)benzoic acid (100 mg, 0.26 mmol), 5-aminoisoindolin-1-one (38 mg, 0.26 mmol), 1-methyl-1H-imidazole (84 mg, 1.02 mmol) and EDCI (196 mg, 1.02 mmol) in DMF (3 mL) was stirred for 16 h at room temperature. Ethyl acetate (5 mL) and water (5 mL) were added. The organic layer was separated and the aqueous phase was extracted with ethyl acetate (20 mL). The organic phases were combined and washed with brine (10 mL) then dried over Na$_2$SO$_4$. The residue was concentrated and triturated with MeOH (2 mL) to give 3-(8-(5,6-dimethoxypyridin-2-ylamino)imidazo[1,2-b]pyridazin-6-yl)-N-(1-oxoisoindolin-5-yl)benzamide (26 mg, 20%) as a yellow solid. $^1$H NMR (300 MHz, DMSO): δ 10.68 (s, 1H), 9.97 (s, 1H), 8.61 (s, 1H), 8.52 (s, 1H), 8.44 (s, 1H), 8.24-8.08 (m, 4 h), 7.82-7.64 (m, 4 h), 7.41 (d, 1H, J=8.7 Hz), 7.11 (d, 1H, J=8.4 Hz), 4.39 (s, 2H), 4.02 (s, 3H), 3.76 (s, 3H). LC-MS: [M+H]$^+$, 521.9, $t_R$=1.434 min, HPLC: 96.12% at 214 nm, 96.79% at 254 nm, $t_R$=3.673 min.

Example 57

Synthesis of 4-(3-(8-(5,6-Dimethoxypyridin-2-ylamino)imidazo[1,2-b]pyridazin-6-yl)benzamido)-2-methoxybenzoic acid

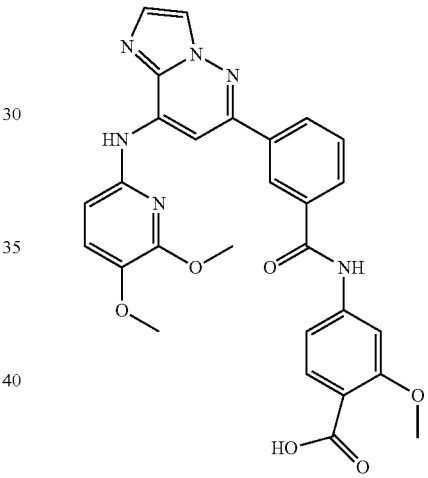

Step 1

Methyl 4-(3-(8-(5,6-dimethoxypyridin-2-ylamino)imidazo[1,2-b]pyridazin-6-yl)benzamido)-2-methoxybenzoate

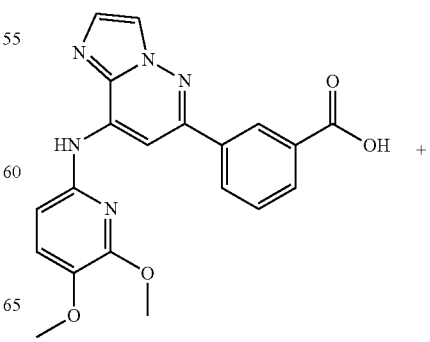

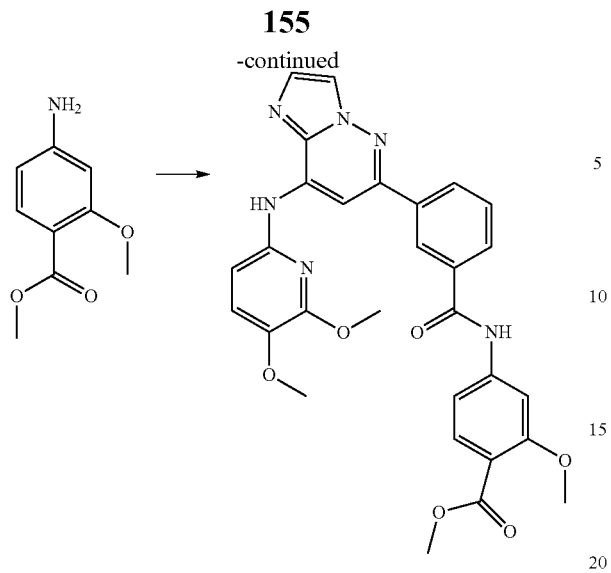

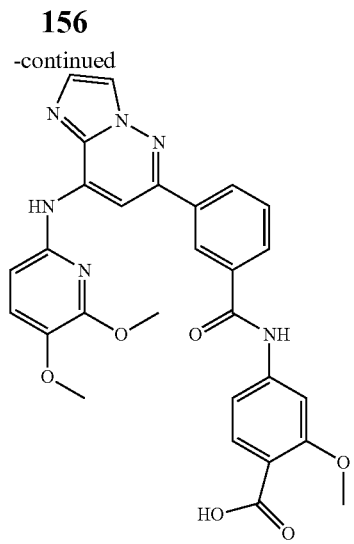

A mixture of 3-(8-(5,6-dimethoxypyridin-2-ylamino)imidazo[1,2-b]pyridazin-6-yl)benzoic acid (150 mg, 0.38 mmol), methyl 4-amino-2-methoxybenzoate (70 mg, 0.38 mmol), 1-methyl-1H-imidazole (126 mg, 1.53 mmol) and EDCI (293 mg, 1.53 mmol) in DMF (3 mL) was stirred for 16 h at room temperature. Ethyl acetate (5 mL) and water (5 mL) were added. The organic layer was separated and the aqueous phase was extracted with ethyl acetate (20 mL). The combined organic phases were washed with brine (10 mL) and dried over $Na_2SO_4$. The residue was concentrated and purified by chromatography (silica gel, 200-300 mesh, dichloromethane:MeOH=50:1) to give methyl 4-(3-(8-(5,6-dimethoxypyridin-2-ylamino)imidazo[1,2-b]pyridazin-6-yl)benzamido)-2-methoxybenzoate (100 mg, 47%) as brown liquid. LC-MS: $[M+H]^+$, 555.1, $t_R$=1.701 min Step 2

4-(3-(8-(5,6-Dimethoxypyridin-2-ylamino)imidazo[1,2-b]pyridazin-6-yl)benzamido)-2-methoxybenzoic acid

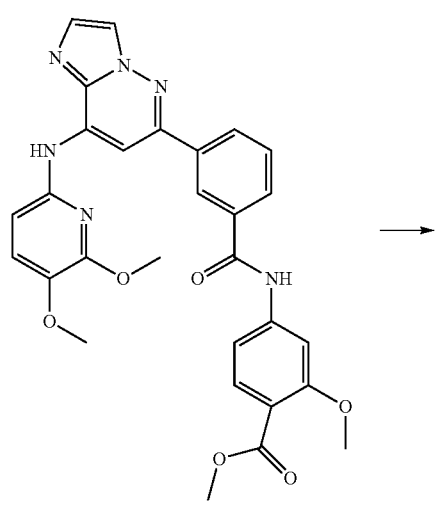

A mixture of methyl 4-(3-(8-(5,6-dimethoxypyridin-2-ylamino)imidazo[1,2-b]pyridazin-6-yl)benzamido)-2-methoxybenzoate (100 mg, 0.18 mmol) and NaOH (100 mg, 2.5 mmol) in 1,4-dioxane (5 mL) and water (5 mL) was stirred for 2 h at 50° C. The mixture was concentrated and adjusted to pH=2 with 3M HCl. The precipitate was filtered and the solid was washed with MeOH (1 mL) and dichloromethane (1 mL) to give 4-(3-(8-(5,6-dimethoxypyridin-2-ylamino)imidazo[1,2-b]pyridazin-6-yl)benzamido)-2-methoxybenzoic acid (24 mg, 25%) as a brown solid. $^1$H NMR (300 MHz, DMSO): δ 10.62 (s, 1H), 10.01 (s, 1H), 8.63 (s, 1H), 8.53 (s, 1H), 8.26-8.21 (m, 2H), 8.09 (d, 1H, J=7.5 Hz), 7.75-7.67 (m, 4 h), 7.50 (dd, 1H, J1=8.4 Hz, J2=1.8 Hz), 7.41 (d, 1H, J=8.4 Hz), 7.10 (d, 1H, J=8.4 Hz), 4.03 (s, 3H), 3.84 (s, 3H), 3.77 (s, 3H). LC-MS: $[M+H]^+$, 541, $t_R$=1.548 min, HPLC: 95.24% at 214 nm, 95.03% at 254 nm, $t_R$=7.943 min.

Example 58

Synthesis of 3-(8-(5,6-Dimethoxypyridin-2-ylamino)imidazo[1,2-b]pyridazin-6-yl)-N-(2-oxoindolin-5-yl)benzamide hydrochloride

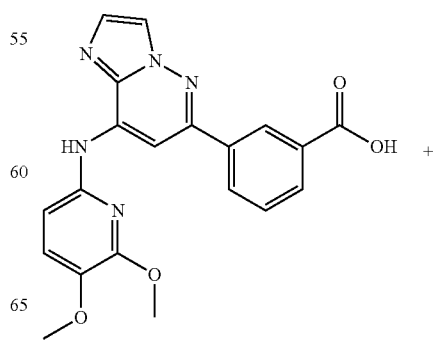

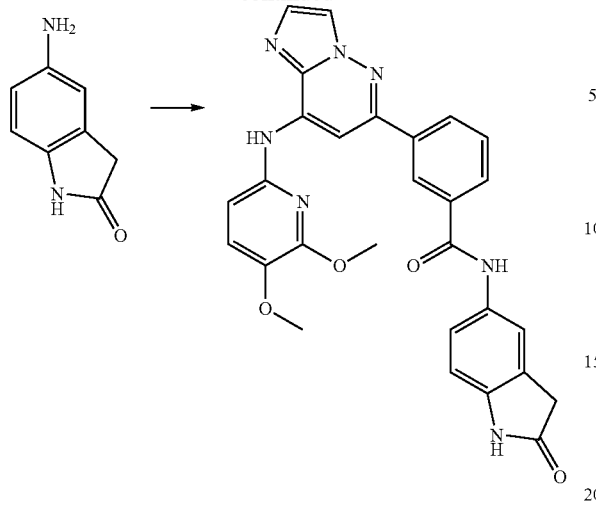

A mixture of 3-(8-(5,6-dimethoxypyridin-2-ylamino)imidazo[1,2-b]pyridazin-6-yl)benzoic acid (100 mg, 0.26 mmol), 5-aminoindolin-2-one (38 mg, 0.26 mmol), 1-methyl-1H-imidazole (84 mg, 1.02 mmol) and EDCI (196 mg, 1.02 mmol) in DMF (3 mL) was stirred at 50° C. for 48 h. Ethyl acetate (5 mL) and water (5 mL) were added. The organic layer was separated and the aqueous phase was extracted with ethyl acetate (20 mL). The organic phases were combined and washed with brine (10 mL) then dried over $Na_2SO_4$. The residue was concentrated and purified by prep-HPLC (Gemini 5u C18 150×21.2 mm; inject volume: 3 mL/inj, flow rate: 20 mL/min; wavelength: 214 nm and 254 nm; gradient conditions: 25% acetonitrile/75% water (0.1% TFA, v/v) initially, proceeding to 50% acetonitrile/50% water (0.1% TFA, v/v) in a linear fashion over 9 min) to give a residue that was treated with 0.5 mL HCl and the suspension stirred for 5 min. Concentration gave 3-(8-(5,6-dimethoxypyridin-2-ylamino)imidazo[1,2-b]pyridazin-6-yl)-N-(2-oxoindolin-5-yl)benzamide hydrochloride (2.3 mg, 2%) as a yellow solid. $^1$H NMR (300 MHz, DMSO): δ 10.67 (s, 1H), 10.36 (s, 1H), 10.31 (s, 1H), 8.88 (s, 1H), 8.51-8.47 (m, 2H), 8.20-8.12 (m, 3H), 7.75-7.68 (m, 2H), 7.54-7.44 (m, 2H), 7.09 (d, 1H, J=8.1 Hz), 6.81 (d, 1H, J=7.8 Hz), 4.03 (s, 3H), 3.78 (s, 3H), 3.08 (s, 2H). LC-MS: $[M+H]^+$, 522, $t_R$=1.48 min, HPLC: 99.05% at 214 nm, 96.91% at 254 nm, $t_R$=5.184 min.

Example 59

Synthesis of 3-(8-(6-(3,3-Dimethylpyrrolidin-1-yl)pyridin-2-ylamino)imidazo[1,2-b]pyridazin-6-yl)benzoic acid

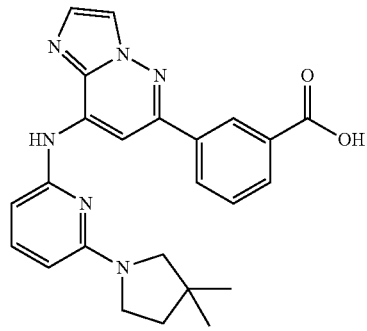 [SMILES: CC1(C)CCN(c2cccc(Nc3cc(-c4cccc(C(=O)O)c4)nn4ccnc34)n2)C1]

Step 1

Methyl 3-(8-(6-(3,3-dimethylpyrrolidin-1-yl)pyridin-2-ylamino)imidazo[1,2-b]pyridazin-6-yl)benzoate

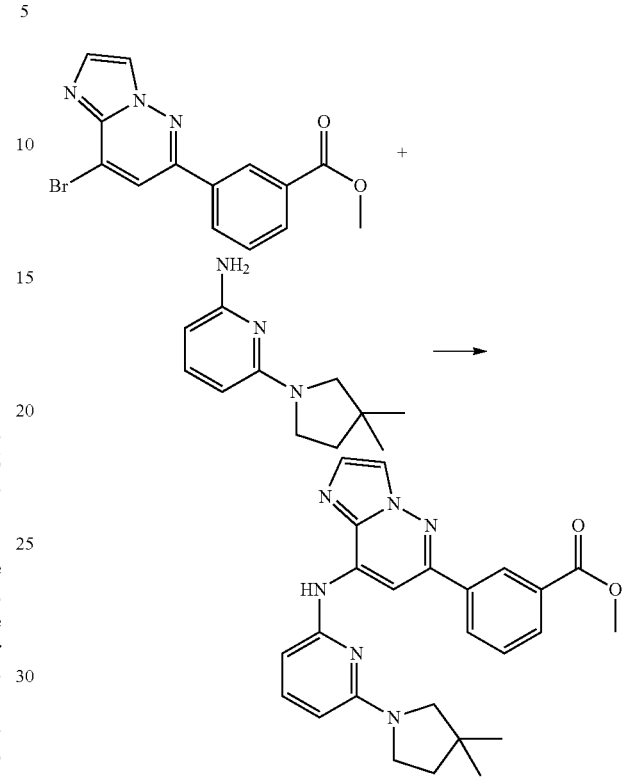

A mixture of methyl 3-(8-bromoimidazo[1,2-b]pyridazin-6-yl)benzoate (0.10 g, 0.3 mmol), 6-(3,3-dimethylpyrrolidin-1-yl)pyridin-2-amine (60 mg, 0.3 mmol), $Pd_2(dba)_3$ (0.014 g, 0.03 mmol), BINAP (0.038 g, 0.06 mmol) and $Cs_2CO_3$ (0.3 g, 0.9 mmol) in dioxane (10 mL) was heated to 100° C. for 15 h in a sealed tube under $N_2$ atmosphere then concentrated in vacuo. The residue was purified by chromatography (silica gel, 10 g, 200~300 mesh, dichloromethane:MeOH=100:1) to afford methyl 3-(8-(6-(3,3-dimethylpyrrolidin-1-yl)pyridin-2-ylamino)imidazo[1,2-b]pyridazin-6-yl)benzoate (110 mg, 83%) as a brown solid. LC-MS: $[M+1]^+$=443, $t_R$=2.065 min.

Step 2

3-(8-(6-(3,3-Dimethylpyrrolidin-1-yl)pyridin-2-ylamino)imidazo[1,2-b]pyridazin-6-yl)benzoic acid

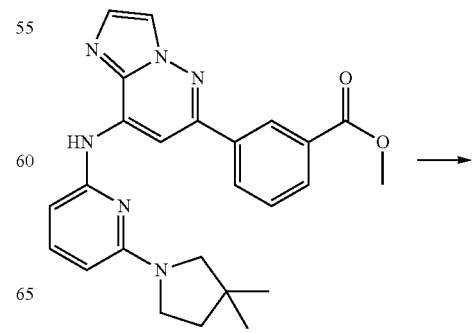

-continued

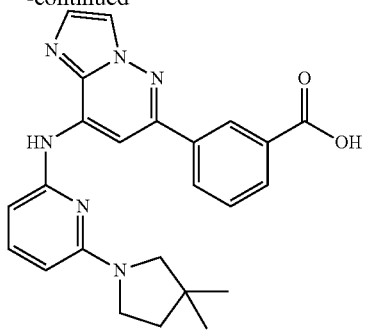

A mixture of methyl 3-(8-(6-(3,3-dimethylpyrrolidin-1-yl) pyridin-2-amino)imidazo[1,2-b]pyridazin-6-yl)benzoate (170 mg, 0.38 mmol) and NaOH (170 mg, 4.25 mmol) in 1,4-dioxane (5 mL) and water (5 mL) was stirred for 2 h at 40° C. The mixture was concentrated to 5 mL and adjusted to pH=2 with 2M HCl. The precipitate was filtered and the solid obtained was purified by prep-HPLC (Gemini 5u C18 150× 21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to give 3-(8-(6-(3,3-dimethylpyrrolidin-1-yl)pyridin-2-ylamino)imidazo[1,2-b]pyridazin-6-yl)benzoic acid (27 mg, 17%) as a yellow solid. $^1$H NMR (300 MHz, DMSO): δ 10.23 (s, 1H), 9.12 (s, 1H), 8.53 (s, 1H), 8.44 (s, 1H), 8.21 (d, 1H, J=7.5 Hz), 8.12 (d, 1H, J=7.8 Hz), 8.00 (brs, 1H), 7.70 (t, 1H, J=7.8 Hz), 7.50 (t, 1H, J=8.1 Hz), 6.70 (d, 1H, J=7.5 Hz), 6.70 (d, 1H, J=8.1 Hz), 3.61 (s, 2H), 3.25 (s, 2H), 1.80-1.75 (m, 2H), 1.23 (s, 6H). LC-MS: [M+H]$^+$, 429, $t_R$=1.73 min, HPLC: 98.58% at 214 nm, 98.61% at 254 nm, $t_R$=6.606 min.

Example 60

Synthesis of 3-(8-(6-(2,5-Dimethylpyrrolidin-1-yl) pyridin-2-ylamino)imidazo[1,2-b]pyridazin-6-yl) benzoic acid

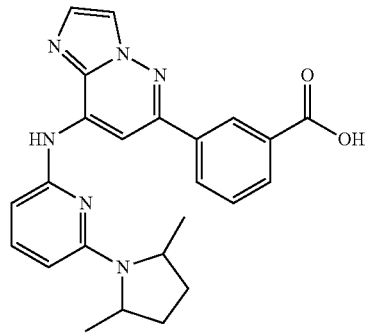

Step 1

Methyl 3-(8-(6-(2,5-dimethylpyrrolidin-1-yl)pyridin-2-ylamino)imidazo[1,2-b]pyridazin-6-yl)benzoate

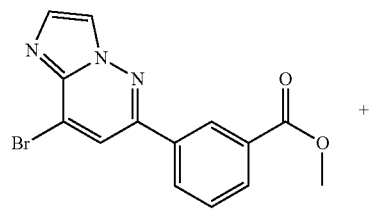

-continued

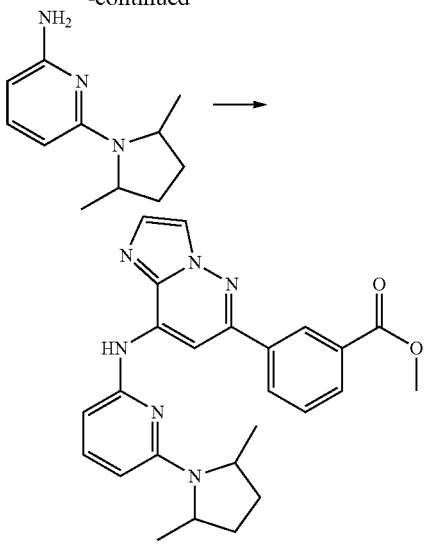

A mixture of methyl 3-(8-bromoimidazo[1,2-b]pyridazin-6-yl)benzoate (0.2 g, 0.6 mmol), 6-(2,5-dimethylpyrrolidin-1-yl)pyridin-2-amine (116 mg, 0.6 mmol), Pd$_2$(dba)$_3$ (0.036 g, 0.06 mmol), BINAP (0.076 g, 0.12 mmol) and Cs$_2$CO$_3$ (0.59 g, 1.8 mmol) in dioxane (5 mL) was heated to 100° C. for 15 h in a sealed tube under N$_2$ atmosphere then concentrated in vacuo. The residue was purified by chromatography (silica gel, 10 g, 200~300 mesh, dichloromethane:MeOH=100:1) to afford methyl 3-(8-(6-(2,5-dimethylpyrrolidin-1-yl)pyridin-2-ylamino)imidazo[1,2-b]pyridazin-6-yl)benzoate (150 mg, 56%) as a brown solid. LC-MS: [M+1]$^+$=443, $t_R$=2.092 min.

Step 2

3-(8-(6-(2,5-Dimethylpyrrolidin-1-yl)pyridin-2-ylamino)imidazo[1,2-b]pyridazin-6-yl)benzoic acid

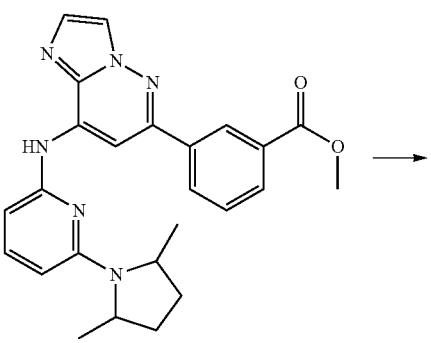

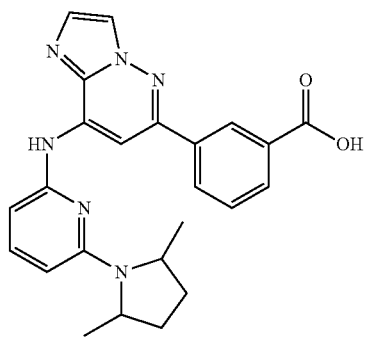 [SMILES: CC1CCC(C)N1c1cccc(Nc2cc(-c3cccc(C(=O)O)c3)nn3ccnc23)n1]

A mixture of methyl 3-(8-(6-(2,5-dimethylpyrrolidin-1-yl)pyridin-2-ylamino)imidazo[1,2-b]pyridazin-6-yl)benzoate (150 mg, 0.34 mmol) and NaOH (150 mg, 3.75 mmol) in 1,4-dioxane (5 mL) and water (5 mL) was stirred for 2 h at 40° C. Then the mixture was concentrated to 5 mL then adjusted to pH=2 with 2M HCl. The precipitate was filtered and the solid was washed with water (2 mL) and dichloromethane (3 mL) to give 3-(8-(6-(2,5-dimethylpyrrolidin-1-yl)pyridin-2-ylamino)imidazo[1,2-b]pyridazin-6-yl)benzoic acid (86 mg, 59%) as a yellow solid. $^1$H NMR (300 MHz, DMSO): δ 10.79 (s, 1H), 9.13 (s, 1H), 8.62 (s, 1H), 8.49 (s, 1H), 8.32-8.14 (m, 3H), 7.75 (t, 1H, J=7.8 Hz), 7.54 (t, 1H, J=8.1 Hz), 6.74 (d, 1H, J=7.8 Hz), 6.23 (d, 1H, J=8.7 Hz), 4.12 (s, 2H), 2.13-2.08 (m, 2H), 1.74-1.68 (m, 2H), 1.18 (s, 3H), 1.16 (s, 3H). LC-MS: [M+H]$^+$, 429, $t_R$=1.708 min, HPLC: 97.23% at 214 nm, 95.49% at 254 nm, $t_R$=6.248 min.

Example 61

Synthesis of 3-(8-(6-(4,4-Dimethylpiperidin-1-yl)pyridin-2-ylamino)imidazo[1,2-b]pyridazin-6-yl)benzoic acid

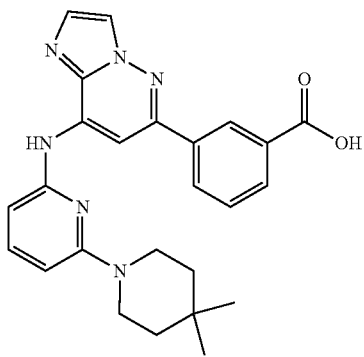 [SMILES: CC1(C)CCN(c2cccc(Nc3cc(-c4cccc(C(=O)O)c4)nn4ccnc34)n2)CC1]

Step 1

Methyl 3-(8-(6-(4,4-dimethylpiperidin-1-yl)pyridin-2-ylamino)imidazo[1,2-b]pyridazin-6-yl)benzoate

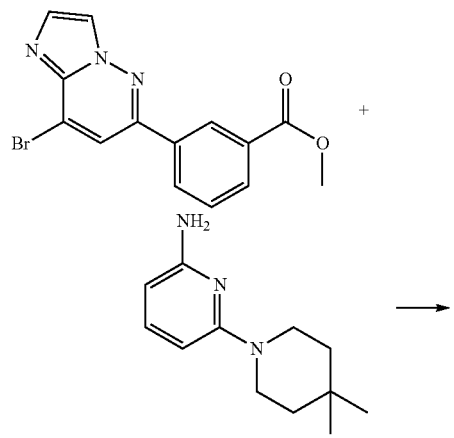

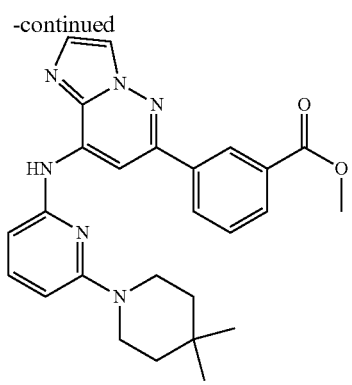

A mixture of methyl 3-(8-bromoimidazo[1,2-b]pyridazin-6-yl)benzoate (0.15 g, 0.45 mmol), 6-(4,4-dimethylpiperidin-1-yl)pyridin-2-amine (93 mg, 0.46 mmol), Pd$_2$(dba)$_3$ (0.026 g, 0.046 mmol), BINAP (0.057 g, 0.09 mmol) and Cs$_2$CO$_3$ (0.442 g, 1.36 mmol) in dioxane (5 mL) was heated to 100° C. for 15 h in a sealed tube under N$_2$ atmosphere then concentrated in vacuo. The residue was purified by chromatography (silica gel, 10 g, 200~300 mesh, dichloromethane:MeOH=100:1) to afford methyl 3-(8-(6-(4,4-dimethylpiperidin-1-yl)pyridin-2-ylamino)imidazo[1,2-b]pyridazin-6-yl)benzoate (200 mg) as a brown liquid. LC-MS: [M+1]$^+$=457.3, $t_R$=2.145 min. This contained unidentified impurities and was used directly without further purification.

Step 2

3-(8-(6-(4,4-Dimethylpiperidin-1-yl)pyridin-2-ylamino)imidazo[1,2-b]pyridazin-6-yl)benzoic acid

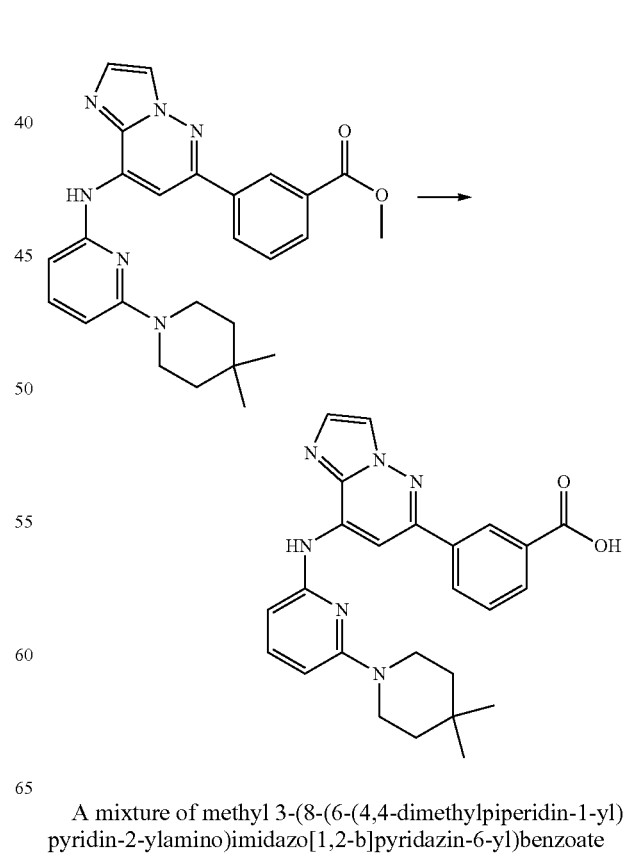

A mixture of methyl 3-(8-(6-(4,4-dimethylpiperidin-1-yl)pyridin-2-ylamino)imidazo[1,2-b]pyridazin-6-yl)benzoate (200 mg, 0.44 mmol) and NaOH (200 mg, 5 mmol) in 1,4-dioxane (5 mL) and water (5 mL) was stirred for 2 h at 40° C. Then the mixture was concentrated to 5 mL and adjusted to pH=2 with 2M HCl. The precipitate was filtered and purified by prep-HPLC to give 3-(8-(6-(4,4-dimethylpiperidin-1-yl)pyridin-2-ylamino)imidazo[1,2-b]pyridazin-6-yl)benzoic acid (18 mg, 9%) as a yellow solid. $^1$H NMR (300 MHz, DMSO): δ 10.53 (s, 1H), 8.94 (s, 1H), 8.52 (s, 2H), 8.18-8.12 (m, 3H), 7.72 (t, 1H, J=7.8 Hz), 7.57 (t, 1H, J=7.8 Hz), 6.76 (d, 1H, J=7.8 Hz), 6.54 (d, 1H, J=8.1 Hz), 3.59-3.57 (m, 4 h), 1.38-1.36 (m, 4 h), 0.98 (s, 6H). LC-MS: [M+H]$^+$, 443, $t_R$=1.788 min, HPLC: 100% at 214 nm, 100% at 254 nm, $t_R$=6.762 min.

Example 62

Synthesis of 6-(3,4-Dimethoxyphenyl)-N-(6-(2-methylpyrrolidin-1-yl)pyridin-2-yl)imidazo[1,2-b]pyridazin-8-amine

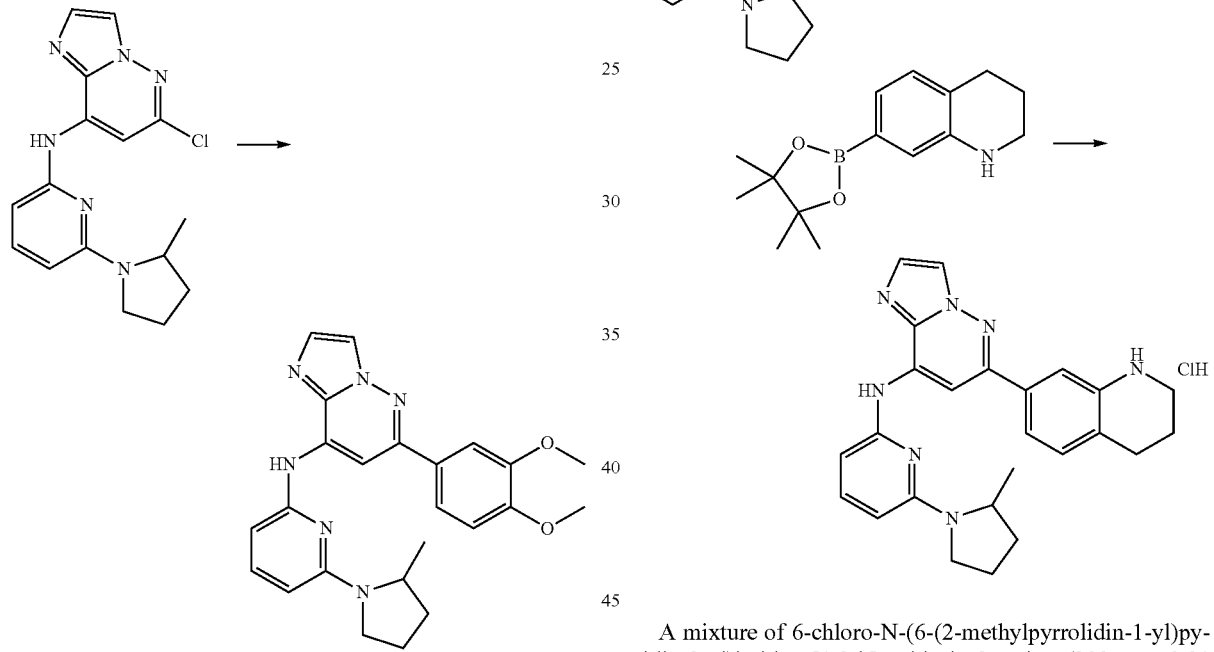

A mixture of 6-chloro-N-(6-(2-methylpyrrolidin-1-yl)pyridin-2-yl)imidazo[1,2-b]pyridazin-8-amine (100 mg, 0.3 mmol), 3,4-dimethoxyphenylboronic acid (82 mg, 0.45 mmol), Pd$_2$(dba)$_3$ (0.018 g, 0.03 mmol), X-phos (0.029 g, 0.06 mmol) and Na$_2$CO$_3$ (0.096 g, 0.9 mmol) in dioxane (3 mL) and water (3 mL) was heated to 100° C. for 15 h in a sealed tube under N$_2$ atmosphere then concentrated in vacuo. The residue was purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to afford 6-(3,4-dimethoxyphenyl)-N-(6-(2-methylpyrrolidin-1-yl)pyridin-2-yl)imidazo[1,2-b]pyridazin-8-amine (18 mg, 14%) as a yellow solid. $^1$H NMR (300 MHz, DMSO): δ 10.19 (s, 1H), 8.93 (s, 1H), 8.40 (s, 1H), 8.08 (s, 1H), 7.50-7.48 (m, 1H), 7.11 (d, 1H, J=8.4 Hz), 6.66 (d, 1H, J=7.2 Hz), 6.12 (d, 1H, J=7.8 Hz), 4.22 (brs, 1H), 3.85 (s, 6H), 3.56-3.37 (m, 3H), 2.07-1.97 (m, 2H), 1.74-1.70 (m, 1H), 1.11 (d, 3H, J=6.3 Hz). LC-MS: [M+H]$^+$, 431, $t_R$=1.769 min, HPLC: 98.38% at 214 nm, 99.04% at 254 nm, $t_R$=7.213 min.

Example 63

Synthesis of N-(6-(2-Methylpyrrolidin-1-yl)pyridin-2-yl)-6-(1,2,3,4-tetrahydroquinolin-7-yl)imidazo[1,2-b]pyridazin-8-amine hydrochloride

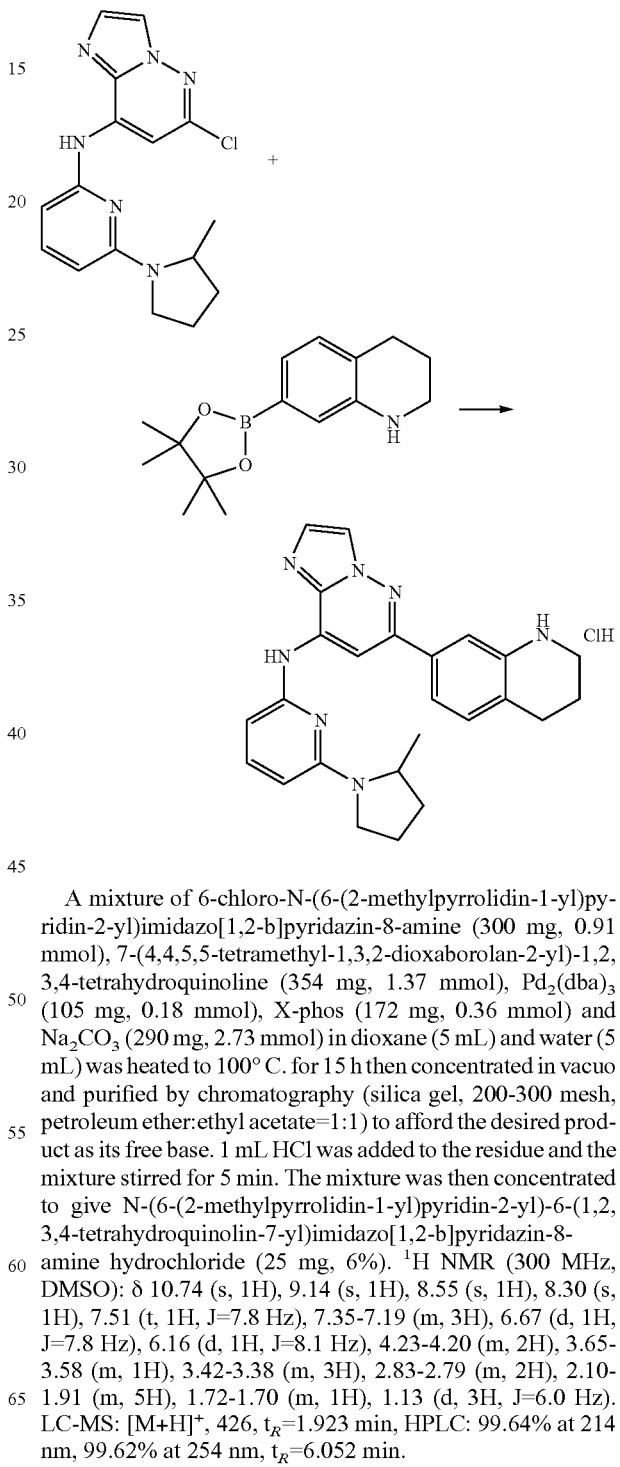

A mixture of 6-chloro-N-(6-(2-methylpyrrolidin-1-yl)pyridin-2-yl)imidazo[1,2-b]pyridazin-8-amine (300 mg, 0.91 mmol), 7-(4,4,5,5-tetramethyl-1,3,2-dioxaborolan-2-yl)-1,2,3,4-tetrahydroquinoline (354 mg, 1.37 mmol), Pd$_2$(dba)$_3$ (105 mg, 0.18 mmol), X-phos (172 mg, 0.36 mmol) and Na$_2$CO$_3$ (290 mg, 2.73 mmol) in dioxane (5 mL) and water (5 mL) was heated to 100° C. for 15 h then concentrated in vacuo and purified by chromatography (silica gel, 200-300 mesh, petroleum ether:ethyl acetate=1:1) to afford the desired product as its free base. 1 mL HCl was added to the residue and the mixture stirred for 5 min. The mixture was then concentrated to give N-(6-(2-methylpyrrolidin-1-yl)pyridin-2-yl)-6-(1,2,3,4-tetrahydroquinolin-7-yl)imidazo[1,2-b]pyridazin-8-amine hydrochloride (25 mg, 6%). $^1$H NMR (300 MHz, DMSO): δ 10.74 (s, 1H), 9.14 (s, 1H), 8.55 (s, 1H), 8.30 (s, 1H), 7.51 (t, 1H, J=7.8 Hz), 7.35-7.19 (m, 3H), 6.67 (d, 1H, J=7.8 Hz), 6.16 (d, 1H, J=8.1 Hz), 4.23-4.20 (m, 2H), 3.65-3.58 (m, 1H), 3.42-3.38 (m, 3H), 2.83-2.79 (m, 2H), 2.10-1.91 (m, 5H), 1.72-1.70 (m, 1H), 1.13 (d, 3H, J=6.0 Hz). LC-MS: [M+H]$^+$, 426, $t_R$=1.923 min, HPLC: 99.64% at 214 nm, 99.62% at 254 nm, $t_R$=6.052 min.

Example 64

Synthesis of 1-(7-(8-(6-(2-Methylpyrrolidin-1-yl)pyridin-2-ylamino)imidazo[1,2-b]pyridazin-6-yl)-3,4-dihydroisoquinolin-2(1H)-yl)ethanone

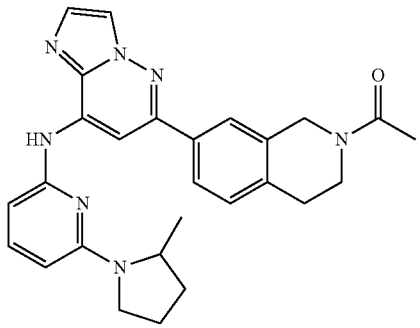 [SMILES: CC(=O)N1CCc2ccc(-c3cc(Nc4cccc(N5CCCC5C)n4)c4nccn4n3)cc2C1]

Step 1

1-(7-Bromo-3,4-dihydroisoquinolin-2(1H)-yl)ethanone

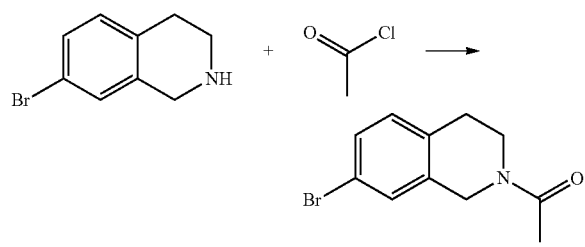

To A mixture of 7-bromo-1,2,3,4-tetrahydroisoquinoline (500 mg, 2.36 mmol) and triethylamine (715 mg, 7.08 mmol) in dichloromethane (10 mL) was added acetyl chloride (221 mg, 2.83 mmol) at 0° C., then the mixture was stirred for 2 h at 0° C. Water (5 mL) was added and the mixture extracted with ethyl acetate (10 mL). The combined organic layers were washed with brine (3×10 mL) and dried with $Na_2SO_4$. The residue was concentrated then purified by chromatography (silica gel, 200-300 mesh, petroleum ether:ethyl acetate=5:1) to give 1-(7-bromo-3,4-dihydroisoquinolin-2(1H)-yl)ethanone (500 mg, 83%) as yellow oil. LC-MS: $[M+H]^+$, 254, $t_R$=1.533 min.

Step 2

1-(7-(4,4,5,5-Tetramethyl-1,3,2-dioxaborolan-2-yl)-3,4-dihydroisoquinolin-2(1H)-yl)ethanone

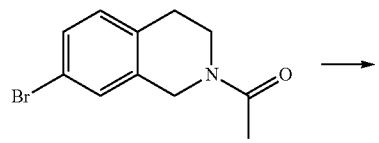

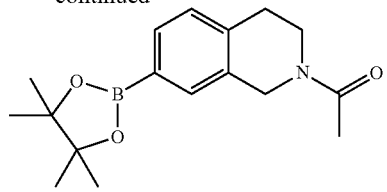

A mixture of 1-(7-bromo-3,4-dihydroisoquinolin-2(1H)-yl)ethanone (300 mg, 1.2 mmol), 4,4,4',4',5,5,5',5'-octamethyl-2,2'-bi(1,3,2-dioxaborolane) (450 mg, 1.8 mmol), Pd(dppf)Cl$_2$ (123 mg, 0.12 mmol), KOAc (348 mg, 3.6 mmol) and DMF (10 mL) was heated to 100° C. for 15 h under $N_2$ atmosphere then concentrated in vacuo. Water (20 mL) was added and extracted with ethyl acetate (20 mL). The organic phase was washed with brine (3×10 mL) then dried with $Na_2SO_4$. The residue was concentrated and purified by chromatography (silica gel, 200-300 mesh, dichloromethane:MeOH=20:1) to give 1-(7-(4,4,5,5-tetramethyl-1,3,2-dioxaborolan-2-yl)-3,4-dihydroisoquinolin-2(1H)-yl)ethanone (300 mg, crude) as black oil. LC-MS: $[M+H]^+$, 301.2, $[2M+H]^+$, 603.4, $t_R$=1.569 min. This contained unidentified impurities and was used directly without further purification.

Step 3

1-(7-(8-(6-(2-Methylpyrrolidin-1-yl)pyridin-2-ylamino)imidazo[1,2-b]pyridazin-6-yl)-3,4-dihydroisoquinolin-2(1H)-yl)ethanone

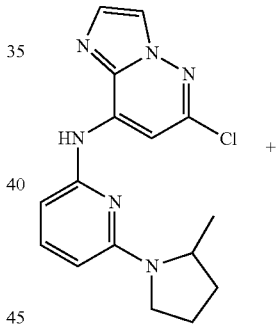

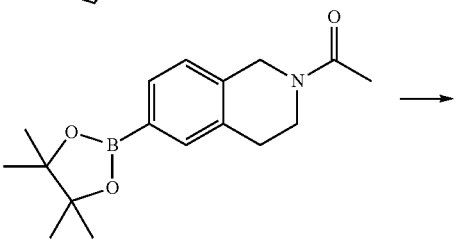

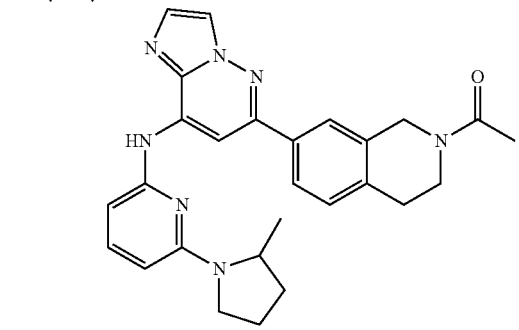

A mixture of 6-chloro-N-(6-(2-methylpyrrolidin-1-yl)pyridin-2-yl)imidazo[1,2-b]pyridazin-8-amine (90 mg, 0.27 mmol), 1-(7-(4,4,5,5-tetramethyl-1,3,2-dioxaborolan-2-yl)-3,4-dihydroisoquinolin-2(1H)-yl)ethanone (500 mg, crude), Pd$_2$(dba)$_3$ (16 mg, 0.027 mmol), X-phos (26 mg, 0.054 mmol) and Na$_2$CO$_3$ (86 mg, 0.81 mmol) in dioxane (5 mL) and water (5 mL) was heated to 100° C. for 15 h then concentrated in vacuo and purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to afford 1-(7-(8-(6-(2-methylpyrrolidin-1-yl)pyridin-2-ylamino)imidazo[1,2-b]pyridazin-6-yl)-3,4-dihydroisoquinolin-2(1H)-yl)ethanone (20 mg, 16%). $^1$H NMR (300 MHz, CD3OD): δ 8.87-8.83 (m, 1H), 8.25 (s, 1H), 7.96 (s, 1H), 7.83-7.81 (m, 1H), 7.71-7.48 (m, 2H), 7.34-7.31 (m, 1H), 6.30-6.19 (m, 2H), 4.78-4.74 (m, 2H), 4.26-4.22 (m, 1H), 3.81-3.77 (m, 2H), 3.68-3.62 (m, 1H), 3.46-3.41 (m, 1H), 3.01-2.93 (m, 2H), 2.23 (s, 3H), 2.18-2.02 (m, 3H), 1.88-1.83 (m, 1H), 1.21-1.19 (m, 3H). LC-MS: [M+H]$^+$, 468, $t_R$=1.726 min, HPLC: 96.93% at 214 nm, 99.52% at 254 nm, $t_R$=6.04 min.

Example 65

Synthesis of Methyl 3-(8-(6-(3-tert-butylpyrrolidin-1-yl)pyridin-2-ylamino)imidazo[1,2-b]pyridazin-6-yl)benzoate

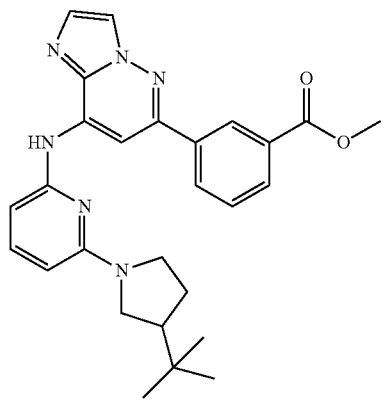 [SMILES: COC(=O)c1cccc(-c2cc(Nc3cccc(N4CCC(C(C)(C)C)C4)n3)c3nccn3n2)c1]

Step 1

6-(3-tert-Butylpyrrolidin-1-yl)pyridin-2-amine

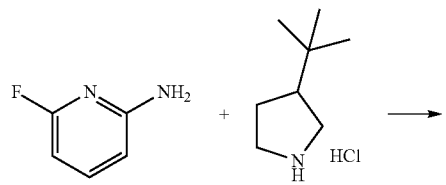

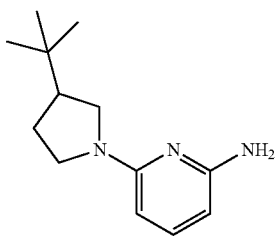

A suspension of 6-fluoropyridin-2-amine (500 mg, 4.46 mmol), 3-tert-butylpyrrolidine (730 mg, 4.46 mmol) in water (0.5 mL) and triethylamine (0.9 g, 8.92 mmol) was heated to 150° C. in a microwave oven for 30 minutes. The reaction mixture was purified by chromatography (silica gel, 200-300 mesh, dichloromethane:MeOH=20:1) to give 6-(3-tert-butylpyrrolidin-1-yl)pyridin-2-amine (540 mg, 55%) as a brown oil. LC-MS: [M+H]$^+$, 220, $t_R$=1.228 min.

Step 2

N-(6-(3-tert-butylpyrrolidin-1-yl)pyridin-2-yl)-6-chloroimidazo[1,2-b]pyridazin-8-amine

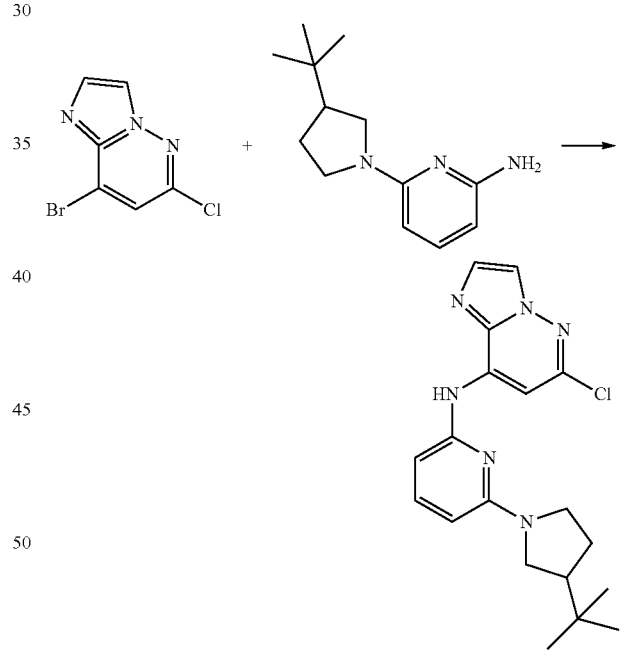

A mixture of 8-bromo-6-chloroimidazo[1,2-b]pyridazine (573 mg, 2.47 mmol), 6-(3-tert-butylpyrrolidin-1-yl)pyridin-2-amine (540 mg, 2.47 mmol), Pd$_2$(dba)$_3$ (142 mg, 0.25 mmol), BINAP (307 mg, 0.50 mmol), Cs$_2$CO$_3$ (2.4 g, 7.41 mmol) and dioxane (20 mL) was heated to reflux with stirring for 15 h under N$_2$. The solvent was removed in vacuo and the resulting mixture was purified by chromatography (silica gel, 200-300 mesh, dichloromethane:MeOH=50:1) to give N-(6-(3-tert-butylpyrrolidin-1-yl)pyridin-2-yl)-6-chloroimidazo[1,2-b]pyridazin-8-amine (400 mg, crude) as a brown oil. LC-MS: [M+H]$^+$, 371.1, $t_R$=2.23 min.

Step 3

Methyl 3-(8-(6-(3-tert-butylpyrrolidin-1-yl)pyridin-2-ylamino)imidazo[1,2-b]pyridazin-6-yl)benzoate

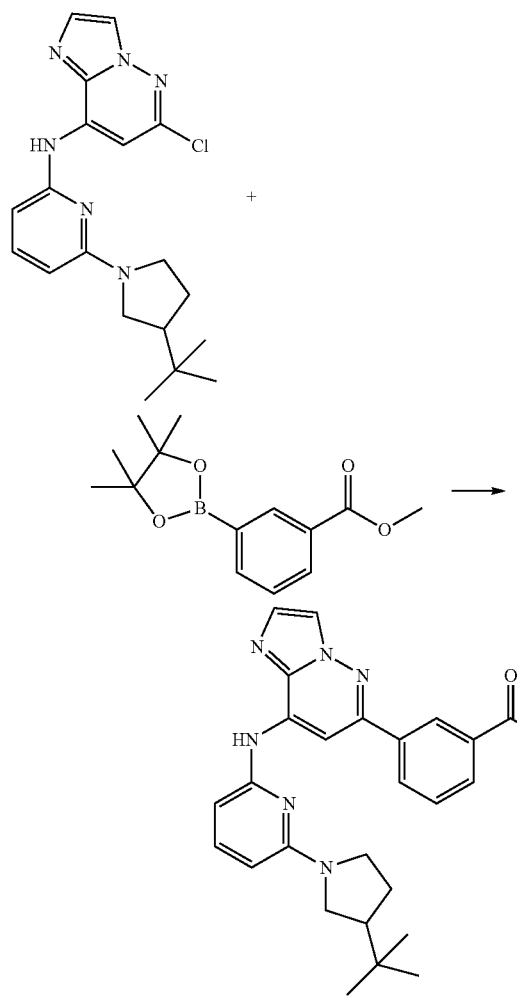

A mixture of N-(6-(3-tert-butylpyrrolidin-1-yl)pyridin-2-yl)-6-chloroimidazo[1,2-b]pyridazin-8-amine (400 mg, 1.08 mmol), methyl 3-(4,4,5,5-tetramethyl-1,3,2-dioxaborolan-2-yl)benzoate (425 mg, 1.62 mmol), Pd$_2$(dba)$_3$ (64 mg, 0.11 mmol), X-phos (105 mg, 0.22 mmol) and Na$_2$CO$_3$ (343 mg, 3.24 mmol) in dioxane (5 mL) and water (5 mL) was heated to reflux for 15 h under N$_2$. The solvent was removed in vacuo and the resulting mixture was purified by prep-HPLC (Gemini 5u C18 150×21.2 mm; inject volume: 3 mL/inj, flow rate: 20 mL/min; wavelength: 214 nm and 254 nm; gradient conditions: 25% acetonitrile/75% water (0.1% TFA, v/v) initially, proceeding to 50% acetonitrile/50% water (0.1% TFA, v/v) in a linear fashion over 9 min) to give methyl 3-(8-(6-(3-tert-butylpyrrolidin-1-yl)pyridin-2-ylamino)imidazo[1,2-b]pyridazin-6-yl)benzoate (60 mg, 12%) as a yellow solid. $^1$H NMR (300 MHz, CD3OD): δ 8.74 (s, 1H), 8.55 (s, 1H), 8.21-8.11 (m, 3H), 7.86 (s, 1H), 7.63-7.47 (m, 2H), 6.27 (d, 1H, J=5.4 Hz), 6.14 (d, 1H, J=7.2 Hz), 3.96 (s, 3H), 3.71-3.68 (m, 1H), 3.48-3.42 (m, 2H), 3.19-3.13 (m, 1H), 2.16-1.98 (m, 2H), 1.82-1.78 (m, 2H). 0.93 (s, 9H). LC-MS: 471, [M+H]$^+$, t$_R$=2.275 min, HPLC: 96.55% at 214 nm, 96.14% at 254 nm, t$_R$=5.449 min.

Example 66

Synthesis of 3-(8-(6-(3-tert-Butylpyrrolidin-1-yl)pyridin-2-ylamino)imidazo[1,2-b]pyridazin-6-yl)benzoic acid

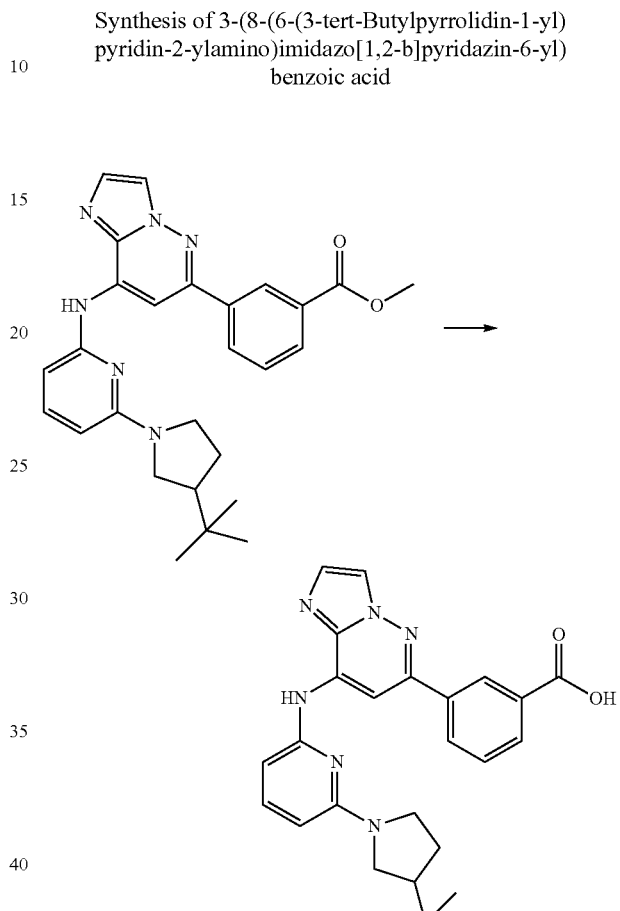

To a solution of methyl 3-(8-(6-(3-tert-butylpyrrolidin-1-yl)pyridin-2-ylamino)imidazo[1,2-b]pyridazin-6-yl)benzoate (55 mg, 0.11 mmol) in dioxane (5 mL) and water (5 mL) was added NaOH (50 mg, 1.25 mmol), then the mixture was heated to 40° C. with stirring for 3 h. The solution was concentrated in vacuo, washed with dichloromethane (10 mL×3), then water (10 mL) was added and the aqueous phase was adjusted to pH=2 by addition of 2M HCl. The solid formed was filtered and washed with water (1 mL) and MeOH (1 mL) to give 3-(8-(6-(3-tert-butylpyrrolidin-1-yl)pyridin-2-ylamino)imidazo[1,2-b]pyridazin-6-yl)benzoic acid (50 mg, 93%) as a yellow solid. $^1$H NMR (300 MHz, DMSO): δ 10.22 (s, 1H), 9.05 (s, 1H), 8.52 (s, 1H), 8.45 (s, 1H), 8.22 (d, 1H, J=8.1 Hz), 8.12 (d, 1H, J=7.5 Hz), 8.01 (s, 1H), 7.72 (t, 1H, J=7.5 Hz), 7.52 (t, 1H, J=7.8 Hz), 6.72 (d, 1H, J=7.5 Hz), 6.15 (d, 1H, J=8.4 Hz), 3.73-3.68 (m, 1H), 3.52-3.43 (m, 2H), 3.13 (t, 1H, J=10.5 Hz), 2.16-2.12 (m, 1H), 1.98-1.93 (m, 1H), 1.78-1.71 (m, 1H), 0.86 (s, 9H). LC-MS: [M+H]$^+$, 457, t$_R$=1.859 min, HPLC: 96.72% at 214 nm, 98.12% at 254 nm, t$_R$=4.654 min.

Example 67

Synthesis of 3-(8-(6-(3-tert-Butylpyrrolidin-1-yl)pyridin-2-ylamino)imidazo[1,2-b]pyridazin-6-yl)benzamide

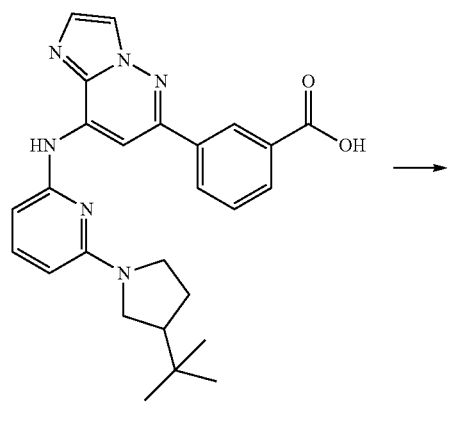

A mixture of 3-(8-(6-(3-tert-butylpyrrolidin-1-yl)pyridin-2-ylamino)imidazo[1,2-b]pyridazin-6-yl)benzoic acid (25 mg, 0.106 mmol), 0.5 M ammonium in dioxane solution (2 mL), EDCI (43 mg, 0.22 mmol), HOBT (30 mg, 0.22 mmol), Et$_3$N (23 mg, 0.22 mmol) and dichloromethane (2 mL) was stirred at room temperature for 16 h. The solution was concentrated in vacuo and purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to give 3-(8-(6-(3-tert-butylpyrrolidin-1-yl)pyridin-2-ylamino)imidazo[1,2-b]pyridazin-6-yl)benzamide (6 mg, 24%) as a yellow solid. $^1$H NMR (300 MHz, DMSO): δ 9.79 (s, 1H), 8.91 (s, 1H), 8.47 (s, 1H), 8.31 (s, 1H), 8.16-8.02 (m, 3H), 7.79 (s, 1H), 7.63 (t, 1H, J=7.6 Hz), 7.52-7.47 (m, 2H), 6.72 (d, 1H, J=7.8 Hz), 6.11 (d, 1H, J=8.4 Hz), 3.72-3.66 (m, 1H), 3.52-3.40 (m, 2H), 3.12 (t, 1H, J=10.0 Hz), 2.13-1.94 (m, 2H), 1.78-1.74 (m, 1H), 0.86 (s, 9H). LC-MS: [M+H]$^+$, 456, t$_R$=1.72 min, HPLC: 99.11% at 214 nm, 99.64% at 254 nm, t$_R$=4.22 min.

Example 68

Synthesis of (3-(8-(6-(2-Methylpyrrolidin-1-yl)pyridin-2-ylamino)imidazo[1,2-b]pyridazin-6-yl)phenyl)methanol

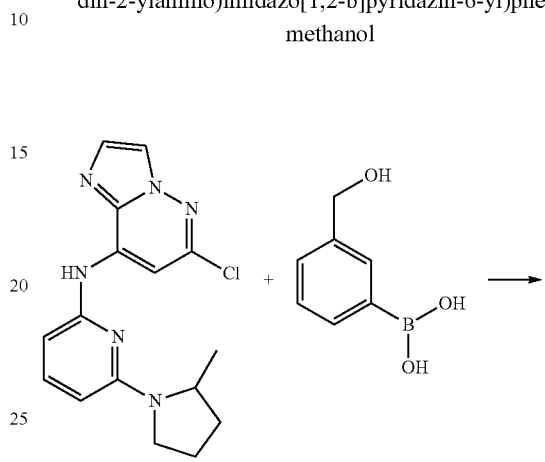

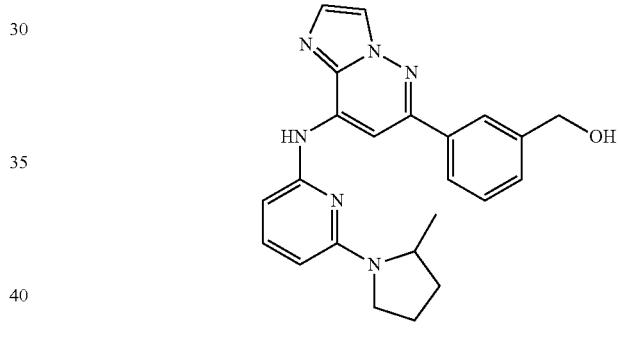

A mixture of 6-chloro-N-(6-(2-methylpyrrolidin-1-yl)pyridin-2-yl)imidazo[1,2-b]pyridazin-8-amine (500 mg, 1.52 mmol), 3-(hydroxymethyl)phenylboronic acid (350 mg, 2.28 mmol), Pd$_2$dba$_3$ (100 mg, 0.15 mmol), X-phos (300 mg, 0.61 mmol) and K$_2$CO$_3$ (625 mg, 4.56 mmol) was dissolved in dioxane/water (50 mL/5 mL). The reaction mixture was degassed with bubbling nitrogen for 5 minutes then heated at 100° C. with stirring for 3 h, the solvent removed in vacuo, The residue purified by chromatography (silica gel, 200-300 mesh, dichloromethane/methanol=40:1) to give (3-(8-(6-(2-methylpyrrolidin-1-yl)pyridin-2-ylamino)imidazo[1,2-b]pyridazin-6-yl)phenyl)methanol (300 mg, 81%) as a white solid. $^1$H NMR (300 MHz, DMSO): δ 9.62 (s, 1H), 8.77 (s, 1H), 8.19 (s, 1H), 7.88 (s, 1H), 7.81-7.78 (m, 1H), 7.63 (s, 1H), 7.49-7.39 (m, 3H), 6.71 (d, 1H, J=7.8 Hz), 6.05 (d, 1H, J=7.8 Hz), 5.31 (t, 1H, J=5.7 Hz), 4.59 (d, 2H, J=5.7 Hz), 4.25-4.20 (m, 1H), 3.58-3.50 (m, 1H), 3.42-3.38 (m, 1H), 2.08-1.97 (m, 3H), 1.70 (brs, 1H), 1.11 (d, 3H, J=6.3 Hz). LC-MS: [M+H]$^+$, 401, t$_R$=1.679 min, HPLC: 99.87% at 214 nm, 99.85% at 254 nm, t$_R$=5.87 min.

Example 69

Synthesis of N-(6-(2-Methylpyrrolidin-1-yl)pyridin-2-yl)-6-(3-(piperidin-1-ylmethyl)phenyl)imidazo[1,2-b]pyridazin-8-amine

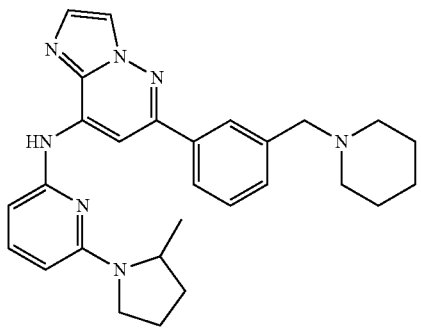 [SMILES: CC1CCCN1c1cccc(Nc2cc(-c3cccc(CN4CCCCC4)c3)nn3ccnc23)n1]

Step 1

3-(8-(6-(2-Methylpyrrolidin-1-yl)pyridin-2-ylamino)imidazo[1,2-b]pyridazin-6-yl)benzaldehyde

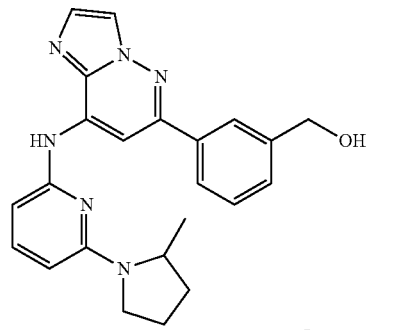

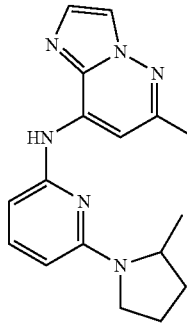

(3-(8-(6-(2-methylpyrrolidin-1-yl)pyridin-2-ylamino)imidazo[1,2-b]pyridazin-6-yl)phenyl)methanol (20 mg, 0.05 mmol) and MnO$_2$ (86 mg, 1.0 mmol) were dissolved in dichloromethane (10 mL), the reaction mixture was heated up to 40° C. with stirring for 24 h, filtered, washed with dichloromethane (30 mL) and then the filtrate was concentrated in vacuo to give a solid which was purified by chromatography on a aluminum oxide eluted with dichloromethane to give 3-(8-(6-(2-methylpyrrolidin-1-yl)pyridin-2-ylamino)imidazo[1,2-b]pyridazin-6-yl)benzaldehyde (9 mg, 45%) as an orange solid. LC-MS: 399 [M+H]$^+$, t$_R$=1.88 min.

Step 2

N-(6-(2-methylpyrrolidin-1-yl)pyridin-2-yl)-6-(3-(piperidin-1-ylmethyl)phenyl)imidazo[1,2-b]pyridazin-8-amine

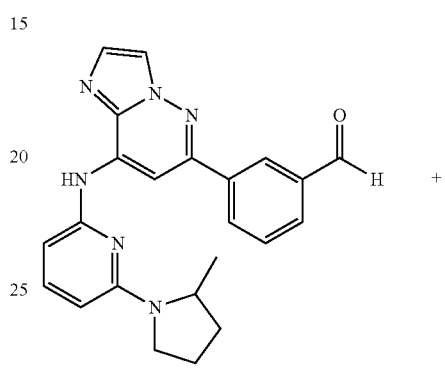

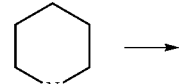

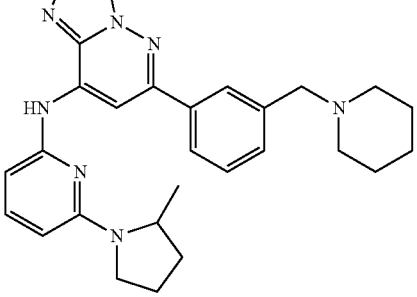

3-(8-(6-(2-methylpyrrolidin-1-yl)pyridin-2-ylamino)imidazo[1,2-b]pyridazin-6-yl)benzaldehyde (28 mg, 0.070 mmol) and piperidine (7 mg, 0.077 mmol) were dissolved in 1,2-dichloroethane (8 mL), stirred for 1 h, then sodium triacetoxyborohydride (44 mg, 0.21 mmol) was added followed by AcOH (0.1 mL). After 15 h, the solvent was removed and the residue was purified by chromatography (silica gel, dichloromethane/methanol 40/1) to give N-(6-(2-methylpyrrolidin-1-yl)pyridin-2-yl)-6-(3-(piperidin-1-ylmethyl)phenyl)imidazo[1,2-b]pyridazin-8-amine (17 mg, 21%) as an orange solid. $^1$H NMR (300 MHz, CD3OD): δ 8.80 (s, 1H), 8.00 (s, 1H), 7.91-7.84 (m, 2H), 7.59 (s, 1H), 7.48-7.41 (m, 3H), 6.30 (d, 1H, J=7.8 Hz), 6.09 (d, 1H, J=8.4 Hz), 4.30-4.26 (m, 1H), 3.60-3.43 (m, 4 h), 2.51-2.47 (m, 4 h), 2.15-2.05 (m, 3H), 1.78 (brs, 1H), 1.63-1.60 (m, 4 h), 1.51-1.46 (m, 2H), 1.19 (d, 3H, J=6.3 Hz). LC-MS: [M+H]$^+$, 468, t$_R$=1.397 min, HPLC: 99.52% at 214 nm, 98.65% at 254 nm, t$_R$=5.76 min.

Example 70

Synthesis of N-(6-(2-Methylpyrrolidin-1-yl)pyridin-2-yl)-6-(3-(pyrrolidin-1-ylmethyl)phenyl)imidazo[1,2-b]pyridazin-8-amine

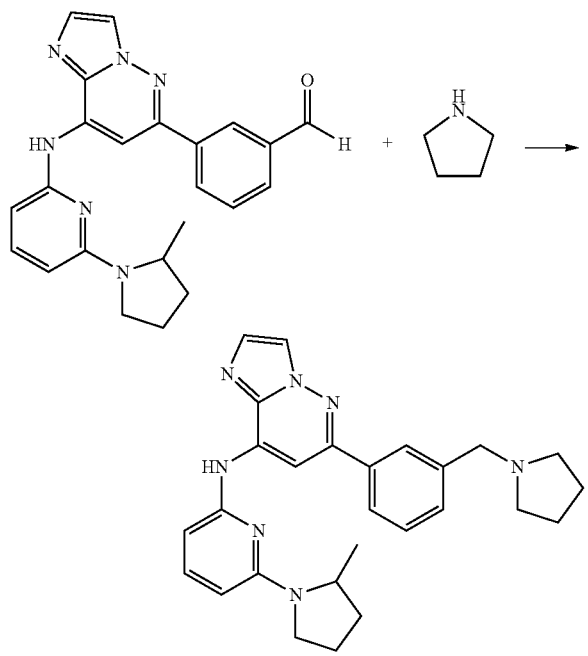

3-(8-(6-(2-methylpyrrolidin-1-yl)pyridin-2-ylamino)imidazo[1,2-b]pyridazin-6-yl)benzaldehyde (70 mg, 0.175 mmol) and pyrrolidine (14 mg, 0.194 mmol) were dissolved in 1,2-dichloroethane (10 mL), stirred for 1 h, then sodium triacetoxyborohydride (111 mg, 0.525 mmol) was added followed by AcOH (0.2 mL). After 15 h, the solvent was removed and the residue purified by chromatography (silica gel, dichloromethane/methanol 90:1) to give N-(6-(2-methylpyrrolidin-1-yl)pyridin-2-yl)-6-(3-(pyrrolidin-1-ylmethyl)phenyl)imidazo[1,2-b]pyridazin-8-amine (18 mg, 23%) as an orange solid. $^1$H NMR (300 MHz, CD3OD): δ 8.70 (s, 1H), 8.05 (s, 1H), 7.91-7.85 (m, 2H), 7.59-7.48 (m, 3H), 7.38-7.35 (m, 1H), 6.21 (d, 1H, J=7.5 Hz), 6.01 (d, 1H, J=7.8 Hz), 4.25-4.17 (m, 3H), 3.55 (s, 1H), 3.37-3.44 (m, 1H), 3.17 (brs, 4h), 2.08-1.97 (m, 7H), 1.72 (brs, 1H), 1.13 (d, 3H, J=4.5 Hz). LC-MS: [M+H]$^+$, 454, $t_R$=1.367 min, HPLC: 99.54% at 214 nm, 99.89% at 254 nm, $t_R$=5.164 min.

Example 71

Synthesis of (S)-6-(3-chlorophenyl)-N-(6-(2-methylpyrrolidin-1-yl)pyridin-2-yl)imidazo[1,2-b]pyridazin-8-amine hydrochloride

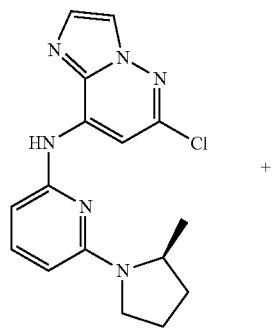

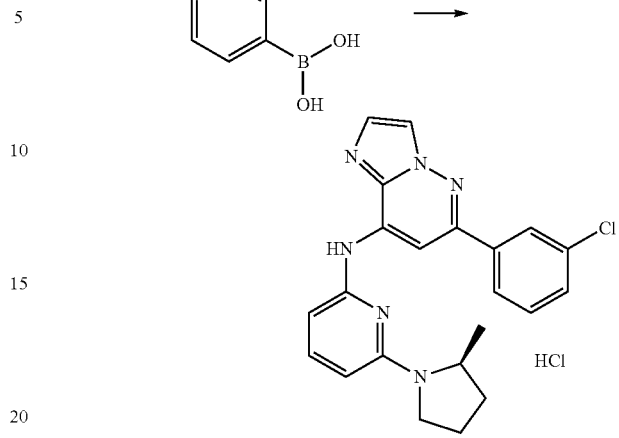

A mixture of (S)-6-chloro-N-(6-(2-methylpyrrolidin-1-yl)pyridin-2-yl)imidazo[1,2-b]pyridazin-8-amine (200 mg, 0.61 mmol), 3-chlorophenylboronic acid (79 mg, 0.67 mmol), Pd$_2$dba$_3$ (26 mg, 0.061 mmol), X-phos (87 mg, 0.24 mmol) and K$_2$CO$_3$ (190 mg, 1.83 mmol) were dissolved in dioxane/water (30 mL/3 mL), the reaction mixture degassed with bubbling nitrogen for 5 minutes, then heated at 100° C. with stirring for 3 h. The solvent was removed in vacuo then purified by chromatography (silica gel, dichloromethane/methanol 80:1) to give a residue which was further purified by preparative-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to afford a product which was dissolved in dichloromethane (10 mL) then concentrated HCl (2 mL) added slowly and stirred at room temperature for 10 min. The solvent was removed in vacuo to afford (S)-6-(3-chlorophenyl)-N-(6-(2-methylpyrrolidin-1-yl)pyridin-2-yl)imidazo[1,2-b]pyridazin-8-amine-hydrochloride (15 mg, 6%) as an orange solid. $^1$H NMR (300 MHz, DMSO): δ 9.78 (s, 1H), 8.88 (s, 1H), 8.33-8.31 (m, 1H), 7.96-7.81 (m, 3H), 7.65-7.46 (m, 3H), 6.73-6.69 (m, 1H), 6.13 (d, 1H, J=8.1 Hz), 4.28-4.24 (m, 1H), 3.63-3.58 (m, 1H), 3.47-3.41 (m, 1H), 2.12-2.02 (m, 3H), 1.74-1.73 (m, 1H), 1.16 (d, 3H, J=6.3 Hz). LC-MS: [M+H]$^+$, 405, $t_R$=2.26 min, HPLC: 99.61% at 214 nm, 95.33% at 254 nm, $t_R$=5.36 min.

Example 72

Synthesis of 4-(1-(8-(5,6-Dimethoxypyridin-2-ylamino)imidazo[1,2-b]pyridazin-6-yl)piperidin-3-ylcarbamoyl)benzoic acid

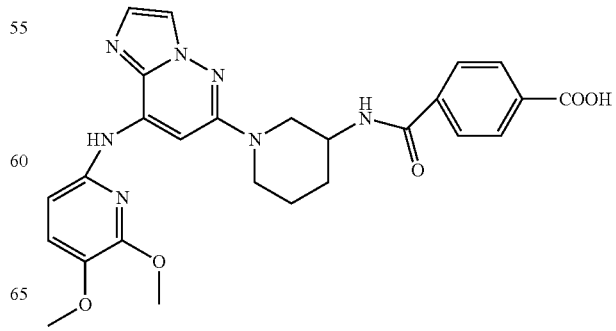

Step 1 tert-Butyl 1-(8-(5,6-dimethoxypyridin-2-ylamino)imidazo[1,2-b]pyridazin-6-yl)piperidin-3-ylcarbamate

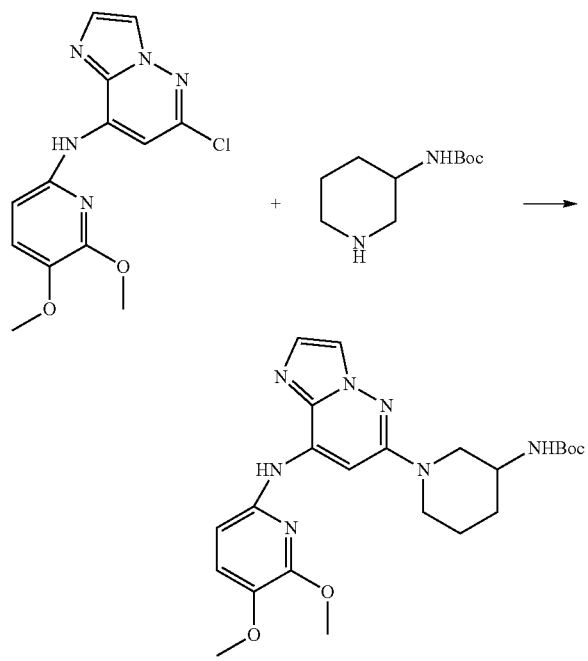

A suspension of 6-chloro-N-(5,6-dimethoxypyridin-2-yl)imidazo[1,2-b]pyridazin-8-amine (1.3 g, 4.24 mmol) and tert-butyl piperidin-3-ylcarbamate (3.4 g, 16.99 mmol) was heated to 160° C. for 2 h. The residue was purified by chromatography (silica gel, 200-300 mesh, dichloromethane:MeOH=120:1) to give the tert-butyl 1-(8-(5,6-dimethoxypyridin-2-ylamino)imidazo[1,2-b]pyridazin-6-yl)piperidin-3-ylcarbamate (300 mg, 15%) as brown solid. LC-MS: 470 [M+1]$^+$, $t_R$=1.44 min

Step 2

6-(3-Aminopiperidin-1-yl)-N-(5,6-dimethoxypyridin-2-yl)imidazo[1,2-b]pyridazin-8-amine

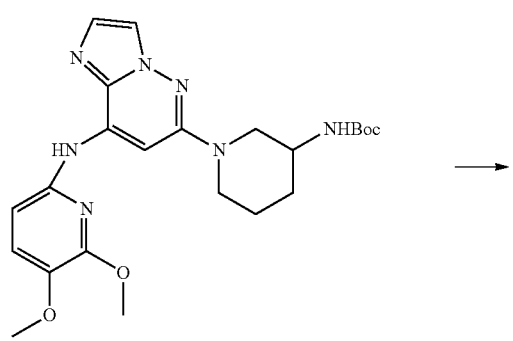

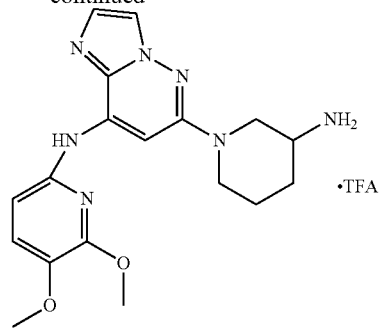

A mixture of tert-butyl 1-(8-(5,6-dimethoxypyridin-2-ylamino)imidazo[1,2-b]pyridazin-6-yl)piperidin-3-ylcarbamate (300 mg, 0.64 mmol) and TFA (5 mL) in dichloromethane (5 mL) was stirred at 25° C. for 6 h. The residue was concentrated to give the crude 6-(3-aminopiperidin-1-yl)-N-(5,6-dimethoxypyridin-2-yl)imidazo[1,2-b]pyridazin-8-amine trifluoroacetate salt (350 mg, crude) as a brown liquid that was used directly without further purification. LC-MS: 370 [M+1]$^+$, $t_R$=1.09 min

Step 3

Methyl 4-(1-(8-(5,6-dimethoxypyridin-2-ylamino)imidazo[1,2-b]pyridazin-6-yl)piperidin-3-ylcarbamoyl)benzoate

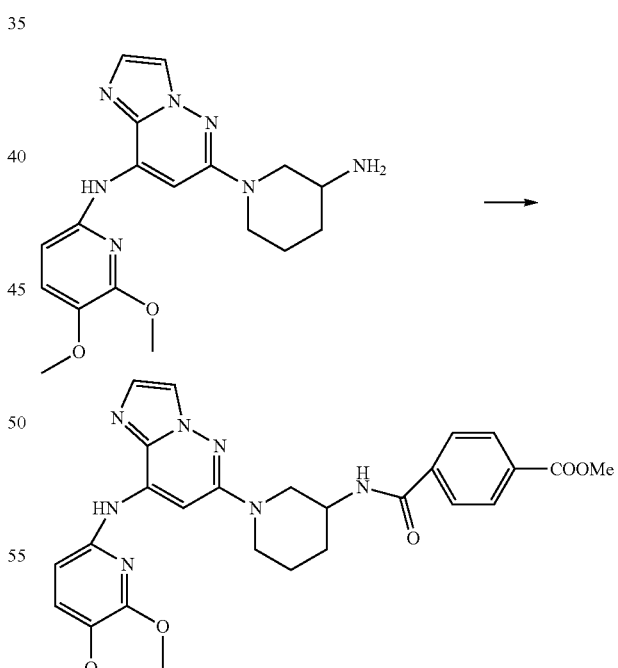

A mixture of 6-(3-aminopiperidin-1-yl)-N-(5,6-dimethoxypyridin-2-yl)imidazo[1,2-b]pyridazin-8-amine trifluoroacetate (350 mg, 0.94 mmol), 4-(methoxycarbonyl)benzoic acid (171 mg, 0.94 mmol), EDCI (725 mg, 3.79 mmol), triethylamine (288 mg, 2.84 mmol) and 1-methyl- 1H-imidazole (311 mg, 3.79 mmol) in dichloromethane (15 mL) was stirred at room temperature for 16 h. The residue was concentrated in vacuo then purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to give methyl 4-(1-(8-(5,6-dimethoxypyridin-2-ylamino)imidazo[1,2-b]pyridazin-6-yl)piperidin-3-ylcarbamoyl)benzoate (50 mg, 10%) as a white solid. LC-MS: 532 [M+1]$^+$, $t_R$=1.58 min.

Step 4

4-(1-(8-(5,6-Dimethoxypyridin-2-ylamino)imidazo[1,2-b]pyridazin-6-yl)piperidin-3-ylcarbamoyl)benzoic acid

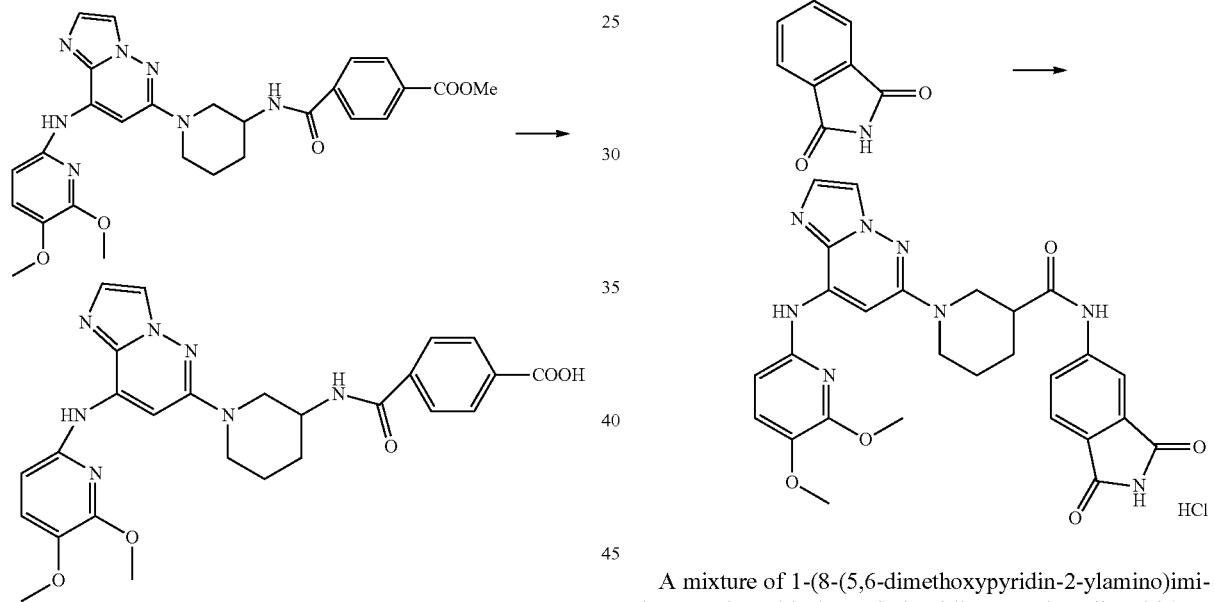

A mixture of methyl 4-(1-(8-(5,6-dimethoxypyridin-2-ylamino)imidazo[1,2-b]pyridazin-6-yl)piperidin-3-ylcarbamoyl)benzoate (50 mg, 0.09 mmol) and sodium hydroxide (50 mg, 1.25 mmol) in 1,4-dioxane (5 mL) and water (5 mL) was stirred at 40° C. for 3 h. The residue was concentrated in vacuo to ~5 mL then adjusted pH to 2 with 1M HCl. The residue was concentrated and triturated with MeOH to give the product 4-(1-(8-(5,6-dimethoxypyridin-2-ylamino)imidazo[1,2-b]pyridazin-6-yl)piperidin-3-ylcarbamoyl)benzoic acid (15 mg, 31%) as yellow solid. $^1$H NMR (300 MHz, DMSO): δ 10.36 (s, 1H), 8.60 (d, 1H, J=7.2 Hz), 8.19 (s, 2H), 8.06-7.92 (m, 4 h), 7.45 (d, 1H, J=8.4 Hz), 6.95 (d, 1H, J=8.4 Hz), 4.18-4.07 (m, 3H), 3.99 (s, 3H), 3.91 (s, 3H), 3.07-2.99 (m, 2H), 1.98-1.88 (m, 2H), 1.70-1.64 (m, 2H). LC-MS: [M+H]$^+$, 518, $t_R$=1.295 min, HPLC: 95.24% at 214 nm, 95.25% at 254 nm, $t_R$=4.981 min.

Example 73

Synthesis of 1-(8-(5,6-Dimethoxypyridin-2-ylamino)imidazo[1,2-b]pyridazin-6-yl)-N-(1,3-dioxoisoindolin-5-yl)piperidine-3-carboxamide hydrochloride

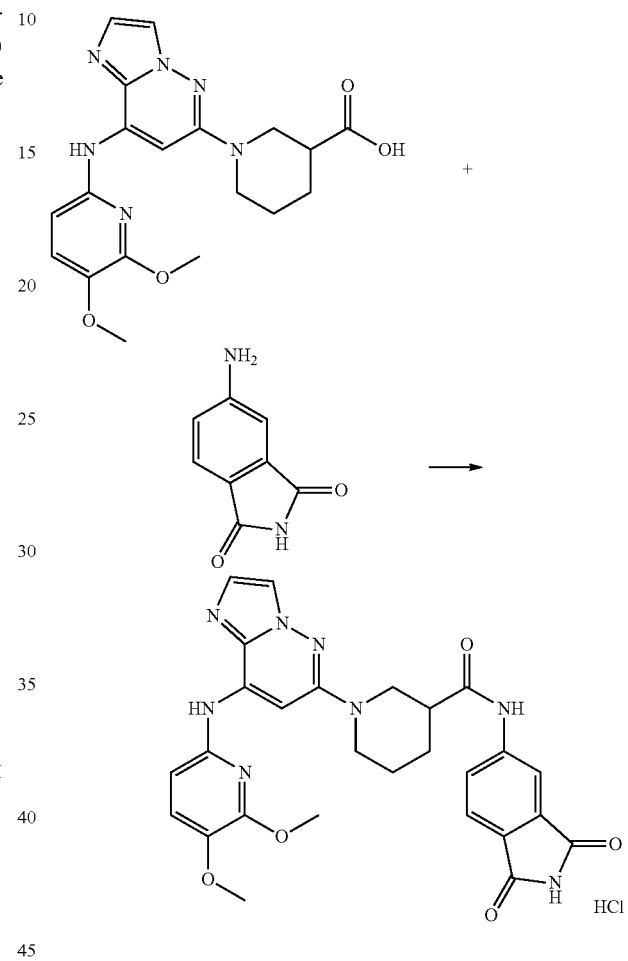

A mixture of 1-(8-(5,6-dimethoxypyridin-2-ylamino)imidazo[1,2-b]pyridazin-6-yl)piperidine-3-carboxylic acid (500 mg, 1.26 mmol), 5-aminoisoindoline-1,3-dione (250 mg, 1.51 mmol) and pyridine (10 mL) was stirred at 0° C. for 2 h. POCl$_3$ (20 drops) was added and stirred for 10 mins, then water (5 mL) was added and the mixture extracted with ethyl acetate (10 mL). The organic layer was washed with brine (10 mL), then dried over Na$_2$SO$_4$, filtered and concentrated in vacuo. The crude product was purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/50% water (0.1% TFA, v/v) in a linear fashion over 9 min) to give the product. HCl (1 mL) was added and then the mixture concentrated in vacuo to give 1-(8-(5,6-dimethoxypyridin-2-ylamino)imidazo[1,2-b]pyridazin-6-yl)-N-(1,3-dioxoisoindolin-5-yl)piperidine-3-carboxamide hydrochloride (10 mg, 2%). $^1$H NMR (300 MHz, DMSO): δ 11.23 (s, 1H), 10.65 (s, 1H), 10.21 (s, 1H), 8.15 (s, 2H), 7.98 (s, 1H), 7.86 (d, 1H, J=8.4 Hz), 7.77 (d, 1H, J=7.8 Hz), 7.43 (d, 1H, J=8.1 Hz), 6.93 (d, 1H, J=8.1 Hz), 4.29 (d, 1H, J=11.7 Hz), 4.14 (d, 1H, J=12.3 Hz), 3.91 (s, 3H), 7.56 (s, 3H), 3.23-3.02 (m, 2H), 2.73 (s, 1H), 2.10-2.06 (s, 1H), 1.82-1.75 (m, 3H). LC-MS: [M+H]$^+$, 543, $t_R$=1.406 min, HPLC: 98.08% at 214 nm, 98.69% at 254 nm, $t_R$=5.25 min.

Example 74

Synthesis of 4-(1-(8-(5,6-Dimethoxypyridin-2-ylamino)imidazo[1,2-b]pyridazin-6-yl)piperidine-3-carboxamido)benzoic acid

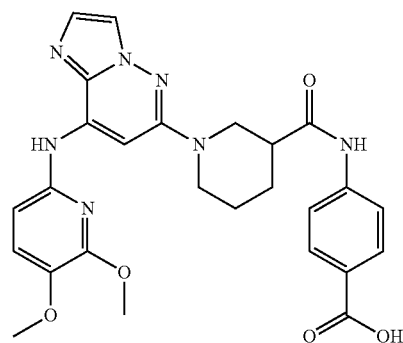 [SMILES: COc1ccc(Nc2cc(N3CCCC(C(=O)Nc4ccc(C(=O)O)cc4)C3)nn3ccnc23)nc1OC]

Step 1

1-(8-(5,6-Dimethoxypyridin-2-ylamino)imidazo[1,2-b]pyridazin-6-yl)piperidine-3-carboxylic acid

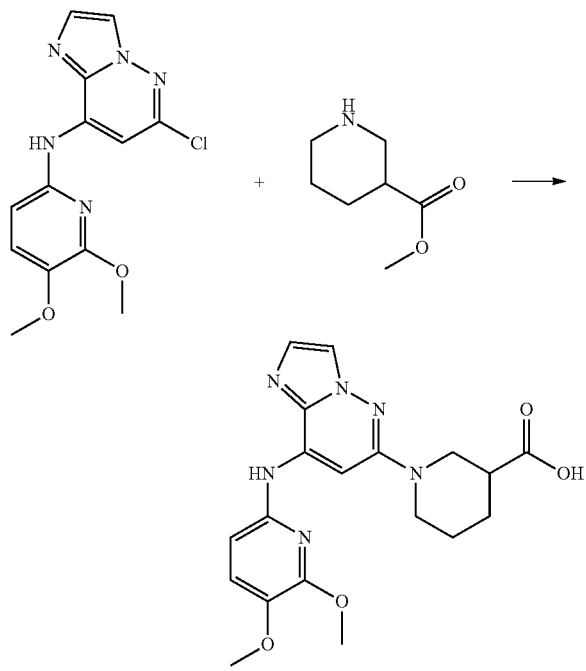

A suspension of 6-chloro-N-(5,6-dimethoxypyridin-2-yl)imidazo[1,2-b]pyridazin-8-amine (200 mg, 0.65 mmol) and methyl piperidine-3-carboxylate (400 mg, 2.8 mmol) was heated at 160° C. for 2 h under N$_2$. After cooling to room temperature, the residue was purified by chromatography (silica gel, 200-300 mesh, dichloromethane:MeOH=20:1) to give 1-(8-(5,6-dimethoxypyridin-2-ylamino)imidazo[1,2-b]pyridazin-6-yl)piperidine-3-carboxylic acid (40 mg, 15%) as a red solid. LC-MS: 399 [M+1]$^+$, $t_R$=1.261 min.

Step 2 tert-Butyl 4-(1-(8-(5,6-dimethoxypyridin-2-ylamino)imidazo[1,2-b]pyridazin-6-yl)piperidine-3-carboxamido)benzoate

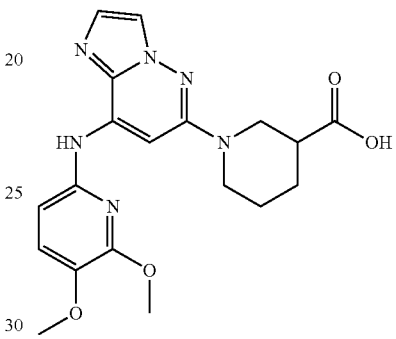

A mixture of 1-(8-(5,6-dimethoxypyridin-2-ylamino)imidazo[1,2-b]pyridazin-6-yl)piperidine-3-carboxylic acid (100 mg, 0.25 mmol), tert-butyl 4-aminobenzoate (49 mg, 0.25 mmol), EDCI (192 mg, 1.0 mmol) and 1-methyl-1H-imidazole (82 mg, 1.0 mmol) in dichloromethane (3 mL) was stirred at room temperature for 16 h. The residue was concentrated to give crude tert-butyl 4-(1-(8-(5,6-dimethoxypyridin-2-ylamino)imidazo[1,2-b]pyridazin-6-yl)piperidine-3-carboxamido)benzoate (200 mg, crude) as brown liquid that was used directly without further purification. LC-MS: 574 [M+1]$^+$, $t_R$=1.720 min.

Step 3
4-(1-(8-(5,6-Dimethoxypyridin-2-ylamino)imidazo[1,2-b]pyridazin-6-yl)piperidine-3-carboxamido)benzoic acid

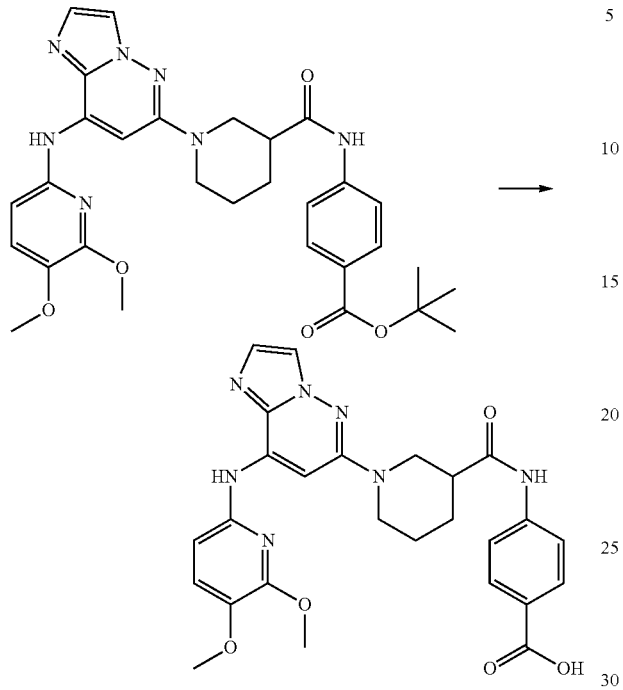

A mixture of tert-butyl 4-(1-(8-(5,6-dimethoxypyridin-2-ylamino)imidazo[1,2-b]pyridazin-6-yl)piperidine-3-carboxamido)benzoate (150 mg, 0.26 mmol) and TFA (2 mL) in dichloromethane (2 mL) was stirred at room temperature for 2 h. The residue was concentrated in vacuo. The crude product was purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 40% acetonitrile/60% water (0.1% TFA, v/v) in a linear fashion over 9 min) to give 4-(1-(8-(5,6-dimethoxypyridin-2-ylamino)imidazo[1,2-b]pyridazin-6-yl)piperidine-3-carboxamido)benzoic acid (5 mg, 4%) as yellow solid. $^1$H NMR (300 MHz, DMSO): δ 10.36 (s, 1H), 10.25 (s, 1H), 8.14 (brs, 2H), 7.90-7.74 (m, 5H), 7.44 (s, 1H), 6.97 (s, 1H), 4.25-4.15 (m, 4 h), 3.91 (s, 3H), 3.77 (s, 3H), 2.67 (brs, 2H), 2.04-1.57 (m, 3H). LC-MS: [M+H]$^+$, 517.9, $t_R$=1.366 min, HPLC: 95.06% at 214 nm, 95.20% at 254 nm, $t_R$=4.927 min.

Example 75
Synthesis of 4-(1-(8-(5,6-Dimethoxypyridin-2-ylamino)imidazo[1,2-b]pyridazin-6-yl)pyrrolidine-3-carboxamido)benzoic acid

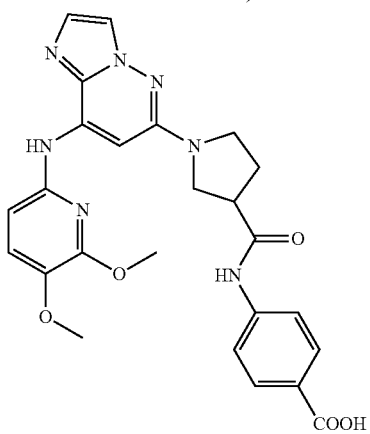

Step 1
1-(8-(5,6-Dimethoxypyridin-2-ylamino)imidazo[1,2-b]pyridazin-6-yl)pyrrolidine-3-carboxylic acid

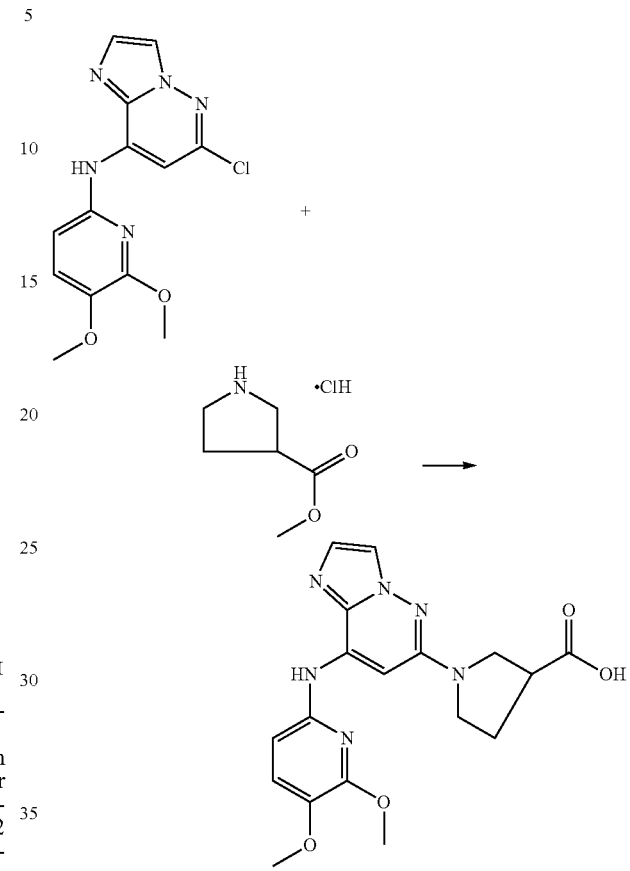

A suspension of 6-chloro-N-(5,6-dimethoxypyridin-2-yl)imidazo[1,2-b]pyridazin-8-amine (1 g, 3.27 mmol), methylpyrrolidine-3-carboxylate (1.69 g, 13.1 mmol), triethylamine (1.32 g, 13.1 mmol) and cesium carbonate (4.26 g, 13.1 mmol) was heated to 180° C. for 2 h. The residue was purified by chromatography (silica gel, 200-300 mesh, dichloromethane:MeOH=20:1) to give 1-(8-(5,6-dimethoxypyridin-2-ylamino)imidazo[1,2-b]pyridazin-6-yl)pyrrolidine-3-carboxylic acid (80 mg, 6%) as a red solid. LC-MS: 385 [M+1]$^+$, $t_R$=1.258 min

Step 2
tert-Butyl 4-(1-(8-(5,6-dimethoxypyridin-2-ylamino)imidazo[1,2-b]pyridazin-6-yl)pyrrolidine-3-carboxamido)benzoate

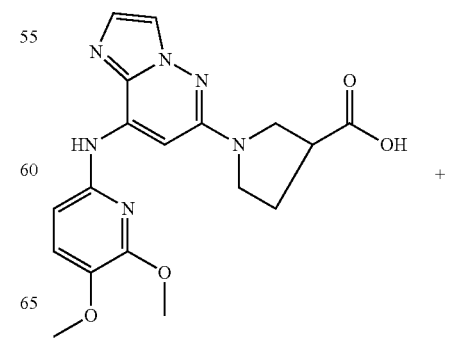

-continued

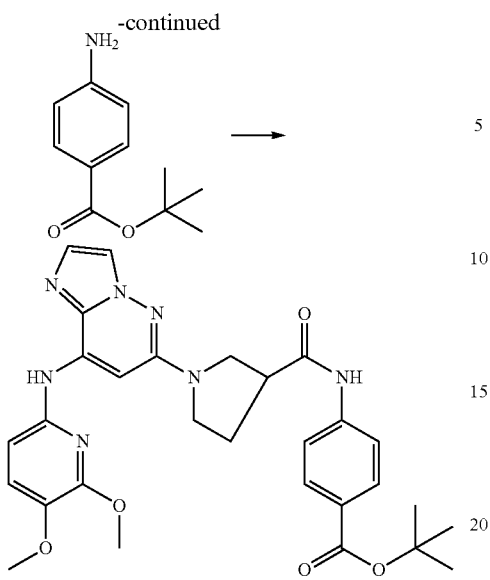

A mixture of 1-(8-(5,6-dimethoxypyridin-2-ylamino)imidazo[1,2-b]pyridazin-6-yl)pyrrolidine-3-carboxylic acid (80 mg, 0.21 mmol), tert-butyl 4-aminobenzoate (40 mg, 0.21 mmol), EDCI (159 mg, 0.08 mmol) and 1-methyl-1H-imidazole (68 mg, 0.8 mmol) in dichloromethane (5 mL) was stirred at room temperature for 16 h. The residue was concentrated to give crude tert-butyl 4-(1-(8-(5,6-dimethoxypyridin-2-ylamino)imidazo[1,2-b]pyridazin-6-yl)pyrrolidine-3-carboxamido)benzoate (200 mg, crude) as brown liquid that was used directly without purification. LC-MS: 560 [M+1]$^+$, $t_R$=1.510 min.

Step 3

4-(1-(8-(5,6-Dimethoxypyridin-2-ylamino)imidazo[1,2-b]pyridazin-6-yl)pyrrolidine-3-carboxamido)benzoic acid

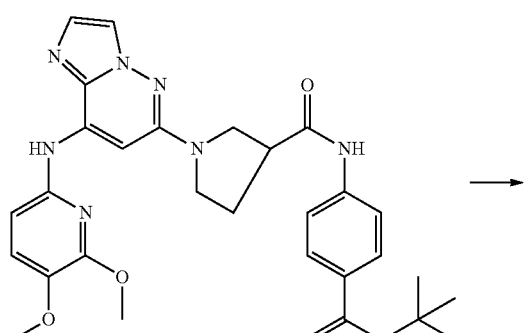

A mixture of tert-butyl 4-(1-(8-(5,6-dimethoxypyridin-2-ylamino)imidazo[1,2-b]pyridazin-6-yl)pyrrolidine-3-carboxamido)benzoate (200 mg, 0.36 mmol) and TFA (2 mL) in dichloromethane (2 mL) was stirred at room temperature for 2 h. The residue was concentrated in vacuo. The crude product was purified by prep-HPLC (Gemini 5u C18 150×21.2 mm; inject volume: 3 mL/inj, flow rate: 20 mL/min; wavelength: 214 nm and 254 nm; gradient conditions: 25% acetonitrile/75% water (0.1% TFA, v/v) initially, proceeding to 50% acetonitrile/50% water (0.1% TFA, v/v) in a linear fashion over 9 min) to give 4-(1-(8-(5,6-dimethoxypyridin-2-ylamino)imidazo[1,2-b]pyridazin-6-yl)pyrrolidine-3-carboxamido)benzoic acid (6 mg, 4%) as a yellow solid. $^1$H NMR (300 MHz, DMSO): δ 10.54 (s, 1H), 8.88 (brs, 2H), 7.95-7.82 (m, 4 h), 7.49-6.69 (m, 3H), 4.06-3.57 (m, 6H), 3.19-3.02 (m, 5H), 2.05 (brs, 2H). LC-MS: [M+H]$^+$, 504, $t_R$=1.269 min, HPLC: 96.47% at 214 nm, 97.69% at 254 nm, $t_R$=4.72 min.

Example 76

Synthesis of 4-(1-(8-(5,6-Dimethoxypyridin-2-ylamino)imidazo[1,2-b]pyridazin-6-yl)pyrrolidin-3-ylcarbamoyl)benzoic acid

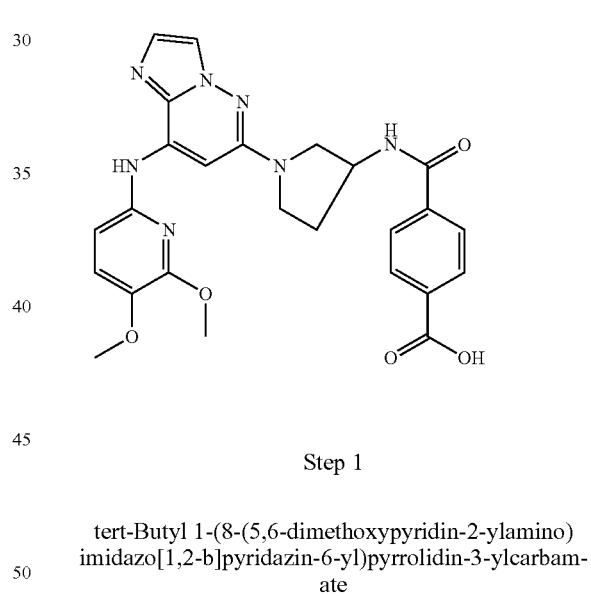

Step 1 tert-Butyl 1-(8-(5,6-dimethoxypyridin-2-ylamino)imidazo[1,2-b]pyridazin-6-yl)pyrrolidin-3-ylcarbamate

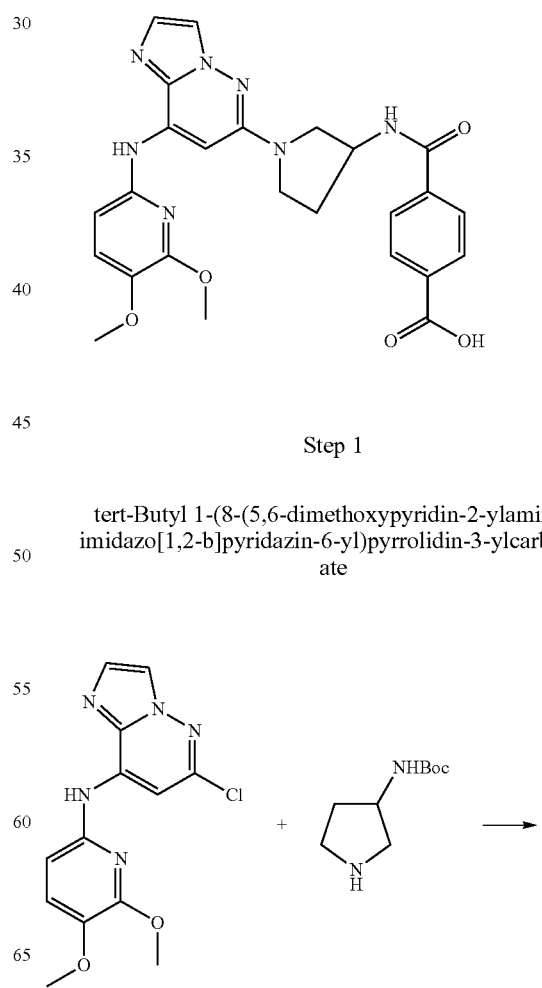

-continued

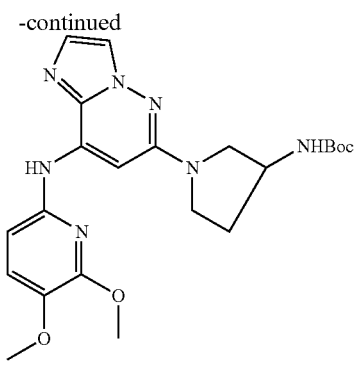

A suspension of 6-chloro-N-(5,6-dimethoxypyridin-2-yl)imidazo[1,2-b]pyridazin-8-amine (1.5 g, 4.9 mmol) and tert-butyl pyrrolidin-3-ylcarbamate (3 g, 16 mmol) was heated to 160° C. for 2 h. The residue was purified by chromatography (silica gel, 200-300 mesh, dichloromethane:MeOH=30:1) to give tert-butyl 1-(8-(5,6-dimethoxypyridin-2-ylamino)imidazo[1,2-b]pyridazin-6-yl)pyrrolidin-3-ylcarbamate (180 mg, 8%) as off-white solid. LC-MS: 456 [M+1]$^+$, $t_R$=1.396 min Step 2

6-(3-Aminopyrrolidin-1-yl)-N-(5,6-dimethoxypyridin-2-yl)imidazo[1,2-b]pyridazin-8-amine

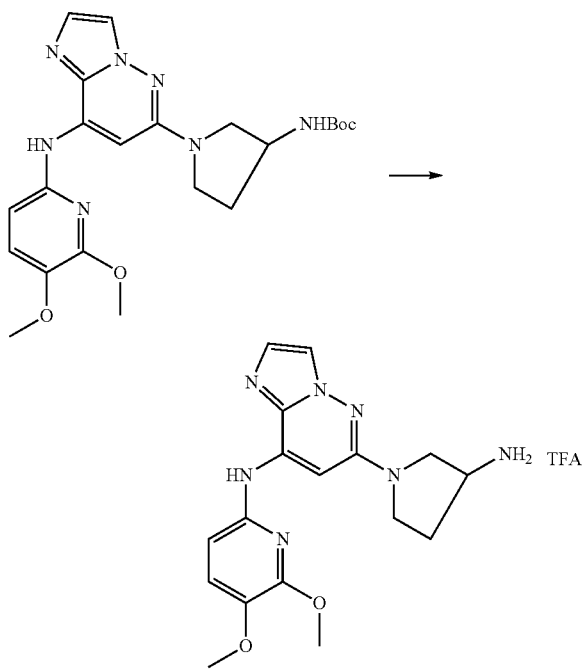

A suspension of tert-butyl 1-(8-(5,6-dimethoxypyridin-2-ylamino)imidazo[1,2-b]pyridazin-6-yl)pyrrolidin-3-ylcarbamate (180 mg, 0.40 mmol) and TFA (2 mL) in dichloromethane (5 mL) was stirred at 25° C. for 6 h. The residue was concentrated to give 6-(3-aminopyrrolidin-1-yl)-N-(5,6-dimethoxypyridin-2-yl)imidazo[1,2-b]pyridazin-8-amine (180 mg, crude) as a red liquid. This was used directly without purification. LC-MS: 356 [M+1]$^+$, $t_R$=1.187 min.

Step 3

Methyl 4-(1-(8-(5,6-dimethoxypyridin-2-ylamino)imidazo[1,2-b]pyridazin-6-yl)pyrrolidin-3-ylcarbamoyl)benzoate

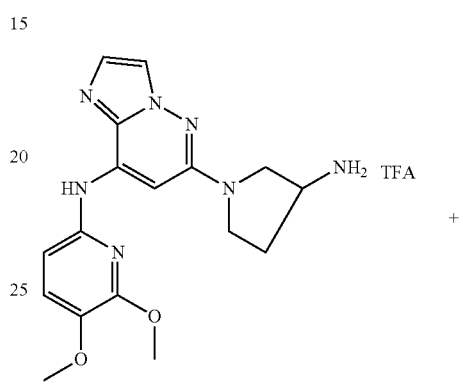

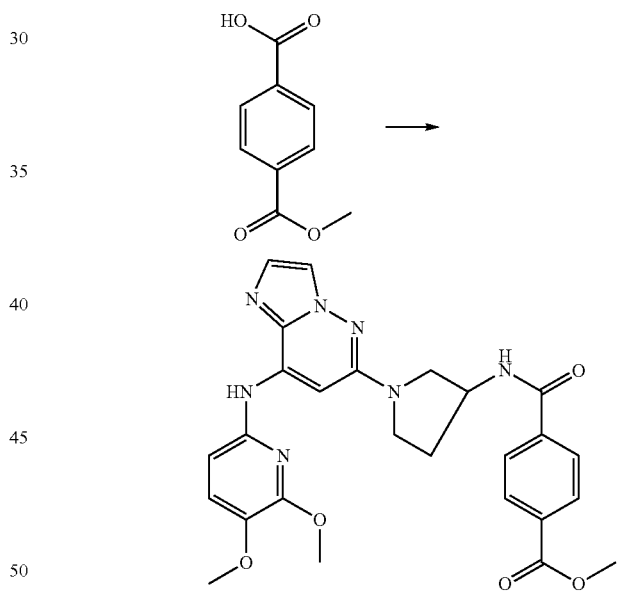

A mixture of 6-(3-aminopyrrolidin-1-yl)-N-(5,6-dimethoxypyridin-2-yl)imidazo[1,2-b]pyridazin-8-amine (180 mg, 0.51 mmol), 4-(methoxycarbonyl)benzoic acid (92 mg, 0.51 mmol), EDCI (389 mg, 2.0 mmol), triethylamine (103 mg, 1.02 mmol) and 1-methyl-1H-imidazole (167 mg, 2.0 mmol) in dichloromethane (10 mL) was stirred at room temperature for 16 h. The residue was concentrated and purified by chromatography (silica gel, 200-300 mesh, dichloromethane:MeOH=20:1) to give 4-(1-(8-(5,6-dimethoxypyridin-2-ylamino)imidazo[1,2-b]pyridazin-6-yl)pyrrolidin-3-ylcarbamoyl)benzoic acid (100 mg, 38%) as a brown liquid. LC-MS: 518 [M+1]$^+$, $t_R$=1.327 min.

189

Step 4

4-(1-(8-(5,6-Dimethoxypyridin-2-ylamino)imidazo[1,2-b]pyridazin-6-yl)pyrrolidin-3-ylcarbamoyl)benzoic acid

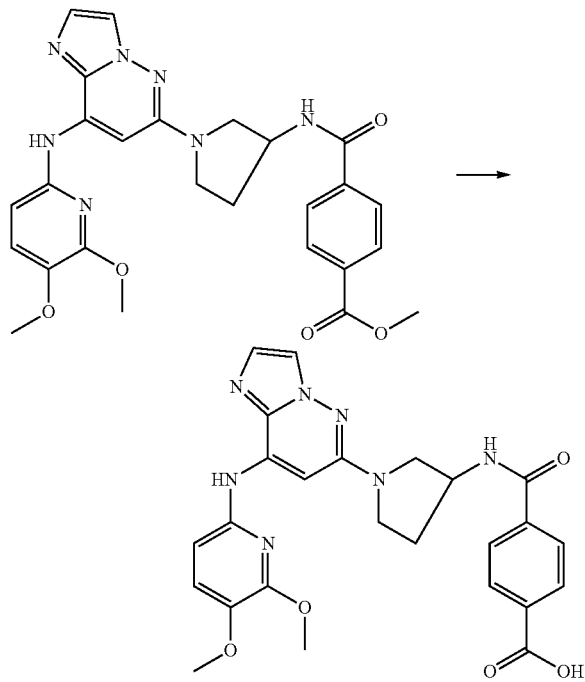

A mixture of methyl 4-(1-(8-(5,6-dimethoxypyridin-2-ylamino)imidazo[1,2-b]pyridazin-6-yl)pyrrolidin-3-ylcarbamoyl)benzoate (100 mg, 0.19 mmol) and sodium hydroxide (100 mg) in 1,4-dioxane (5 mL) and water (5 mL) was stirred at 40° C. for 2 h. The residue was concentrated to ~5 mL in vacuo and adjusted pH=2 with 1M HCl. The crude mixture was concentrated and purified by prep-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 45% acetonitrile/55% water (0.1% TFA, v/v) in a linear fashion over 9 min) to give 4-(1-(8-(5,6-dimethoxypyridin-2-ylamino)imidazo[1,2-b]pyridazin-6-yl)pyrrolidin-3-ylcarbamoyl)benzoic acid (9.5 mg, 10%) as a yellow solid. $^1$H NMR (300 MHz, DMSO): δ 10.29 (s, 1H), 8.80 (d, 1H, J=5.4 Hz), 8.13 (s, 1H), 8.00-7.92 (m, 5H), 7.51-7.40 (m, 2H), 6.98-6.92 (m, 2H), 4.58 (brs, 2H), 3.99 (s, 3H), 3.85 (s, 3H), 2.28-1.98 (m, 5H). LC-MS: [M+H]$^+$, 504, $t_R$=1.236 min, HPLC: 98.3% at 214 nm, 98.4% at 254 nm, $t_R$=4.52 min.

Example 77

Synthesis of 4-(8-(6-(2-Methylpyrrolidin-1-yl)pyridin-2-ylamino)imidazo[1,2-b]pyridazin-6-yl)phenol

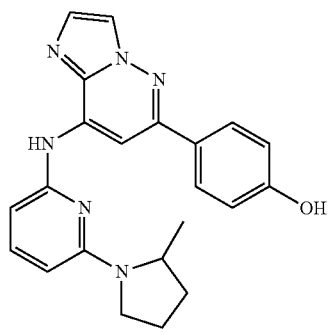 [SMILES: CC1CCCN1c1cccc(Nc2cc(-c3ccc(O)cc3)nn3ccnc23)n1]

190

Step 1

4-(8-(6-(2-Methylpyrrolidin-1-yl)pyridin-2-ylamino)imidazo[1,2-b]pyridazin-6-yl)phenol

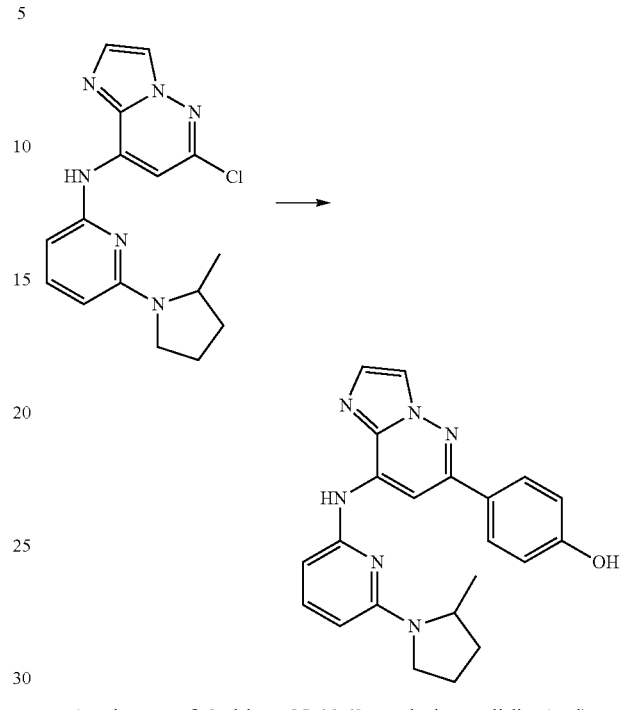

A mixture of 6-chloro-N-(6-(2-methylpyrrolidin-1-yl)pyridin-2-yl)imidazo[1,2-b]pyridazin-8-amine (0.05 g, 0.15 mmol), 4-hydroxyphenylboronic acid (0.025 g, 4 mmol), Pd(dba)$_2$ (0.02 g, 0.035 mmol), X-Phos (0.02 g, 0.042 mmol) and Na$_2$CO$_3$ (0.032 g, 0.3 mmol) in dioxane/H$_2$O (20 mL/2 mL) was stirred at 95° C. for 18 h under N$_2$. The solvent was removed in vacuo and the residue purified by chromatography (silica gel, petroleum ether/ethyl acetate 3:1) to give 4-(8-(6-(2-methylpyrrolidin-1-yl)pyridin-2-ylamino)imidazo[1,2-b]pyridazin-6-yl)phenol (0.03 g, 51%) as a yellow solid. $^1$H NMR (300 MHz, DMSO): δ 9.85 (s, 1H), 9.54 (s, 1H), 8.70 (s, 1H), 8.14 (s, 1H), 7.78-7.75 (m, 2H), 7.62 (s, 1H), 7.43 (t, 1H, J=8.0 Hz), 6.91-6.88 (m, 2H), 6.70 (d, 1H, J=7.8 Hz), 6.07 (d, 1H, J=8.1 Hz), 4.22 (brs, 1H), 3.57 (brs, 2H), 2.08-1.98 (m, 3H), 1.69 (brs, 1H), 1.15 (d, 3H, J=6.3 Hz). LC/MS: 387 [M+H]$^+$, 385 [M−H]$^-$, $t_R$=1.59 min. HPLC: 96.77% at 214 nm, 97.82% at 254 nm, $t_R$=6.12 min.

Example 78

Synthesis of N-(6-(2-Methylpyrrolidin-1-yl)pyridin-2-yl)-6-(pyridin-3-yl)imidazo[1,2-b]pyridazin-8-amine

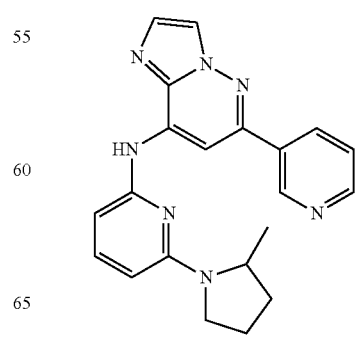

Step 1

N-(6-(2-Methylpyrrolidin-1-yl)pyridin-2-yl)-6-(pyridin-3-yl)imidazo[1,2-b]pyridazin-8-amine

Step 1

6-(4-Fluorophenyl)-N-(6-(2-methylpyrrolidin-1-yl)pyridin-2-yl)imidazo[1,2-b]pyridazin-8-amine

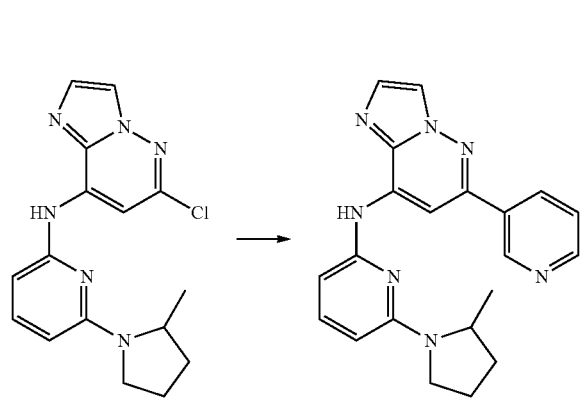 [SMILES: CC1CCCN1c1cccc(Nc2cc(Cl)nn3ccnc23)n1 ; CC1CCCN1c1cccc(Nc2cc(-c3cccnc3)nn3ccnc23)n1]

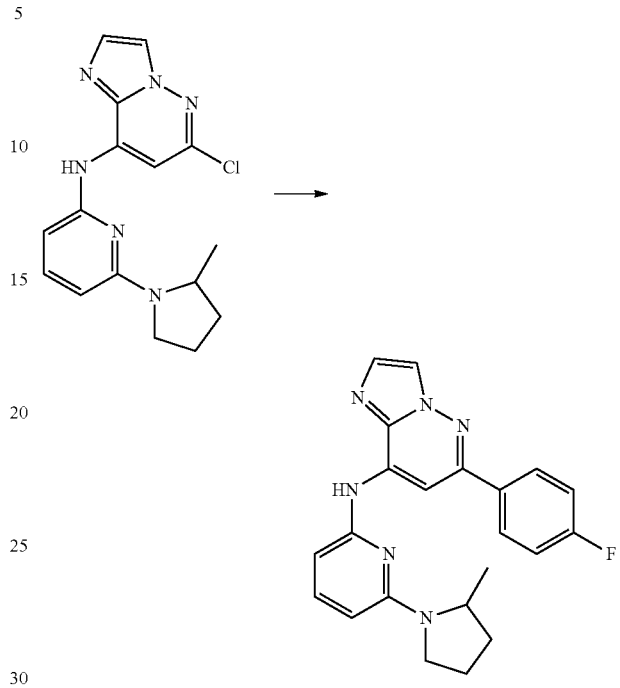

Procedure:

A mixture of 6-chloro-N-(6-(2-methylpyrrolidin-1-yl)pyridin-2-yl)imidazo[1,2-b]pyridazin-8-amine (0.05 g, 0.15 mmol), pyridin-3-ylboronic acid (0.022 g, 0.18 mmol), Pd(dba)$_2$ (0.02 g, 0.035 mmol), X-Phos (0.02 g, 0.042 mmol) and Na$_2$CO$_3$ (0.032 g, 0.3 mmol) in dioxane/H$_2$O (20 mL/2 mL) was stirred at 95° C. for 18 h under N$_2$ atmosphere. The solvent was removed in vacuo and the residue purified by chromatography (silica gel, petroleum ether/ethyl acetate 3:1) to give N-(6-(2-methylpyrrolidin-1-yl)pyridin-2-yl)-6-(pyridin-3-yl)imidazo[1,2-b]pyridazin-8-amine (0.025 g, 44%) as a yellow solid. $^1$H NMR (300 MHz, CDCl$_3$): δ 9.20 (s, 1H), 8.74-8.72 (m, 2H), 8.32-8.19 (m, 2H), 7.95 (s, 1H), 7.63 (s, 1H), 7.47-7.41 (m, 2H), 6.26 (d, 1H, J=8.1 Hz), 6.07 (d, 1H, J=8.4 Hz), 4.27 (t, 1H, J=6.2 Hz), 3.69-3.64 (m, 1H), 3.50-3.47 (m, 1H), 2.17-2.05 (m, 3H), 1.79 (brs, 1H), 1.27 (d, 3H, J=6.0 Hz). LC/MS: 372 [M+H]$^+$, $t_R$=1.71 min. HPLC: 98.37% at 214 nm, 99.69% at 254 nm, $t_R$=4.70 min.

Example 79

Synthesis of 6-(4-Fluorophenyl)-N-(6-(2-methylpyrrolidin-1-yl)pyridin-2-yl)imidazo[1,2-b]pyridazin-8-amine Procedure:

A mixture of 6-chloro-N-(6-(2-methylpyrrolidin-1-yl)pyridin-2-yl)imidazo[1,2-b]pyridazin-8-amine (0.05 g, 0.15 mmol), 4-fluorophenylboronic acid (0.025 g, 0.18 mmol), Pd(dba)$_2$ (0.02 g, 0.035 mmol), X-Phos (0.02 g, 0.042 mmol) and Na$_2$CO$_3$ (0.032 g, 0.3 mmol) in dioxane/H$_2$O (20 mL/2 mL) was stirred at 95° C. for 18 h under N$_2$ atmosphere. The solvent was removed in vacuo and the residue purified by chromatography (silica gel, petroleum ether/ethyl acetate 3:1) to give 6-(4-fluorophenyl)-N-(6-(2-methylpyrrolidin-1-yl)pyridin-2-yl)imidazo[1,2-b]pyridazin-8-amine (0.025 g, 43%) as a yellow solid. $^1$H NMR (300 MHz, CD3OD): δ 8.85 (s, 1H), 8.03-7.98 (m, 3H), 7.63 (s, 1H), 7.48 (t, 1H, J=7.9 Hz), 7.30-7.24 (m, 2H), 6.34 (d, 1H, J=7.8 Hz), 6.13 (d, 1H, J=8.1 Hz), 4.30 (brs, 1H), 3.65-3.33 (m, 2H), 2.18-2.05 (m, 3H), 1.81 (brs, 1H), 1.24 (d, 3H, J=6.0 Hz) LC/MS: 389 [M+H]$^+$, $t_R$=2.03 min. HPLC: 95.87% at 214 nm, 99.64% at 254 nm, $t_R$=4.79 min.

Example 80

Synthesis of 41583-131 3-(8-(6-(2-Methylpyrrolidin-1-yl)pyridin-2-ylamino)imidazo[1,2-b]pyridazin-6-yl)benzonitrile

Step 1

3-(8-(6-(2-Methylpyrrolidin-1-yl)pyridin-2-ylamino)imidazo[1,2-b]pyridazin-6-yl)benzonitrile

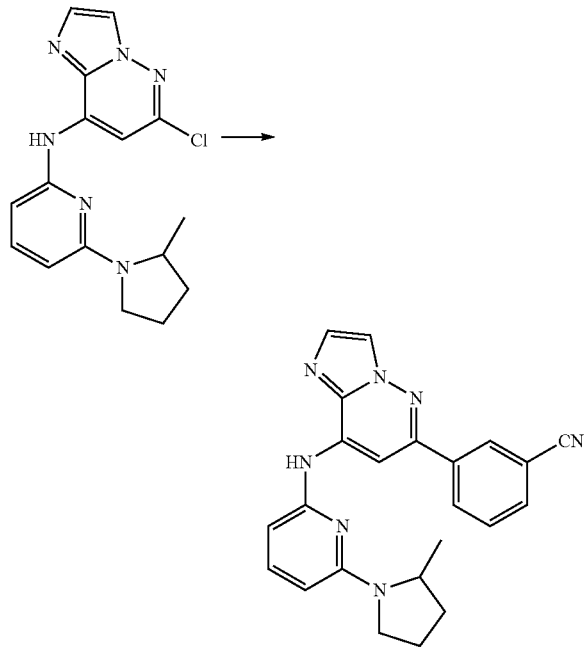

Procedure:
A mixture of 6-chloro-N-(6-(2-methylpyrrolidin-1-yl)pyridin-2-yl)imidazo[1,2-b]pyridazin-8-amine (0.05 g, 0.15 mmol), 3-cyanophenylboronic acid (0.026 g, 0.18 mmol), Pd(dba)$_2$ (0.02 g, 0.035 mmol), X-Phos (0.02 g, 0.042 mmol) and Na$_2$CO$_3$ (0.032 g, 0.3 mmol) in dioxane/H$_2$O (20 mL/2 mL) was stirred at 95° C. for 18 h under N$_2$ atmosphere. The solvent was removed in vacuo and the residue purified by chromatography (silica gel, petroleum ether and ethyl acetate 3:1) to give 3-(8-(6-(2-methylpyrrolidin-1-yl)pyridin-2-ylamino)imidazo[1,2-b]pyridazin-6-yl)benzo nitrile (0.03 g, 50%) as a yellow solid. $^1$H NMR (300 MHz, CDCl$_3$): δ 8.77 (s, 1H), 8.42 (brs, 1H), 8.26-8.21 (m, 2H), 7.90 (s, 1H), 7.75-7.36 (m, 4 h), 6.17 (d, 1H, J=7.5 Hz), 6.04 (d, 1H, J=8.1 Hz), 4.25-4.21 (m, 1H), 3.67-3.63 (m, 1H), 3.51-3.46 (m, 1H), 2.16-2.08 (m, 3H), 1.81-1.76 (m, 1H), 0.98 (d, 3H, J=6.6 Hz). LC/MS: 396 [M+H]$^+$, t$_R$=1.91 min. HPLC: 95.63% at 214 nm, 98.93% at 254 nm, t$_R$=4.59 min.

Example 81

Synthesis of N-(6-(2-Methylpyrrolidin-1-yl)pyridin-2-yl)-6-(pyridin-4-yl)imidazo[1,2-b]pyridazin-8-amine

Step 1

N-(6-(2-Methylpyrrolidin-1-yl)pyridin-2-yl)-6-(pyridin-4-yl)imidazo[1,2-b]pyridazin-8-amine

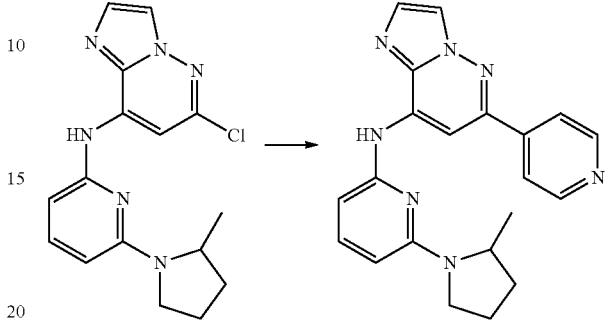

Procedure:
A mixture of 6-chloro-N-(6-(2-methylpyrrolidin-1-yl)pyridin-2-yl)imidazo[1,2-b]pyridazin-8-amine (0.05 g, 0.15 mmol), pyridin-4-ylboronic acid (0.022 g, 0.18 mmol), Pd(dba)$_2$ (0.02 g, 0.035 mmol), X-Phos (0.02 g, 0.042 mmol) and Na$_2$CO$_3$ (0.032 g, 0.3 mmol) in dioxane/H$_2$O (20 mL/2 mL) was stirred at 95° C. for 18 h under N$_2$ atmosphere. The solvent was removed in vacuo and the residue purified by chromatography (silica gel, petroleum ether/ethyl acetate 3:1) to give N-(6-(2-methylpyrrolidin-1-yl)pyridin-2-yl)-6-(pyridin-4-yl)imidazo[1,2-b]pyridazin-8-amine (0.025 g, 44%) as a yellow solid. $^1$H NMR (300 MHz, CDCl$_3$): δ 8.75-8.70 (m, 3H), 8.15 (brs, 1H), 7.93 (s, 1H), 7.86 (d, 1H, J=5.7 Hz), 7.62 (s, 1H), 7.41 (t, 1H, J=7.9 Hz), 6.22 (d, 1H, J=7.5 Hz), 6.05 (d, 1H, J=8.4 Hz), 4.26-4.22 (m, 1H), 3.68-3.63 (m, 1H), 3.49-3.46 (m, 1H), 2.16-2.04 (m, 3H), 1.77 (brs, 1H), 1.24 (t, 3H, J=6.3 Hz). LC/MS: 372 [M+H]$^+$, 370 [M−H]$^−$, t$_R$=1.68 min. HPLC: 100% at 214 nm, 100% at 254 nm, t$_R$=4.57 min.

Example 82

Synthesis of 6-(5-Methoxypyridin-3-yl)-N-(6-(2-methylpyrrolidin-1-yl)pyridin-2-yl)imidazo[1,2-b]pyridazin-8-amine

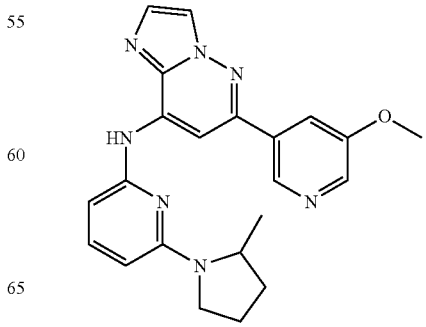

Step 1

6-(5-Methoxypyridin-3-yl)-N-(6-(2-methylpyrrolidin-1-yl)pyridin-2-yl)imidazo[1,2-b]pyridazin-8-amine

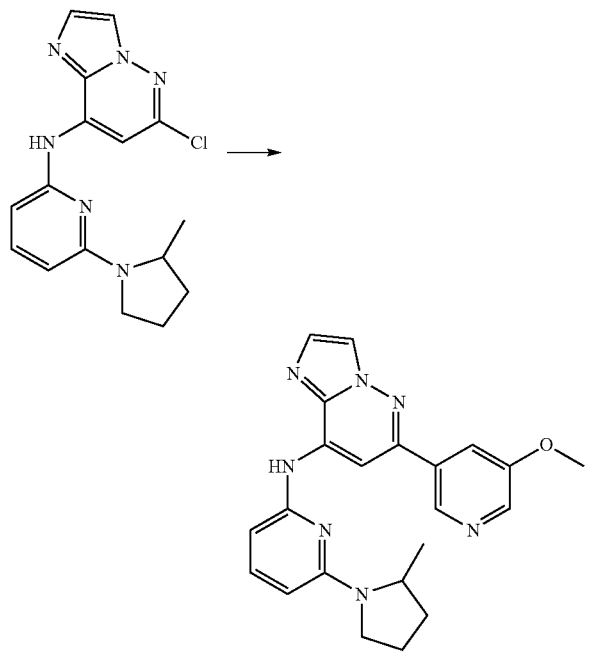

Procedure:

A mixture of 6-chloro-N-(6-(2-methylpyrrolidin-1-yl)pyridin-2-yl)imidazo[1,2-b]pyridazin-8-amine (0.05 g, 0.15 mmol), 5-methoxypyridin-3-ylboronic acid (0.028 g, 0.18 mmol), Pd(dba)$_2$ (0.02 g, 0.035 mmol), X-Phos (0.02 g, 0.042 mmol) and Na$_2$CO$_3$ (0.032 g, 0.3 mmol) in dioxane/H$_2$O (20 mL/2 mL) was stirred at 95° C. for 18 h under N$_2$ atmosphere. The solvent was removed in vacuo and the residue purified by chromatography (silica gel, petroleum ether/ethyl acetate 3:1) to give 6-(5-methoxypyridin-3-yl)-N-(6-(2-methylpyrrolidin-1-yl)pyridin-2-yl)imidazo[1,2-b]pyridazin-8-amine (0.03 g, 49%) as a yellow solid. $^1$H NMR (300 MHz, CD3OD): δ 8.28 (s, 1H), 8.72 (s, 1H), 8.40 (s, 1H), 8.12 (s, 1H), 7.98 (s, 1H), 7.72 (s, 1H), 7.49 (t, 1H, J=7.9 Hz), 6.34 (d, 1H, J=7.8 Hz), 6.17 (d, 1H, J=7.8 Hz), 4.31-4.27 (m, 1H), 4.01 (s, 3H), 3.68-3.63 (m, 1H), 3.51-3.43 (m, 1H), 2.20-2.07 (m, 3H), 1.81 (brs, 1H), 1.23 (d, 3H, J=6.0 Hz). LC/MS: 402 [M+H]$^+$, t$_R$=1.73 min. HPLC: 99.91% at 214 nm, 99.92% at 254 nm, t$_R$=5.59 min.

Example 83

Synthesis of N-(6-(2-Methylpyrrolidin-1-yl)pyridin-2-yl)-6-(4-(2-(pyrrolidin-1-yl)ethoxy)phenyl)imidazo[1,2-b]pyridazin-8-amine hydrochloride

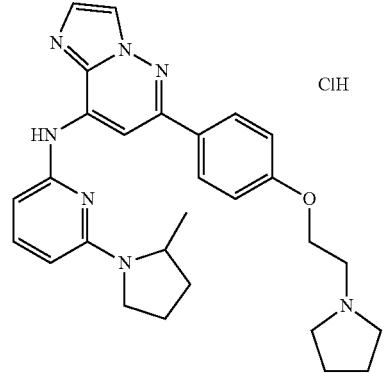 [SMILES: CC1CCCN1c1cccc(Nc2cc(-c3ccc(OCCN4CCCC4)cc3)nn3ccnc23)n1 ; Cl]

Step 1

N-(6-(2-Methylpyrrolidin-1-yl)pyridin-2-yl)-6-(4-(2-(pyrrolidin-1-yl)ethoxy)phenyl)imidazo[1,2-b]pyridazin-8-amine hydrochloride

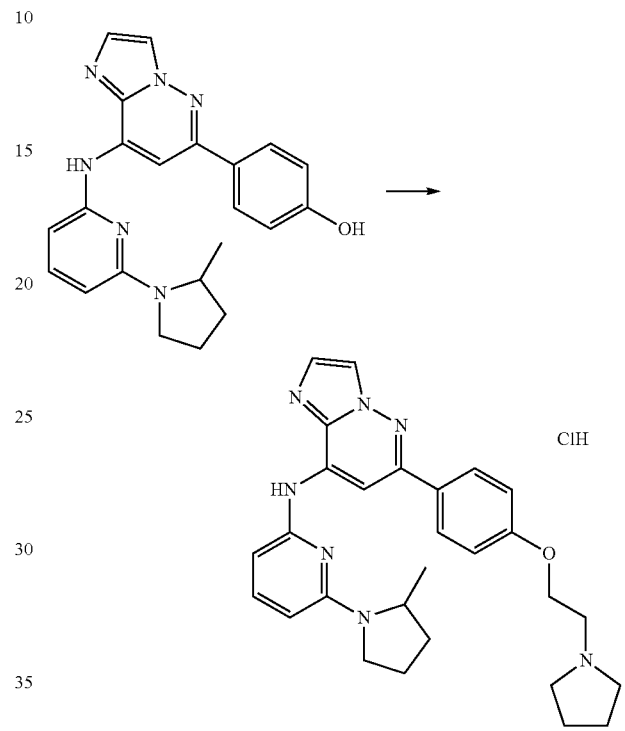

Procedure:

A mixture of 4-(8-(6-(2-methylpyrrolidin-1-yl)pyridin-2-ylamino)imidazo[1,2-b]pyridazin-6-yl)phenol (0.05 g, 0.13 mmol), 1-(2-bromoethyl)pyrrolidine (0.05 g, 0.26 mmol) and K$_2$CO$_3$ (0.05 g, 0.36 mmol) in DMF (15 mL) was stirred at 50° C. for 3 h. The solvent was removed in vacuo and the residue was purified by preparative-HPLC (Gemini 5u C18 150×21.2 mm; inject volume: 3 mL/inj, flow rate: 20 mL/min; wavelength: 214 nm and 254 nm; gradient conditions: 20% acetonitrile/80% water (0.1% TFA, v/v) initially, proceeding to 50% acetonitrile/530% water (0.1% TFA, v/v) in a linear fashion over 9 min). The preparative solvent was adjusted to pH=2 with 1M HCl before being evaporated to dryness, giving N-(6-(2-methylpyrrolidin-1-yl)pyridin-2-yl)-6-(4-(2-(pyrrolidin-1-yl)ethoxy)phenyl)imidazo[1,2-b]pyridazin-8-amine hydrochloride (0.015 g, 24%) as a yellow solid. $^1$H NMR (300 MHz, CD3OD): δ 8.78 (s, 1H), 6.35 (s, 1H), 8.08-8.02 (m, 3H), 7.59 (t, 1H, J=8.1 Hz), 7.24-7.22 (m, 2H), 6.43 (d, 1H, J=7.8 Hz), 6.30 (d, 1H, J=8.4 Hz), 4.46 (t, 2H, J=4.8 Hz), 4.30 (brs, 1H), 3.77-3.71 (m, 5H), 3.54-3.50 (m, 1H), 3.30 (brs, 1H), 2.22-2.07 (m, 8H), 1.82 (brs, 1H), 1.23 (d, 3H, J=6.3 Hz). LC/MS: 484 [M+H]$^+$, t$_R$=1.10 min. HPLC: 100% at 214 nm, 100% at 254 nm, t$_R$=5.01 min.

Example 84

Synthesis of 6-(3-(Aminomethyl)phenyl)-N-(6-(2-methylpyrrolidin-1-yl)pyridin-2-yl)imidazo[1,2-b]pyridazin-8-amine hydrochloride

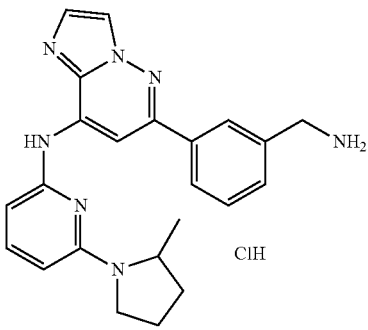 [SMILES: CC1CCCN1c1cccc(Nc2cc(-c3cccc(CN)c3)nn3ccnc23)n1 ; Cl]

Step 1

6-(3-(Aminomethyl)phenyl)-N-(6-(2-methylpyrrolidin-1-yl)pyridin-2-yl)imidazo[1,2-b]pyridazin-8-amine hydrochloride

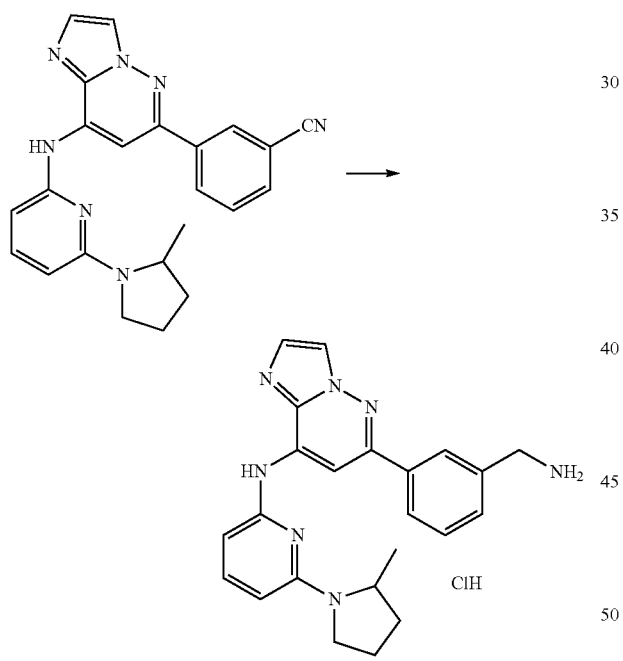

To a stirred mixture of LiAlH₄ (0.10 g, 2.6 mmol) in THF (30 mL), a solution of 3-(8-(6-(2-methylpyrrolidin-1-yl)pyridin-2-ylamino)imidazo[1,2-b]pyridazin-6-yl)benzonitrile (0.12 g, 0.3 mmol) in THF (10 mL) was added dropwise at ambient temperature. After 2 h, 0.3 mL of water was added slowly and then stirred for additional 30 min. The mixture was filtered and the filtrate was concentrated and purified by preparative-HPLC (Gemini 5u C18 150×21.2 mm; inject volume: 3 mL/inj, flow rate: 20 mL/min; wavelength: 214 nm and 254 nm; gradient conditions: 25% acetonitrile/75% water (0.1% TFA, v/v) initially, proceeding to 40% acetonitrile/60% water (0.1% TFA, v/v) in a linear fashion over 9 min). The preparative solution was adjusted to pH=2 with 1M HCl and then evaporated to give 6-(3-(aminomethyl)phenyl)-N-(6-(2-methylpyrrolidin-1-yl)pyridin-2-yl)imidazo[1,2-b]pyridazin-8-amine hydrochloride (0.07 g, 53%) as a yellow solid. $^1$H NMR (300 MHz, CD3OD): δ 8.80 (s, 1H), 8.43 (s, 1H), 8.23-8.10 (m, 3H), 7.72-7.65 (m, 3H), 6.58 (d, 1H, J=7.8 Hz), 6.43 (d, 1H, J=8.4 Hz), 4.37-4.29 (m, 3H), 3.76-3.73 (m, 1H), 3.58-3.55 (m, 1H), 2.24-2.12 (m, 3H), 1.87 (brs, 1H), 1.26 (d, 3H, J=6.3 Hz). LC/MS: 400 [M+H]⁺, $t_R$=1.03 min. HPLC: 100% at 214 nm, 100% at 254 nm, $t_R$=4.72 min.

Example 85

Synthesis of 6-(4-tert-Butylphenyl)-N-(6-(2-methylpyrrolidin-1-yl)pyridin-2-yl)imidazo[1,2-b]pyridazin-8-amine

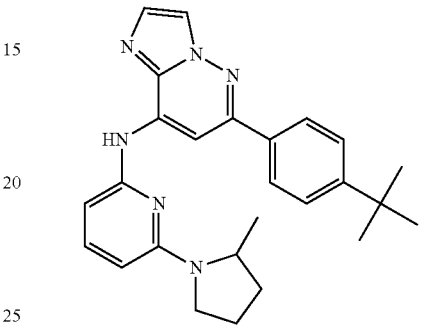

Step 1

6-(4-tert-Butylphenyl)-N-(6-(2-methylpyrrolidin-1-yl)pyridin-2-yl)imidazo[1,2-b]pyridazin-8-amine

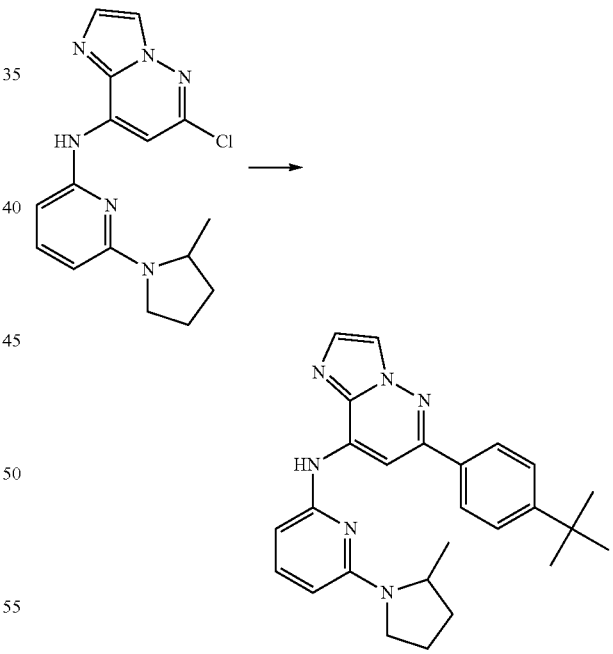

Procedure:

To a solution of 6-chloro-N-(6-(2-methylpyrrolidin-1-yl)pyridin-2-yl)imidazo[1,2-b]pyridazin-8-amine (60 mg, 0.183 mmol) and 4-tert-butylphenylboronic acid (49 mg, 0.274 mmol) in dioxane/H₂O (10 mL/1 mL) was added Na₂CO₃ (39 mg, 0.366 mmol) followed by Pd(dba)₂ (21 mg) and X-Phos (9 mg) under nitrogen with stirring. The mixture was refluxed for 15 h under nitrogen. After cooling, the solvent was concentrated in vacuo. The residue was purified by chromatography (silica, dichloromethane:MeOH=100:1) to give 6-(4-tert-butylphenyl)-N-(6-(2-methylpyrrolidin-1-yl)pyridin-2-yl)imidazo[1,2-b]pyri-dazin-8-amine (30 mg, 38%) as a solid. $^1$H NMR (300 MHz, CDCl$_3$): δ 8.70 (s, 1H), 8.30 (brs, 1H), 7.90 (d, 1H, J=7.5 Hz), 7.60 (s, 1H), 7.51-7.38 (m, 4 h), 6.31 (d, 1H, J=7.2 Hz), 6.03 (d, 1H, J=8.1 Hz), 4.24 (brs, 1H), 3.66 (brs, 1H), 3.49-3.47 (m, 1H), 2.15-2.09 (m, 3H), 1.75 (brs, 1H), 1.38 (s, 9H), 1.23 (d, 3H, J=6.3 Hz). LC/MS: 427 [M+H]$^+$, t$_R$=2.51 min. HPLC: 95.63% at 214 nm, 99.19% at 254 nm, t$_R$=99.79% min.

Example 86

Synthesis of 3-(8-(6-(2-Methylpyrrolidin-1-yl)pyridin-2-ylamino)imidazo[1,2-b]pyridazin-6-yl)phenol

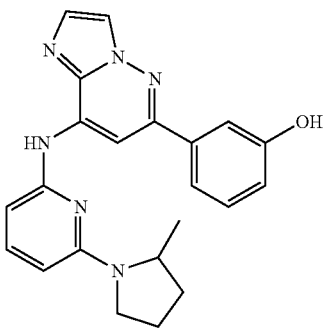

Step 1

3-(8-(6-(2-Methylpyrrolidin-1-yl)pyridin-2-ylamino)imidazo[1,2-b]pyridazin-6-yl)phenol

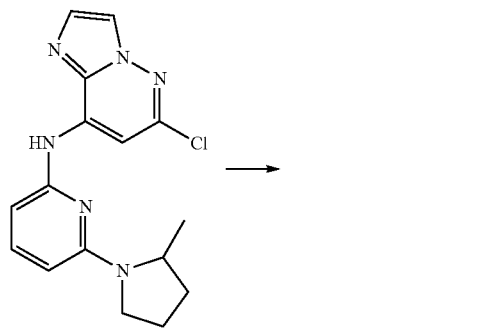

Procedure:

To a solution of 6-chloro-N-(6-(2-methylpyrrolidin-1-yl)pyridin-2-yl)imidazo[1,2-b]pyridazin-8-amine (550 mg, 1.68 mmol) and 4-tert-butylphenylboronic acid (345 mg, 2.52 mmol) in dioxane/H$_2$O (20 mL/2 mL) was added Na$_2$CO$_3$ (356 mg, 3.36 mmol) followed by Pd(dba)$_2$ (193 mg, 0.336 mmol) and X-Phos (80 mg, 0.168 mmol) under nitrogen with stirring. The mixture was refluxed for 16 h under nitrogen. After cooling, the solvent was concentrated in vacuo. The residue was purified by chromatography (silica, petroleum ether:EtOAc=3:1 to 1:1) to give 3-(8-(6-(2-methylpyrrolidin-1-yl)pyridin-2-ylamino)imidazo[1,2-b]pyridazin-6-yl)phenol (565 mg, 87%) as a yellow solid. $^1$H NMR (300 MHz, DMSO): δ 9.61 (s, 1H), 9.58 (s, 1H), 8.72 (s, 1H), 8.16 (s, 1H), 7.62 (s, 1H), 7.44-7.26 (m, 2H), 6.90-6.86 (m, 2H), 6.71 (d, 1H, J=7.8 Hz), 6.05 (d, 1H, J=8.1 Hz), 4.22-4.18 (m, 1H), 3.55-3.53 (m, 1H), 3.42-3.37 (m, 1H), 2.10-1.96 (m, 3H), 1.66 (brs, 1H), 1.13 (d, 3H, J=6.0 Hz). LC/MS: 387 [M+H]$^+$; 385 [M−H]$^−$, t$_R$=1.72 min. HPLC: 95.63% at 214 nm, 95.18% at 254 nm, t$_R$=2.72 min.

Example 87

Synthesis of N-(6-(2-Methylpyrrolidin-1-yl)pyridin-2-yl)-6-(3-(2-(piperidin-1-yl)ethoxy)phenyl)imidazo[1,2-b]pyridazin-8-amine

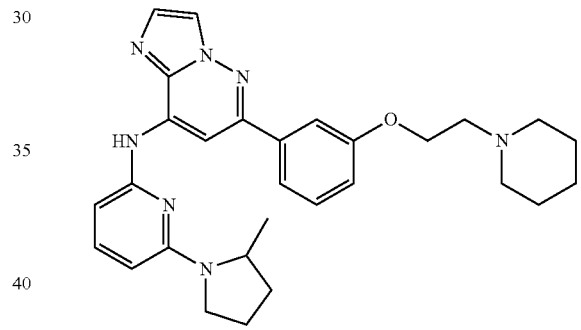

Step 1

2-(Piperidin-1-yl)ethyl methanesulfonate

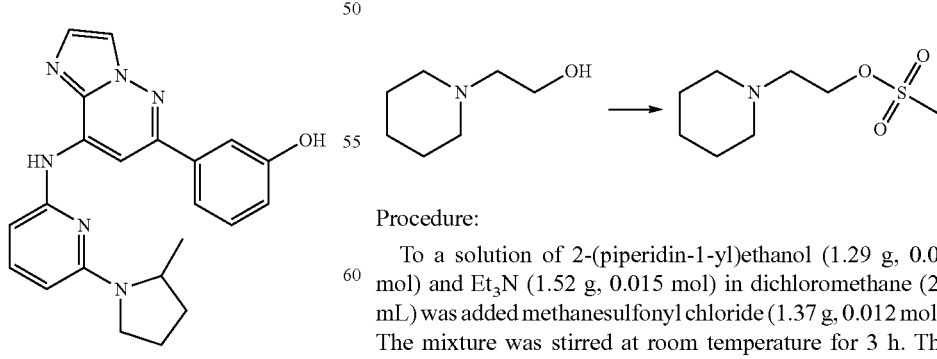

Procedure:

To a solution of 2-(piperidin-1-yl)ethanol (1.29 g, 0.01 mol) and Et$_3$N (1.52 g, 0.015 mol) in dichloromethane (20 mL) was added methanesulfonyl chloride (1.37 g, 0.012 mol). The mixture was stirred at room temperature for 3 h. The mixture was washed with brine. The organic layer was concentrated in vacuo to give crude product which was used to the next step without purification or characterization. (1.9 g, 91%).

Step 2

N-(6-(2-Methylpyrrolidin-1-yl)pyridin-2-yl)-6-(3-(2-(piperidin-1-yl)ethoxy)phenyl)imidazo[1,2-b]pyridazin-8-amine

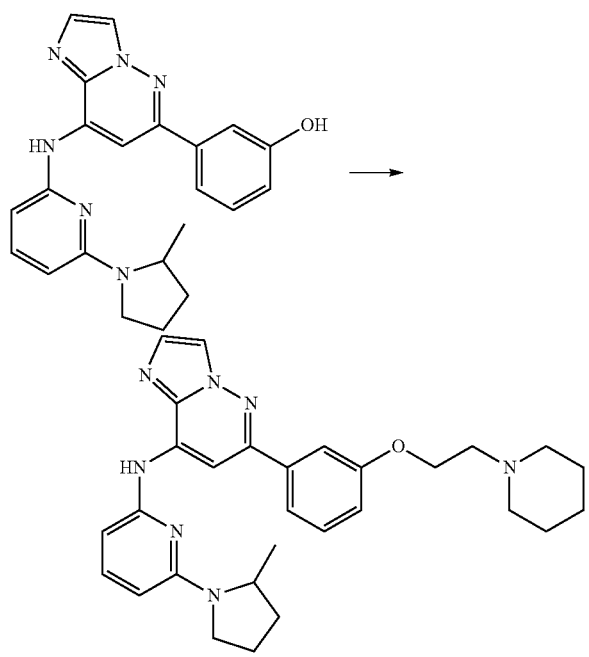

Procedure:

To a mixture of 3-(8-(6-(2-methylpyrrolidin-1-yl)pyridin-2-ylamino)imidazo[1,2-b]pyridazin-6-yl)phenol (40 mg, 0.1 mmol) and $K_2CO_3$ (28 mg, 0.2 mmol) in DMF (5 mL) was added 2-(piperidin-1-yl)ethyl methanesulfonate (25 mg, 0.12 mmol). The mixture was heated at 50° C. for 16 h. After cooling, the mixture was poured into water and extracted with EtOAc (8 mL 3). The combined organic layers were washed with brine, then dried over $MgSO_4$. After filtration and concentration, the residue was purified by chromatography (silica gel, EtOAc) to give N-(6-(2-methylpyrrolidin-1-yl)pyridin-2-yl)-6-(3-(2-(piperidin-1-yl)ethoxy)phenyl)imidazo[1,2-b]pyridazin-8-amine (20 mg, 40%). $^1$H NMR (300 MHz, $CDCl_3$): δ 8.67 (s, 1H), 8.08 (s, 1H), 7.93 (s, 1H), 7.60-7.53 (m, 3H), 7.45-7.37 (m, 2H), 7.05-7.01 (m, 1H), 6.23 (d, 1H, J=7.5 Hz), 6.04 (d, 1H, J=8.4 Hz), 4.31-4.21 (m, 3H), 3.71-3.65 (m, 1H), 3.54-3.48 (m, 1H), 2.85 (t, 2H, J=6.0 Hz), 2.57 (brs, 4 h), 2.17-2.04 (m, 3H), 1.76-1.62 (m, 5H), 1.48 (brs, 2H), 1.26 (d, 3H, J=6.6 Hz). LC/MS: 498 [M+H]$^+$, $t_R$=1.15 min. HPLC: 99.14% at 214 nm, 99.51% at 254 nm, $t_R$=3.97 min.

Example 88

Synthesis of N-(6-(2-Methylpyrrolidin-1-yl)pyridin-2-yl)-6-(3-(2-morpholinoethoxy)phenyl)imidazo[1,2-b]pyridazin-8-amine

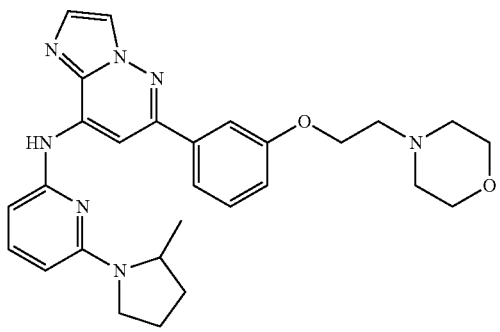 [SMILES: CC1CCCN1c1cccc(Nc2cc(-c3cccc(OCCN4CCOCC4)c3)nn3ccnc23)n1]

Step 1

2-Morpholinoethyl methanesulfonate

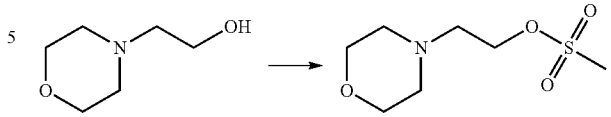

Procedure:

To a solution of 2-morpholinoethanol (1.31 g, 0.01 mol) and $Et_3N$ (1.52 g, 0.015 mol) in dichloromethane (20 mL) was added methanesulfonyl chloride (1.37 g, 0.012 mol) at 0° C. The mixture was stirred at room temperature for 3 h. The mixture was washed with brine. The organic layer was concentrated in vacuo to give crude product. The product was used to the next step without purification or characterization. (2 g, 95%).

Step 2

N-(6-(2-Methylpyrrolidin-1-yl)pyridin-2-yl)-6-(3-(2-morpholinoethoxy)phenyl)imidazo[1,2-b]pyridazin-8-amine

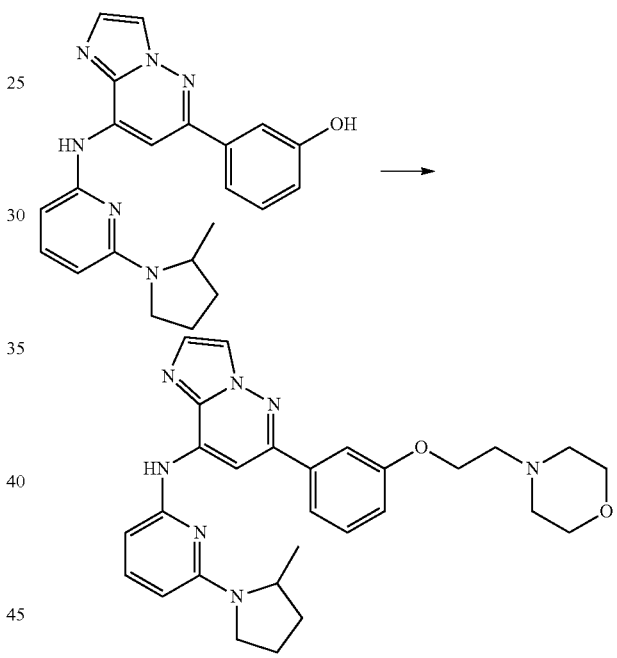

Procedure:

To a mixture of 3-(8-(6-(2-methylpyrrolidin-1-yl)pyridin-2-ylamino)imidazo[1,2-b]pyridazin-6-yl)phenol (40 mg, 0.1 mmol) and $K_2CO_3$ (28 mg, 0.2 mmol) in DMF (5 mL) was added 2-(piperidin-1-yl)ethyl methanesulfonate (25 mg, 0.12 mmol). The mixture was heated at 50° C. for 16 h. After cooling, the mixture was poured into water and extracted with EtOAc (10 mL×3). The combined organic layers were washed with brine, then dried over $MgSO_4$. After filtration and concentration, the residue was purified by chromatography (silica, EtOAc) to give N-(6-(2-methylpyrrolidin-1-yl)pyridin-2-yl)pyridin-2-yl)-6-(3-(2-morpholinoethoxy)phenyl)imidazo[1,2-b]pyridazin-8-amine (20 mg, 40%). $^1$H NMR (300 MHz, $CDCl_3$): δ 8.65 (s, 1H), 8.06 (s, 1H), 7.93 (s, 1H), 7.59-7.54 (m, 3H), 7.45-7.40 (m, 2H), 7.04-7.02 (m, 2H), 6.22 (d, 1H, J=7.5 Hz), 6.04 (d, 1H, J=7.8 Hz), 4.25-4.20 (m, 3H), 3.79-3.76 (m, 4 h), 3.68 (brs, 1H), 3.51-3.48 (m, 1H), 2.87 (t, 2H, J=5.7 Hz), 2.64 (brs, 4 h), 2.14-2.06 (m, 3H), 1.78 (brs, 1H), 1.67-1.62 (m, 4h), 1.50-1.48 (m, 2H), 1.25 (d, 3H, J=6.3 Hz). LC/MS: 500 [M+H]$^+$, $t_R$=1.13 min. HPLC: 95.85% at 214 nm, 95.41% at 254 nm, $t_R$=5.12 min.

Example 89

Synthesis of N-(6-(2-Methylpyrrolidin-1-yl)pyridin-2-yl)-6-(4-(2-(piperidin-1-yl)ethoxy)phenyl)imidazo[1,2-b]pyridazin-8-amine

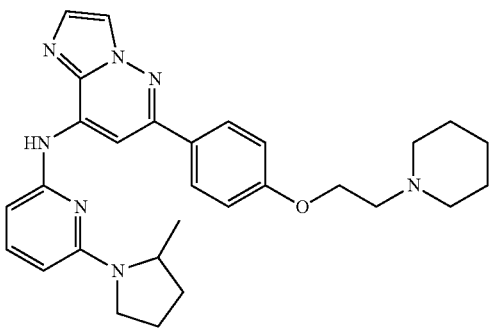 [SMILES: CC1CCCN1c1cccc(Nc2cc(-c3ccc(OCCN4CCCCC4)cc3)nn3ccnc23)n1]

Step 1

N-(6-(2-Methylpyrrolidin-1-yl)pyridin-2-yl)-6-(4-(2-(piperidin-1-yl)ethoxy)phenyl)imidazo[1,2-b]pyridazin-8-amine

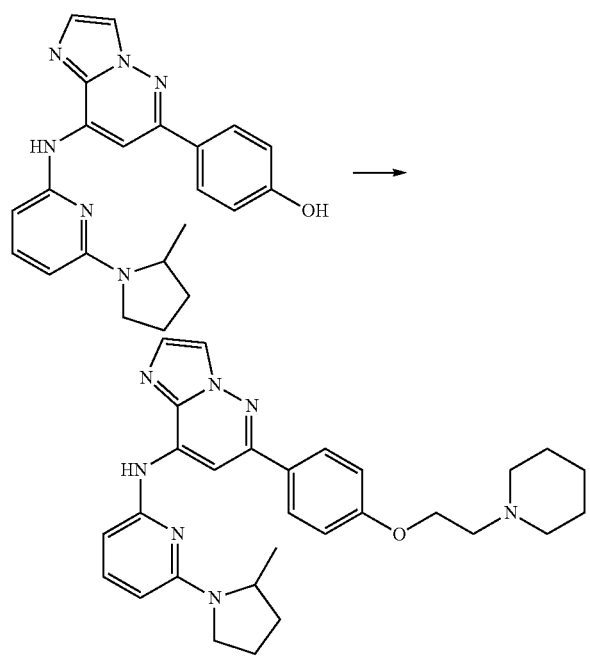

Procedure:

To a mixture of 4-(8-(6-(2-methylpyrrolidin-1-yl)pyridin-2-ylamino)imidazo[1,2-b]pyridazin-6-yl)phenol (40 mg, 0.1 mmol) and $K_2CO_3$ (28 mg, 0.2 mmol) in DMF (5 mL) was added 2-(piperidin-1-yl)ethyl methanesulfonate (25 mg, 0.12 mmol). The mixture was heated at 50° C. for 16 h. After cooling, the mixture was poured into water and extracted with EtOAc (3×10 mL). The combined organic layers were washed with brine then dried over $MgSO_4$. After filtration and concentration, the residue was purified by chromatography (silica, EtOAc) to give N-(6-(2-methylpyrrolidin-1-yl)pyridin-2-yl)-6-(4-(2-(piperidin-1-yl)ethoxy)phenyl)imidazo[1,2-b]pyridazin-8-amine (20 mg, 40%). $^1$H NMR (300 MHz, $CDCl_3$): δ 8.63 (s, 1H), 8.01-7.90 (m, 4 h), 7.57 (s, 1H), 7.42 (t, 1H, J=7.8 Hz), 7.05-7.01 (m, 2H), 6.21 (d, 1H, J=7.8 Hz), 6.04 (d, 1H, J=8.7 Hz), 4.30-4.20 (m, 3H), 3.70-3.64 (m, 1H), 3.53-3.45 (m, 1H), 2.84 (t, 2H, J=6.2 Hz), 2.56 (brs, 4 h), 2.20-2.03 (m, 3H), 1.78 (brs, 1H), 1.67-1.62 (m, 4 h), 1.50-1.48 (m, 2H), 1.27 (d, 3H, J=6.3 Hz). LC/MS: 498 [M+H]$^+$, $t_R$=1.13 min. HPLC: 99.24% at 214 nm, 99.34% at 254 nm, $t_R$=5.70 min.

Example 90

Synthesis of N-(6-(2-Methylpyrrolidin-1-yl)pyridin-2-yl)-6-(4-(2-morpholinoethoxy)phenyl)imidazo[1,2-b]pyridazin-8-amine

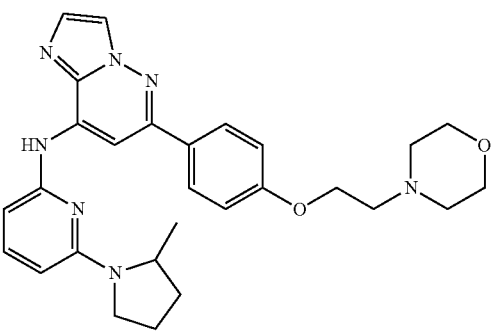 [SMILES: CC1CCCN1c1cccc(Nc2cc(-c3ccc(OCCN4CCOCC4)cc3)nn3ccnc23)n1]

Step 1

N-(6-(2-Methylpyrrolidin-1-yl)pyridin-2-yl)-6-(4-(2-morpholinoethoxy)phenyl)imidazo[1,2-b]pyridazin-8-amine

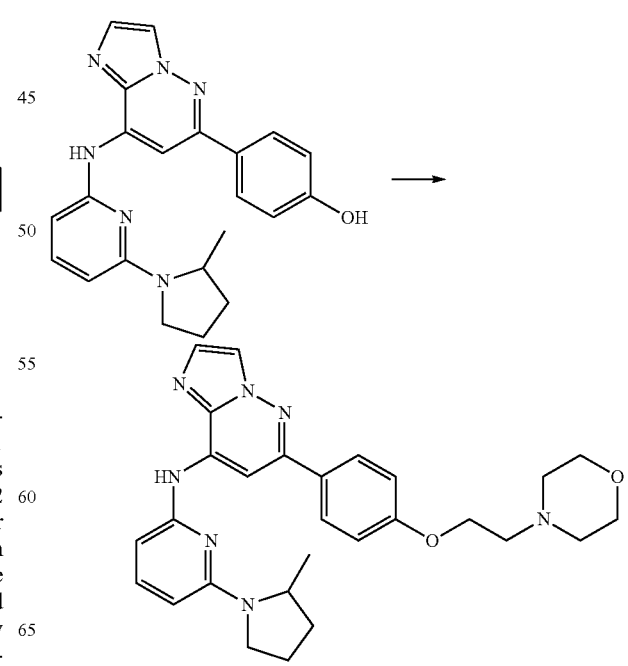

Procedure:

To a mixture of 4-(8-(6-(2-methylpyrrolidin-1-yl)pyridin-2-ylamino)imidazo[1,2-b]pyridazin-6-yl)phenol (40 mg, 0.1 mmol) and K$_2$CO$_3$ (28 mg, 0.2 mmol) in DMF (5 mL) was added 2-(piperidin-1-yl)ethyl methanesulfonate (25 mg, 0.12 mmol). The mixture was heated at 50° C. for 16 h. After cooling, the mixture was poured into water and extracted with EtOAc (3×10 mL). The combined organic layers were washed with brine, dried over MgSO$_4$, filtered and concentrated in vacuo. The residue was purified by chromatography (silica, EtOAc) to give N-(6-(2-Methylpyrrolidin-1-yl)pyridin-2-yl)-6-(4-(2-morpholinoethoxy)phenyl)imidazo[1,2-b]pyridazin-8-amine (40 mg, 80%). $^1$H NMR (300 MHz, CDCl$_3$): δ 8.63 (s, 1H), 8.05-7.90 (m, 4 h), 7.57 (s, 1H), 7.42 (t, 1H, J=8.0 Hz), 7.04-7.01 (m, 2H), 6.22 (d, 1H, J=7.5 Hz), 6.04 (d, 1H, J=8.4 Hz), 4.30-4.19 (m, 3H), 3.80-3.77 (m, 4 h), 3.70-3.64 (m, 1H), 3.51-3.48 (m, 1H), 2.87 (t, 2H, J=5.7 Hz), 2.65-2.62 (m, 4 h), 2.17-2.05 (m, 3H), 1.78 (brs, 1H), 1.26 (d, 3H, J=6.3 Hz). LC/MS: 500 [M+H]$^+$, t$_R$=1.11 min. HPLC: 99.73% at 214 nm, 99.60% at 254 nm, t$_R$=99.73% min.

Example 91

Synthesis of 6-(3-(2-(Diethylamino)ethoxy)phenyl)-N-(6-(2-methylpyrrolidin-1-yl)pyridin-2-yl)imidazo[1,2-b]pyridazin-8-amine

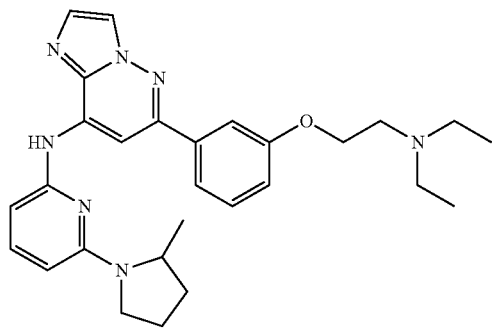 [SMILES: CCN(CC)CCOc1cccc(-c2cc(Nc3cccc(N4CCCC4C)n3)c3nccn3n2)c1]

Step 1

2-(Diethylamino)ethyl methanesulfonate

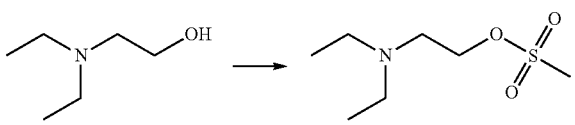

Procedure:

To a solution of 2-(diethylamino)ethanol (1.76 g, 0.015 mol) and Et$_3$N (2.27 g, 0.00225 mol) in dichloromethane (25 mL) was added methanesulfonyl chloride (2.05 g, 0.018 mol) at 0° C. The mixture was stirred at room temperature for 3 h. The mixture was washed with brine. The organic layer was concentrated in vacuo to give crude product. The product was used to the next step without purification. (2 g, 69%).

Step 2

6-(3-(2-(Diethylamino)ethoxy)phenyl)-N-(6-(2-methylpyrrolidin-1-yl)pyridin-2-yl)imidazo[1,2-b]pyridazin-8-amine

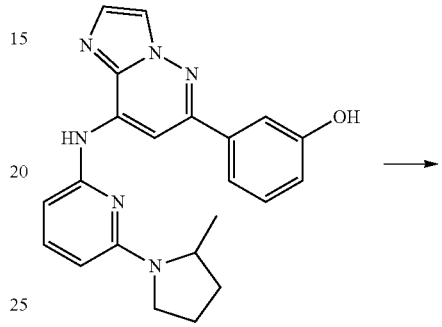

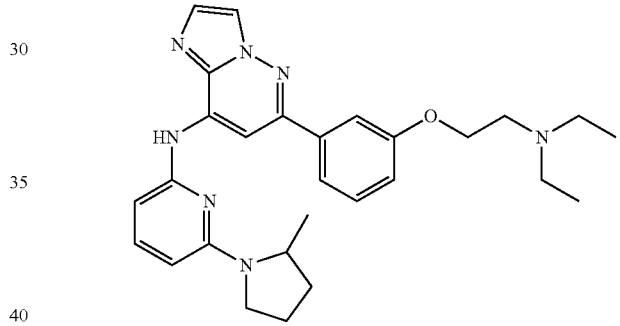

Procedure:

To a mixture of 3-(8-(6-(2-methylpyrrolidin-1-yl)pyridin-2-ylamino)imidazo[1,2-b]pyridazin-6-yl)phenol (40 mg, 0.1 mmol) and K$_2$CO$_3$ (28 mg, 0.2 mmol) in DMF (5 mL) was added 2-(diethylamino)ethyl methanesulfonate (30 mg, 0.15 mmol). The mixture was heated at 50° C. for 15 h. After cooling, the mixture was poured into water and extracted with EtOAc (3×10 mL). The combined organic layers were washed with brine, dried over MgSO$_4$, filtrated and concentrated. The residue was purified by chromatography (silica, EtOAc) to give 6-(3-(2-(diethylamino)ethoxy)phenyl)-N-(6-(2-methylpyrrolidin-1-yl)pyridin-2-yl)imidazo[1,2-b]pyridazin-8-amine (18 mg, 37%). $^1$H NMR (300 MHz, CDCl$_3$): δ 8.64 (s, 1H), 8.04 (s, 1H), 7.93 (s, 1H), 7.59-7.53 (m, 3H), 7.45-7.36 (m, 2H), 7.28 (s, 1H), 7.04 (d, 1H, J=8.4 Hz), 6.23 (d, 1H, J=8.1 Hz), 6.04 (d, 1H, J=8.4 Hz), 4.29-4.15 (m, 3H), 3.68 (brs, 1H), 3.52-3.49 (m, 1H), 2.97-2.93 (m, 2H), 2.72-2.65 (m, 4H), 2.15-2.04 (m, 3H), 1.77 (brs, 3H), 1.26 (d, 3H, J=6.3 Hz), 1.11 (t, 6H, J=7.1 Hz). LC/MS: 486 [M+H]$^+$, t$_R$=1.48 min. HPLC: 95.50% at 214 nm, 96.62% at 254 nm, t$_R$=5.45 min.

Example 92

Synthesis of 6-(4-(2-(Diethylamino)ethoxy)phenyl)-N-(6-(2-methylpyrrolidin-1-yl)pyridin-2-yl)imidazo[1,2-b]pyridazin-8-amine

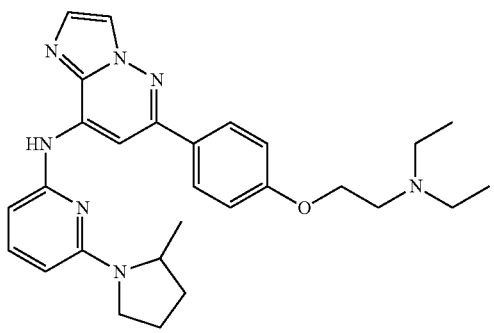 [SMILES: CCN(CC)CCOc1ccc(-c2cc(Nc3cccc(N4CCCC4C)n3)c3nccn3n2)cc1]

Step 1

6-(4-(2-(Diethylamino)ethoxy)phenyl)-N-(6-(2-methylpyrrolidin-1-yl)pyridin-2-yl)imidazo[1,2-b]pyridazin-8-amine

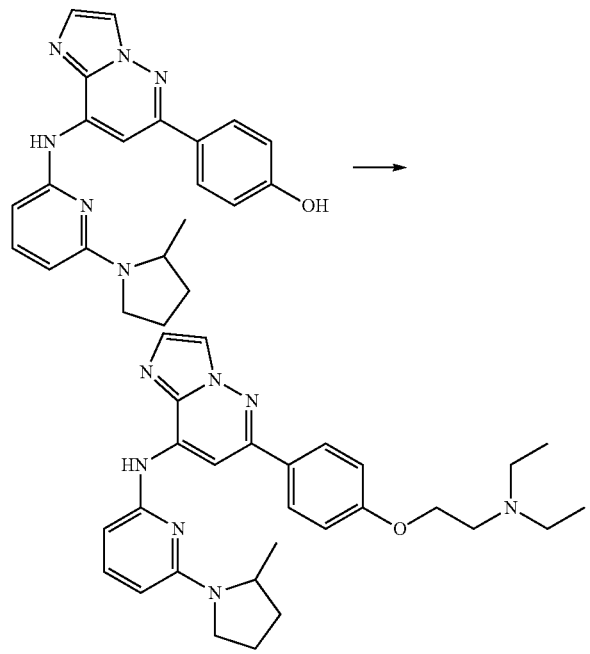

Procedure:

To a mixture of 4-(8-(6-(2-methylpyrrolidin-1-yl)pyridin-2-ylamino)imidazo[1,2-b]pyridazin-6-yl)phenol (40 mg, 0.1 mmol) and K$_2$CO$_3$ (28 mg, 0.2 mmol) in DMF (5 mL) was added 2-(diethylamino)ethyl methanesulfonate (30 mg, 0.15 mmol). The mixture was heated at 50° C. for 15 h. After cooling, the mixture was poured into water and extracted with EtOAc (3×10 mL). The combined organic layers were washed with brine and dried over MgSO$_4$. After filtration and concentration, the residue was purified by chromatography (silica, EtOAc) to give 6-(4-(2-(diethylamino)ethoxy)phenyl)-N-(6-(2-methylpyrrolidin-1-yl)pyridin-2-yl)imidazo[1,2-b]pyridazin-8-amine (20 mg, 40%). $^1$H NMR (300 MHz, CDCl$_3$): δ 8.59 (s, 1H), 8.06-7.90 (m, 4 h), 7.58 (s, 1H), 7.42 (t, 1H, J=7.6 Hz), 7.03-7.00 (m, 2H), 6.23 (d, 1H, J=7.2 Hz), 6.05 (d, 1H, J=8.1 Hz), 4.57 (brs, 2H), 4.27 (brs, 1H), 3.67 (brs, 1H), 3.52-3.41 (m, 3H), 3.22-3.20 (m, 4 h), 2.16-2.06 (m, 3H), 1.80 (brs, 1H), 1.45 (t, 6H, J=6.9 Hz), 1.28 (d, 3H, J=6.3 Hz). LC/MS: 486 [M+H]$^+$, t$_R$=1.12 min. HPLC: 98.72% at 214 nm, 99.10% at 254 nm, t$_R$=5.46 min.

Example 93

Synthesis of N-(6-(2-Methylpyrrolidin-1-yl)pyridin-2-yl)-6-(3-((piperidin-4-ylamino)methyl)phenyl)imidazo[1,2-b]pyridazin-8-amine hydrochloride

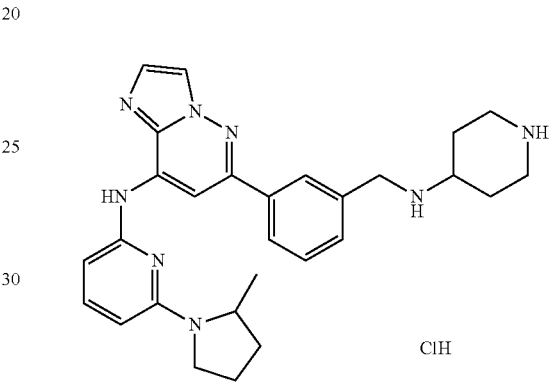

Step 1

3-(8-(6-(2-Methylpyrrolidin-1-yl)pyridin-2-ylamino)imidazo[1,2-b]pyridazin-6-yl)benzonitrile

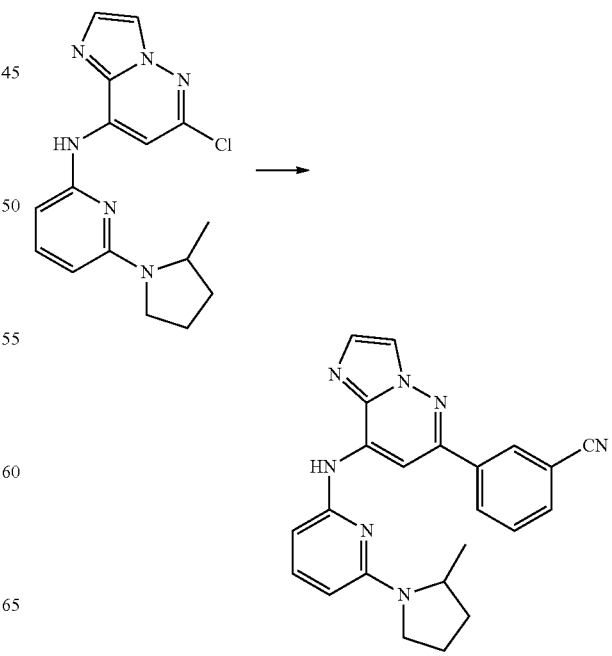

Procedure:

To a solution of 6-chloro-N-(6-(2-methylpyrrolidin-1-yl)pyridin-2-yl)imidazo[1,2-b]pyridazin-8-amine (500 mg, 1.52 mmol) and 3-cyanophenylboronic acid (336 mg, 2.29 mmol) in dioxane/H$_2$O (10 mL/2 mL) was added Na$_2$CO$_3$ (322 mg, 3.04 mmol) followed by Pd(dba)$_2$ (175 mg, 0.30 mmol) and X-Phos (73 mg, 0.15 mmol) under nitrogen with stirring. The mixture was stirred at reflux for 15 h under nitrogen. After cooling, the solvent was concentrated in vacuo. The residue was purified by chromatography (silica, ethyl acetate) to give 3-(8-(6-(2-methylpyrrolidin-1-yl)pyridin-2-ylamino)imidazo[1,2-b]pyridazin-6-yl)benzonitrile (310 mg, 52%) as a yellow oil. LC-MS: 396.2 [M+H]$^+$, t$_R$=1.89 min.

Step 2

6-(3-(Aminomethyl)phenyl)-N-(6-(2-methylpyrrolidin-1-yl)pyridin-2-yl)imidazo[1,2-b]pyridazin-8-amine

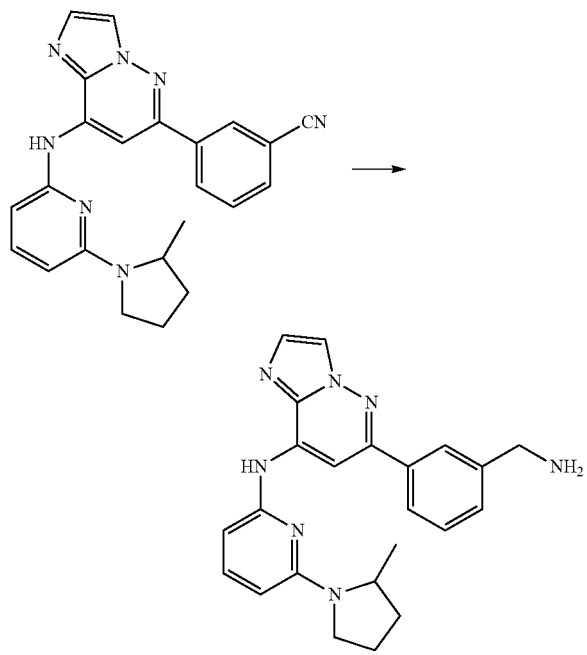

Procedure:

To a mixture of LiAlH$_4$ (114 mg, 3 mmol) in THF (10 mL) was added dropwise 3-(8-(6-(2-methylpyrrolidin-1-yl)pyridin-2-ylamino)imidazo[1,2-b]pyridazin-6-yl)benzonitrile (235 mg, 0.6 mmol) in THF (5 mL). The mixture was stirred at room temperature for 2 h. The reaction was quenched with water, and the mixture was filtered. The filtrate was dried over Na$_2$SO$_4$ and concentrated to give the product (210 mg, 88%) as an oil that was used directly without purification. LC/MS: 400.3 [M+H]$^+$, t$_R$=1.33 min.

Step 3 tert-Butyl 4-oxopiperidine-1-carboxylate

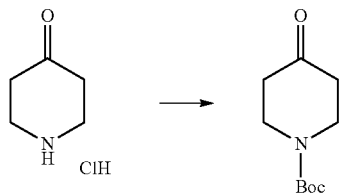 [SMILES: O=C1CCNCC1 ; Cl ; CC(C)(C)OC(=O)N1CCC(=O)CC1]

Procedure:

To a solution of piperidin-4-one hydrochloride (1.53 g, 0.01 mol) and (Boc)$_2$O (2.62 g, 0.012 mol) in MeOH (20 mL) was added Et$_3$N (2.02 g, 0.02 mol). The mixture was stirred at room temperature for 2 h. The solvent was removed in vacuo. The residue was diluted with water and extracted with EtOAc (3×15 mL). The combined organic layers were washed with brine then dried over MgSO$_4$. After filtration and concentration, tert-butyl 4-oxopiperidine-1-carboxylate (1.5 g, 75%) was obtained as a white solid. $^1$H NMR (300 MHz, CDCl$_3$): δ 3.71 (t, 4 h, J=6.2 Hz), 2.44 (t, 4 h, J=6.3 Hz), 1.49 (s, 9H).

Step 4 tert-Butyl-4-(3-(8-(6-(2-methylpyrrolidin-1-yl)pyridin-2-ylamino)imidazo[1,2-b]pyridazin-6-yl)benzylamino)piperidine-1-carboxylate

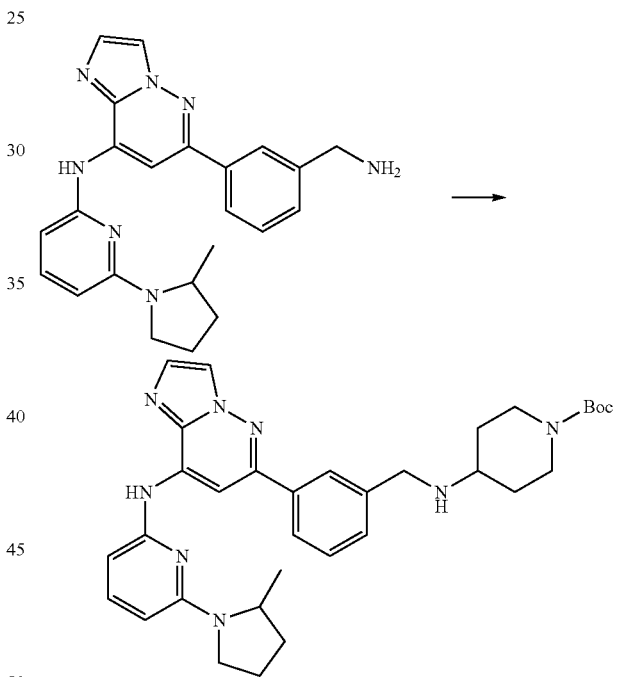

Procedure:

To a solution of 6-(3-(aminomethyl)phenyl)-N-(6-(2-methylpyrrolidin-1-yl)pyridin-2-yl)imidazo[1,2-b]pyridazin-8-amine (50 mg, 1.52 mmol), tert-butyl 4-oxopiperidine-1-carboxylate (38 mg, 0.188 mmol) and NaBH(OAc)$_3$ (80 mg, 0.375 mmol) in dichloromethane (5 mL) was added HOAc (12 mg). The mixture was stirred at room temperature for 3 h. The solvent was concentrated in vacuo. The residue was purified by chromatography (silica, EtOAc) to give tert-butyl 4-(3-(8-(6-(2-methylpyrrolidin-1-yl)pyridin-2-ylamino)imidazo[1,2-b]pyridazin-6-yl)benzylamino)piperidine-1-carboxylate (35 mg, 48%) as a yellow oil. LC/MS: 583.3 [M+H]$^+$, t$_R$=1.52 min.

Step 5

N-(6-(2-Methylpyrrolidin-1-yl)pyridin-2-yl)-6-(3-((piperidin-4-ylamino)methyl)phenyl)imidazo[1,2-b]pyridazin-8-amine hydrochloride

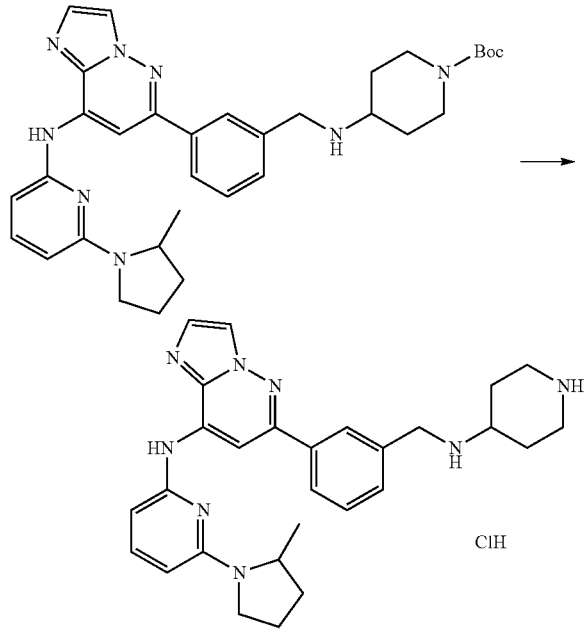

Procedure:

tert-Butyl-4-(3-(8-(6-(2-methylpyrrolidin-1-yl)pyridin-2-ylamino)imidazo[1,2-b]pyridazin-6-yl)benzylamino)piperidine-1-carboxylate (35 mg, 0.06 mmol) was dissolved in HCl gas in dichloromethane (5 mL). The solution was stirred at room temperature for 2 h. The solvent was concentrated in vacuo to give N-(6-(2-methylpyrrolidin-1-yl)pyridin-2-yl)-6-(3-((piperidin-4-ylamino)methyl)phenyl)imidazo[1,2-b]pyridazin-8-amine hydrochloride (35 mg, 109%) as a yellow solid. $^1$H NMR (300 MHz, DMSO+D$_2$O): δ 9.18 (s, 1H), 8.49 (s, 1H), 8.27 (s, 1H), 8.17 (s, 1H), 7.99 (d, 1H, J=7.5 Hz), 7.80 (d, 1H, J=7.5 Hz), 7.68 (t, 1H, J=7.5 Hz), 7.53 (t, 1H, J=7.8 Hz), 6.60 (d, 1H, J=7.5 Hz), 6.19 (d, 1H, J=8.4 Hz), 4.28-4.21 (m, 3H), 3.53-3.38 (m, 5H), 2.95 (t, 2H, J=12.3 Hz), 2.31-2.28 (m, 2H), 2.07-1.68 (m, 6H), 1.06 (d, 3H, J=6.0 Hz). LC/MS: 486 [M+H]$^+$, t$_R$=0.85 min. HPLC: 100% at 214 nm, 99.89% at 254 nm, t$_R$=4.58 min.

Example 94

Synthesis of N-(6-(2-Methylpyrrolidin-1-yl)pyridin-2-yl)-6-(3-(2-(piperazin-1-yl)ethoxy)phenyl)imidazo[1,2-b]pyridazin-8-amine hydrochloride

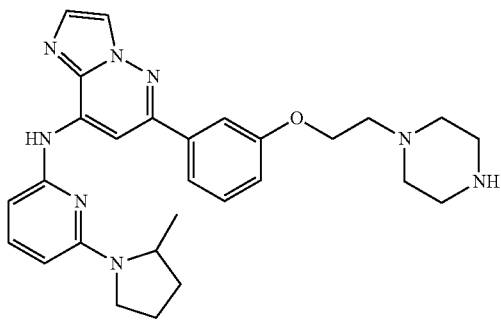 [SMILES: CC1CCCN1c1cccc(Nc2cc(-c3cccc(OCCN4CCNCC4)c3)nn3ccnc23)n1]

Step 1

Tert-Butyl 4-(2-hydroxyethyl)piperazine-1-carboxylate

Procedure:

To a solution of 2-(piperazin-1-yl)ethanol (1.3 g, 0.01 mol) and (Boc)$_2$O (2.4 g, 0.011 mol) in MeOH (15 mL) was added Et$_3$N (1.52 g, 0.015 mol). The mixture was stirred at room temperature for 3 h. The solvent was removed in vacuo. The residue was diluted with water and extracted with EtOAc (3×20 mL). The combined organic layers were washed with brine then dried over MgSO$_4$. After filtration and concentration, the product (2 g, 87%) was obtained as an oil. $^1$H NMR (300 MHz, CDCl$_3$): δ 3.74 (t, 2H, J=5.3 Hz), 3.56 (t, 4 h, J=5.0 Hz), 2.72 (t, 2H, J=5.1 Hz), 2.66 (t, 4 h, J=5.0 Hz), 1.44 (s, 9H). LCMS: No molecular ion observed for desired mass.

Step 2 tert-Butyl 4-(2-(methylsulfonyloxy)ethyl)piperazine-1-carboxylate

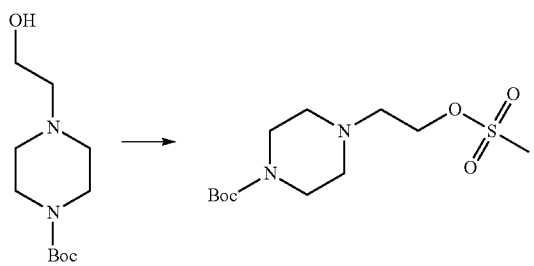 [SMILES: CC(C)(C)OC(=O)N1CCN(CCO)CC1 ; CC(C)(C)OC(=O)N1CCN(CCOS(C)(=O)=O)CC1]

Procedure:

To a solution of tert-butyl 4-(2-hydroxyethyl)piperazine-1-carboxylate (1.7 g, 7.4 mmol) and Et$_3$N (1.12 g, 11.1 mmol) in dichloromethane (20 mL) was added methanesulfonyl chloride (1 g, 8.87 mmol) at 0° C. The mixture was stirred at room temperature for 3 h. The mixture was washed with brine. The organic layer was concentrated in vacuo to give crude tert-butyl 4-(2-(methylsulfonyloxy)ethyl)piperazine-1-carboxylate (2.1 g, 94%). This was used in the next step without purification. $^1$H NMR (300 MHz, CDCl$_3$): δ 4.38 (t, 2H, J=5.3 Hz), 3.49-3.44 (m, 4 h), 3.09 (s, 3H), 2.79 (t, 2H, J=5.1 Hz), 2.58 (t, 4 h, J=5.0 Hz), 1.49 (s, 9H). LCMS: No molecular ion observed for desired mass.

213

Step 3 tert-Butyl-4-(2-(3-(8-(6-(2-methylpyrrolidin-1-yl)pyridin-2-ylamino)imidazo[1,2-b]pyridazin-6-yl)phenoxy)ethyl)piperazine-1-carboxylate

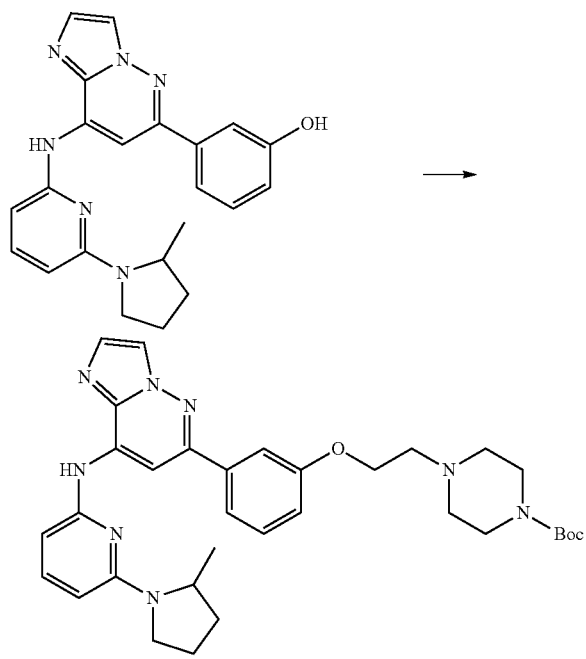

Procedure:

To a mixture of 3-(8-(6-(2-methylpyrrolidin-1-yl)pyridin-2-ylamino)imidazo[1,2-b]pyridazin-6-yl)phenol (50 mg, 0.129 mmol) and $K_2CO_3$ (36 mg, 0.258 mmol) in DMF (5 mL) was added tert-butyl 4-(2-(methylsulfonyloxy)ethyl)piperazine-1-carboxylate (48 mg, 0.155 mmol). The mixture was heated at 50° C. for 16 h. After cooling, the mixture was poured into water and extracted with EtOAc (3×10 mL). The combined organic layers were washed with brine and dried over $MgSO_4$. After filtration and concentration, the residue was washed by petroleum ether to give tert-butyl-4-(2-(3-(8-(6-(2-methylpyrrolidin-1-yl)pyridin-2-ylamino)imidazo[1,2-b]pyridazin-6-yl)phenoxy)ethyl)piperazine-1-carboxylate (25 mg, 33%) as crude oil. LC-MS: 599.4 $[M+H]^+$, $t_R$=1.53 min.

Step 4

N-(6-(2-Methylpyrrolidin-1-yl)pyridin-2-yl)-6-(3-(2-(piperazin-1-yl)ethoxy)phenyl)imidazo[1,2-b]pyridazin-8-amine

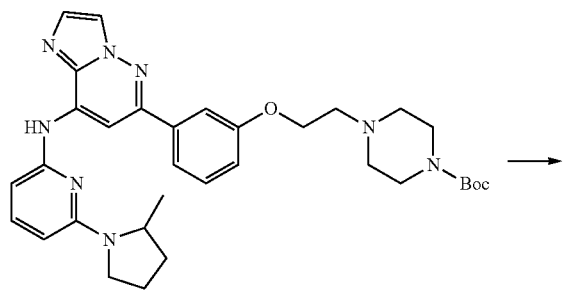

214

-continued

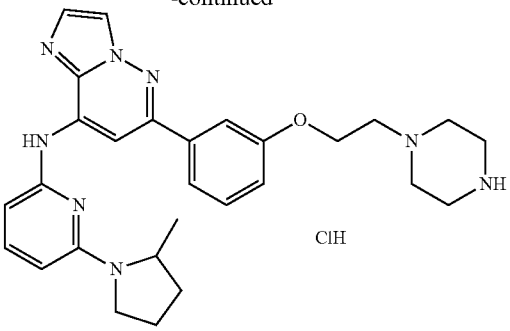

Procedure:

tert-butyl-4-(2-(3-(8-(6-(2-methylpyrrolidin-1-yl)pyridin-2-ylamino)imidazo[1,2-b]pyridazin-6-yl)phenoxy)ethyl)piperazine-1-carboxylate (25 mg, 0.042 mmol) was dissolved in dichloromethane (5 mL) that had been saturated by bubbling HCl gas. The solution was stirred at room temperature for 2 h. The solvent was concentrated in vacuo. The residue was purified by preparative-HPLC (Gemini 5u C18 150×21.2 mm; inject volume: 3 mL/inj, flow rate: 20 mL/min; wavelength: 214 nm and 254 nm; gradient conditions: 10% acetonitrile/90% water (0.1% TFA, v/v) initially, proceeding to 60% acetonitrile/40% water (0.1% TFA, v/v) in a linear fashion over 9 min) to give N-(6-(2-methylpyrrolidin-1-yl)pyridin-2-yl)-6-(3-(2-(piperazin-1-yl)ethoxy)phenyl)imidazo[1,2-b]pyridazin-8-amine hydrochloride (15 mg, 71%) as a yellow solid. $^1$H NMR (300 MHz, DMSO+$D_2$O): δ 9.12 (s, 1H), 8.49 (s, 1H), 8.21 (s, 1H), 7.58-7.52 (m, 4 h), 7.27-7.26 (m, 1H), 6.66 (d, 1H, J=7.8 Hz), 6.19 (d, 1H, J=8.4 Hz), 4.51 (brs, 2H), 4.25 (brs, 1H), 3.69-3.37 (m, 12H), 2.08-1.99 (m, 3H), 1.72 (brs, 1H), 1.12 (d, 3H, J=6.3 Hz). LC/MS: 499 $[M+H]^+$, $t_R$=1.08 min. HPLC: 99.25% at 214 nm, 99.12% at 254 nm, $t_R$=4.99 min.

Example 95

Synthesis of 3-(8-(5,6-dimethoxypyridin-2-ylamino)imidazo[1,2-b]pyridazin-6-yl)benzoic acid

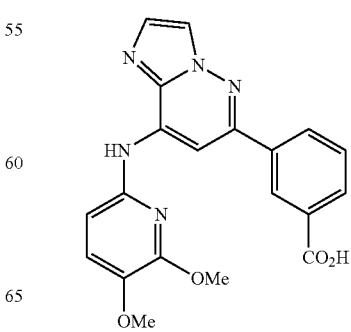

Step 1

6-Chloro-N-(5,6-dimethoxypyridin-2-yl)imidazo[1,2-b]pyridazin-8-amine

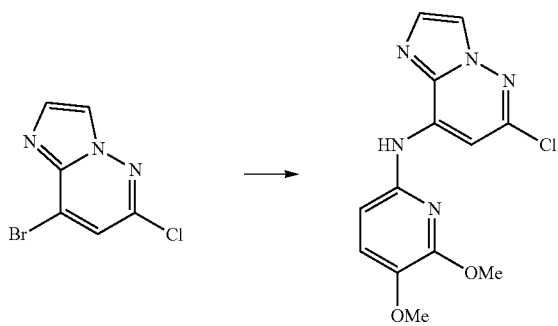 [SMILES: Clc1cc(Br)c2nccn2n1 ; COc1ccc(Nc2cc(Cl)nn3ccnc23)nc1OC]

A mixture of 8-bromo-6-chloroimidazo[1,2-b]pyridazine (2 g, 8.6 mmol) and 5,6-dimethoxypyridin-2-amine (1.39 g, 9.03 mmol) in DMF (72 ml) was cooled to 0° C. To the mixture was added sodium hydride (1.1 g, 27.5 mmol, 60% dispersion in mineral oil). The reaction was stirred for 10 min then warmed to room temperature. After 15 h the reaction was quenched with saturated sodium bicarbonate solution, and then diluted with water and EtOAc. An insoluble solid was filtered off. The filtrate was separated and the aqueous phase was washed with EtOAc. The combined organic extracts were concentrated in vacuo and the residue obtained was crystallized from methanol to give 6-chloro-N-(5,6-dimethoxypyridin-2-yl)imidazo[1,2-b]pyridazin-8-amine (2.4 g, 7.85 mmol, 91.2%) as light brown needles. $^1$H NMR (300 MHz, CHLOROFORM-d) δ ppm 8.26 (br. s., 1H) 7.95 (s, 1H) 7.81 (s, 1H) 7.55 (s, 1H) 7.15 (d, J=7.93 Hz, 1H) 6.58 (d, J=8.31 Hz, 1H) 4.12 (s, 3H) 3.89 (s, 3H); LC/MS: 305.9 [MH]$^+$.

Step 2

Ethyl 3-(8-(5,6-dimethoxypyridin-2-ylamino)imidazo[1,2-b]pyridazin-6-yl)benzoate

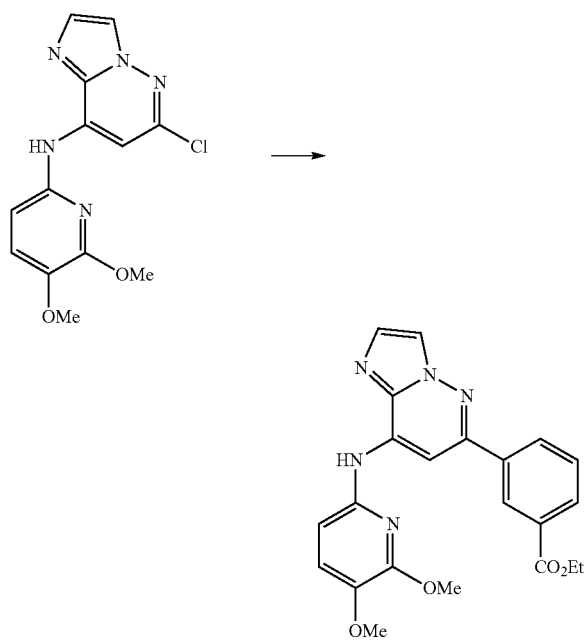

6-Chloro-N-(5,6-dimethoxypyridin-2-yl)imidazo[1,2-b]pyridazin-8-amine (611 mg, 2 mmol), ethyl 3-(4,4,5,5-tetramethyl-1,3,2-dioxaborolan-2-yl)benzoate (828 mg, 3.00 mmol), potassium phosphate (1.06 g, 5.00 mmol) and X-phos (381 mg, 800 μmol) were combined with dioxane (29.4 ml) and water (2.94 ml) to give a light yellow suspension. The mixture was evacuated and back-filled with argon three times, then Pd$_2$(dba)$_3$ (183 mg, 200 μmol) was added and the mixture heated to 125° C. in a microwave for 60 min. The mixture was filtered and the filtrate concentrated. The residue was purified by chromatography (silica, 160 g, 20% to 50% EtOAc in hexanes, gradient over 20 min) to give ethyl 3-(8-(5,6-dimethoxypyridin-2-ylamino)imidazo[1,2-b]pyridazin-6-yl)benzoate (284 mg, 677 μmol, 34%) as an off-white powder. $^1$H NMR (300 MHz, CHLOROFORM-d) δ ppm 8.55-8.68 (m, 2H) 8.20 (dd, J=13.79, 7.74 Hz, 2H) 7.96 (d, J=1.51 Hz, 1H) 7.52-7.71 (m, 2H) 7.19 (d, J=8.31 Hz, 1H) 6.73 (d, J=8.31 Hz, 1H) 4.45 (q, J=7.18 Hz, 2H) 4.20 (s, 3H) 3.82-3.97 (m, 3H) 1.44 (t, J=7.18 Hz, 3H); LC/MS: 420.2 [MH]$^+$.

Step 3

3-(8-(5,6-Dimethoxypyridin-2-ylamino)imidazo[1,2-b]pyridazin-6-yl)benzoic acid

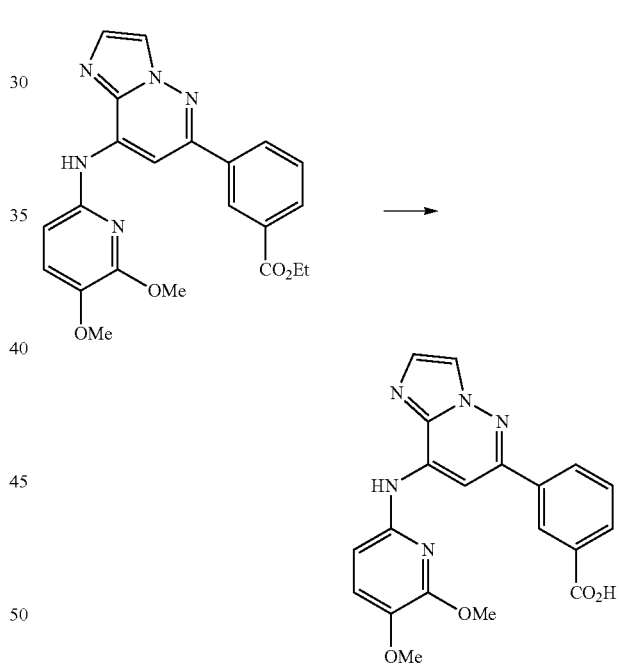

Ethyl 3-(8-(5,6-dimethoxypyridin-2-ylamino)imidazo[1,2-b]pyridazin-6-yl)benzoate (150 mg, 358 μmol) was dissolved in dioxane (18 mL). To this was added a solution of LiOH (85.6 mg, 3.58 mmol) in water (9 mL). The mixture was stirred for 4 h, acidified with 1N HCl, and concentrated in vacuo to give the crude acid which was recrystallized from isopropyl alcohol and methanol to give 3-(8-(5,6-dimethoxypyridin-2-ylamino)imidazo[1,2-b]pyridazin-6-yl)benzoic acid (123 mg, 314 μmol, 88%) as a light brown powder. $^1$H NMR (300 MHz, DMSO-d$_6$) δ ppm 9.97 (s, 1H) 8.60 (s, 1H) 8.52 (s, 1H) 8.17-8.30 (m, 2H) 8.05 (d, J=7.55 Hz, 1H) 7.60-7.72 (m, 2H) 7.41 (d, J=8.31 Hz, 1H) 7.12 (d, J=8.31 Hz, 1H) 4.05 (s, 3H) 3.76 (s, 3H); LC/MS: 391.8 [MH]$^+$.

Example 96

Synthesis of 3-(8-(5,6-Dimethoxypyridin-2-ylamino)imidazo[1,2-b]pyridazin-6-yl)-N-(4-(methylcarbamoyl)phenyl)benzamide

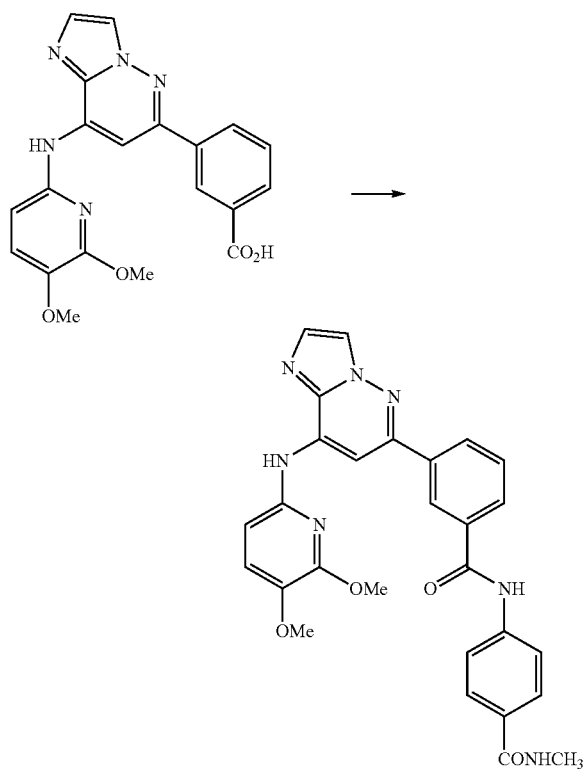

3-(8-(5,6-Dimethoxypyridin-2-ylamino)imidazo[1,2-b]pyridazin-6-yl)benzoic acid (58 mg, 148 μmol), HOBt (34.0 mg, 222 μmol) and EDCI (42.6 mg, 222 μmol) were combined with DMF (10 mL) to give a light yellow suspension. After 1 h, a clear yellow solution had been generated. DIPEA (47.9 mg, 64.7 μL, 370 μmol) and 4-amino-N-methylbenzamide (31.2 mg, 207 μmol) were added. After 15 h the mixture was concentrated in vacuo then diluted with water (10 mL) and filtered. The collected solid was washed with water (3×3 mL) and dried in vacuo. Purification by chromatography (silica, 50 g, Supelco VersaFlash, 0-5% methanol in dichloromethane, gradient over 15 min) gave a residue that was recrystallized from methanol to give 3-(8-(5,6-dimethoxypyridin-2-ylamino)imidazo[1,2-b]pyridazin-6-yl)-N-(4-(methylcarbamoyl)phenyl)benzamide (22 mg, 42.0 μmol, 28%) as an off-white powder. $^1$H NMR (300 MHz, DMSO-$d_6$) δ ppm 10.60 (s, 1H) 9.98 (s, 1H) 8.62 (s, 1H) 8.53 (s, 1H) 8.36 (d, J=4.91 Hz, 1H) 8.16-8.27 (m, 2H) 8.10 (d, J=7.93 Hz, 1H) 7.87 (d, J=1.51 Hz, 4H) 7.61-7.76 (m, 2H) 7.42 (d, J=8.31 Hz, 1H) 7.13 (d, J=8.31 Hz, 1H) 4.03 (s, 3H) 3.77 (s, 3H) 2.79 (d, J=4.53 Hz, 3H); LC/MS: 524.1 [MH]$^+$.

BIOLOGICAL EXAMPLES

SYK Assay Information

Determination of $IC_{50}$ of Spleen Tyrosine Kinase (SYK) Inhibition:

SYK kinase assay is a standard kinase assay adapted to a 96 well plate format. This assay is performed in 96-well format for $IC_{50}$ determination with 8 samples which represented 10 half log dilutions and a 40 μL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)

Streptavidin coated beads: Streptavidin Sepharose™, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.:0.0005 μM.

Peptide 1: biotinylated peptide is derived from a naturally occurring phosphor-acceptor consensus sequence (Biotin-EPEGDYEEVLE), special order from QCB, stock solution 20 mM, final conc.: 5.0 μM.

ATP: Adenosine-5'-triphosphate 20 mM, (ROCHE Cat. No.: 93202720), final concentration: 20 μM Buffer: HEPES: 2-Hydroxyethyl piperazine-2-ethanesulfonic acid (Sigma™, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM $MgCl_2 \times 6H_2O$: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM $MgCl_2$, 1 mM DTT, 0.1% BSA, pH 7.5

Bead wash buffer: 10 g/L PBS (Phosphate buffered saline) with 2M NaCl+1% phosphoric acid.

Experimental Method:

In 40 μL volume, 26 μL of ADB diluted, purified recombinant human SYK360-635 [0.5 nM] was mixed with 4 μL of 10× concentrations of the test compounds, [usually 100 μM-0.003 μM] in [10%] DMSO and the mixture was incubated for 10 min at RT.

The kinase reaction was initiated by the addition of 10 μL 4× substrate cocktail containing the DYE peptide substrate [0 or 5 μM], ATP [20 μM] and $^{33}$PγATP [2 μCi/rxn]. After incubation at 30° C. for 15 min, the reaction was terminated by the transfer of 25 μL of the reaction sample to a 96 well 0.65 μm Millipore MADVNOB membrane/plate containing 200 μL 5 mM EDTA and 20% Streptavidine coated beads in PBS.

The unbound radionucleotides were washed under vacuum with 3×250 μL 2M NaCl; 2×250 μL 2M NaCl+1% phosphoric acid; 1×250 μL $H_2O$. After the last wash membrane/plates were transferred to an adaptor plate, heat dried for 15 min at 60° C., and 50 μL scintillation cocktail was added to each well and 4 h later the amount of radioactivity was counted in a top counter.

The percent inhibition was calculated based on the uninhibited enzyme rate:

% Inhibition=100/(1+($IC_{50}$/Inhibitor conc)$^n$)

The IC$_{50}$ was calculated using a non-linear curve fit with XLfit software (ID Business Solution Ltd., Guilford, Surrey, UK).

| Compound | ENZYME_FILTRATION_IC50 (uM) |
|---|---|
| I-1 | >10 |
| I-2 | 0.18555 |
| I-3 | 0.4064 |
| I-4 | 0.35125 |
| I-5 | 0.1273 |
| I-6 | |
| I-7 | |
| I-8 | 0.4778 |
| I-9 | 0.1173 |
| I-10 | 0.00165 |
| I-11 | 0.3495 |
| I-12 | 0.0486 |
| I-13 | 3.49915 |
| I-14 | 0.36885 |
| I-15 | 0.0842 |
| I-16 | 0.08758 |
| I-17 | 0.03312 |
| I-18 | 0.11495 |
| I-19 | 0.075 |
| I-20 | 0.258 |
| I-21 | 0.65425 |
| I-22 | 0.43365 |
| I-23 | 0.44245 |
| I-24 | 0.1943 |
| I-25 | 0.0885 |
| I-26 | 0.26515 |
| I-27 | |
| I-28 | 0.18685 |
| I-29 | 0.6378 |
| I-30 | 1.95725 |
| I-31 | 0.27 |
| I-32 | 0.88917 |
| I-33 | 0.07895 |
| I-34 | 1.04783 |
| I-35 | 0.8337 |
| I-36 | 0.3449 |
| I-37 | 0.0981 |
| I-38 | 0.90435 |
| I-39 | 0.29185 |
| I-40 | 0.0425 |
| I-41 | 0.1297 |
| I-42 | 0.2189 |
| I-43 | 0.1066 |
| I-44 | 0.04765 |
| I-45 | 0.07122 |
| I-46 | 0.14144 |
| I-47 | 0.1594 |
| I-48 | 0.41005 |
| I-49 | 0.10838 |
| I-50 | 0.01895 |
| I-51 | 0.01605 |
| I-52 | 0.03615 |
| I-53 | 0.6378 |
| I-54 | 0.001 |
| I-55 | 0.00733 |
| I-56 | 0.59335 |
| I-57 | 0.00155 |
| I-58 | |
| I-59 | 0.59945 |
| I-60 | 0.23065 |
| I-61 | 1.3836 |
| I-62 | 0.30648 |
| I-63 | 0.1513 |
| I-64 | 0.0566 |
| I-65 | 1.2595 |
| I-66 | 0.69595 |
| I-67 | 0.2803 |
| I-68 | 0.0247 |
| I-69 | 0.5994 |
| I-70 | 0.06077 |
| I-71 | 0.24605 |
| I-72 | 0.0022 |
| I-73 | 0.21483 |
| I-74 | 0.01495 |
| I-75 | 0.4606 |
| I-76 | 0.04215 |
| I-77 | 0.0639 |
| I-78 | 0.06515 |
| I-79 | 0.48826 |
| I-80 | 0.61395 |
| I-81 | 0.1885 |
| I-82 | 0.05988 |
| I-83 | 0.0475 |
| I-84 | 0.01563 |
| I-85 | 0.60965 |
| I-86 | 0.10155 |
| I-87 | 0.20976 |
| I-88 | 0.05105 |
| I-89 | 0.08955 |
| I-90 | 0.15665 |
| I-91 | 0.2612 |
| I-92 | 0.0606 |
| I-93 | 0.02437 |
| I-94 | 0.1756 |
| I-95 | 0.949 |
| I-96 | 0.103 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of Formula I

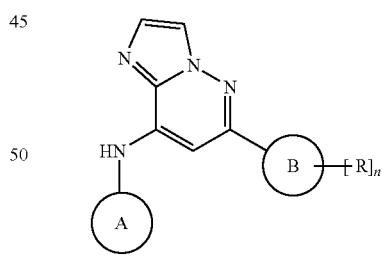

wherein:

A is pyridyl, pyrrolidinyl, or pyrazolyl, substituted with one or more A';

each A' is independently pyrrolidinyl or piperidinyl, optionally substituted with lower alkyl;

n is 0, 1 or 2;

B is phenyl, pyridyl, pyrrolidinyl, or piperidinyl;

each R is independently halo, hydroxy, lower alkyl, lower alkoxy, lower haloalkyl, cyano, heterocycloalkyl lower alkyl, —NH(C═O)R$^1$, —C(═O)R$^1$, —C(═O)OR', —O(CH$_2$)$_p$R$^1$, CH$_2$R$^1$, CH$_2$NHR$^1$, or —C(═O)NHR$^1$;

or two R together form a bicyclic heteroaryl or heterocycloalkyl ring system;

R$^1$ is H or R$^{1'}$;

R$^{1'}$ is lower alkyl, phenyl, indolyl, indazolyl, heteroaryl lower alkyl, or heterocycloalkyl, optionally substituted with one or more R$^{1''}$;

each R$^{1''}$ is hydroxy, lower alkyl, lower alkoxy, carboxy, amido, amino, dialkyl amino, or oxo; and p is 0, 1, or 2;

or a pharmaceutically acceptable salt thereof.

2. The compound of claim 1, wherein A is pyridyl, substituted with one or more A'.

3. The compound of claim 2, wherein B is phenyl.

4. The compound of claim 3, wherein A' is pyrrolidinyl, optionally substituted with one or more lower alkyl.

5. The compound of claim 4, wherein A' is methyl pyrrolidinyl or dimethyl pyrrolidinyl.

6. The compound of claim 5, wherein R is C(=O)NHR$^1$.

7. The compound of claim 5, wherein R is —C(=O)OH.

8. The compound of claim 5, wherein R is —NH(C=O)R$^1$.

9. The compound of claim 3, wherein n is 0 or two R together form a bicyclic heteroaryl or heterocycloalkyl ring system.

10. The compound of claim 6, wherein R1 is phenyl, indolyl, or indazolyl, optionally substituted with one or more R$^{1''}$.

11. A compound selected from the group consisting of:
(6-Phenyl-imidazo[1,2-b]pyridazin-8-yl)-(6-trifluoromethyl-pyridin-2-yl)-amine;
(5-Ethyl-pyridin-2-yl)-(6-phenyl-imidazo[1,2-b]pyridazin-8-yl)-amine;
(6-Phenyl-imidazo[1,2-b]pyridazin-8-yl)-(3,4,5,6-tetrahydro-2H-[1,2]bipyridinyl-6'-yl)-amine;
(6-Phenyl-imidazo[1,2-b]pyridazin-8-yl)-(6-pyrrolidin-1-yl-pyridin-2-yl)-amine;
[6-(2-Methyl-pyrrolidin-1-yl)-pyridin-2-yl]-(6-phenyl-imidazo[1,2-b]pyridazin-8-yl)-amine;
(1-tert-Butyl-1H-pyrazol-3-yl)-(6-phenyl-imidazo[1,2-b]pyridazin-8-yl)-amine;
8-(2,2-Dimethyl-pyrrolidin-1-yl)-6-phenyl-imidazo[1,2-b]pyridazine;
3-{8-[6-(2-Methyl-pyrrolidin-1-yl)-pyridin-2-ylamino]-imidazo[1,2-b]pyridazin-6-yl}-benzoic acid methyl ester;
3-{8-[6-(2-Methyl-pyrrolidin-1-yl)-pyridin-2-ylamino]-imidazo[1,2-b]pyridazin-6-yl}-benzoic acid;
4-(3-{8-[6-(2-Methyl-pyrrolidin-1-yl)-pyridin-2-ylamino]-imidazo[1,2-b]pyridazin-6-yl}-benzoylamino)-benzoic acid;
Sodium 3-(8-(6-(2-methylpyrrolidin-1-yl)pyridin-2-ylamino)imidazo[1,2-b]pyridazin-6-yl)benzoate;
3-{8-[6-(2-Methyl-pyrrolidin-1-yl)-pyridin-2-ylamino]-imidazo[1,2-b]pyridazin-6-yl}-benzamide;
(2-Methyl-3,4,5,6-tetrahydro-2H-[1,2']bipyridinyl-6'-yl)-(6-phenyl-imidazo[1,2-b]pyridazin-8-yl)-amine;
4-{8-[6-(2-Methyl-pyrrolidin-1-yl)-pyridin-2-ylamino]-imidazo[1,2-b]pyridazin-6-yl}-benzoic acid methyl ester;
4-{8-[6-(2-Methyl-pyrrolidin-1-yl)-pyridin-2-ylamino]-imidazo[1,2-b]pyridazin-6-yl}-benzoic acid;
4-{8-[6-(2-Methyl-pyrrolidin-1-yl)-pyridin-2-ylamino]-imidazo[1,2-b]pyridazin-6-yl}-N-(2-pyridin-4-yl-ethyl)-benzamide;
4-{8-[6-(2-Methyl-pyrrolidin-1-yl)-pyridin-2-ylamino]-imidazo[1,2-b]pyridazin-6-yl}-benzamide;
(6-Benzo[1,3]dioxol-5-yl-imidazo[1,2-b]pyridazin-8-yl)-[6-(2-methyl-pyrrolidin-1-yl)-pyridin-2-yl]-amine;
[6-(1H-Indazol-6-yl)-imidazo[1,2-b]pyridazin-8-yl]-[6-(2-methyl-pyrrolidin-1-yl)-pyridin-2-yl]-amine;
3-{8-[6-(2-Hydroxymethyl-pyrrolidin-1-yl)-pyridin-2-ylamino]-imidazo[1,2-b]pyridazin-6-yl}-benzoic acid;
[6-((R)-2-Methyl-pyrrolidin-1-yl)-pyridin-2-yl]-(6-phenyl-imidazo[1,2-b]pyridazin-8-yl)-amine;
3-[8-(6-Pyrrolidin-1-yl-pyridin-2-ylamino)-imidazo[1,2-b]pyridazin-6-yl]-benzoic acid;
3-{8-[6-(3-Aza-bicyclo[3.1.0]hex-3-yl)-pyridin-2-ylamino]-imidazo[1,2-b]pyridazin-6-yl}-benzoic acid;
2-Methyl-3-{8-[6-((S)-2-methyl-pyrrolidin-1-yl)-pyridin-2-ylamino]-imidazo[1,2-b]pyridazin-6-yl}-benzoic acid;
[6-(3-Methyl-pyrrolidin-1-yl)-pyridin-2-yl]-(6-phenyl-imidazo[1,2-b]pyridazin-8-yl)-amine;
4-[8-(5,6-Dimethoxy-pyridin-2-ylamino)-imidazo[1,2-b]pyridazin-6-yl]-benzoic acid;
4-[8-(5,6-Dimethoxy-pyridin-2-ylamino)-imidazo[1,2-b]pyridazin-6-yl]-N-(2-pyridin-4-yl-ethyl)-benzamide;
4-[8-(5,6-Dimethoxy-pyridin-2-ylamino)-imidazo[1,2-b]pyridazin-6-yl]-N-[2-(2-oxo-1,2-dihydro-pyridin-4-yl)-ethyl]-benzamide;
[6-(2,5-Dimethyl-pyrrolidin-1-yl)-pyridin-2-yl]-(6-phenyl-imidazo[1,2-b]pyridazin-8-yl)-amine;
[6-(2-Ethyl-pyrrolidin-1-yl)-pyridin-2-yl]-(6-phenyl-imidazo[1,2-b]pyridazin-8-yl)-amine;
{1-[6-(6-Phenyl-imidazo[1,2-b]pyridazin-8-ylamino)-pyridin-2-yl]-pyrrolidin-2-yl}-methanol;
[6-(2,2-Dimethyl-pyrrolidin-1-yl)-pyridin-2-yl]-(6-phenyl-imidazo[1,2-]pyridazin-8-yl)-amine,
4-[8-(5,6-Dimethoxy-pyridin-2-ylamino)-imidazo[1,2-b]pyridazin-6-yl]-N-[2-(1-methyl-2-oxo-1,2-dihydro-pyridin-4-yl)-ethyl]-benzamide;
[6-(3,3-Dimethyl-pyrrolidin-1-yl)-pyridin-2-yl]-(6-phenyl-imidazo[1,2-b]pyridazin-8-yl)-amine;
[6-(2-Methoxymethyl-pyrrolidin-1-yl)-pyridin-2-yl]-(6-phenyl-imidazo[1,2-b]pyridazin-8-yl)-amine;
3-{8-[6-(2-Methoxymethyl-pyrrolidin-1-yl)-pyridin-2-ylamino]-imidazo[1,2-b]pyridazin-6-yl}-benzoic acid;
[6-(1H-Indazol-5-yl)-imidazo[1,2-b]pyridazin-8-yl]-[6-(2-methyl-pyrrolidin-1-yl)-pyridin-2-yl]amine;
3-[8-(3,5-Dimethyl-3,4,5,6-tetrahydro-2H-[1,2']bipyridinyl-1-ylamino)-imidazo[1,2-b]pyridazin-6-yl]-benzoic acid;
[6-(3-Methoxy-phenyl)-imidazo[1,2-b]pyridazin-8-yl]-[6-(2-methyl-pyrrolidin-1-yl)-pyridin-2-yl]-amine;
N-(2-Hydroxy-ethyl)-3-{8-[6-(2-methyl-pyrrolidin-1-yl)-pyridin-2-ylamino]-imidazo[1,2-b]pyridazin-6-yl}-benzamide;
N-(2-Hydroxy-1-methyl-ethyl)-3-{8-[6-(2-methyl-pyrrolidin-1-yl)-pyridin-2-ylamino]imidazo[1,2-b]pyridazin-6-yl}-benzamide;
(3-{8-[6-(2-Methyl-pyrrolidin-1-yl)-pyridin-2-ylamino]-imidazo[1,2-b]pyridazin-6-yl}-phenyl)-morpholin-4-yl-methanone;
[6-((S)-2-Methyl-pyrrolidin-1-yl)-pyridin-2-yl]-(6-phenyl-imidazo[1,2-b]pyridazin-8-yl)-amine;
(5,6-Dimethoxy-pyridin-2-yl)-(6-phenyl-imidazo[1,2-b]pyridazin-8-yl)-amine;
[6-(2-Chloro-phenyl)-imidazo[1,2-b]pyridazin-8-yl]-[6-(2-methyl-pyrrolidin-1-yl)-pyridin-2-yl]amine;
N-(2-Dimethylamino-ethyl)-3-{8-[6-(2-methyl-pyrrolidin-1-yl)-pyridin-2-ylamino]-imidazo[1,2-b]pyridazin-6-yl}-benzamide;

[6-(2-Methyl-pyrrolidin-1-yl)-pyridin-2-yl]-(6-o-tolyl-imidazo[1,2-b]pyridazin-8-yl)-amine;
[6-(2-Methyl-pyrrolidin-1-yl)-pyridin-2-yl]-[6-(2-trifluoromethyl-phenyl)-imidazo[1,2-b]pyridazin-8-yl]-amine;
3-{8-[6-((S)-2-Methyl-pyrrolidin-1-yl)-pyridin-2-ylamino]-imidazo[1,2-b]pyridazin-6-yl}-benzoic acid;
4-{8-[6-((S)-2-Methyl-pyrrolidin-1-yl)-pyridin-2-ylamino]-imidazo[1,2-b]pyridazin-6-yl}-benzamide;
3-{8-[6((S)-2-Methyl-pyrrolidin-1-yl)-pyridin-2-ylamino]-imidazo[1,2-b]pyridazin-6-yl}-benzamide;
(6-Benzothiazol-6-yl-imidazo[1,2-b]pyridazin-8-yl)-[6-((S)-2-methyl-pyrrolidin-1-yl)-pyridin-2-yl]-amine;
[6-(2,5-Dimethyl-pyrrolidin-1-yl)-pyridin-2-yl]-(6-phenyl-imidazo[1,2-b]pyridazin-8-yl)-amine;
4-{3-[8-(5,6-Dimethoxy-pyridin-2-ylamino)-imidazo[1,2-b]pyridazin-6-yl]-benzoylamino}-benzoic acid;
3-[8-(5,6-Dimethoxy-pyridin-2-ylamino)-imidazo[1,2-b]pyridazin-6-yl]-N-(1H-indazol-5-yl)-benzamide;
3-[8-(5,6-Dimethoxy-pyridin-2-ylamino)-imidazo[1,2-b]pyridazin-6-yl]-N-(1-oxo-2,3-dihydro-H-isoindol-5-yl)-benzamide;
4-{3-[8-(5,6-Dimethoxy-pyridin-2-ylamino)-imidazo[1,2-b]pyridazin-6-yl]-benzoylamino}-2-methoxy-benzoic acid;
3-[8-(5,6-Dimethoxy-pyridin-2-ylamino)-imidazo[1,2-b]pyridazin-6-yl]-N-(2-oxo-2,3-dihydro-1H-indol-5-yl)-benzamide;
3-{8-[6-(3,3-Dimethyl-pyrrolidin-1-yl)-pyridin-2-ylamino]-imidazo[1,2-b]pyridazin-6-yl}-benzoic acid;
3-{8-[6-(2,5-Dimethyl-pyrrolidin-1-yl)-pyridin-2-ylamino]-imidazo[1,2-b]pyridazin-6-yl}-benzoic acid;
3-[8-(4,4-Dimethyl-3,4,5,6-tetrahydro-2H-[1,2]bipyridinyl-6-ylamino)-imidazo[1,2-b]pyridazin-6-yl]-benzoic acid;
[6-(3,4-Dimethoxy-phenyl)-imidazo[1,2-b]pyridazin-8-yl]-[6-(2-methyl-pyrrolidin-1-yl)-pyridin-2-yl]-amine;
[6-(2-Methyl-pyrrolidin-1-yl)-pyridin-2-yl]-[6-(1,2,3,4-tetrahydro-quinolin-7-yl)-imidazo[1,2-b]pyridazin-8-yl]-amine;
1-(7-{8-[6-(2-Methyl-pyrrolidin-1-yl)-pyridin-2-ylamino]-imidazo[1,2-b]pyridazin-6-yl}-3,4-dihydro-1H-isoquinolin-2-yl)-ethanone;
3-{8-[6-(3-tert-Butyl-pyrrolidin-1-yl)-pyridin-2-ylamino]-imidazo[1,2-b]pyridazin-6-yl}-benzoic acid methyl ester;
3-{8-[6-(3-tert-Butyl-pyrrolidin-1-yl)-pyridin-2-ylamino]-imidazo[1,2-b]pyridazin-6-yl}-benzoic acid;
3-{8-[6-(3-tert-Butyl-pyrrolidin-1-yl)-pyridin-2-ylamino]-imidazo[1,2-b]pyridazin-6-yl}-benzamide;
(3-{8-[6-(2-Methyl-pyrrolidin-1-yl)-pyridin-2-ylamino]-imidazo[1,2-b]pyridazin-6-yl}-phenyl)-methanol;
[6-(2-Methyl-pyrrolidin-1-yl)-pyridin-2-yl]-[6-(3-piperidin-1-ylmethyl-phenyl)-imidazo[1,2-b]pyridazin-8-yl]-amine;
[6-(2-Methyl-pyrrolidin-1-yl)-pyridin-2-yl]-[6-(3-pyrrolidin-1-ylmethyl-phenyl)-imidazo[1,2-b]pyridazin-8-yl]-amine;
[6-(3-Chloro-phenyl)-imidazo[1,2-b]pyridazin-8-yl]-[6-((S)-2-methyl-pyrrolidin-1-yl)-pyridin-2-yl]-amine;
N-{1-[8-(5,6-Dimethoxy-pyridin-2-ylamino)-imidazo[1,2-b]pyridazin-6-yl]-piperidin-3-yl}-terephthalamic acid;
1-[8-(5,6-Dimethoxy-pyridin-2-ylamino)-imidazo[1,2-b]pyridazin-6-yl]-piperidine-3-carboxylic acid (1,3-dioxo-2,3-dihydro-1H-isoindol-5-yl)-amide;
4-({1-[8-(5,6-Dimethoxy-pyridin-2-ylamino)-imidazo[1,2-b]pyridazin-6-yl]-piperidine-3-carbonyl}-amino)-benzoic acid;
4-({1-[8-(5,6-Dimethoxy-pyridin-2-ylamino)-imidazo[1,2-b]pyridazin-6-yl]-pyrrolidine-3-carbonyl}-amino)-benzoic acid;
N-{1-[8-(5,6-Dimethoxy-pyridin-2-ylamino)-imidazo[1,2-b]pyridazin-6-yl]-pyrrolidin-3-yl}-terephthalamic acid;
4-{8-[6-(2-Methyl-pyrrolidin-1-yl)-pyridin-2-ylamino]-imidazo[1,2-b]pyridazin-6-yl}-phenol;
[6-(2-Methyl-pyrrolidin-1-yl)-pyridin-2-yl]-(6-pyridin-3-yl-imidazo[1,2-b]pyridazin-8-yl)-amine;
[6-(4-Fluoro-phenyl)-imidazo[1,2-b]pyridazin-8-yl]-[6-(2-methyl-pyrrolidin-1-yl)-pyridin-2-yl]-amine;
3-{8-[6-(2-Methyl-pyrrolidin-1-yl)-pyridin-2-ylamino]-imidazo[1,2-b]pyridazin-6-yl}-benzonitrile;
[6-(2-Methyl-pyrrolidin-1-yl)-pyridin-2-yl]-(6-pyridin-4-yl-imidazo[1,2-b]pyridazin-8-yl)-amine;
[6-(5-Methoxy-pyridin-3-yl)-imidazo[1,2-b]pyridazin-8-yl]-[6-(2-methyl-pyrrolidin-1-yl)-pyridin-2-yl]-amine;
[6-(2-Methyl-pyrrolidin-1-yl)-pyridin-2-yl]-{6-[4-(2-pyrrolidin-1-yl-ethoxy)-phenyl]-imidazo[1,2-b]pyridazin-8-yl}-amine;
[6-(3-Aminomethyl-phenyl)-imidazo[1,2-b]pyridazin-8-yl]-[6-(2-methyl-pyrrolidin-1-yl)-pyridin-2-yl]-amine;
[6-(4-tert-Butyl-phenyl)-imidazo[1,2-b]pyridazin-8-yl]-[6-(2-methyl-pyrrolidin-1-yl)-pyridin-2-yl]-amine;
3-{8-[6-(2-Methyl-pyrrolidin-1-yl)-pyridin-2-ylamino]-imidazo[1,2-b]pyridazin-6-yl}-phenol;
[6-(2-Methyl-pyrrolidin-1-yl)-pyridin-2-yl]-{6-[3-(2-piperidin-1-yl-ethoxy)-phenyl]-imidazo[1,2-b]pyridazin-8-yl}-amine;
[6-(2-Methyl-pyrrolidin-1-yl)-pyridin-2-yl]-{6-[3-(2-morpholin-4-yl-ethoxy)-phenyl]imidazo[1,2-b]pyridazin-8-yl}-amine;
[6-(2-Methyl-pyrrolidin-1-yl)-pyridin-2-yl]-{6-[4-(2-piperidin-1-yl-ethoxy)-phenyl]-imidazo[1,2-b]pyridazin-8-yl}-amine;
[6-(2-Methyl-pyrrolidin-1-yl)-pyridin-2-yl]-{6-[4-(2-morpholin-4-yl-ethoxy)-phenyl]-imidazo[1,2-b]pyridazin-8-yl}-amine;
{6-[3-(2-Diethylamino-ethoxy)-phenyl]-imidazo[1,2-b]pyridazin-8-yl}-[6-(2-methyl-pyrrolidin-1-yl)-pyridin-2-yl]-amine;
{6-[4-(2-Diethylamino-ethoxy)-phenyl]-imidazo[1,2-b]pyridazin-8-yl}-[6-(2-methyl-pyrrolidin-1-yl)-pyridin-2-yl]-amine;
[6-(2-Methyl-pyrrolidin-1-yl)-pyridin-2-yl]-{6-[3-(piperidin-4-ylaminomethyl)-phenyl]-imidazo[1,2-b]pyridazin-8-yl}-amine;
[6-(2-Methyl-pyrrolidin-1-yl)-pyridin-2-yl]-{6-[3-(2-piperazin-1-yl-ethoxy)-phenyl]-imidazo[1,2-b]pyridazin-8-yl}-amine;
3-[8-(5,6-Dimethoxy-pyridin-2-ylamino)-imidazo[1,2-b]pyridazin-6-yl]-benzoic acid; and
3-(8-(5,6-Dimethoxypyridin-2-ylamino)imidazo[1,2-b]pyridazin-6-yl)-N-(4-(methylcarbamoyl)phenyl)benzamide,
or a pharmaceutically acceptable salt thereof.

12. A method for treating an inflammatory or autoimmune condition comprising administering to a patient in need thereof a therapeutically effective amount of the compound of claim 1.

13. The method of claim 12, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

14. A method for treating an inflammatory condition comprising administering to a patient in need thereof a therapeutically effective amount of the compound of claim 1.

15. A method for treating rheumatoid arthritis comprising administering to a patient in need thereof a therapeutically effective amount of the compound of claim 1.

16. A method for treating asthma comprising administering to a patient in need thereof a therapeutically effective amount of the compound of claim 1.

17. A method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of claim 1.

18. A method for treating an inflammatory condition comprising co-administering to a patient in need thereof a therapeutically effective amount of an anti-inflammatory compound in combination with a therapeutically effective amount of the compound of claim 1.

19. A method for treating an immune disorder comprising co-administering to a patient in need thereof a therapeutically effective amount of an immunosuppressant compound in combination with a therapeutically effective amount of the compound of claim 1.

20. A pharmaceutical composition comprising a therapeutically effective amount of the compound of claim 1, or a pharmaceutically acceptable salt thereof, admixed with at least one pharmaceutically acceptable carrier, excipient or diluent.

21. The pharmaceutical composition of claim 20, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

* * * * *